US008838395B2

(12) United States Patent
Matsiev et al.

(10) Patent No.: US 8,838,395 B2
(45) Date of Patent: Sep. 16, 2014

(54) SYSTEMS AND METHODS FOR INTRAVENOUS DRUG MANAGEMENT USING IMMITTANCE SPECTROSCOPY

(75) Inventors: Leonid F. Matsiev, San Jose, CA (US); Michael J. Weickert, Emerald Hills, CA (US); James W. Bennett, Santa Clara, CA (US); Matthew F. Smith, San Jose, CA (US); Svetlana Litvintseva, San Jose, CA (US); Kit Blanke, Milpitas, CA (US)

(73) Assignee: S.E.A. Medical Systems, Inc., Emerald Hills, CA (US)

( * ) Notice: Subject to any disclaimer, the term of this patent is extended or adjusted under 35 U.S.C. 154(b) by 79 days.

(21) Appl. No.: 13/229,597

(22) Filed: Sep. 9, 2011

(65) Prior Publication Data

US 2012/0065617 A1    Mar. 15, 2012

Related U.S. Application Data

(60) Provisional application No. 61/381,076, filed on Sep. 9, 2010, provisional application No. 61/394,775, filed on Oct. 20, 2010, provisional application No. 61/462,325, filed on Dec. 5, 2010, provisional application No. 61/429,461, filed on Jan. 4, 2011.

(51) Int. Cl.
*G01N 31/00* (2006.01)

(52) U.S. Cl.
USPC ............................................................ 702/22

(58) Field of Classification Search
USPC .................................................. 702/1, 22, 23
See application file for complete search history.

(56) References Cited

U.S. PATENT DOCUMENTS

| | | | |
|---|---|---|---|
| 3,286,992 A | 11/1966 | Armeniades et al. |
| 4,132,944 A | 1/1979 | Bentz |
| 4,601,820 A | 7/1986 | Leason |
| 4,810,963 A | 3/1989 | Blake et al. |
| 5,260,665 A | 11/1993 | Goldberg et al. |
| 5,260,667 A | 11/1993 | Garcia-Golding et al. |

(Continued)

FOREIGN PATENT DOCUMENTS

| | | |
|---|---|---|
| EP | 0499217 B1 | 1/1996 |
| EP | 1739585 A2 | 1/2007 |

(Continued)

OTHER PUBLICATIONS

Tian et al.; Drug signature using impedance spectroscopy technique; BMES/EMBS Proc. Of the First Joint Conf., Atlanta, Georgia; vol. 2; pp. 813; Oct. 13, 1999.*

(Continued)

*Primary Examiner* — Kevin C Sirmons
*Assistant Examiner* — Deanna K Hall
(74) *Attorney, Agent, or Firm* — Shay Glenn LLP

(57) ABSTRACT

Described herein are devices, systems, and methods for determining the composition of liquids, including the identity of one or more drugs in the liquid, the concentration of the drug, and the type of diluent using immittance spectroscopy. These devices, systems and methods are particularly useful for describing the identity and, in some variations, concentration of one or more components of a medical liquid such as intravenous fluid. In particular, described herein are devices, systems and methods that may operate in low ionic strength diluents. Also described are methods of recognizing complex immittance spectrograph patterns to determine the composition of a liquid by pattern recognition.

19 Claims, 166 Drawing Sheets

(56) References Cited

U.S. PATENT DOCUMENTS

| | | | |
|---|---|---|---|
| 5,425,867 | A | 6/1995 | Dawson et al. |
| 5,569,591 | A | 10/1996 | Kell et al. |
| 5,612,622 | A | 3/1997 | Goldman et al. |
| 5,772,688 | A | 6/1998 | Muroki |
| 5,792,668 | A | 8/1998 | Fuller et al. |
| 5,992,643 | A | 11/1999 | Scrogham et al. |
| 6,182,504 | B1 | 2/2001 | Gaisford |
| 6,449,580 | B1 | 9/2002 | Bardetsky et al. |
| 6,556,001 | B1 | 4/2003 | Wiegand et al. |
| 6,690,181 | B1 | 2/2004 | Dowdeswell et al. |
| 6,771,074 | B2 | 8/2004 | Zou et al. |
| 6,853,203 | B2 | 2/2005 | Beylich et al. |
| 6,885,960 | B2 | 4/2005 | Wagner et al. |
| 6,969,468 | B2 | 11/2005 | Stone et al. |
| 6,970,738 | B1 | 11/2005 | Othman et al. |
| 6,989,680 | B2 | 1/2006 | Sosnowski et al. |
| 6,990,422 | B2 | 1/2006 | Laletin et al. |
| 7,011,631 | B2 | 3/2006 | Davis et al. |
| 7,043,372 | B2 | 5/2006 | Koehler et al. |
| 7,049,831 | B2 | 5/2006 | Wooton et al. |
| 7,078,910 | B2 | 7/2006 | Hirthe et al. |
| 7,106,075 | B2 | 9/2006 | Hu |
| 7,109,729 | B2 | 9/2006 | Schilowitz et al. |
| 7,124,120 | B2 | 10/2006 | Wikiel et al. |
| 7,143,637 | B1 | 12/2006 | McBrearty et al. |
| 7,154,102 | B2 | 12/2006 | Poteet et al. |
| 7,218,395 | B2 * | 5/2007 | Kaye et al. .............. 356/301 |
| 7,250,775 | B1 | 7/2007 | Collins et al. |
| 7,253,644 | B2 | 8/2007 | Song |
| 7,270,733 | B2 | 9/2007 | Wikiel et al. |
| 7,315,767 | B2 | 1/2008 | Caduff et al. |
| 7,317,525 | B2 | 1/2008 | Rzasa et al. |
| 7,474,971 | B2 | 1/2009 | Hu et al. |
| 7,581,434 | B1 | 9/2009 | Discenzo et al. |
| 7,621,181 | B2 | 11/2009 | Cammarata et al. |
| 8,328,083 | B1 | 12/2012 | Bochenko et al. |
| 8,355,753 | B2 | 1/2013 | Bochenko et al. |
| 8,385,972 | B2 | 2/2013 | Bochenko et al. |
| 8,394,053 | B2 | 3/2013 | Bochenko et al. |
| 2002/0180570 | A1 | 12/2002 | Facer et al. |
| 2002/0183693 | A1 | 12/2002 | Peterson et al. |
| 2003/0072549 | A1 | 4/2003 | Facer et al. |
| 2003/0159741 | A1 | 8/2003 | Sparks |
| 2003/0204330 | A1 | 10/2003 | Allgeyer |
| 2004/0020772 | A1 | 2/2004 | Bas et al. |
| 2004/0079652 | A1 | 4/2004 | Vreeke et al. |
| 2004/0126814 | A1 | 7/2004 | Singh et al. |
| 2004/0142405 | A1 | 7/2004 | Alfonta et al. |
| 2004/0171983 | A1 | 9/2004 | Sparks et al. |
| 2005/0023155 | A1 | 2/2005 | Sawyer et al. |
| 2005/0266582 | A1 | 12/2005 | Modlin et al. |
| 2006/0105467 | A1 | 5/2006 | Niksa et al. |
| 2007/0072286 | A1 | 3/2007 | Orsel et al. |
| 2007/0191700 | A1 | 8/2007 | Say et al. |
| 2007/0293817 | A1 | 12/2007 | Feng et al. |
| 2008/0053202 | A1 | 3/2008 | Rohklin et al. |
| 2008/0105565 | A1 | 5/2008 | Davalos et al. |
| 2008/0116908 | A1 | 5/2008 | Potyrailo et al. |
| 2008/0167823 | A1 | 7/2008 | Koehler et al. |
| 2008/0172187 | A1 | 7/2008 | Koehler et al. |
| 2009/0102450 | A1 | 4/2009 | Da Silva et al. |
| 2009/0115435 | A1 | 5/2009 | Tomlinson |
| 2009/0115436 | A1 | 5/2009 | Koehler, III et al. |
| 2009/0261847 | A1 | 10/2009 | Petrovsky et al. |
| 2009/0293590 | A1 | 12/2009 | Zeng et al. |
| 2010/0300899 | A1 | 12/2010 | Levine et al. |
| 2010/0305499 | A1 | 12/2010 | Matsiev et al. |
| 2011/0009817 | A1 | 1/2011 | Bennett et al. |
| 2011/0060198 | A1 | 3/2011 | Bennett et al. |
| 2012/0037266 | A1 | 2/2012 | Bochenko |
| 2012/0323208 | A1 | 12/2012 | Bochenko et al. |
| 2012/0325330 | A1 | 12/2012 | Prince et al. |
| 2013/0018356 | A1 | 1/2013 | Prince et al. |
| 2013/0204227 | A1 | 8/2013 | Bochenko et al. |

FOREIGN PATENT DOCUMENTS

| | | |
|---|---|---|
| EP | 2042719 A2 | 4/2009 |
| EP | 2068139 A1 | 6/2009 |
| JP | 2006-138770 | 6/2006 |
| JP | 2008-76227 | 4/2008 |
| WO | WO2004/033003 A1 | 4/2004 |
| WO | WO2005/007223 A2 | 1/2005 |
| WO | WO2006/010310 A1 | 2/2006 |
| WO | WO2007/047004 A2 | 4/2007 |
| WO | WO2007/054700 A1 | 5/2007 |
| WO | WO2008/073931 A2 | 6/2008 |
| WO | WO2008/133656 A2 | 11/2008 |
| WO | WO2008131609 A1 | 11/2008 |
| WO | WO 2009/114115 A1 | 9/2009 |

OTHER PUBLICATIONS

Bow, Sing-Tze; Pattern Recognition and Image Preprocessing; 2nd ed.; Marcel Dekker; pp. 16-20, 29-32, 112-117, 197-199, and 511-513 (21 total pgs.); Jan. 28, 2002.

Bruun, H. H.; Hot-wire anemometry: principles and signal analysis; Oxford University Press; pp. 34-37 & 112-121 (14 total pgs); Jun. 28, 1995.

Carter, C.W.; Graphic Representation of the impedance of networks containing resistance and two reactances: Bell Sys. Tech. J.;vol. 4; pp. 387-401; Jul. 1925.

Cole-Parmer (Tech. Library); Why Measure Viscosity? What is it?; 10 pgs.; printed Sep. 8, 2010 (http://www.coleparmer.com/techinfo/techinfo.asp?htmlfile=why-meas-viscosity.htm&ID=933).

Endress+Hauser; Bubble Detection Sensor OUSAF13; Tech. Info. Doc. No. TI921C/24/ae; 4 pgs.; printed/accessed Sep. 10, 2010 (https://portal.endress.com/wa001/dla/50001951410/000/00/TI921CAE.pdf).

Fouke et al.; Sensor for measuring surface fluid conductivity in vivo; IEEE Trans Biomed Eng.; vol. 35; No. 10; pp. 877-881; Oct. 1988.

Gonzalez et al.; Fluid flow induced by nonuniform ac electric fields in electrolytes on microelectrodes. ii. a linear double-layer analysis; Phys. Rev. E; vol. 61; No. 4; pp. 4019R4028; Apr. 2000.

Green et al.; Fluid flow induced by nonuniform ac electric fields in electrolytes on microelectrodes. i. experimental measurements; Phys. Rev. E; vol. 61; No. 4; pp. 4011R4018; Apr. 2000.

Green et al.; Fluid flow induced by nonuniform ac electric fields in electrolytes on microelectrodes. iii. observation of streamlines and numerical simulation; Phys. Rev. E; 66; 026305; Aug. 19, 2002.

Green et al.; Impedance based flow sensors; Microtechnologies for the New Millennium; 2005 SPIE; May 9-11, 2005.

Helmholtz; Studien über elektrische Grenzschichten. Annalen der Physik und Chemie; Neue Folge; 7 (7), p. 337-382; Jul. 1879— (translation: P. E. Bocque; Studies of electric boundary layers; Dep. Engineering Research Univ. Mich.; 33; pp. 5-47; 1951 (month unavailable).

Homola, Jiri (Ed.); Surface Plasmon Resonance Based Sensors; Springer Series on Chemical Sensors and Biosensors; vol. 4; pp. 134-138; Jul. 2006.

Kikutani et al.; Flowing thermal lens micro-flow velocimeter; Sensors and Actuators B: Chemical; vol. 133; iss. 1; pp. 91-96; Jul. 28, 2008.

Krasser et al.; Simultaneous Measurements at U-tube Density Sensors in Fundamental and Harmonic Oscillation; EUROCON; The Int'l Conf. on "Computer as a tool"; pp. 551-555; Sep. 9-12, 2007.

Kumar et al.; A fibre optic evanescent wave sensor used for the detection of trace nitrites in water; Journal of Optics A: Pure and Applied Optics; vol. 4; pp. 247-250; Mar. 8, 2002.

MacDonald et al.; Analysis of impedance and admittance data for solids and liquids; J. Electrochem. Soc.; vol. 124; No. 7; pp. 1022-1030; Jul. 1977.

MacDonald; Impedance spectroscopy-emphasizing solid materials and systems; 1st ed.; John Wiley and Sons; pp. 1-4; Jun. 1987.

MacDonald; Theory of ac space-charge polarization effects in photoconductors, semiconductors, and electrolytes; Physical Review; vol. 92; No. 1; pp. 4-17; Oct. 1, 1953.

Maltoni et al.; Handbook of Fingerprint Recognition; Springer, NY; pp. 137-141; May 20, 2003.

(56) References Cited

OTHER PUBLICATIONS

Mathioulakis et al.; A pulsed-wire technique for velocity and temperature measurements in natural convection flows; Experiments in Fluids; vol. 18; Nos. 1-2; pp. 82-86; Dec. 1994.

Nixon, M.S. et al.; Feature Extraction and Image Processing; 1st ed.; MPG Books Ltd.; pp. 164-169; Feb. 28, 2002.

Oh et al.; Minimization of electrode polarization effect by nanogap electrodes for biosensor applications; The 16th Ann Int'l Conf on Micro Electro Mech Sys 2003; MEMS-03 Kyoto. IEEE; pp. 52-55; Jan. 19-23, 2003.

Omega Engineering; Turbidity Measurement; 4 pgs.; printed/accessed Sep. 10, 2010 (http://www.omega.com/techref/ph-6.html).

Optek; Inline process color measurement (Application note from website; 2 pgs.; printed Sep. 8, 2010 (http://www.optek.com/Application_Note/General/English/7/Inline_Process_Color_Measureme nt.asp).

Orazem et al.; History of Impedance Spectroscopy; Electrochemical Impedance Spectroscopy; John Wiley & Sons; pp. XXV-XXXI; (published online) Feb. 7, 2008.

Potyrailo et al.; Near-Ultraviolet Evanescent-Wave Absorption Sensor Based on a Multimode Optical Fiber; Anal. Chem.; vol. 70; No. 8; pp. 1639-1645; Apr. 15, 1998.

Resonance; ElectroChemical Methods; 11 pgs.; printed/accessed from archive Sep. 10, 2010 (http://web.archive.org/web/20061023171937/http://www.resonancepub.com/electrochem.htm).

Richter, Andreas; Differential optical absorption spectroscopy as a tool to measure pollution from space; Spectroscopy Europe; vol. 18; No. 6; pp. 14-21; 2006 (month unavailable).

Sarmousakis et al.; Impedance at polarized platinum electrodes in various electrolytes; Journal of the Electrochemical Society; vol. 104; No. 7; pp. 454-459; Jul. 1957.

Schirmer et al.; A new method for the determination of membrane permeability by spatially resolved concentration measurements; Meas. Sci. Technol.; vol. 15; No. 1; pp. 195-202; Jan. 2004.

Schwan; Linear and nonlinearelectrode polarization and biological materials; Ann. Biomed. Eng.; vol. 20; No. 3; pp. 269R288; May 1992.

Sensorland.com; How Sensors Work—Understanding pH measurement; 7 pgs.; printed Sep. 8, 2010 (http://www.sensorland.com/HowPage037.html).

Singh, Shyam; Refractive Index Measurement and its Applications; Physica Scripta; vol. 65; No. 2; pp. 167-180; Feb. 2002.

Smith, P.H.; Transmission line calculator; Electronics.; pp. 29-31; Jan. 1939.

Stachowiak et al.; A thermoelectric sensor for fluid flow measurement. principles, calibration and solution for self temperature compensation; Flow Measurement and Instrumentation; vol. 9; iss. 3; pp. 135-141; Sep. 1998.

Test & Measurement World; Analysis of dielectric material properties using LCR meters; www.tmworld.com/contents/pdf/tmw03_05D1_jr.doc; printed/accessed Oct. 26, 2010.

Überall, Herbert; Interference and Steady-State Scattering of Sound Waves; In: Handbook of Acoustics (M. J. Crocker (Ed.); Chap. 4; pp. 47-60; Mar. 1998.

Walton et al.; Platinum pacemaker electrodes: origins and effects of the electrode-tissue interface impedance; Pacing Clin. Electrophysiol; vol. 10; pp. 87R99; Jan.-Feb. 1978.

Way et al.; Hot-wire probes for measuring velocity and concentration in helium-air mixtures; AIAA Journal; vol. 8; No. 5; pp. 976R978; May 1970.

Bauerle, J.E.; Study of solid electrolyte polarization by a complex admittance method: J. of Physics and Chem. of Solids; vol. 30; No. 12; pp. 2657-2670; Dec. 1969.

Cole et al.; Dispersion and absorption in dielectrics I. alternation current characteristics: J. Chem. Phys.; vol. 9 No. 4; pp. 341-351; Apr. 1941.

Fischler et al.; Polarisation impedance of pacemaker electrodes: in vitro studies simulating practical operation; Med. Biol. Eng. and Comput.; vol. 19; No. 5; pp. 579-588; Sep. 1981.

Sluyters J.H.; On the impedance of galvanic cells: I. Theory.; Rec. Trav Chim.; vol. 79; No. 10; pp. 1092-1100; (the year of publication is sufficiently earlier than the effective U.S. filing date and any foreign priority date) 1960.

Sluyters J.H.; On the impedance of galvanic cells: II. Experimental verification.; Rec. Trav Chim.; vol. 79; No. 10; pp. 1101-1110; (the year of publication is sufficiently earlier than the effective U.S. filing date and any foreign priority date) 1960.

Smith, P.H.; An improved transmission line calculator; Electronics.; vol. 17; No. 1; pp. 130-133; Jan. 1944.

MacDonald et al.; Fundamentals of Impedance Spectroscopy (Ch. 1/pp. 1-4); in Impedance Spectroscopy: Theory, Experiment, and Applications 2nd Ed.; Barsoukov & MacDonald; pp. 1-4; Mar. 2005.

* cited by examiner

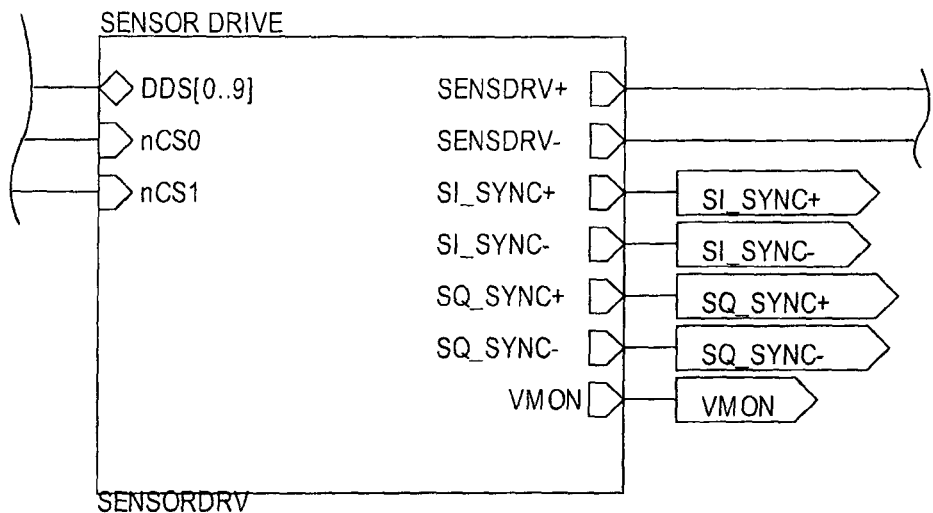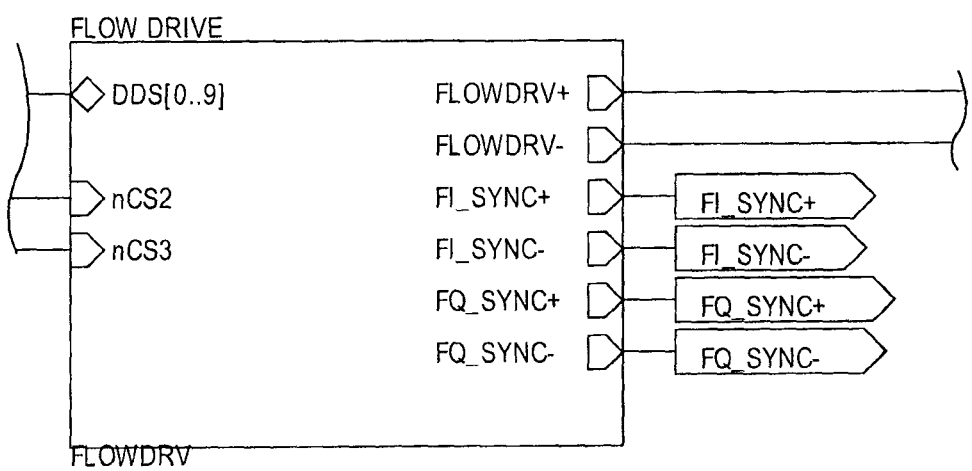
FIG. 3 (cont.)

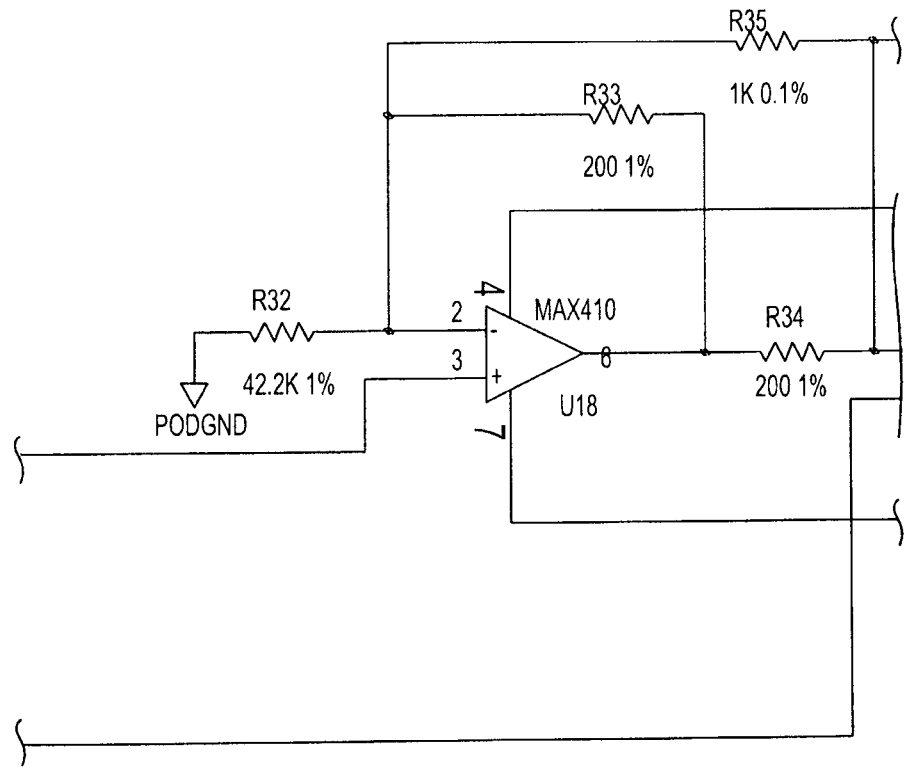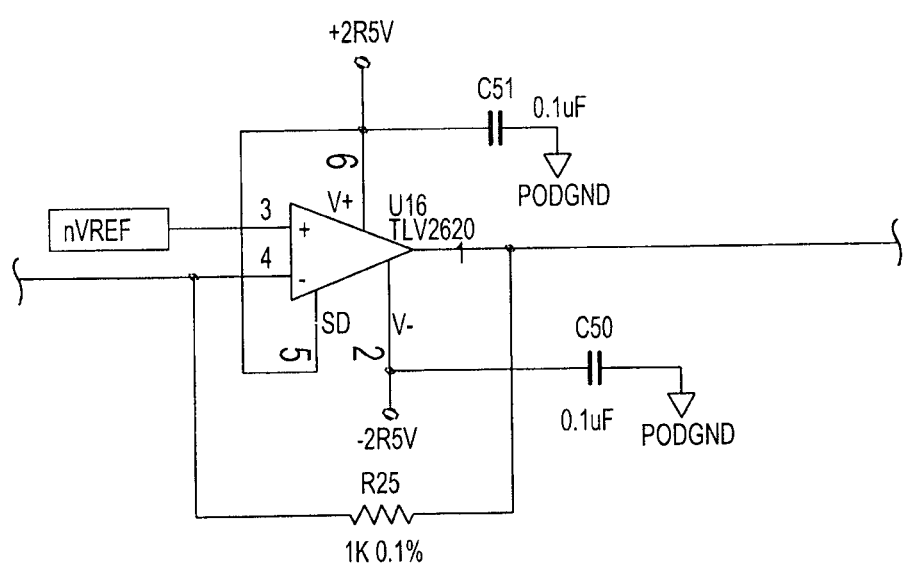
FIG. 8 (CONT.)

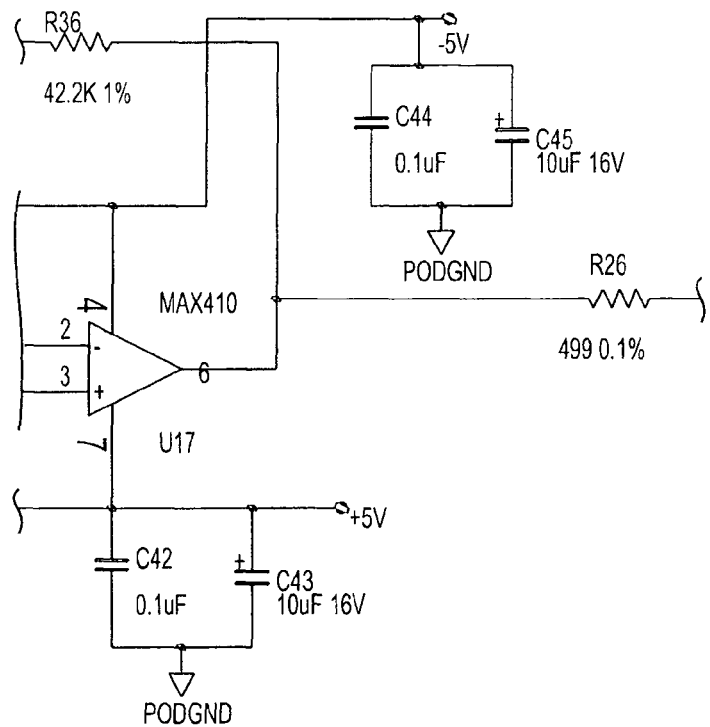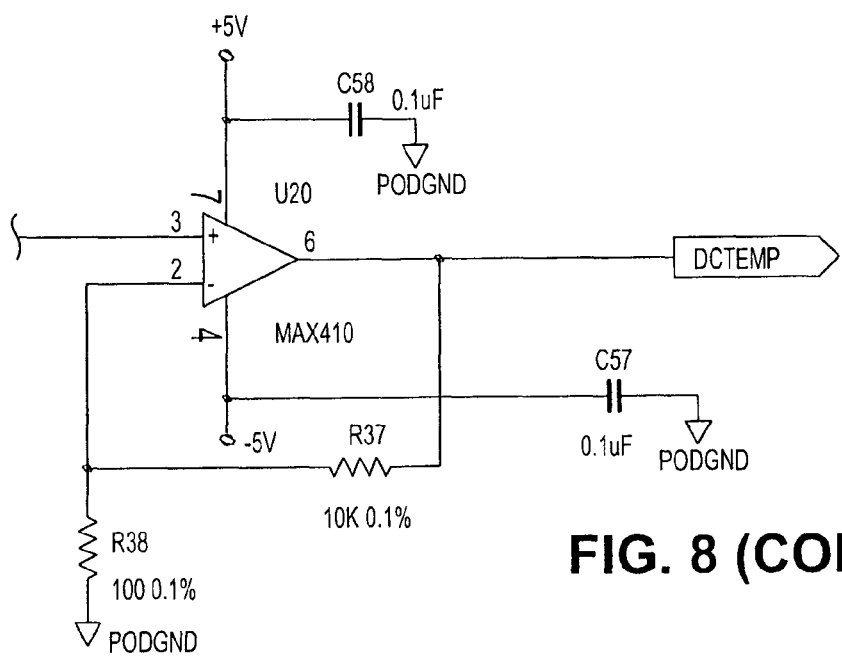
FIG. 8 (CONT.)

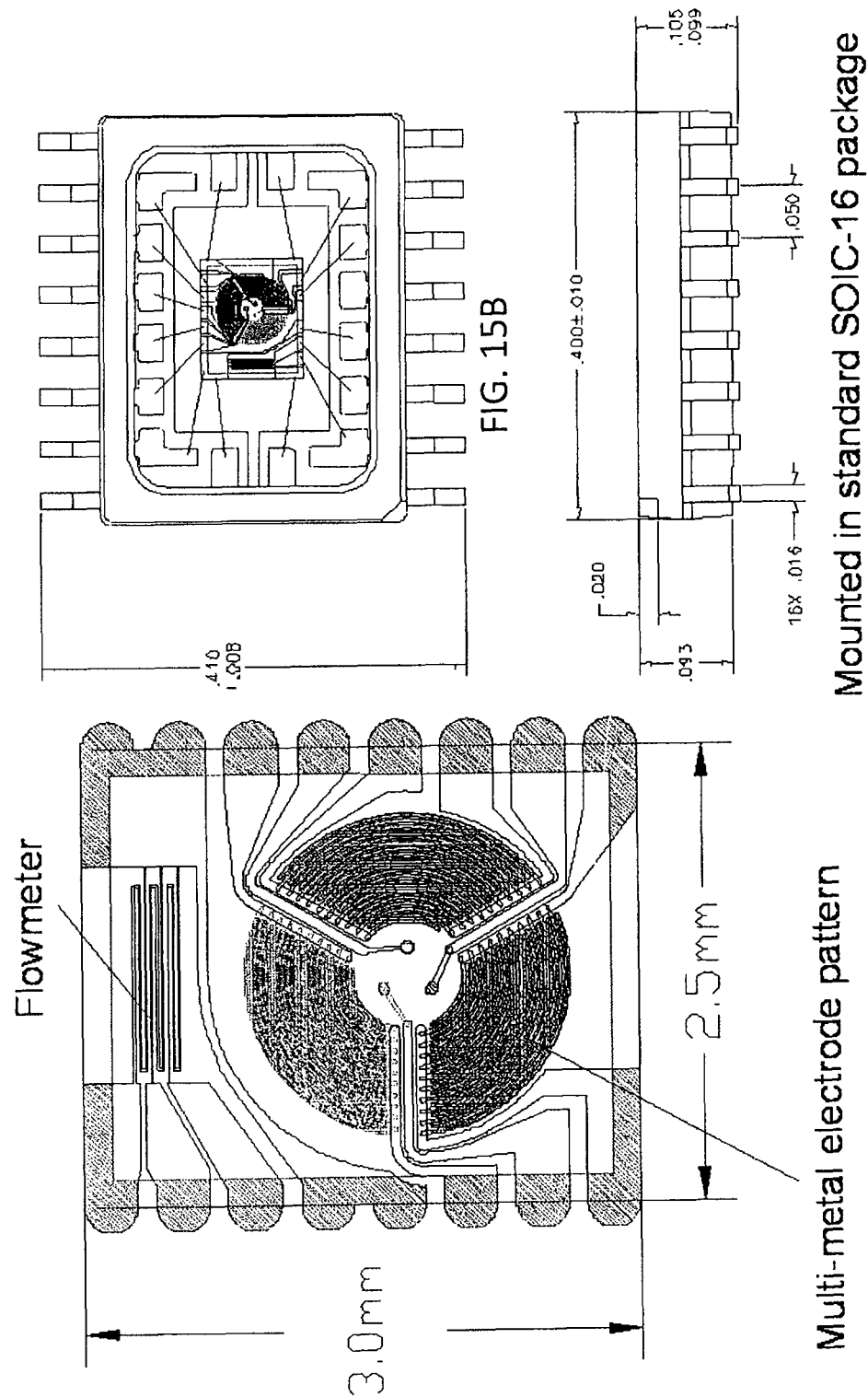

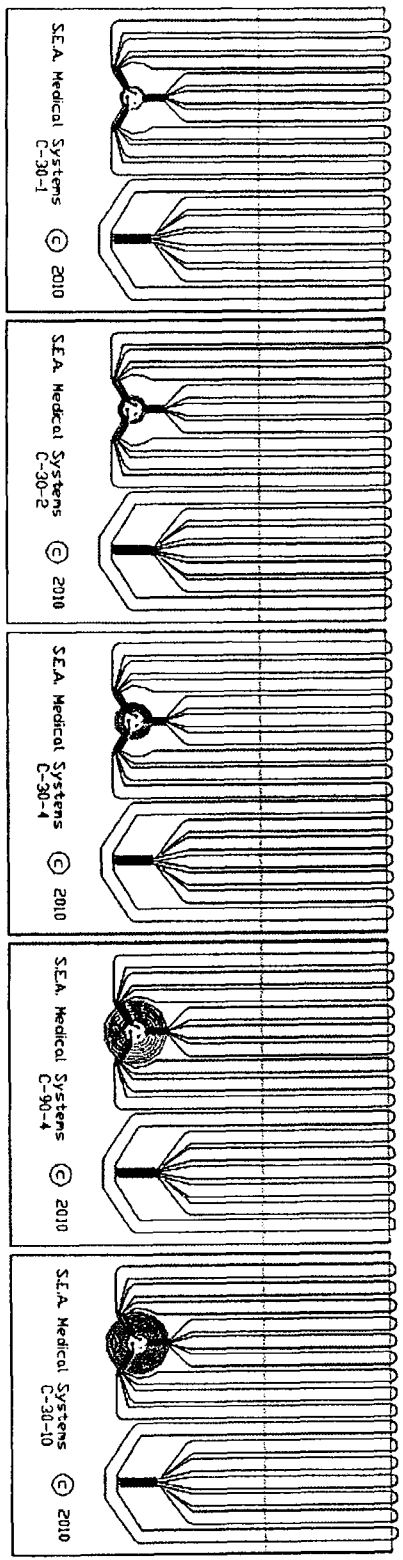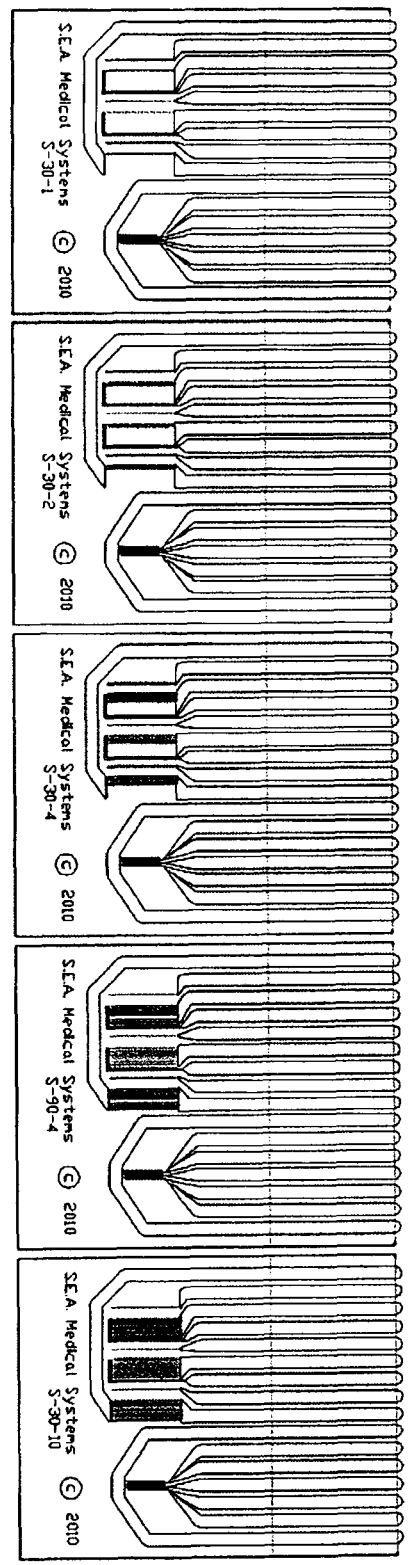

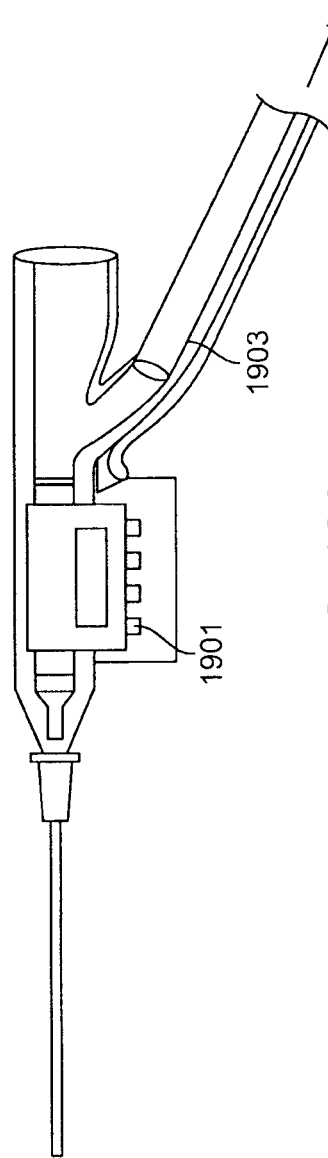
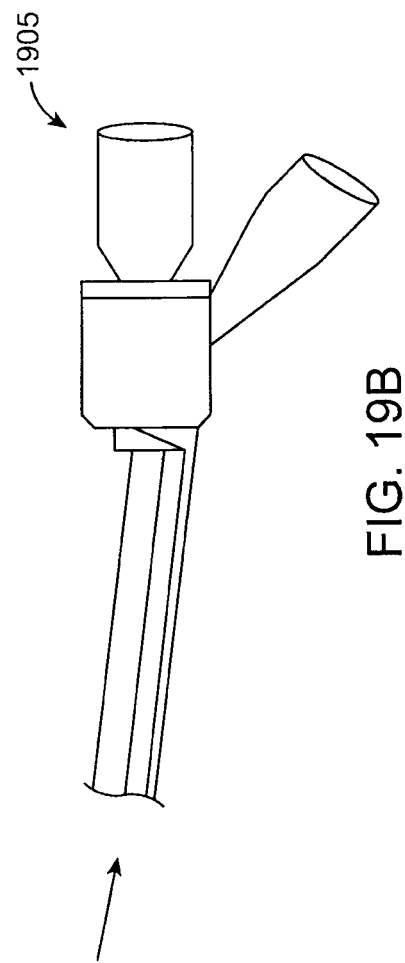
FIG. 19A
FIG. 19B

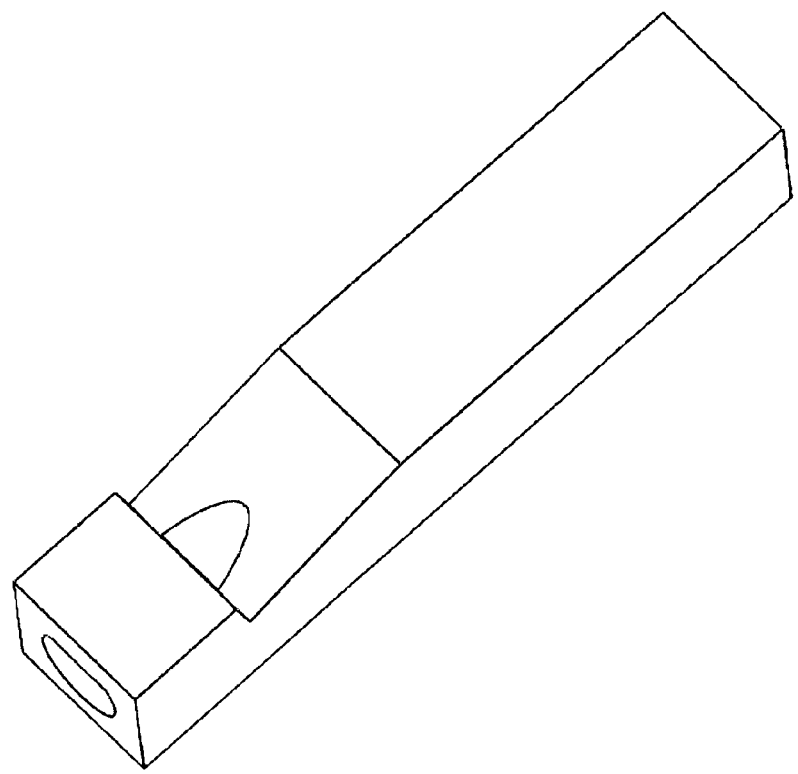
FIG. 39A
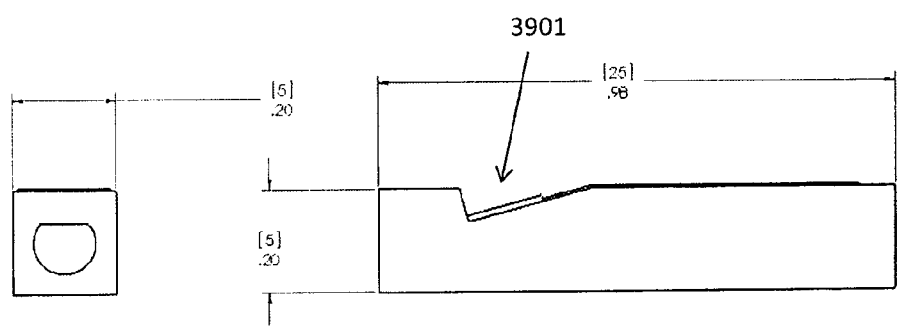
FIG. 39B
FIG. 39C

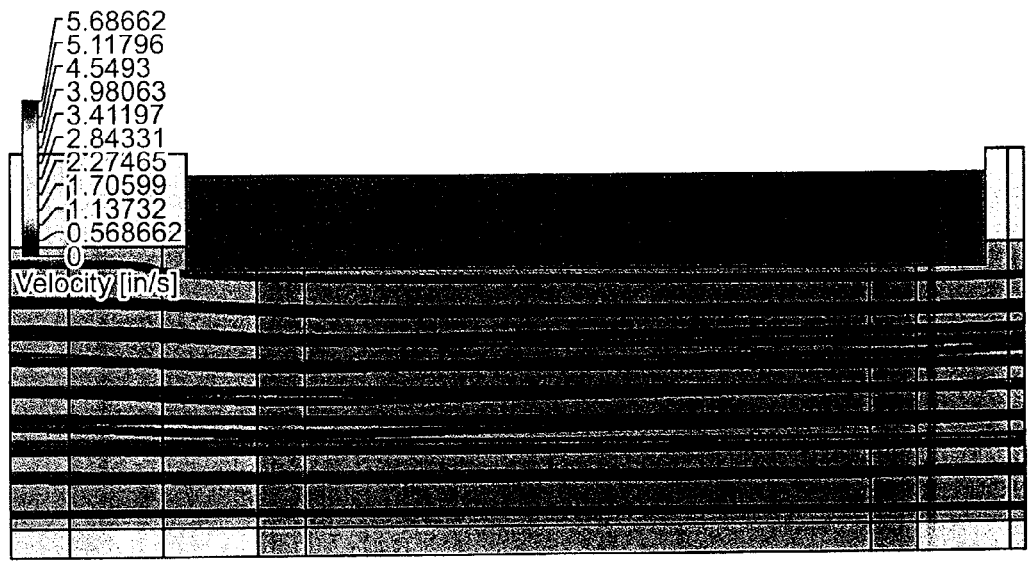
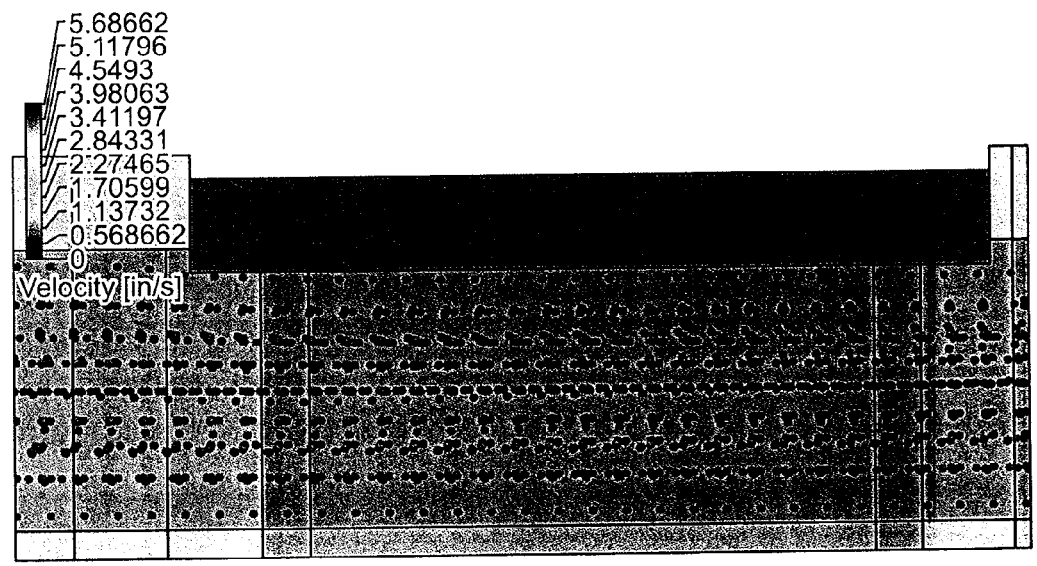
FIG. 45

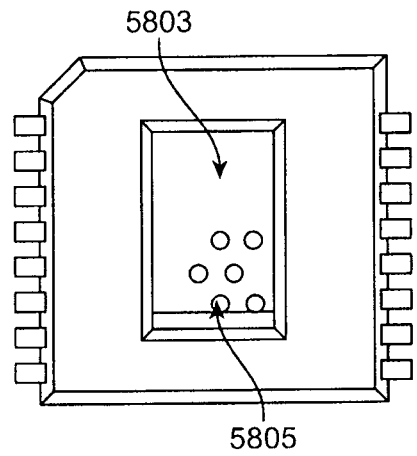 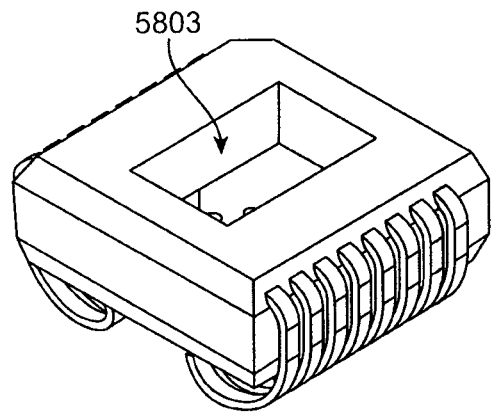
FIG. 58A  FIG. 58B
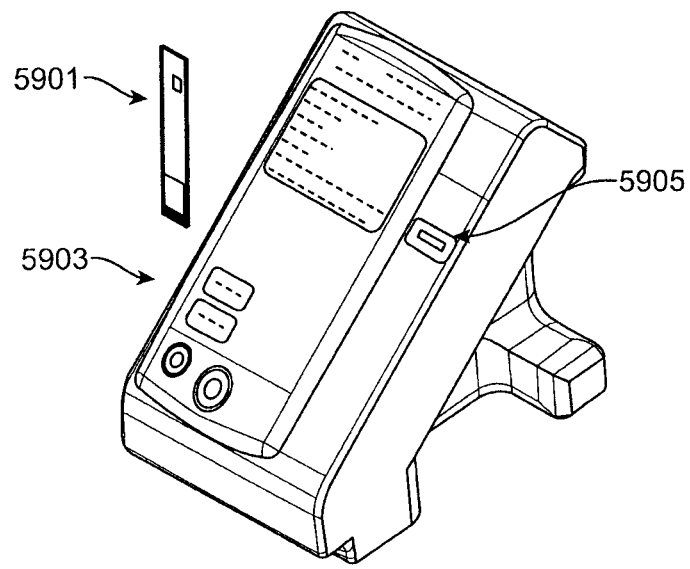
FIG. 59

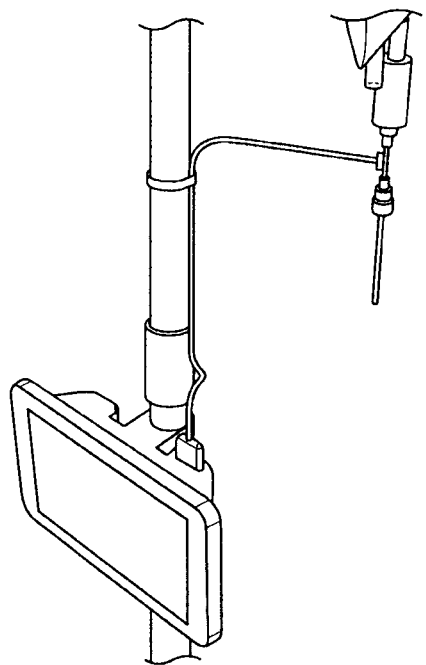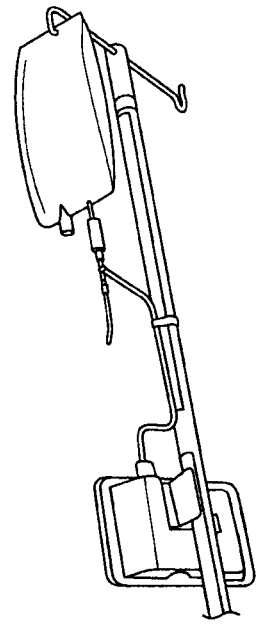
FIG. 67A        FIG. 67B
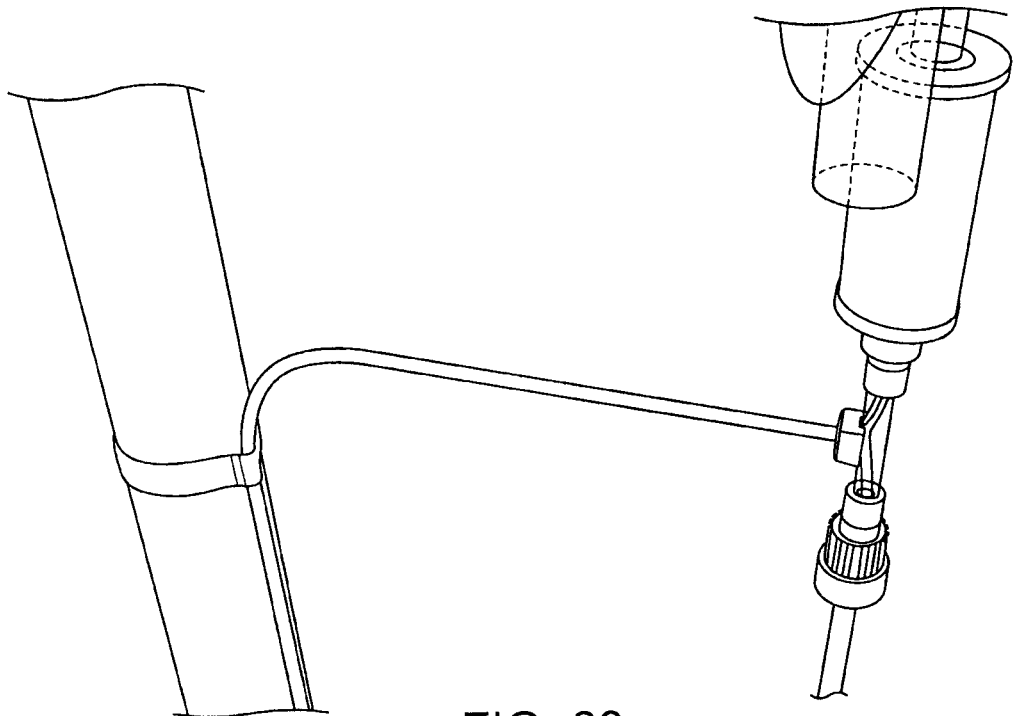
FIG. 68

Noise = ±4%, Error Rate = 0%

Noise = ±6%, Error Rate = 0.6%

FIG. 96A (CONT.)

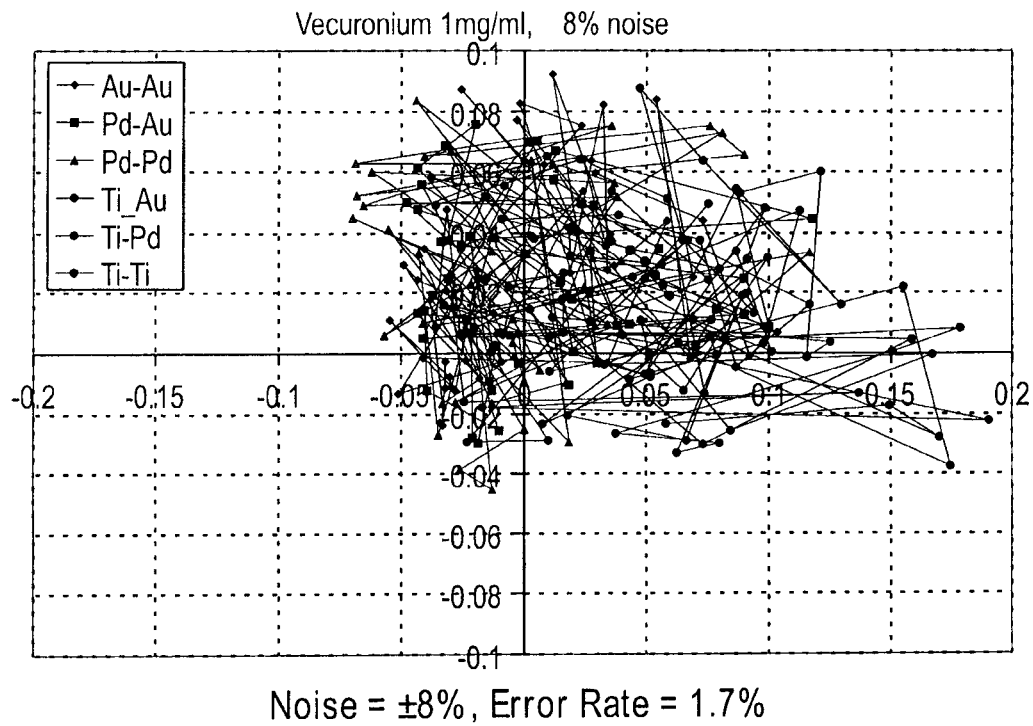
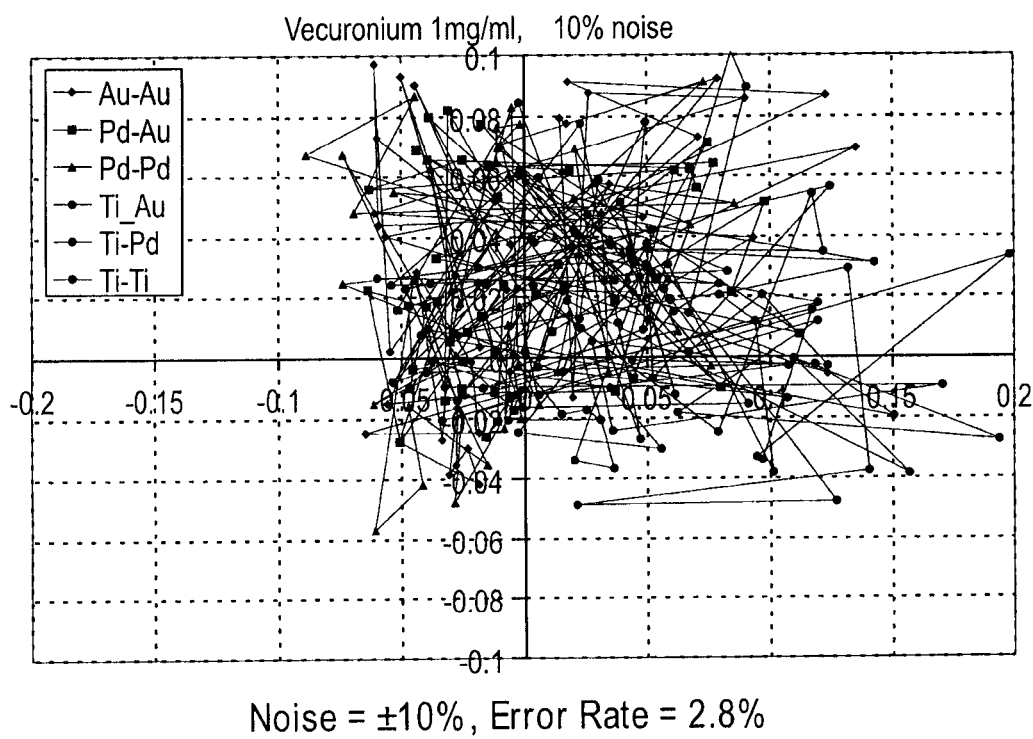
FIG. 96A (CONT.)

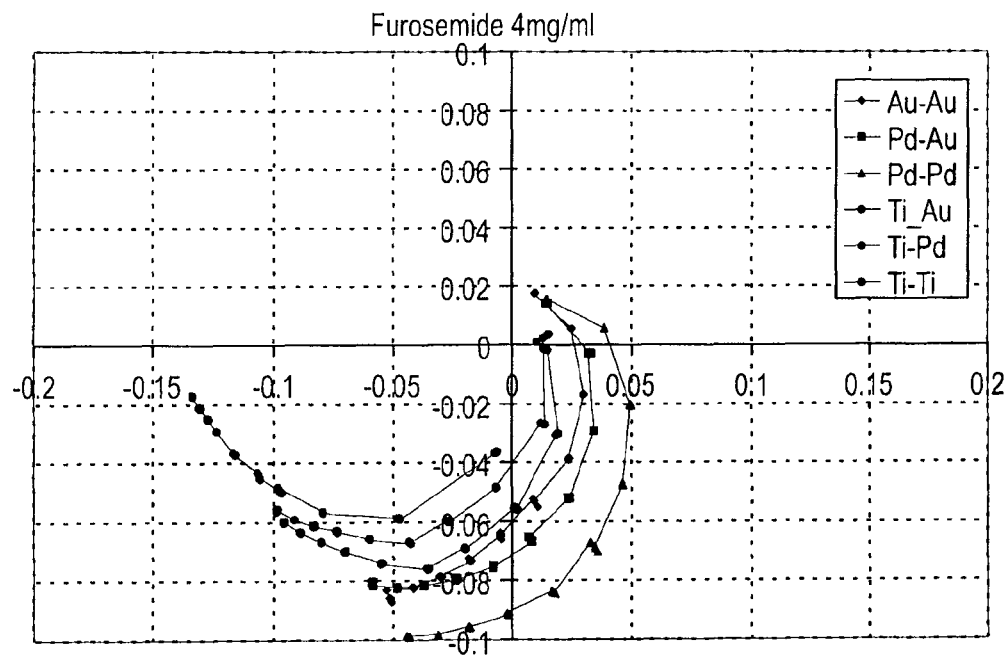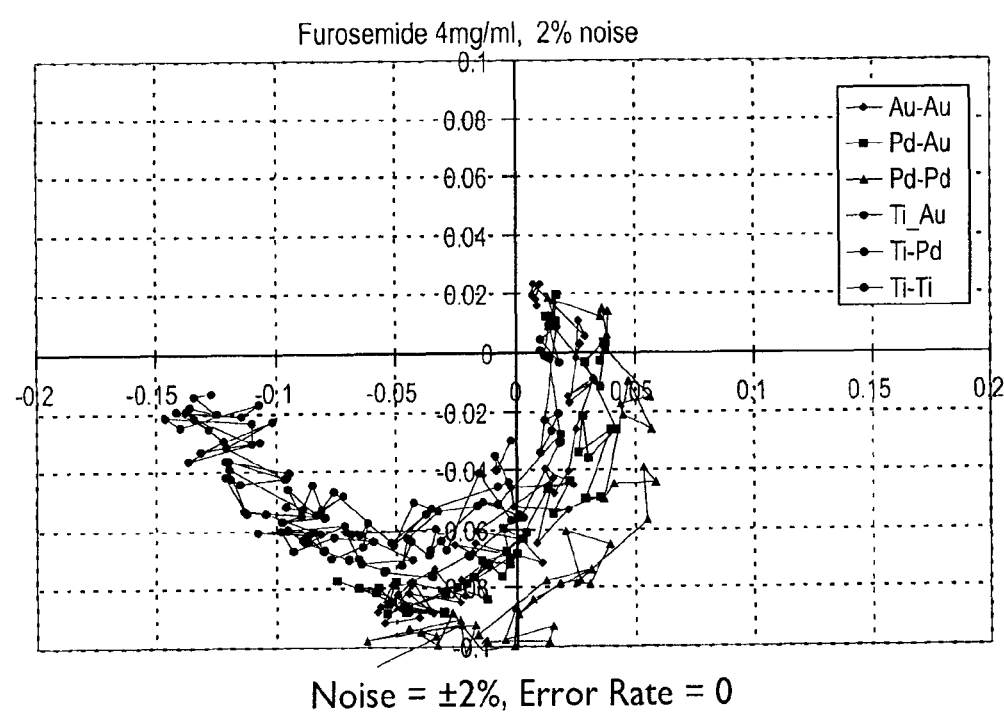
FIG. 96B

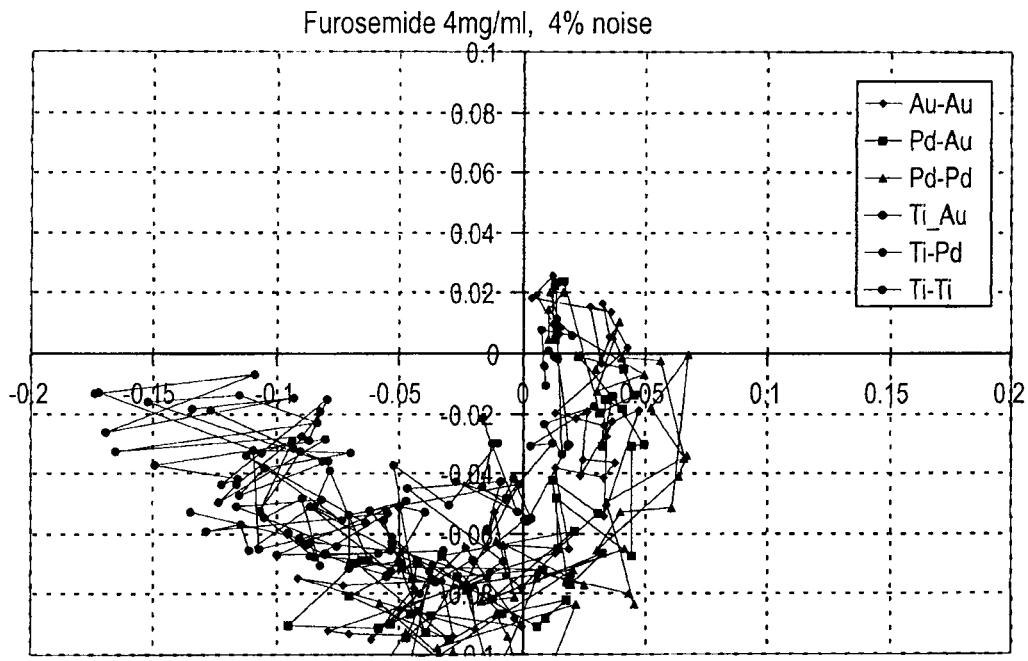
Noise = ±4%, Error Rate = 0
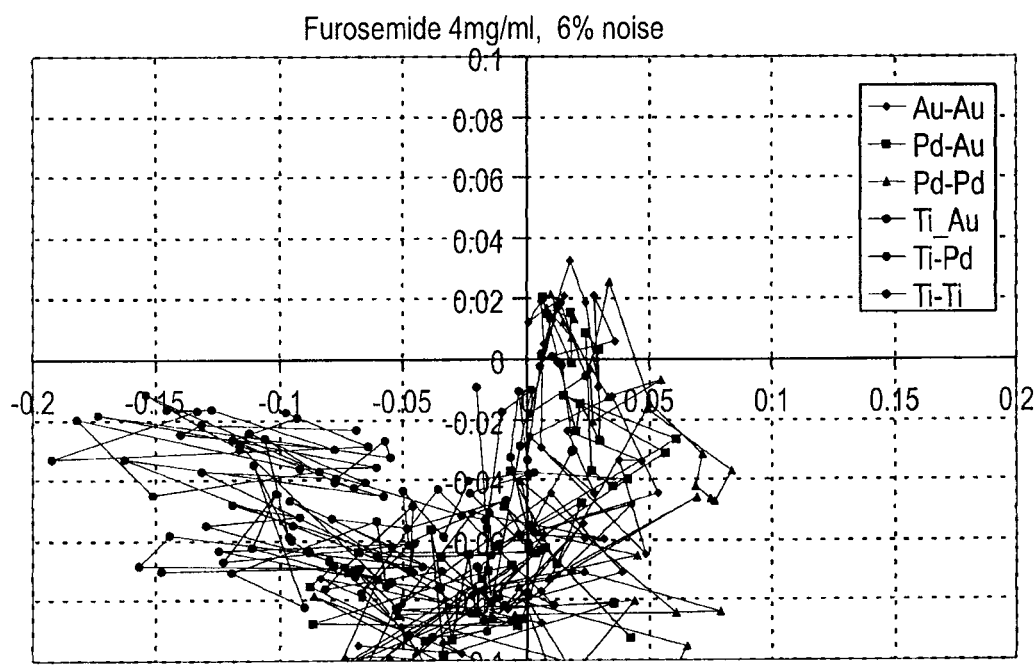
Noise = ±6%, Error Rate = 0.3%
FIG. 96B (CONT.)

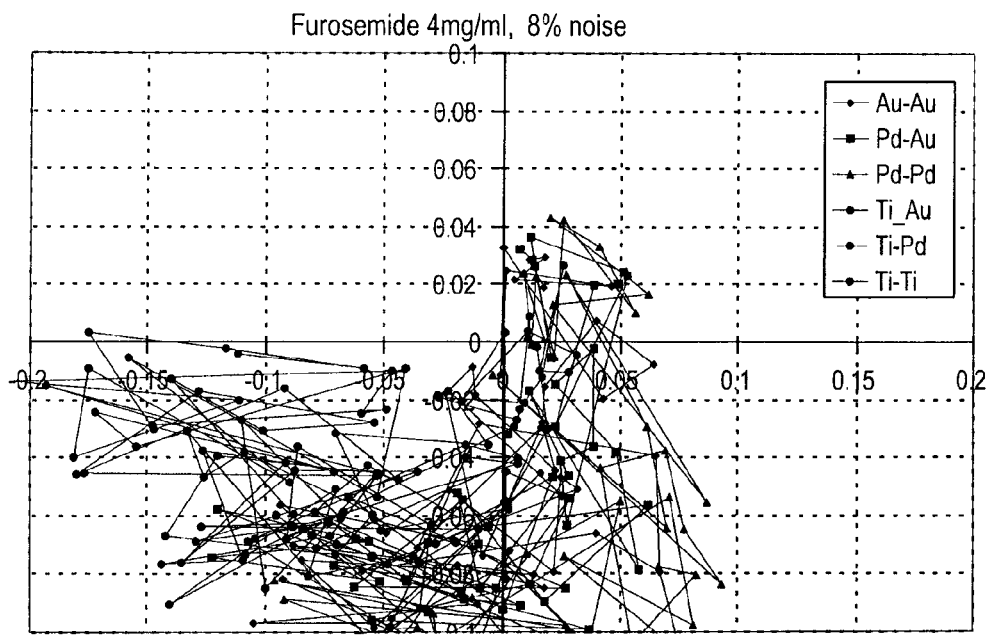
Noise = ±8%, Error Rate = 4.3%
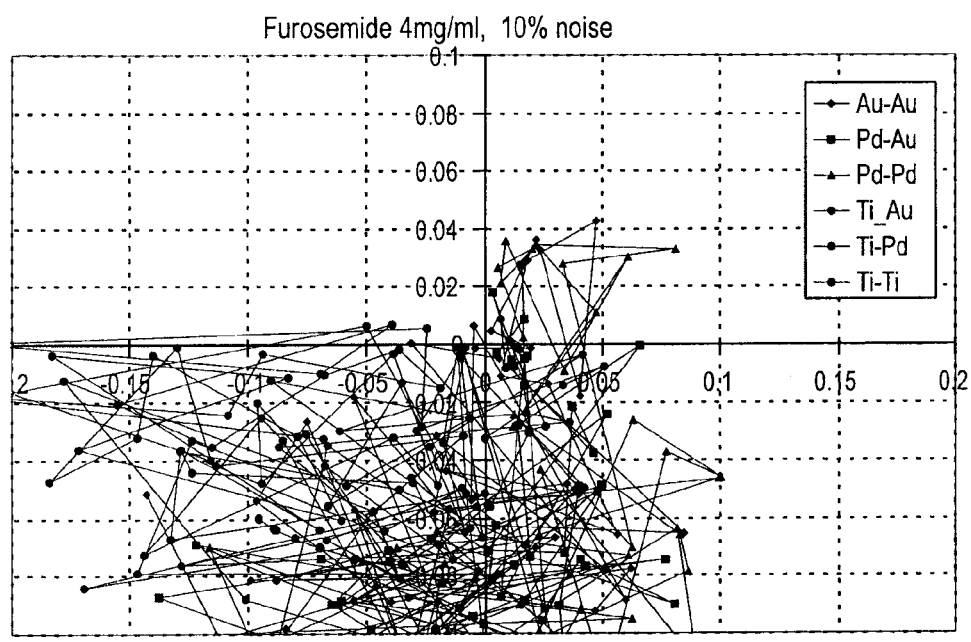
Noise = ±10%, Error Rate = 14.2%
FIG. 96B (CONT.)

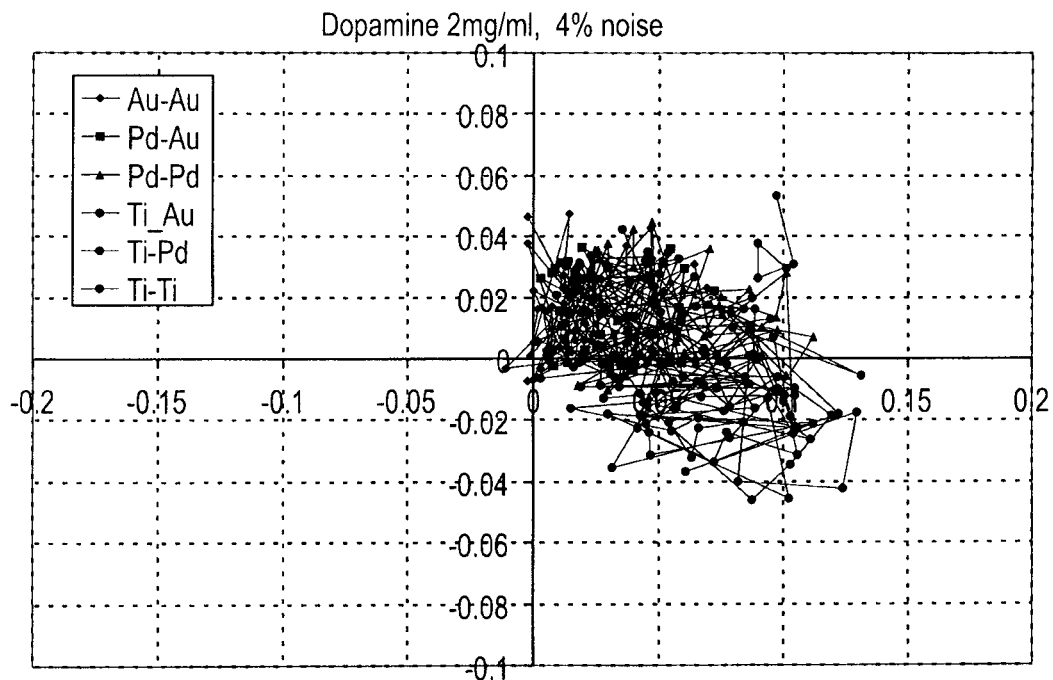
Noise = ±4%, Error Rate = 0
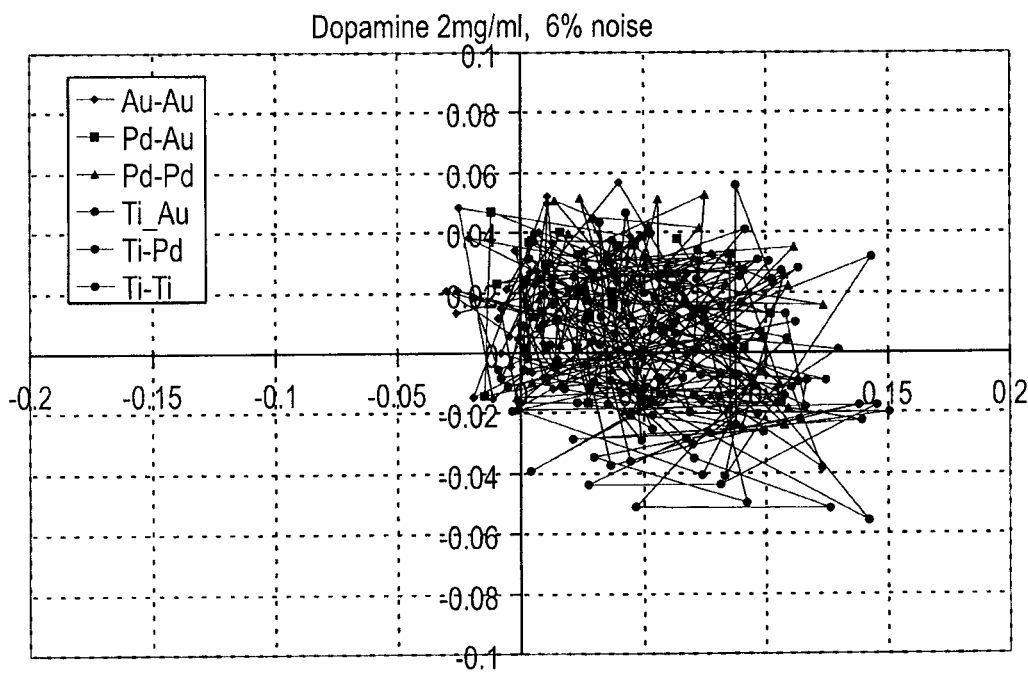
Noise = ±6%, Error Rate = 0%
FIG. 96C (CONT.)

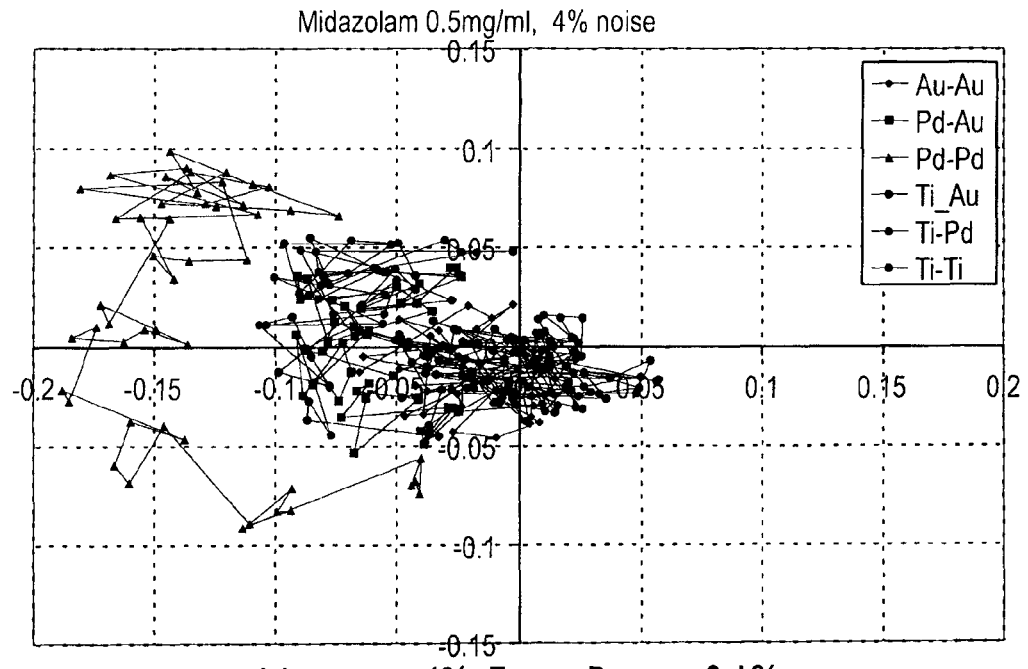
Noise = ±4%, Error Rate = 0.1%
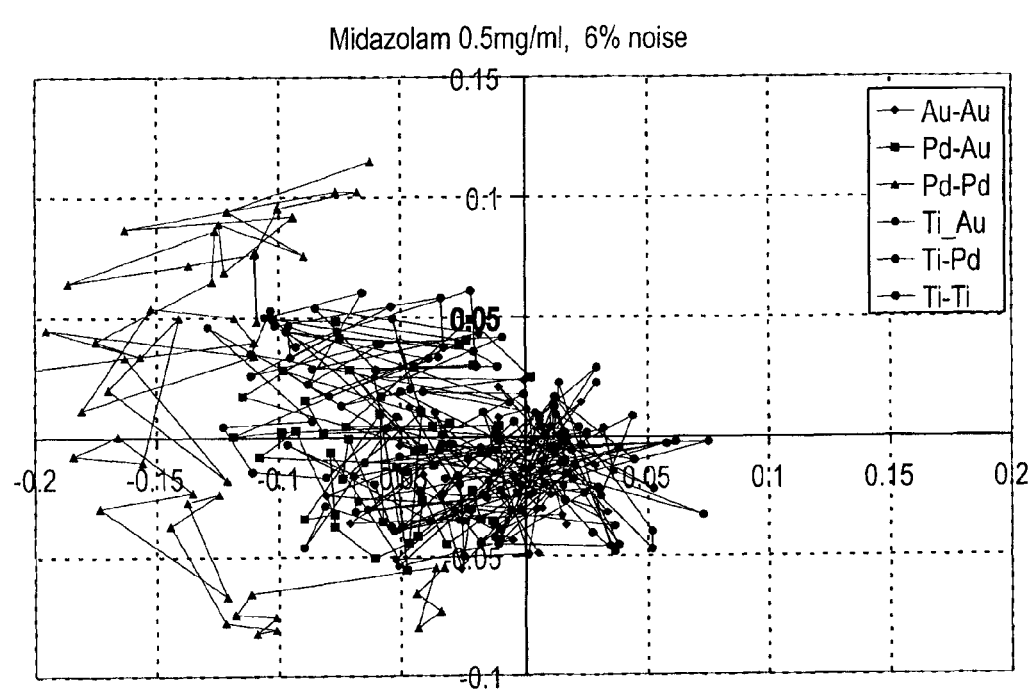
Noise = ±6%, Error Rate = 2.2%
FIG. 96D (CONT.)

|     | DOP      | FUR      | MID      | SAL      | VEC      |
|-----|----------|----------|----------|----------|----------|
| DOP | 6.43E-16 | 1.1      | 0.555    | 0.696    | 0.594    |
| FUR | 0.964    | 5.32E-16 | 0.779    | 0.575    | 1.15     |
| MID | 0.94     | 0.71     | 4.85E-16 | 0.545    | 0.32     |
| SAL | 1.04     | 0.442    | 1.31     | 7.56E-16 | 1.49     |
| VEC | 0.563    | 1.07     | 0.364    | 0.641    | 6.29E-16 |

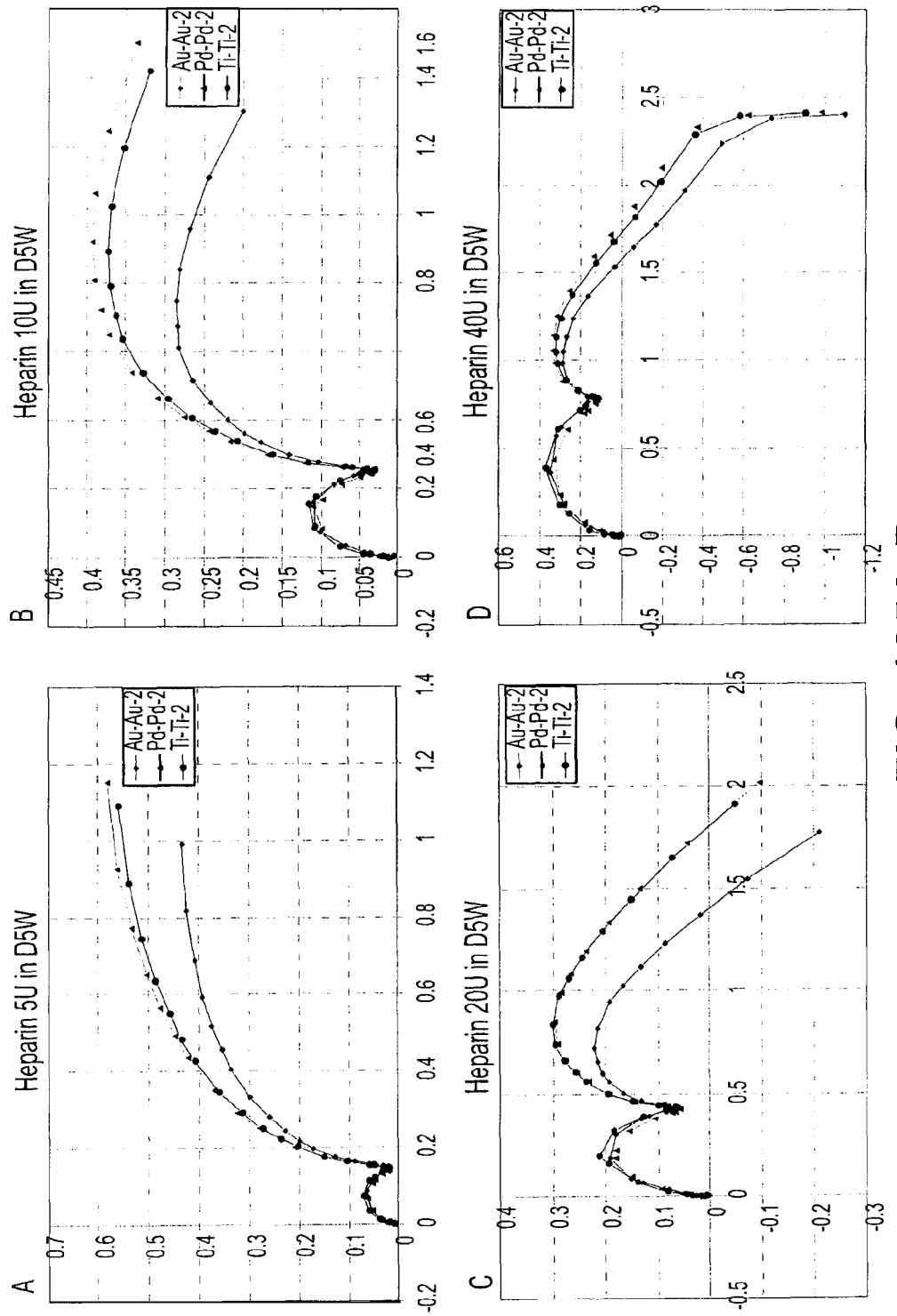
FIG. 105A-D

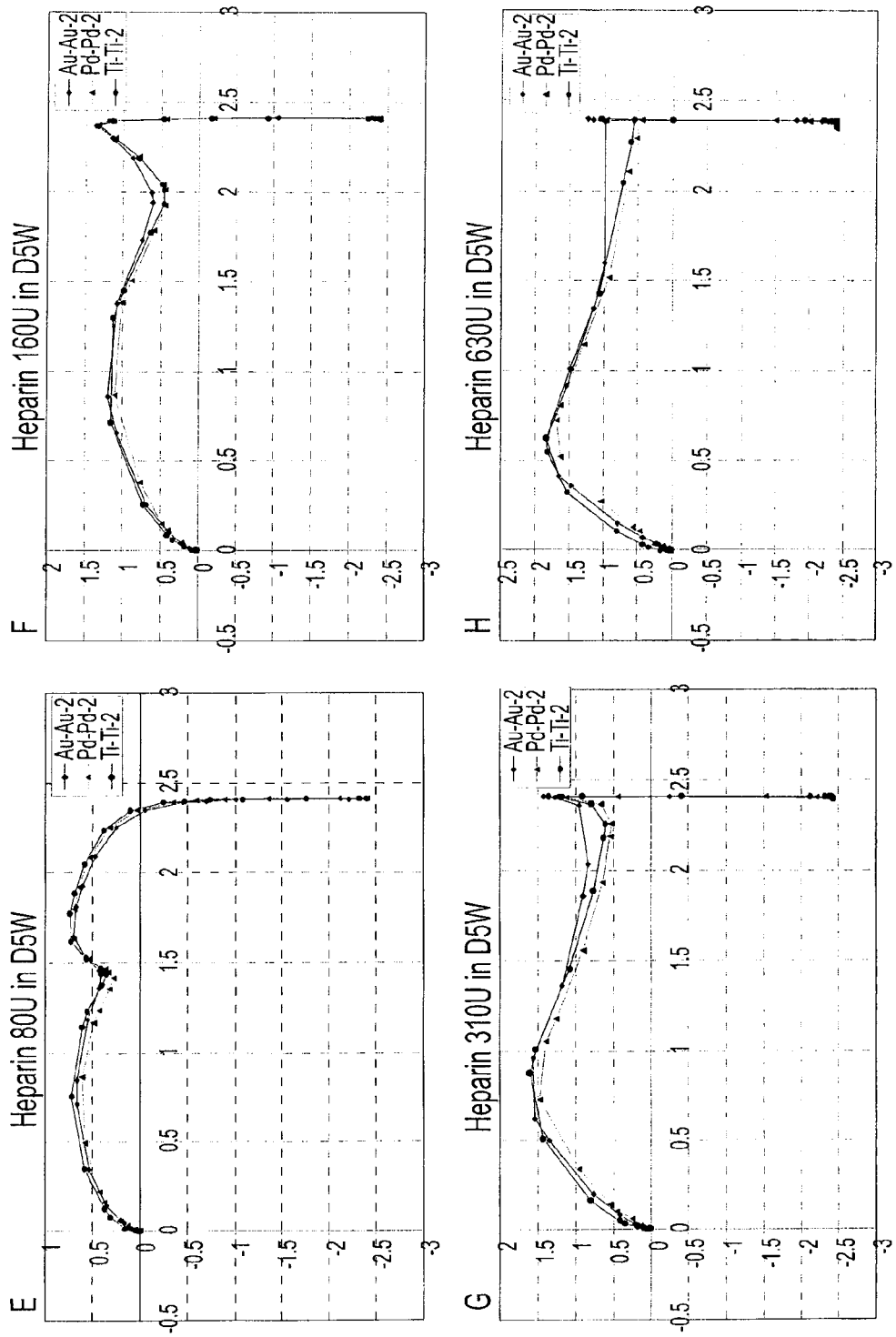
FIG. 105E-H

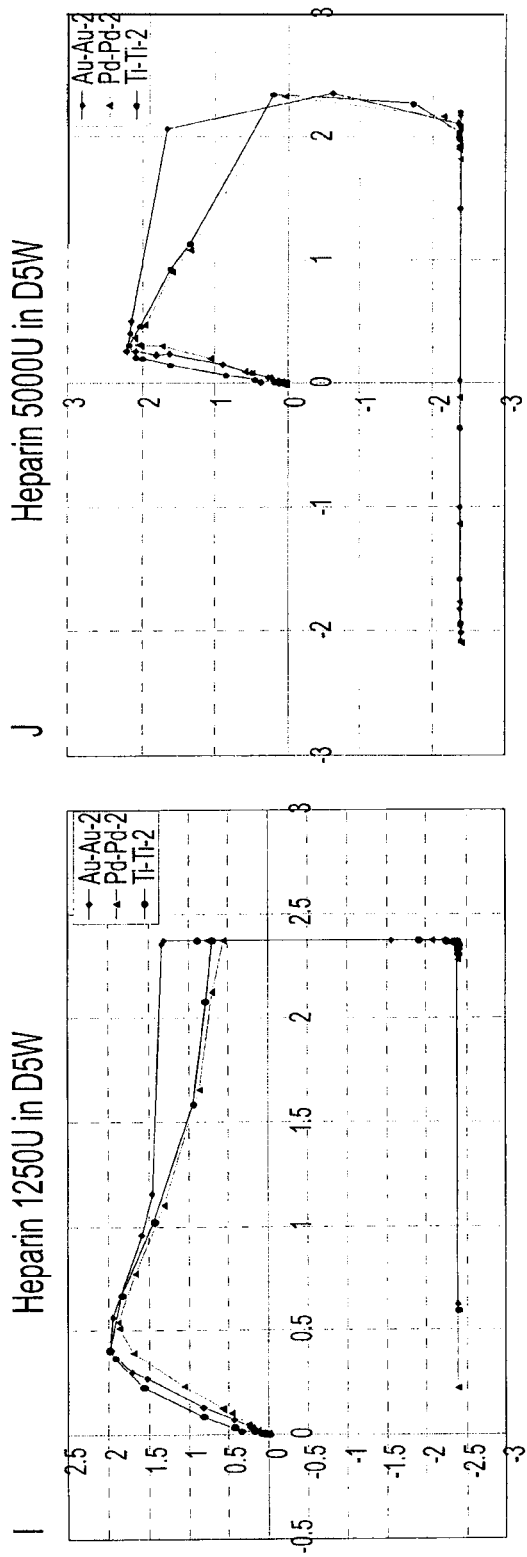
FIG. 105I-J

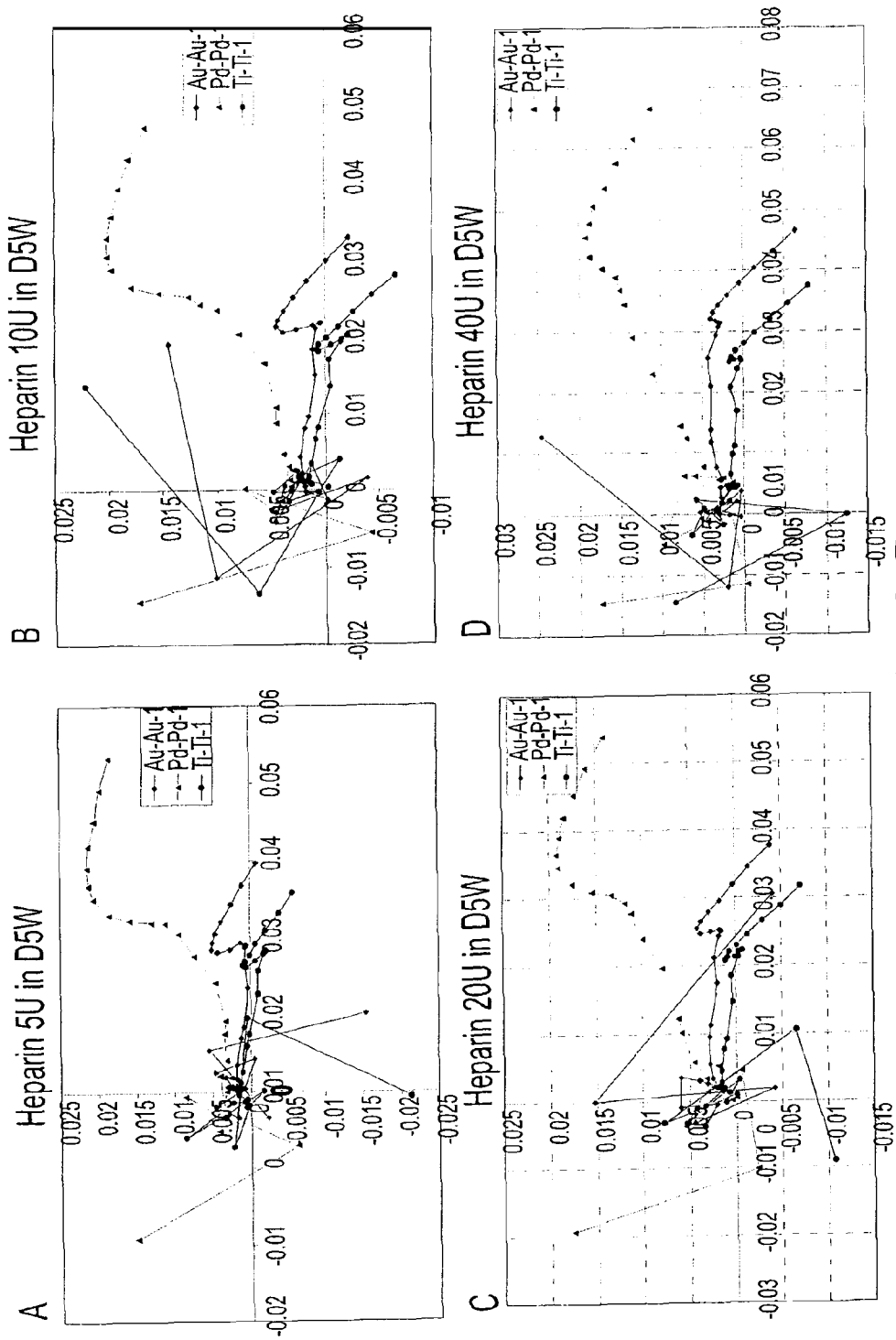
FIG. 106A-D

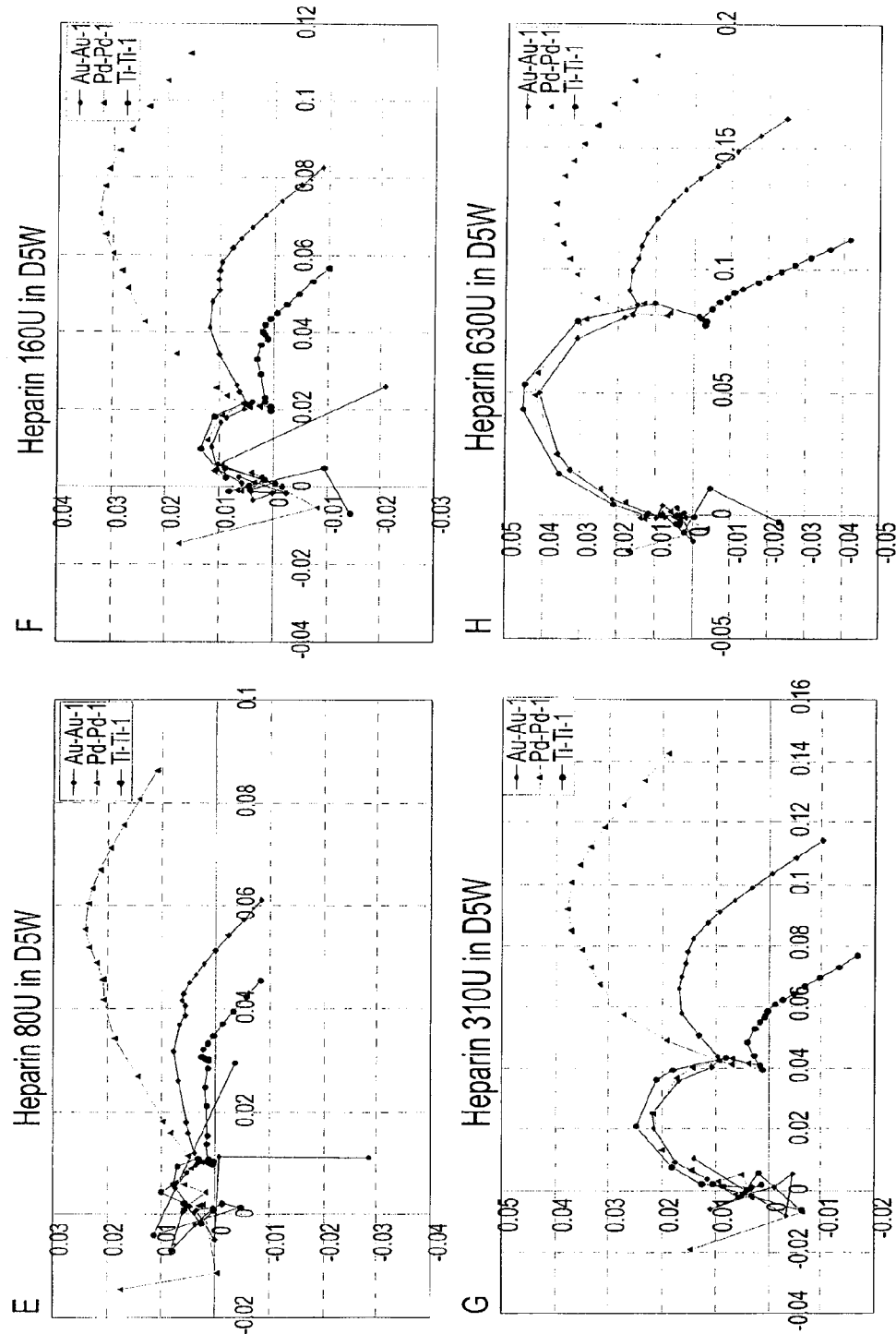
FIG. 106E-H

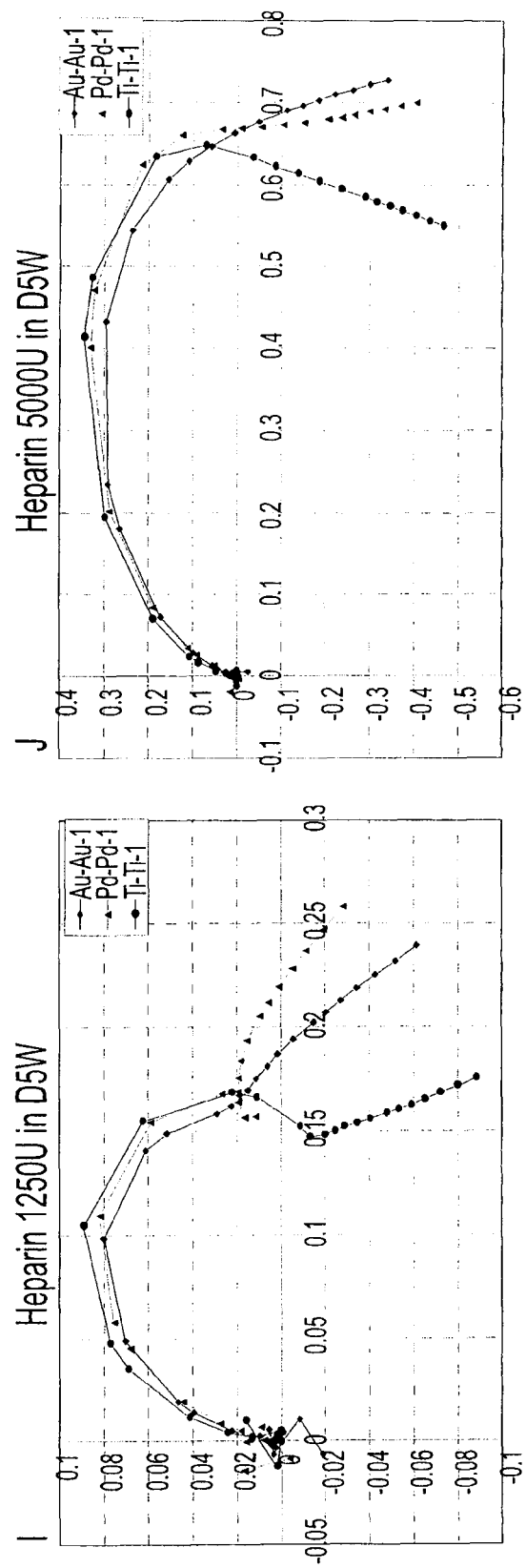
FIG. 106I-J

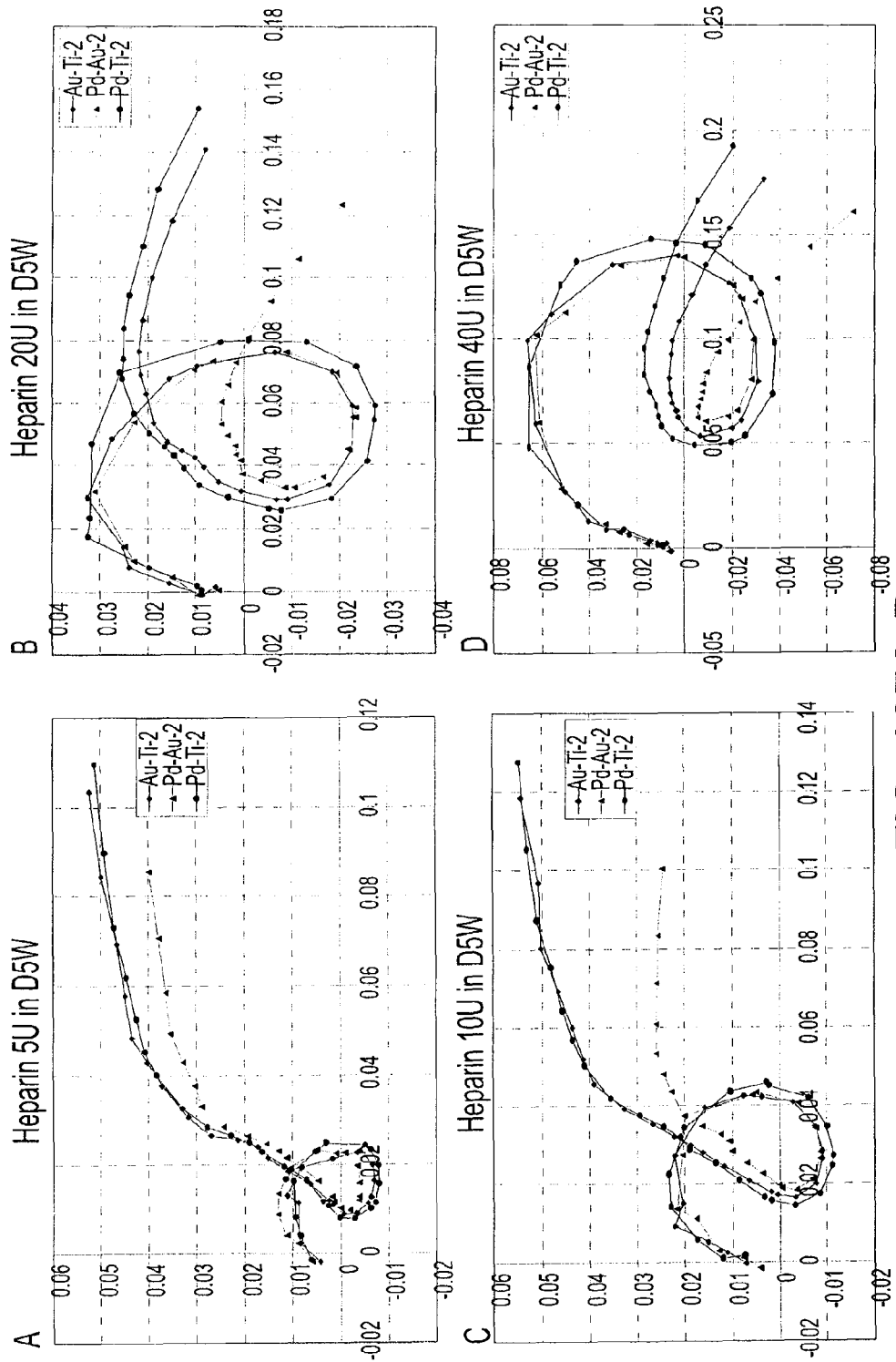
FIG. 107A-D

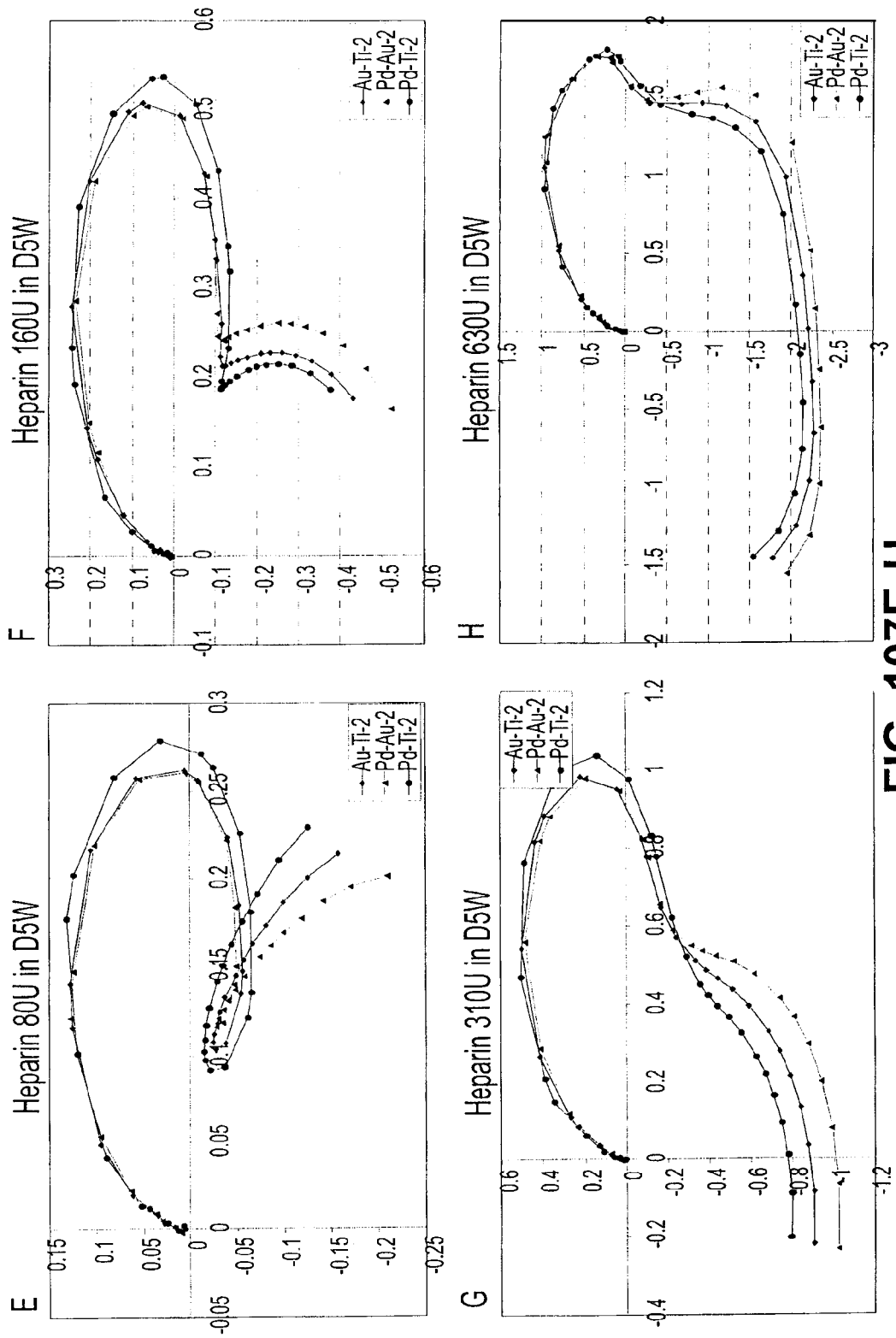
FIG. 107E-H

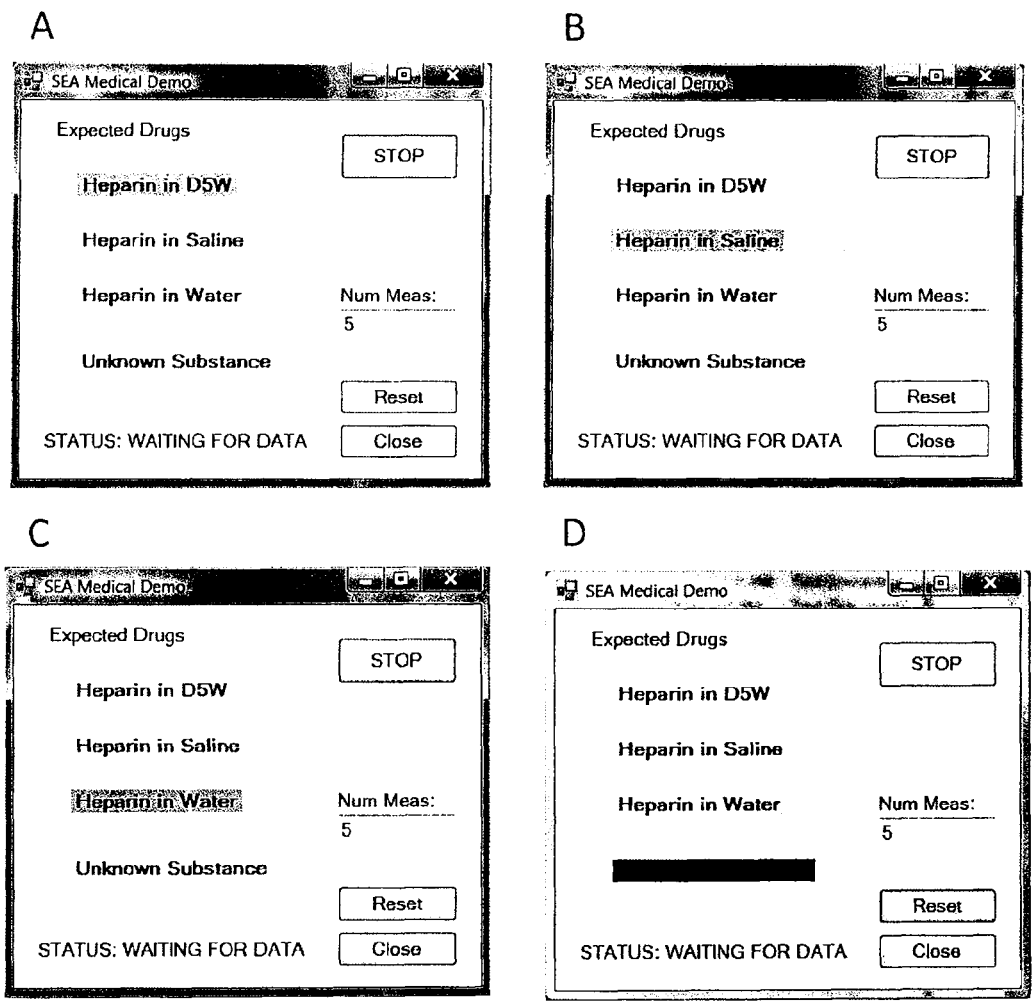
FIG. 108A-D

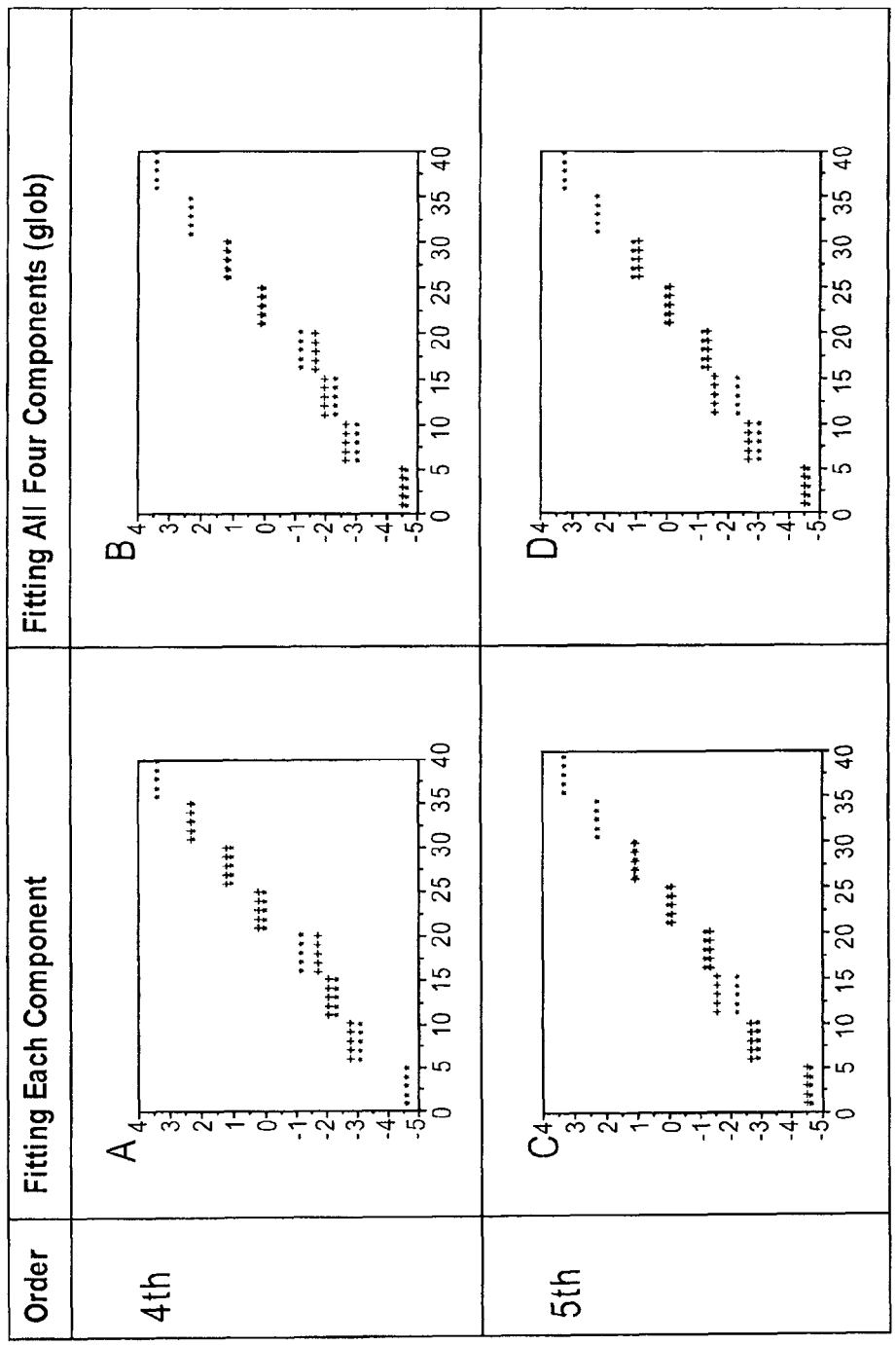
FIG. 109A-D

| Performance | Drug-Solvent(Sulfame thoxazole/Trime thoprim/Enalipri lat-NS) | Drug-Solvent(Sulfame thoxazole/Trime thoprim-NS) | Drug-Solvent(Ropivac aine-NS) | Drug-Solvent(Lorazep am=D5W) | Drug-Solvent(Insulin-D5W) | Drug-Solvent(Heparin-D5W) | Drug-Solvent(Furose mide-NS) | Drug-Solvent(Fentany l_citrate-D5W) | Drug-Solvent(Epineph rine-D5W) | Drug-Solvent(Enalapri lat-D5W) | Drug-Solvent(Atracuri um-D5W) |
|---|---|---|---|---|---|---|---|---|---|---|---|
| MSE | 2.11329E-33 | 2.11329E-33 | 1.33151E-33 | 3.78493E-13 | 1.73476E-33 | 9.11174E-06 | 1.33151E-33 | 9.11174E-06 | 2.89508E-33 | 1.54455E-33 | 5.80796E-18 |
| NMSE | 2.64678E-32 | 2.64678E-32 | 1.66764E-32 | 4.74042E-12 | 2.50566E-32 | 9.126E-05 | 1.66764E-32 | 0.000155507 | 2.89961E-32 | 1.54697E-32 | 7.27416E-17 |
| MAE | 2.48258E-17 | 2.48258E-17 | 2.15877E-17 | 6.87834E-08 | 2.43632E-17 | 0.000428444 | 2.15877E-17 | 0.000428513 | 2.8064E-17 | 2.28213E-17 | 2.69443E-10 |
| Min Abs Error | 0 | 0 | 0 | 0 | 0 | 0 | 0 | 0 | 0 | 0 | 0 |
| Max Abs Error | 2.22045E-16 | 2.22045E-16 | 6.16791E-17 | 5.50267E-06 | 1.23358E-16 | 0.025550054 | 6.16791E-7 | 0.025550054 | 2.22045E-16 | 1.11022E-16 | 2.15554E-08 |
| r | 1 | 1 | 1 | 1 | 1 | 0.999958736 | 1 | 0.999924493 | 1 | 1 | 1 |
| Percent Correct | 100 | 100 | 100 | 100 | 100 | 100 | 100 | 100 | 100 | 100 | 100 |

FIG. 110

| NormLog2 Conc | NormLog2Conc Output | Log2MinC | Log2MaxC | Log2Conc_Output | Conc_Output | Conc_Desired | Error_% |
|---|---|---|---|---|---|---|---|
| 0 | 0 | -3.321928095 | 3.321928095 | -3.321928095 | 0.1 | 0.1 | 0.000000% |
| 0.349485 | 0.349485002 | -3.321928095 | 3.321928095 | -1.000000001 | 0.5 | 0.5 | 0.000000% |
| 0.5 | 0.5 | -3.321928095 | 3.321928095 | 0 | 1 | 1 | 0.000000% |
| 0.650515 | 0.650514998 | -3.321928095 | 3.321928095 | 1.000000001 | 2.000000002 | 2 | 0.000000% |
| 0.80103 | 0.801029996 | -3.321928095 | 3.321928095 | 2.000000002 | 4.000000006 | 4 | 0.000000% |
| 0.88907563 | 0.889075625 | -3.321928095 | 3.321928095 | 2.584962499 | 5.999999995 | 6 | 0.000000% |
| 1 | 1 | -3.321928095 | 3.321928095 | 3.321928095 | 10 | 10 | 0.000000% |
| 0 | -6.16791E-17 | -3.321928095 | 3.321928095 | -9.321928095 | 0.0015625 | 0.0015625 | 0.000000% |
| 0.2407676 | 0.240767598 | -3.321928095 | 3.321928095 | -7.000000005 | 0.0078125 | 0.0078125 | 0.000000% |
| 0.34446056 | 0.344460559 | -3.321928095 | 3.321928095 | -6.000000001 | 0.015625 | 0.015625 | 0.000000% |
| 0.5184648 | 0.518464803 | -3.321928095 | 3.321928095 | -4.321928095 | 0.05 | 0.05 | 0.000000% |
| 0.58522816 | 0.585228158 | -3.321928095 | 3.321928095 | -3.678071901 | 0.078125 | 0.078125 | 0.000000% |
| 0.79848139 | 0.798481392 | -3.321928095 | 3.321928095 | -1.62148838 | 0.324999999 | 0.325 | 0.000000% |
| 0.89630704 | 0.896307039 | -3.321928095 | 3.321928095 | -0.678071909 | 0.624999998 | 0.625 | 0.000000% |
| 0.96661832 | 0.966618323 | -3.321928095 | 3.321928095 | 2.52585E-09 | 1.000000002 | 1 | 0.000000% |
| 1 | 1 | -3.321928095 | 3.321928095 | 0.321928095 | 1.25 | 1.25 | 0.000000% |
| 0 | 0 | -9.965784285 | 0 | -9.965784285 | 0.001 | 0.001 | 0.000000% |
| 0.10034333 | 0.100343332 | -9.965784285 | 0 | -8.965784284 | 0.002 | 0.002 | 0.000000% |
| 0.20068666 | 0.200686664 | -9.965784285 | 0 | -7.965784282 | 0.004 | 0.004 | 0.000000% |
| 0.30103 | 0.301029996 | -9.965784285 | 0 | -6.965784281 | 0.008 | 0.008 | 0.000000% |
| 0.33333333 | 0.333333333 | -9.965784285 | 0 | -6.643856193 | 0.01 | 0.01 | 0.000000% |
| 0.49237375 | 0.492373752 | -9.965784285 | 0 | -5.058893685 | 0.03 | 0.03 | 0.000000% |
| 0.66666667 | 0.666666667 | -9.965784285 | 0 | -3.321928092 | 0.1 | 0.1 | 0.000000% |
| 0.82570709 | 0.825707085 | -9.965784285 | 0 | -1.736965593 | 0.3 | 0.3 | 0.000000% |
| 1 | 1 | -9.965784285 | 0 | 0 | 1 | 1 | 0.000000% |
| 0 | 0 | -8.965784285 | -4.64385619 | -8.965784285 | 0.002 | 0.002 | 0.000000% |
| 0.30586536 | 0.305865361 | -8.965784285 | -4.64385619 | -7.643856188 | 0.005 | 0.005 | 0.000000% |
| 0.53724357 | 0.537243944 | -8.965784285 | -4.64385619 | -6.643854589 | 0.010000011 | 0.01 | 0.000111% |
| 0.76862179 | 0.768621784 | -8.965784285 | -4.64385619 | -5.643856203 | 0.02 | 0.02 | -0.000001% |
| 1 | 1 | -8.965784285 | -4.64385619 | -4.64385619 | 0.04 | 0.04 | 0.000000% |
| 0 | 0 | -4.64385619 | 3.321928095 | -4.64385619 | 0.04 | 0.04 | 0.000000% |

FIG. 111

SYSTEMS AND METHODS FOR INTRAVENOUS DRUG MANAGEMENT USING IMMITTANCE SPECTROSCOPY

CROSS REFERENCE TO RELATED APPLICATIONS

This patent application claims priority to the following U.S. Provisional Patent Applications: U.S. Provisional Patent Application No. 61/381,076, titled "SYSTEMS AND METHODS UTILIZING MULTI-ELECTRODE ADMITTANCE SPECTROSCOPY FOR MEDICAL APPLICATIONS" filed on Sep. 9, 2010; Provisional Patent Application No. 61/394,775, titled "SYSTEMS AND METHODS FOR UTILIZING MULTI-ELECTRODE ADMITTANCE SPECTROSCOPY FOR MEDICAL APPLICATIONS" filed on Oct. 20, 2010; Provisional Patent Application No. 61/462,325, titled "SYSTEMS AND METHODS FOR UTILIZING MULTI-ELECTRODE ADMITTANCE SPECTROSCOPY FOR MEDICAL APPLICATIONS" filed on Dec. 5, 2010; and U.S. Provisional Patent Application No. 61/429,461, titled "SYSTEMS AND METHODS FOR INTRAVENOUS DRUG MANAGEMENT THROUGH THE APPLICATION OF ADMITTANCE SPECTROSCOPY" filed on Jan. 4, 2011.

This application may also be related to U.S. patent application Ser. No. 12/920,203 (titled "INTRAVENOUS FLUID MONITORING") and filed on Aug. 30, 2010, and U.S. patent application Ser. No. 12/796,567 (titled "SYSTEMS AND METHODS FOR THE IDENTIFICATION OF COMPOUNDS IN MEDICAL FLUIDS USING ADMITTANCE SPECTROSCOPY") and filed on Jun. 8, 2010.

All of these patent applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The devices, systems and methods described may be used to determine the identity and concentration of one or more, or in some variations all, components in an aqueous solution using immittance spectroscopy. In particular, described herein are devices, systems and methods for using immittance spectroscopy to determine the composition of intravenous drug solutions, including drug solutions having low ionic strengths.

BACKGROUND

Errors in medication provided to a patient are recognized as a serious, and potentially avoidable, problem associated with the delivery of health care.

Medication errors are estimated to account for 7,000 deaths annually, and adverse drug events cause more than 770,000 injuries and deaths each year. Patients who suffer from unintended drug events remain in the hospital an average of 8 to 12 days longer than patients who did not experience such mistakes. Two recent studies, one conducted in Colorado and Utah and the other in New York, found that adverse events occurred in 2.9 and 3.7 percent of hospitalizations, respectively.

Infusion devices are believed to account for up to 35% of all medication errors that result in significant harm (Class 4 and 5). Mistakes typically arise from manually programming incorrect infusion parameters, and the failure to ensure the right patient receives the right medication. The most common error is manually programming infusion parameters such as delivery rate, drug, and drug dose, into the device.

Unfortunately, there is currently no commercially available device capable of reliably determining both the identity and concentration (and thus dosage) of a wide variety of unknown intravenous fluids as they are being delivered to a patient.

Although systems for verifying the presence of a drug or its concentration have been proposed, the majority of these systems rely solely on optical methods (such as optical spectroscopy). For example, U.S. Pat. No. 6,847,899 to Allgeyer et al. describes a spectroscopic analysis device for identifying medications in an IV solution. Similar systems are described in U.S. Pat. No. 7,154,102 to Poteet et al. (florescence spectroscopy), PCT/US2007/087062 and PCT/US2006/036612 by Potuluri et al. (verification of solid drug identity by optical spectroscopy) and U.S. Pat. No. 7,317,525 to Rzasa et al.

Because these systems rely on spectroscopic analysis, they typically suffer from the limitations inherent in optical systems. These limitations may include a limited ability to distinguish between compounds, and particularly mixtures of compounds having multiple components, as well as difficulty in reliably distinguishing concentrations of different compounds.

Thus, there is a need for devices, systems and methods for checking or confirming an IV drug composition has been correctly formulated, e.g., by a pharmacy by directly sampling and testing the formulation. There is also a need to confirm that a drug being delivered to a patient is correct and corresponds to the prescribed medication, by directly sampling and testing the formulation. Drugs are often formulated in low ionic strength liquids. Such fluids have proven extremely difficult to examine electrically, because of the low ionic strength. Thus, it would be particularly helpful to provide devices, systems and method of applying immittance spectroscopy to low ionic strength liquids.

In addition, it would be helpful to provide a method of determining the identity and composition of IV drug waste. Hospitals and other institutions are increasingly required to document proper disposal of environmentally sensitive waste and monitor for diversion of scheduled drugs. Thus, it would be helpful to provide devices, systems and method for confirming the amount and type of drug waste, and providing an accurate record of drug waste collected and/or disposed of. It would also be beneficial to sort drug waste so that different drug waste could be disposed of appropriately according to the compounds in the waste fluid.

Described herein are immittance spectroscopy devices and methods that use multiple electrical immittance measurements to determine the identity, and in some variations concentration, of one or more components of a medical solution such as an intravenous solution.

SUMMARY

Described herein are systems, devices and methods for determining the components of a fluid (e.g., liquid, diluent or solution) using immittance spectroscopy. As used herein, the term immittance spectroscopy may refer to both impedance spectroscopy and admittance spectroscopy. The devices, systems and methods described herein may be useful for determining the identity, concentration, or identity and concentration of one or more (or all) components of a liquid. The solution may be an aqueous solution (an aqueous fluid). For example, the solution may be a medical liquid such as an intravenous fluid, and epidural fluid, a parenteral fluid, or the like. Thus, the components of the liquid may be drugs. In general, the components of the liquid may be any compound, including (but not limited to): ions, molecules, macromolecules, proteins, etc.

As described in more detail below, the immittance spectroscopy systems described here typically take an immittance spectrographic "fingerprint" of an aqueous solution by reading a plurality of complex impedance measurements taken at a plurality different frequencies of applied electrical energy; in addition, a plurality of different electrode pairs may be used. For each pair of electrodes having a slightly different configuration (e.g., shape, size, composition) the complex impedance measurements taken with that set of electrodes may provide another set of data forming the "fingerprint" (e.g., the initial dataset). Different electrodes exposed to the liquid may have different surface interactions between the liquid and the electrodes. Electrode surfaces may be coated, doped, or treated to create different surface interactions.

In general an electrode surface may be reactive or non-reactive. The surface may be coated, treated, smooth, roughened, or the like. Electrode surfaces may include bound active (e.g., binding) agents (such as antibodies, charged elements, etc.). Electrode pairs composed of different electrically conductive metals (e.g. silver, gold, platinum, titanium, etc.).

Electrical energy may be applied between an electrode pair to determine the surface interactions on the electrodes. Immittance spectroscopy applied at appropriate energy (e.g., typically low energy) may be used to poll or test the surface interactions between the liquid and an electrode surface without disturbing the naturally occurring surface interactions. The surface interactions between a particular electrode surface and a particular solution are characteristic of the particular electrode surface and the nature of the solution (e.g., the components in the solution and the carrier solution). If the electrode surface is a known, the (unknown) nature of the solution may be determined. For example, polling may comprise applying an electrical signal to the first surface and measuring the complex immittance. Thus, the step of polling may comprise applying a plurality of electrical signals and measuring the complex immittance at each signal. In particular, the polling step may be performed in a manner that preserves the surface interaction between the solution and the electrode surface. For example, the step of applying energy to determine complex impedance (polling) may comprise applying an electrical signal below the threshold for electrochemical reaction. The polling step may also be performed so that it does not disturb the dynamic equilibrium of the boundary layer on the first surface. The energy applied to poll the surface interaction may be below the threshold for disrupting the surface interaction (e.g., within what is referred to as the electrode polarization effect). In some variations this is a voltage between a threshold of approximately 0.5 V and 1 V.

The sensors described herein take advantage of the electrode polarization effect which was first reported in 1879 by Helmholtz. However, in the intervening century, this effect has not been successfully used to characterize the composition of a liquid. Instead, the electrode polarization effect has typically been viewed as a nuisance to be avoided or eliminated. The polarization effect prevents electrons from crossing the interfaces between non-reacting metals and electrolytes unless a substantial external electric field is applied (so-called "blocking behavior" of fully polarizable electrodes). The effect is considered mostly undesirable as it makes accurate measurements of fluid bulk conductivity difficult. For example, see Macdonald J R., "Impedance Spectroscopy—Emphasizing Solid Materials and Systems" (Wiley-Interscience, John Wiley and Sons. 1987, p. 1-346) ("Analysis of small-signal data can almost always yield estimates of bulk conductivity of new materials free from the electrode polarization effects which plague steady-state d-c measurements"); Schwan H P, "Linear and nonlinear electrode polarization and biological materials." (Annals of biomedical engineering, 1992; 20(3), p. 269-288) ("Electrode polarization is a major nuisance while determining dielectric properties of cell and particle suspensions and tissues, particularly at low frequencies."); and Macdonald J R and Garber J., "Analysis of impedance and admittance data for solids and liquids" (J Electrochem Soc. 1977; 124(7), p. 1022-30) ("The electrode polarization is a major source of error in determining the impedance of biological samples in solution. The unwanted double layer impedance due to the electrode polarization impedance is caused by the accumulation of ions on the surface of electrode.").

Electrode polarization has been most extensively studied in the field of implantable electrodes for pacemakers, where the presence of this effect impedes efficient cardiac activity sensing and stimulation. For example, when a platinum pacemaker electrode (Telectronics type 030-239) is immersed in a bath of physiological saline and a DC voltage was applied to it within a range of potentials, there is virtually no current flowing through the electrolyte unless the voltage exceeds values of approximately ±1 V; see, e.g., FIG. 1. Below this voltage the electrodes demonstrate capacitive behavior. To achieve successful pacing with the limited available electrode area the pacemakers rely on chemical reactions at the electrode interface to pass sufficient charge to the tissue.

The device, systems and methods described herein operate within this electrode polarization regime by probing the parameters of the polarization effect in IV fluids. This technique is referred to herein as Immittance Spectroscopy (IS), which encompasses a variety of techniques for the measurement and analysis of impedance-related functions, including complex impedance Z, complex admittance Y and complex dielectric constant E as a function of frequency, and the plotting of these functions in the complex plane. The complex plane is the standard orthogonal xy frame of reference in which the complex impedance $Z = Z'_i + iZ'_i$, admittance $Y = Y'_i + iY'_i$ and/or dielectric constant $\in = \in' + i\in''$ is plotted so that $x=Z'$, $y=Z'_i$, $x=Y'$, $y=Y'_i$, $x=\in'$, $y=\in''$, where ' and " are real and quadrature components of the complex value. Such plotting can be very helpful in interpreting the small-signal AC response of the electrode-electrolyte system being investigated.

Historically, the use of Z and Y in analyzing the response of electrical circuits made up of lumped (ideal) elements (R, L, and C) goes back to the beginning of electrical engineering as a discipline. For the analysis of the dielectric systems distributed in space, Cole and Cole plotted $\in'$ and $\in''$ in the complex plane, now known as a Cole-Cole plot, which was an adaptation of the circle diagram of electrical engineering, exemplified by the Smith chart impedance diagram. Further, Z and/or Y have been widely used in theoretical treatments of semiconductor and ionic systems, interfaces and devices. The first plotting of impedance in the impedance plane for aqueous electrolytes was Sluyters (1960, theory) and Sluyters and Oomen (1960, experiment). The use of complex admittance plane plotting for solid electrolytes conductivity determination was introduced by Bauerle (1969).

In general, the sensors described herein may be based, in part, on the following principles: (1) the sensor electrodes are made of metals non-reactive with the components of the intravenous fluids; (2) ions of the utilized metals are not present in the intravenous fluids; (3) excitation voltage applied between the sensor electrodes is kept below the threshold voltage of any electrochemical reactions that may occur in the intravenous fluid; and (4) preferably, the excitation voltage applied between the sensor electrodes is kept below the characteristic value of the voltage associated with the naturally occurring thermal fluctuations. Metals falling within categories 1 and 2 when exposed to an IV solution exhibit highly pronounced polarization behavior. The sensors described herein typically operate at voltages significantly lower than IV, thus not triggering electrochemical reactions at the electrode-fluid interface. While the nonlinear sensor response can generate important information regarding the nature and condition of the electrode-fluid interface, for the response to be described in terms of the cell AC admittance, all the measurements may be performed within the voltage range where current is proportional to a voltage-linear regime.

As mentioned, the nonlinear response of the electrode-fluid interface is well documented in pacemaker-related studies, where the response of the interface to pulsed voltage has been investigated. Our experiments with sensors in normal saline and Ringer's Lactate showed no evidence of nonlinear response below 0.7V excitation. Nonlinear response above this voltage typically results from an electric field strong enough to disturb the natural arrangement of fluid components within the double layer adjacent to the electrode surface.

The structure of the fluid layers adjacent to the electrode interface is not static, but rather exists in dynamic equilibrium under naturally occurring thermal fluctuation. The fluctuating voltage associated with thermal motion of an ionic media can be estimated as kT/e, where k is Boltzmann's constant, T is absolute temperature in K°, and e is electron charge, which at room temperature is about 25 mV. Any of the sensors described herein may operate at excitation voltage of 30 mV amplitude (~21.2 mV RMS), which is of the same magnitude as the voltage associated with natural thermal fluctuation. This operation regime ensures that sensor measures response of the fluid cell without considerable disturbance of the electrode/fluid interface.

For example, described herein are sensors for immittance spectroscopy configured to operate in low ionic strength liquid. The sensor may include: a first electrode comprising a plurality of elongate lengths of an electrically conductive material; a second electrode comprising a plurality of elongate lengths of an electrically conductive material; wherein the plurality of elongate lengths of electrically conductive material of the first electrode are interdigitated with the plurality of elongate lengths of electrically conductive material of the second electrode to form an electrode pair.

The sensor may also include a second electrode pair comprising a plurality of elongate lengths of an electrically conductive material forming a third electrode and a plurality of elongate lengths of an electrically conductive material forming a fourth electrode, wherein the plurality of elongate lengths of electrically conductive material of the third electrode are interdigitated with the plurality of elongate lengths of electrically conductive material of the fourth electrode. The electrically conductive material forming the first electrode may be different from the electrically conductive material forming the second electrode. For example, the electrically conductive material forming the first electrode and the electrically conductive material forming the second electrode are selected from the group consisting of: Au, Ti, and Pd.

In general, the elongate lengths of the first electrode of the low ionic strength pair may be separated from the elongate lengths of the second electrode of the low ionic strength pair by less than 100 p.m. The elongate lengths of the first and second electrode may be linear or curved. The sensor may also include electrodes configured for operation in a high ionic strength fluids (small pad electrodes); pairs of small pad electrodes may be operated together, or a small pad electrode may be operated as a pair with one of the low ionic strength electrodes.

Each length of the plurality of elongate lengths of the first and second electrode may have a length that is greater than 10 times its width.

In some variations the sensor includes a printed circuit board substrate onto which the first and second electrodes are formed.

Also described herein are sensors for immittance spectroscopy configured to operate in both high and low ionic strength liquids, the sensor comprising: at least a first pair of electrodes configured to operate in low ionic strength liquids, the first pair comprising a first electrode having a plurality parallel elongate lengths of an electrically conductive material and a second electrode comprising a plurality of parallel elongate lengths of an electrically conductive material, wherein the elongate lengths of the first electrode are interdigitated with the elongate lengths of the second electrode; and at least a second pair of electrodes configured to operate in high ionic strength liquids.

In some variations the sensor includes a flow sensor. The flow sensor may be a hot wire anemometer. The sensor may also include a temperature sensor. In some variations the sensor includes a heating element to regulate the temperature of fluid being sensed by the sensor.

Also described herein are sensors for immittance spectroscopy configured to operate in both high and low ionic strength liquids, the sensor comprising: three pairs of electrodes configured to operate in low ionic strength liquids, wherein each first pair comprises a first electrode having a plurality parallel elongate lengths of an electrically conductive material and a second electrode comprising a plurality of parallel elongate lengths of an electrically conductive material, wherein the elongate lengths of the first electrode for a pair are interdigitated with the elongate lengths of the second electrode for that pair; and three electrodes configured to operate in high ionic strength liquids.

In some variations the sensors described herein include a capillary port configured to wick sample liquid onto all of the electrodes of the sensor. In some variations the sensor includes a retractable needle configured to load sample liquid onto all of the electrodes of the sensor.

Also described herein are immittance spectroscopy systems configured to operate in low ionic strength liquids, the system comprising: a sensor having at least one pair of electrodes configured to operate in a low ionic strength liquid; a signal generator configured to provide electrical excitation at a plurality of frequencies including a low frequency range from less than about 100 milliHertz to greater than about 1 KHz; a processor configured to receive complex admittance data from the sensor at the plurality of frequencies and to determine the identity, concentration or the identity and the concentration of one or more compounds in the liquids.

Any of the systems described herein may also include at least a first pair of electrodes configured to operate in low ionic strength liquids, the first pair comprising a first electrode having a plurality parallel elongate lengths of an electrically conductive material and a second electrode comprising a plurality of parallel elongate lengths of an electrically conductive material, wherein the elongate lengths of the first electrode are interdigitated with the elongate lengths of the second electrode.

The signal generator may be configured to provide electrical excitation at a plurality of frequencies including a low frequency range. The low frequency range may mean from less than about 1 Hz, less than about 100 milliHertz, less than about 10 milliHertz, etc. In some variations the applied frequency range may extend to a relatively high frequency range as well (e.g., greater than about 1 KHz, 10 KHz, 100 KHz, 1 MHz, etc.).

Also described herein are immittance spectroscopy system configured to operate in both low and high ionic strength liquids, the system comprising: a sensor having at least one pair of electrodes configured to operate with a low ionic strength liquid and at least one pair of electrodes configured to operate with a high ionic strength liquid; a signal generator configured to provide electrical excitation at a plurality of frequencies including a low frequency range from less than about 100 milliHertz to greater than about 10 KHz; a processor configured to receive complex admittance data from either or both pairs of electrodes of the sensor at the plurality of frequencies and to determine the identity, concentration or the identity and the concentration of one or more compounds in the liquids.

The pair of electrodes configured to operate in low ionic strength liquids comprises a first electrode having a plurality parallel elongate lengths of an electrically conductive material and a second electrode comprising a plurality of parallel elongate lengths of an electrically conductive material, wherein the elongate lengths of the first electrode are interdigitated with the elongate lengths of the second electrode.

Also described herein are methods of determining the identify and/or concentration of a drug in a low ionic strength liquid, the methods comprising: contacting a low ionic strength liquid and an electrode pair comprising a first electrode having a plurality parallel elongate lengths of an electrically conductive material and a second electrode comprising a plurality of parallel elongate lengths of an electrically conductive material, wherein the elongate lengths of the first electrode are interdigitated with the elongate lengths of the second electrode; applying electrical excitation to the liquid at a plurality of frequencies including a low frequency range from less than about 100 milliHertz to greater than about 1 Hz; and determining the identity, concentration or identity and concentration of one or more compounds in the liquid based on a complex immittance measured between the electrode pair.

The step of contacting the low ionic strength liquid may comprise contacting the low ionic strength liquid and a plurality of electrode pairs each having a first electrode with a plurality of parallel elongate lengths and a second electrode with a plurality of parallel elongate lengths, wherein the elongate lengths of the first electrode are interdigitated with the elongate lengths of the second electrode.

The method may also include the step of contacting the low ionic strength liquid and at least one pair of electrodes configured to measure complex immittance in high ionic strength liquids. Applying electrical excitation may comprise applying electrical excitation at a plurality of frequencies including a low frequency range from less than about 100 milliHertz to greater than about 1 KHz. In some variations applying electrical excitation comprises applying electrical excitation to the electrode pair. Applying electrical excitation may be chosen so that it results in a voltage that is below a threshold level for electrochemical reaction at the surfaces of the first and second electrodes; for example, in some variations applying electrical excitation results in a voltage that is below 500 mV.

The method may also include recording the complex immittance at a plurality of the applied frequencies. The step of determining may include comparing the complex immittance with a library of complex immittances.

Also described herein are methods of determining the identify and/or concentration of a drug in a low or high ionic strength liquid, the methods comprising: contacting a liquid and both a low ionic strength electrode pair and a high ionic strength electrode pair; applying electrical excitation to the electrodes at a plurality of frequencies from less than about 100 milliHertz to greater than about 1 KHz; detecting the complex immittance at both the low ionic strength electrode pair and the high ionic strength electrode pair; and determining the identity, concentration or identity and concentration of one or more compounds in the liquid based on either or both the complex immittances measured between the low ionic strength electrode pair and the high ionic strength electrode pair.

Contacting the liquid and the low ionic strength electrode pair may comprise comprising a first electrode having a plurality parallel elongate lengths of an electrically conductive material and a second electrode comprising a plurality of parallel elongate lengths of an electrically conductive material, wherein the elongate lengths of the first electrode are interdigitated with the elongate lengths of the second electrode.

The method may also include the step of determining if the liquid is high ionic strength or low ionic strength.

In some variations, contacting comprises contacting the liquid with a plurality of both low ionic strength electrode pairs and a high ionic strength electrode pairs. Applying electrical excitation may comprise applying electrical excitation to the electrodes at a plurality of frequencies from less than about 100 milliHertz to greater than about 10 KHz.

In some variations, the method also includes the step of recording the complex immittance at both the low ionic strength electrode pair and the high ionic strength electrode pair.

Applying electrical excitation may comprise applying electrical excitation to the electrode pair. In some variations, applying electrical excitation results in a voltage that is below a threshold level for electrochemical reaction at the surfaces of the electrodes. For example, applying electrical excitation may result in a voltage that is below 500 mV.

Determining may comprise comparing the complex immittance against a library of complex immittances. Determining may comprise comparing the complex immittances at a plurality of frequencies against a library of complex immittances.

Also described herein are systems for collecting and identifying drug waste in a liquid, the system comprising: a waste input port to receive liquid drug waste; a sample chamber coupled to the waste input port, wherein the sample chamber comprises a plurality of electrode pairs configured to contact received liquid drug waste; a signal generator configured to provide electrical energy to liquid drug waste within the sample chamber at a plurality of frequencies; a processor configured to receive complex immittance information at a plurality of frequencies from the plurality of electrode pairs, and to determine the identity and amount of drug in the liquid drug waste; and a collection chamber to collect liquid drug waste.

The system may also include a plurality of collection chambers. In some variations, the system includes a replaceable cartridge holding the plurality of electrode pairs. The sample chamber may be a flow-through chamber configured to pass liquid drug waste therethrough, or a static sample chamber. The sample chamber and plurality of electrode pairs may form part of a replaceable cartridge.

The system may also include a flow sensor to determine the flow rate of liquid drug waste entering the input port. The signal generator may be configured to provide electrical energy at a plurality of frequencies from less than about 100 milliHertz to greater than about 10 Hz. The processor may be configured to log and/or report the identity and amount of drug in a received liquid drug waste.

In some variations, the system includes an output to report the identity and amount of drug received.

The processor may be configured to direct the collection of liquid drug waste to one of a plurality of collection chambers based on the identity of the drug in a received liquid drug waste.

Any of the systems described herein may also include a rinse module connected to a source of rinsate to rinse the sample chamber after delivery of a liquid (e.g., liquid drug waste).

The processor may be configured to compare determine the identity and amount of drug in the liquid drug waste received by comparing the complex immittance to a library of complex immittances of known drugs.

Also described herein are systems for collecting and identifying drug waste in a liquid, the system comprising: a waste input port to receive liquid drug waste; a sample chamber coupled to the waste input port, wherein the sample chamber comprises a plurality of electrode pairs configured to contact received liquid drug waste; a flow sensor configured to determine the flow of liquid into the system; a signal generator configured to provide electrical energy to liquid drug waste within the sample chamber at a plurality of frequencies; a processor configured to receive complex immittance information at a plurality of frequencies from the plurality of electrode pairs, and to determine the identity and amount of drug in the liquid drug waste from the immittance information and the flow sensor; and a collection chamber to collect liquid drug waste.

Also described herein are systems for collecting and identifying drug waste in a liquid, the system comprising: a waste input port to receive liquid drug waste; a sample chamber coupled to the waste input port, wherein the sample chamber comprises a plurality of electrode pairs configured to contact received liquid drug waste; a signal generator configured to provide electrical energy to liquid drug waste within the sample chamber at a plurality of frequencies; a processor configured to receive complex immittance information for a plurality of frequencies from the plurality of electrode pairs, and to determine the identity and amount of drug in a received liquid drug waste from the complex immittance information; and a plurality of collection chambers to collect liquid drug waste, wherein the processor directs the collection of liquid drug waste to one of the plurality of collection chambers based on the identity of the drug in a received liquid drug waste.

Also described herein are methods of collecting and identifying drug waste in a liquid, the method comprising: receiving a liquid drug waste; determining complex immittance information from the liquid drug waste using each of a plurality of electrode pairs for a plurality of frequencies; determining the identity and amount of drug in the liquid drug waste; and collecting the liquid drug waste in a collection chamber.

A method of collecting and identifying drug waste may also include recording the amount of drug in the liquid waste received. In some variations, receiving the liquid drug waste comprises pumping the liquid drug waste into a waste input port of a system for collecting and identifying drug waste in a liquid.

Determining complex immittance information may comprise applying electrical energy at a plurality of frequencies across the plurality of electrode pairs when they are in contact with the liquid drug waste. In some variations determining the identity and amount of drug comprises using the complex immittance information to determine the identity and amount of drug in the liquid drug waste. For example, determining the identity and amount of drug may comprise comparing the complex immittance information with a library of complex immittance information of known drugs to determine the identity and amount of drug in the liquid drug waste.

The step of collecting the liquid drug waste may comprise collecting liquid drug waste containing different drugs into different collection chambers.

Also described herein are methods of determining the identity of a drug or drug formulation by recognizing a pattern of complex immittance from a library of known complex immittances, the methods comprising: receiving an initial dataset comprising complex immittance spectrographic information for an unknown liquid sample, the complex immittance spectrographic information taken from a plurality of different electrode pairs at a plurality of different frequencies; using a processor to apply one or more pattern recognition techniques to compare the initial dataset to an identification space database comprising a plurality of identification datasets wherein the identification datasets comprise complex immittance data corresponding to known drug compositions to determine if the initial dataset matches an identification dataset from the identification space database within a threshold range; and reporting that the initial dataset does or does not match an identification dataset, and if the initial dataset does match an identification dataset within the threshold range, reporting which drug or drugs correspond to the identification dataset matched.

The step of using the processor to apply one or more pattern recognition techniques may comprise using a Neural Network, for example, a Probabilistic Neural Network. In some variations, using the processor to apply one or more pattern recognition techniques comprises reducing the dimension of the initial dataset and performing a regression analysis.

The step of receiving the initial dataset may comprise receiving an initial dataset having greater than 30 dimensions (or in some variations greater than 10 dimensions, greater than 20 dimensions, greater than 50 dimensions, etc.).

The method of determining the identity of a drug or drug formulation by recognizing a pattern of complex immittance may also include setting the threshold range.

The step of using a processor to apply one or more pattern recognition techniques may comprise applying two pattern recognition techniques. For example, the method may include using the processor to apply one or more pattern recognition techniques comprises initially applying a PCA method to reduce the dimension of the data and then applying another pattern recognition technique to determine if the initial dataset matches an identification dataset. The step of using the processor to apply one or more pattern recognition techniques may comprise initially applying a PCA method to reduce the dimension of the dataset and then using a neural network to determine if the initial dataset matches an identification dataset. In some variations using the processor to apply one or more pattern recognition techniques comprises applying a linear technique selected from the group consisting of: principal component analysis, factor analysis, projection pursuit, independent component analysis, multi-objective functions, one-unit objective functions, adaptive methods, batch-mode algorithms, and random projections methods. Using the processor to apply one or more pattern recognition techniques may comprise applying a non-linear technique selected from the group consisting of: non-linear principle component analysis, non-linear independent component analysis, principle curves, multidimensional scaling, and topologically continuous maps.

The method of determining the identity of a drug or drug formulation by recognizing a pattern of complex immittance may also include the step of interpolating to get an estimate of the concentration of the drug or drug corresponding to the matching identification dataset when the initial dataset matches the identification dataset within the threshold range. Reporting that the initial dataset does or does not match an identification dataset may comprise reporting the concentration of the drug or drugs correspond to the identification dataset when the initial dataset does match the identification dataset within the threshold range.

The step of using the processor to apply one or more pattern recognition techniques may comprise reducing the initial dataset down to four dimensions.

Also described herein are methods of determining the identity of a drug or drug formulation by recognizing a pattern of complex immittance from a library of known complex immittances, the methods comprising: receiving an initial dataset comprising multi-dimensional, complex immittance spectrographic information for an unknown liquid sample, the complex immittance spectrographic information taken from a plurality of different electrode pairs at a plurality of different frequencies; reducing the dimensions of the initial dataset using a linear or non-linear technique to form a reduced dataset; determining how closely the reduced dataset matches an identification dataset of an identification space database, wherein the identification space database comprises a plurality of identification datasets corresponding to known drug compositions; and reporting that the known drug composition corresponding to the identification space database having the closest match to the reduced dataset if the closeness of the match is within a threshold range, or report that the unknown liquid sample does not match a known drug composition of those drugs included in the identification space database if the closeness of match is outside of the threshold range.

The step of reducing the dimensions of the initial dataset may comprise applying a linear technique selected from the group consisting of: principal component analysis, factor analysis, projection pursuit, independent component analysis, multi-objective functions, one-unit objective functions, adaptive methods, batch-mode algorithms, and random projections methods. In some variations the step of reducing the dimensions of the initial dataset comprises applying a non-linear technique selected from the group consisting of: non-linear principle component analysis, non-linear independent component analysis, principle curves, multidimensional scaling, and topologically continuous maps. Reducing the dimensions of the initial dataset may comprise reducing the initial dataset down to four dimensions.

Also described are methods of determining the identity and concentration of a drug by recognizing a pattern of complex immittance from a library of known complex immittances, the methods comprising: receiving an initial dataset comprising multi-dimensional, complex immittance spectrographic information for an unknown liquid sample, the complex immittance spectrographic information taken from a plurality of different electrode pairs at a plurality of different frequencies; reducing the dimensions of the initial dataset using a linear or non-linear technique to form a reduced dataset; matching the reduced dataset to an identification space database, the identification space database comprising a plurality of identification datasets corresponding to known drug compositions; determining the closeness of the match for the reduced dataset relative to each of the identification datasets; determining a proposed drug composition by applying a threshold to the closeness of the match for each of the identification datasets, wherein the proposed drug composition is unknown if the closeness of match is outside of the threshold range; and determining a concentration of drug in the unknown liquid sample by applying a regression of the proposed drug composition for the known drug composition.

Also described are fully automated medical system configured to monitor a patient and deliver necessary medication, the system comprising: a patient monitor configured to receive information on a patient's health; a processor configured to receive information on the patient's health from the patient monitor and to prepare and administer an intravenous drug based on the patient's health; an IV drug compounding system in communication with the processor and configured to compound a drug requested by the processor, wherein the IV drug compounding system confirms the drug identity and concentration after compounding; and an IV drug delivery system comprising a drug pump, the IV drug delivery system in communication with the IV drug compounding system and the processor, wherein IV drug delivery system confirms the identity and concentration of the IV drug as it is being delivered to the patient.

Also described herein are methods for accurately and automatically delivering a drug to a patient, the methods comprising: electronically communicating medical information about a patient to an automatic IV delivery system, wherein the automatic IV delivery system determines a drug and drug dosage from the patient's medical information; and administering a drug solution comprising the determined drug and drug dosage to the patient using the automatic IV delivery system, wherein the automatic IV delivery system monitors and confirms the composition of the drug solution as it is being administered.

The method for accurately and automatically delivering a drug to a patient may also include the step of connecting the patient to the automatic IV delivery system.

In some variations, the method includes the step of automatically compounding the drug solution with the automatic IV delivery system.

The automatic IV delivery system may confirm that the composition of the drug solution is correct prior to administering the drug solution. The method may also comprise confirming the identity of the patient.

The automatic IV delivery system may comprise an immittance spectrographic system that confirms the composition of the drug solution by determining a complex immittance fingerprint from the drug solution.

Also described herein are methods for accurately and automatically delivering a drug to a patient, the method comprising: electronically communicating medical information about a patient to an automatic IV delivery system, wherein the automatic IV delivery system determines a drug and drug dosage from the patient's medical information; compounding a drug solution of the determined drug, wherein the automatic IV delivery system confirms that the composition of the drug solution corresponds to the drug and dose from the patient's medical information; administering a drug solution comprising the determined drug and drug dosage to the patient using the automatic IV delivery system, wherein the automatic IV delivery system includes a pump and monitors and confirms the composition of the drug solution as it is being administered.

BRIEF DESCRIPTION OF THE DRAWINGS

FIG. 3 shows one example of a main electronic board circuit diagram.

FIG. 4 is a circuit diagram of one variation of a signal synthesis circuit, and FIG. 5 is an example of a synchronous detector circuit with four filter output.

FIG. 6 is an example of the inline peripheral operation device ("POD") board circuit, and FIG. 7 shows an example of a POD board signal switching system.

FIG. 8 shows an example of a POD Flow sensor circuit.

FIG. 15A is an example of another variation of a sensor including three pairs of low ionic strength electrodes as well as three high ionic strength electrodes and a flow meter. FIGS. 15B and 15C show the sensor of FIG. 15A mounted in an SOIC-16 dual inline integrated circuit package.

FIGS. 17A-17J illustrate variations of sensors having different configurations of low ionic strength electrodes.

FIGS. 19A and 19B show one variation of a mount for an in-line configuration of a sensor.

FIG. 30A is a side perspective view, FIG. 30B is top view and FIG. 30C is a side view.

FIG. 31 shows the sensor onto which the well-forming layer may be attached, as shown in FIG. 31B. FIG. 31C is a partial section though a perspective view, showing the well with the sensor on the bottom. Any sensor may be used, including those having low ionic strength electrodes (not shown).

FIG. 35A shows the assembly including the connector and sensor along with additional connecting elements for connecting to fluid tubing elements. FIG. 35B shows a transparent view of the side of a housing/mount for a sensor; FIG. 35C shows the side view of FIG. 35B non-transparent. FIG. 35D shows the bottom view of the housing/mount, where a sensor may be connected.

FIGS. 39A-39E show another sensor mount similar to the one shown in FIG. 37. FIG. 39A shows a side perspective view without a sensor attached; FIG. 39B shows an end view and FIG. 39C shows a side view with a sensor attached. FIG. 39D illustrates the direction of fluid flow though the mount. FIG. 39E shows a perspective view of a sensor attached to the mount.

FIG. 42A shows the mount assembly in an exploded view; FIG. 42B shows the assembled sensor mount, and FIG. 42C shows a partial section though the mount.

FIG. 44A shows the connector coupling to the mount, and the assembled mount is shown in FIGS. 44B and 44C.

FIG. 45 is a modeled flow profile though a mount/housing such as the one shown in FIGS. 44A-44C.

FIGS. 57, 58A-58B and 59 illustrate variations of IV check systems as described herein.

FIGS. 67A and 67B illustrate one variation of an IV delivery system coupled to an IV bag.

FIG. 68 is another view of the IV delivery system of claim 67A and 87B.

FIG. 70 illustrates one variation of a monitoring screen for monitoring multiple IV delivery systems.

FIG. 81A is an exemplary display for a monitoring screen for monitoring multiple active (pump controlling) IV delivery systems.

FIG. 96B shows the patterns with artificial noise added for Furocemide at 4 mg/ml (FUR)

FIGS. 105A-105J show complex immittance plots of Heparin solutions at increasing concentrations in D5W, frequency scan from 100 HZ to 1 MHz, taken with the low ionic-strength (interdigitated) electrodes.

FIGS. 106A-106J show complex immittance plots of Heparin solutions at increasing concentrations in D5W, frequency scan from 100 HZ to 1 MHz, taken with small pad electrodes.

FIGS. 107A-107H show complex immittance plots of Heparin solutions at increasing concentrations in D5W, frequency scan from 100 HZ to 1 MHz, taken with electrode pairs of mismatched metals.

FIGS. 108A-108D show screenshots from a program for identifying a drug in a low-ionic strength diluent using the data including that shown in FIGS. 105A-107H.

FIGS. 109A-109D illustrate curve fitting using a fourth and fifth order polynomial fit of complex immittance spectrographic data.

FIG. 110 is a table showing the testing result for a system implementing a Probabilistic Neural Network (PNN) technique to identify the composition of a solution (drug identity).

FIG. 111 is a table showing the results for testing a system implementing a PNN function approximation model to estimate the concentration of the drug from immittance measurements.

DETAILED DESCRIPTION

Described herein are devices, systems, and methods for determining the composition of liquids. The composition to be determined may include the identity of one or more compounds in the fluid solution (diluent), and thus may refer to the identity and in some contexts both identity and concentration of one or more of these compounds. In some variations, all of the components of a liquid may be determined, including the identity of the liquid (e.g., saline, etc.). The systems, methods and devices described herein are immittance spectrographic systems (which may be, for convenience referred to as admittance or impedance spectrographic systems), methods and devices which determine the complex electrical admittance of the liquid under multiple surface conditions (either sequentially or in parallel) and/or at multiple applied frequencies in order to determine characteristic properties that may be used to determine the composition. In particular, the systems described herein may be adapted for use with low (or low and high) ionic strength liquids.

A liquid immittance measurement typically involves the measurement of the real and imaginary components of the alternating current (ac) response of a liquid to applied electrical current at a particular frequency, set of frequencies or within a range of frequencies. These components are also sometimes referred to as the in-phase and quadrature or the resistive and reactive components of an ac response. This technique is herein demonstrated for the identification of liquids, components in liquids, and particularly to the identification of medical liquids, particularly fluid medications, as well as determination of their concentration and dosage.

Figure 1:
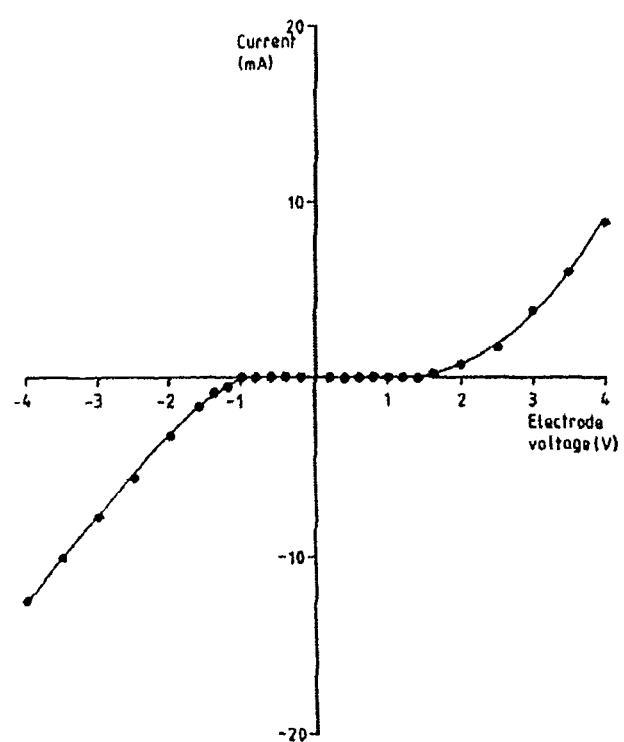
FIG. 1 is a graph showing the electrode polarization effect (adapted from Walton C, Gergely S, Economides AP, "Platinum pacemaker electrodes: origins and effects of the electrode-tissue interface impedance," Pacing Clin Electrophysiol. 1987;10:87-99).
Figure 2:
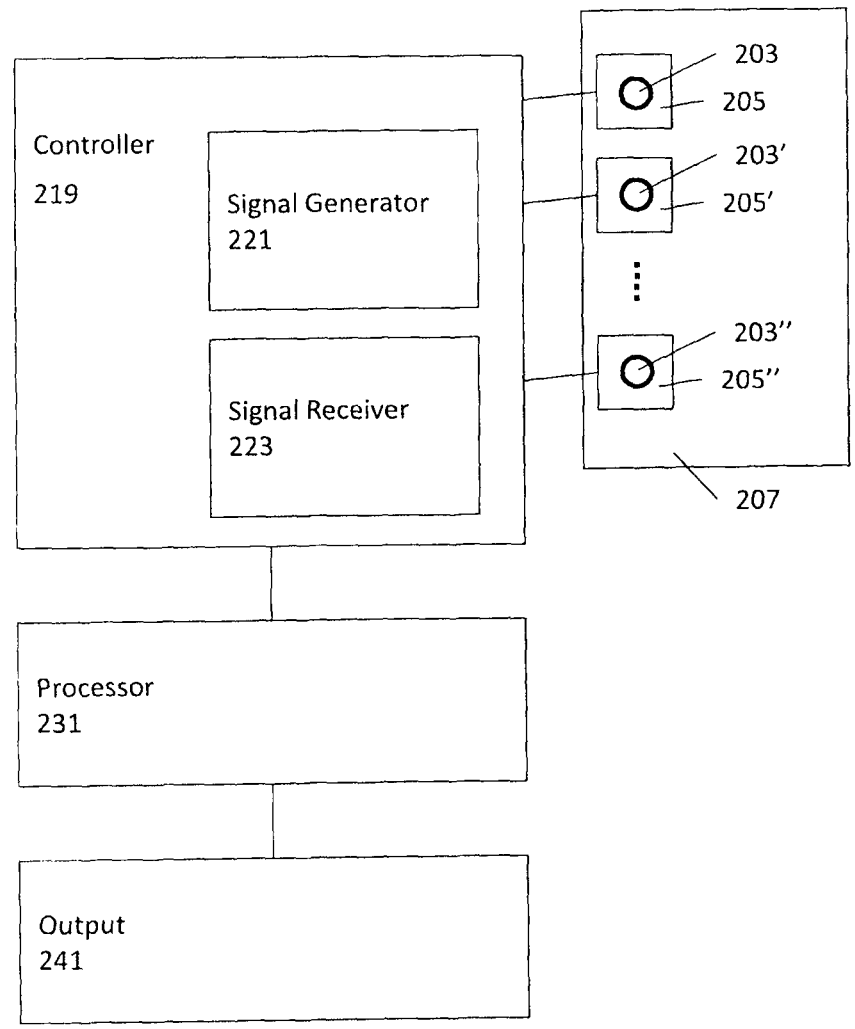
FIG. 2 is a schematic of one variation of an immittance spectrographic system for determining the composition of a liquid.

FIG. 2 shows one variation of a generic description of a system (which may be configured as a device) for determining the composition of an aqueous solution. This generic system may be modified in a variety of unique ways as described in greater detail below in order to improve its functioning and adapt the device for specific applications.

For example, a system or device may include a sensor 207. Typically, the sensor 207 includes a plurality of electrodes (205, 205', ..., 205"), each having a liquid-contacting region (203, 203', ..., 203"). These electrodes may be arranged in pairs. The liquid-contacting region may be co-extensive with the electrode itself, or it may be a surface sub-region of the electrode. The electrodes are electrically conductive material. At least some of the electrodes may have different liquid-contacting surfaces. As mentioned, the complex admittance (immittance) determined across individual pairs of electrodes may depend upon the interaction of the aqueous solution and the components within the solution at the surface of the electrode (the liquid-contacting surface). Thus, the surface properties (including the size and materials forming the surface) may be controlled and matched to known or standardized liquid-contacting regions of the electrodes. Typically each electrode pair may have at least one liquid-contacting surface that is different from liquid-contacting surfaces in other pairs, in variations of the systems in which multiple electrode pairs are used. The sensor electrodes may be formed as part of a separate or separable sensor, an integrated sensor, probe, test cell or test chamber, tubing, or may be integrated into another device, such as a pump (e.g., IV pump), or the like. Disposable or semi-disposable sensors are also included. A semi-disposable sensor may be configured for use with multiple solutions and may be rinsed between uses, but may be replaced periodically.

A system or device may also include a signal generator 221 for applying an electrical signal to the liquid being examined, and particularly across one or more pairs of the electrodes in the sensor. The system generator may operate over a range of frequencies (e.g., from the miliHz range up to the MHz range) and sensor amplitudes in the range of 10 to 30 mV. The generator may apply frequencies and amplitudes larger or smaller than these ranges.

The system may also include a signal receiver 223 for receiving an electrical signal representing the complex immittance (e.g., impedance, admittance). In one example, detection using the signal receiver may be done with a single board lockin such as the Scitec Instruments model 441. Output signals from the lock-in typically range from 1 mV to 10V depending on the nature and ionic content of the liquid being measured, the excitation voltage applied and the frequency of operation. The signals may be maintained in such a range to take full advantage of the dynamic range of the analog to digital circuits incorporated into the sbRIO board.

The sensor and/or the signal receiver may include processing (amplification, filtering, or the like). In some variations the system includes a controller 219 for coordinating the application of the electrical signal to the one or more pairs of electrodes, and for receiving the complex admittance data. For example, a controller may include a trigger, clock or other timing mechanisms for coordinating the application of energy to the electrodes and receiving complex immittance data. The system or device, including controller 219, may also include a memory for recording/aggregating/storing the complex admittance data, and/or communications elements (not shown) for passing the data on, including wired or wireless communication means. The controller may generate datasets corresponding to the multiple complex immittance data from the plurality of electrode pairs on the sensor at different frequencies.

As mentioned, a controller may include software, firmware, and/or hardware for control, data acquisition, data display and data storage. For example, one variation of a system utilizes a National Instruments Model 9632 sbRIO board in conjunction with LabView software that controls the system, acquires and displays data and stores that data in a spreadsheet formatted text file.

An additional sensor or sensors (not shown) may also be included, or the sensor 207 may include one or more additional elements for measuring other fluid properties, such as flow, temperature, or the like. A controller may control multiple sensors, including multiple immittance sensors.

A system or device may also include a processor 231 for analyzing the complex immittance data to determine the composition of the liquid, and/or for controlling other aspects of the system, as described below (e.g., pumps, fluid delivery, fluid collection, etc.). The controller and/or processor may also process any additional (not immittance) data collected from the sensor 207 or additional sensors, such as temperature, flow, etc.

In some variations the processor 231 determines the composition of the aqueous solution based on the complex immittance data. The processor may be integrated with the system, or it may be separate (e.g., remote) or shared with other controllers and/or sensors. Details and examples of the processor are described in greater detail below. A processor 231 may include logic (executable as hardware, software, firmware, or the like) that processes and/or analyzes the initial dataset to determine the composition and/or concentration of the one or more compounds in the liquid (solution). The processor may also determine the total amount of composition (in a solution or delivered). Thus, a processor may receive information from one or more sensors that may also be used to help characterize the administration of the liquid, or the operation of other devices associated with the liquid.

Finally, a device or system may include an output 241 for reporting, recording and/or acting on the identified composition of the aqueous solution. A reporting output may be visual, audible, printed, digital, or any other appropriate signal. In some variations described herein, the system or device may regulate or modify activity of one or more devices associated with the liquid or with a patient receiving liquid. For example, a system may turn off or limit delivery of a substance by controlling operation of a pump or valve based on the analysis of the composition of the fluid.

FIGS. 3 through 9 illustrate circuit diagrams of one variation of a system including features that may be included in any of the devices described herein. For example, a system for examining fluid composition by generation of sensor signals to capture "fingerprints" indicative of the composition of a compound in the solution in a compact format may include custom electronics circuits. The circuit shown in FIG. 3 includes an optional flow sensor; in some variations flow sensors are not included.

In this example, the customized electronics may be used with a well-known processor, such as the sbRIO 9632 data acquisition and processor system from National Instruments. For example, the system may use two circuit boards, shown in FIGS. 3 and 6, one plugged directly to the sbRIO board and a second one, which can be connected directly or remotely via a cable. Additional circuits implemented in the design may allow invocation of the on-chip flow meter. Direct connection of the main board and sbRIO may eliminate the need for flat cables and may simplify the design, thus improving reliability, in-box heat exchange and reducing overall volume (footprint) of the device. The second board (peripheral operation device or "POD") may perform functions for signal condition and buffering as well as signal transfer through the cables. Both boards in this example provide functions for flow measurements as well as a number of internal electronics control functions such as excitation voltage calibration, transfer function calibration, chip and board temperatures.

Figure 3:
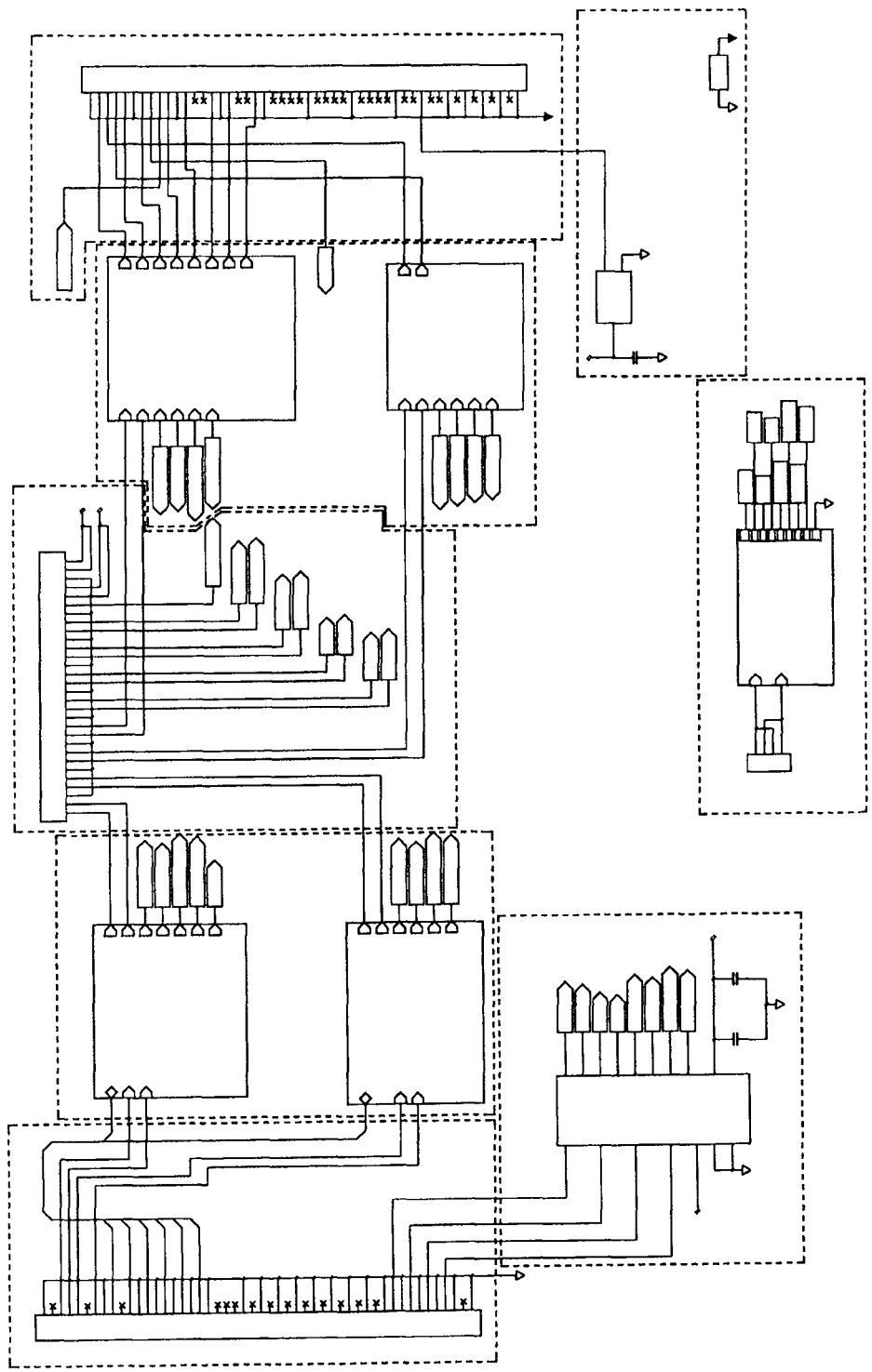
FIGS. 3 through 8 are circuit diagrams showing one variation of a system for performing immittance spectroscopy to determine the composition of a liquid.
Figure 3:
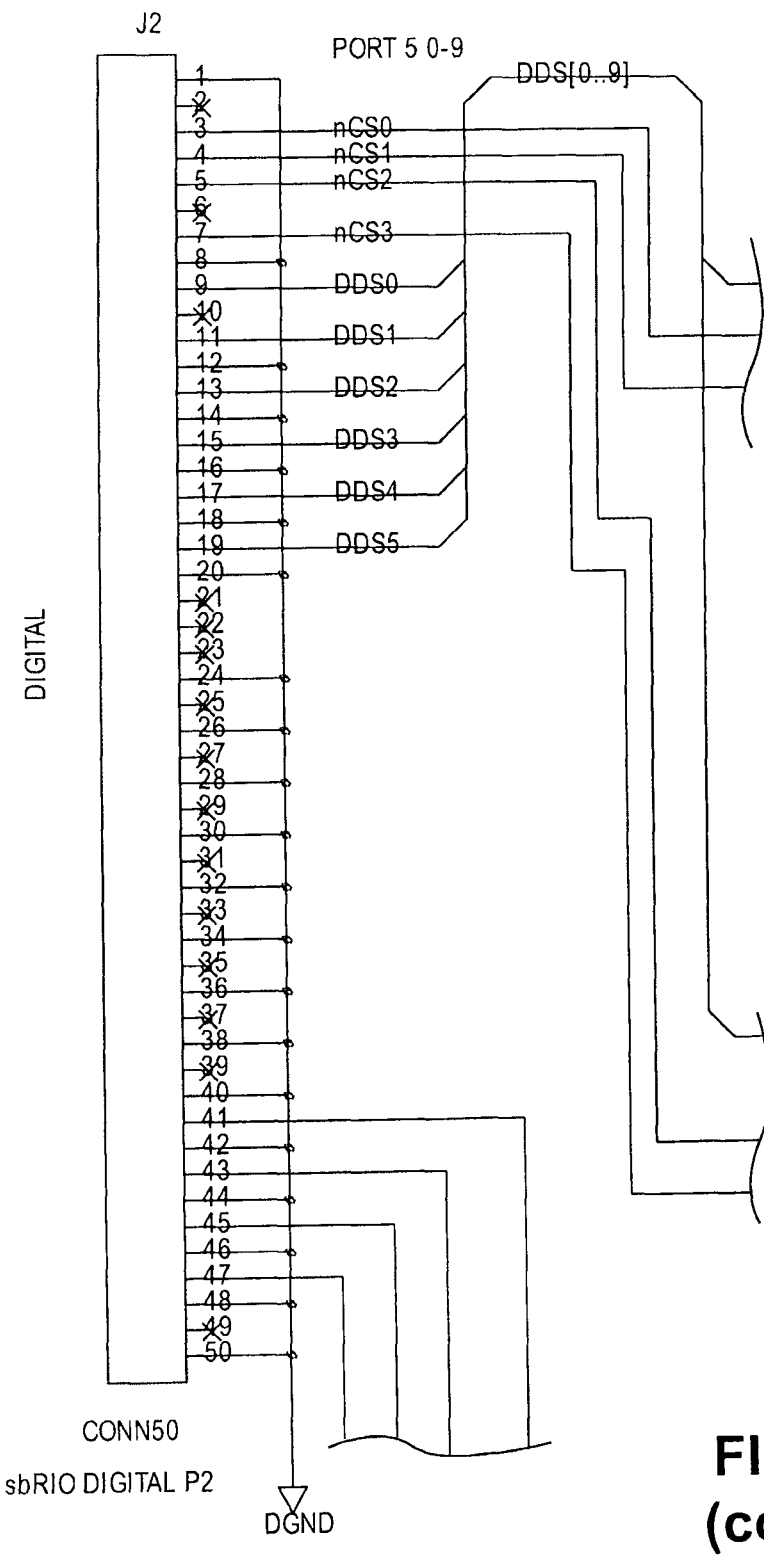
Figure 3:
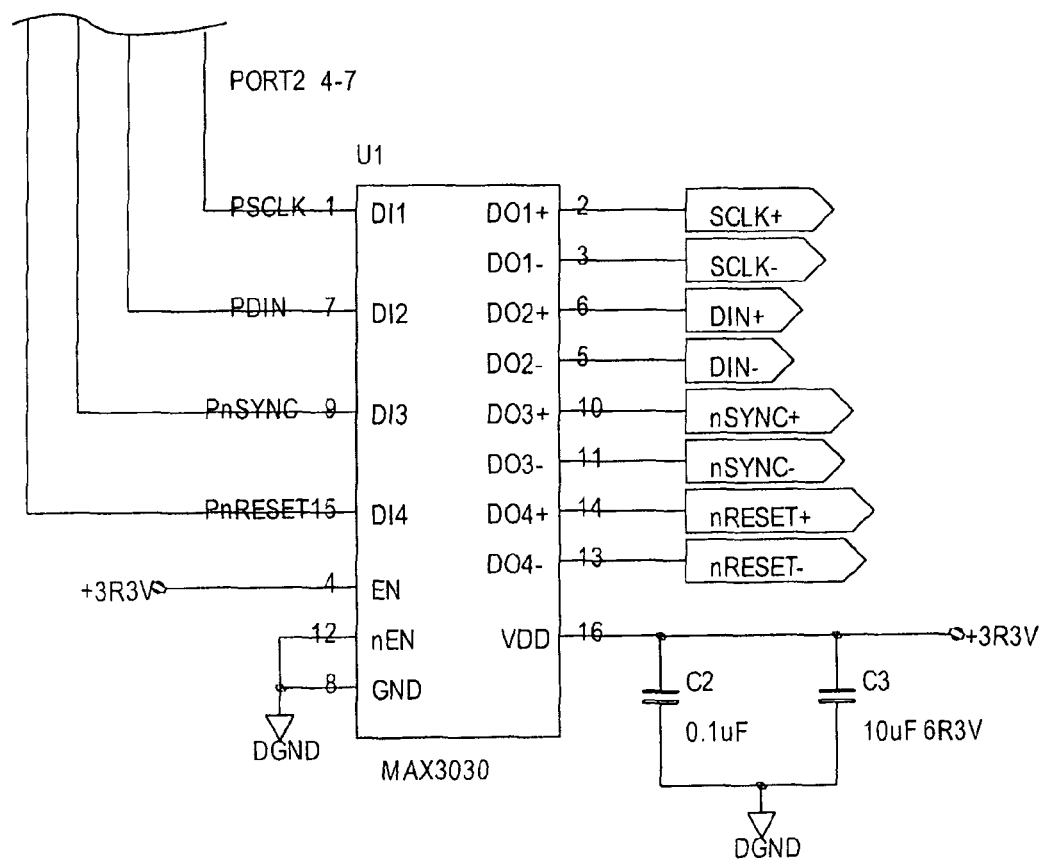
Figure 3:
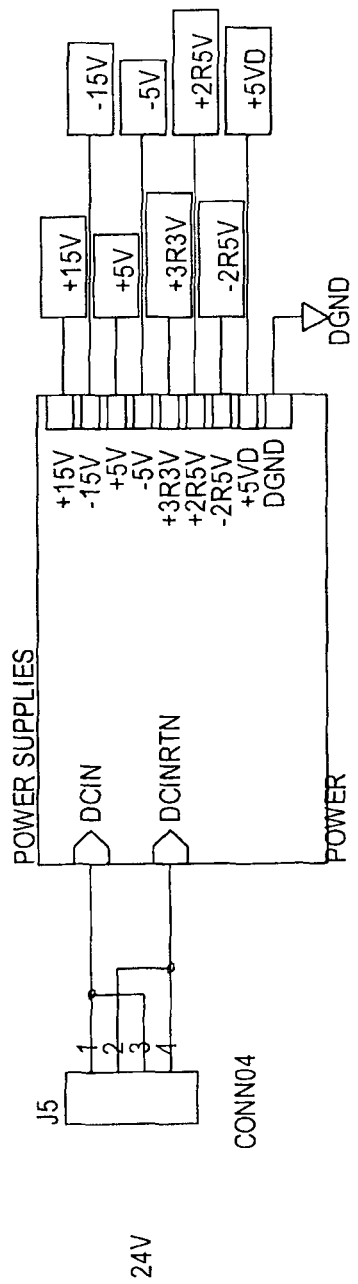
Figure 3:
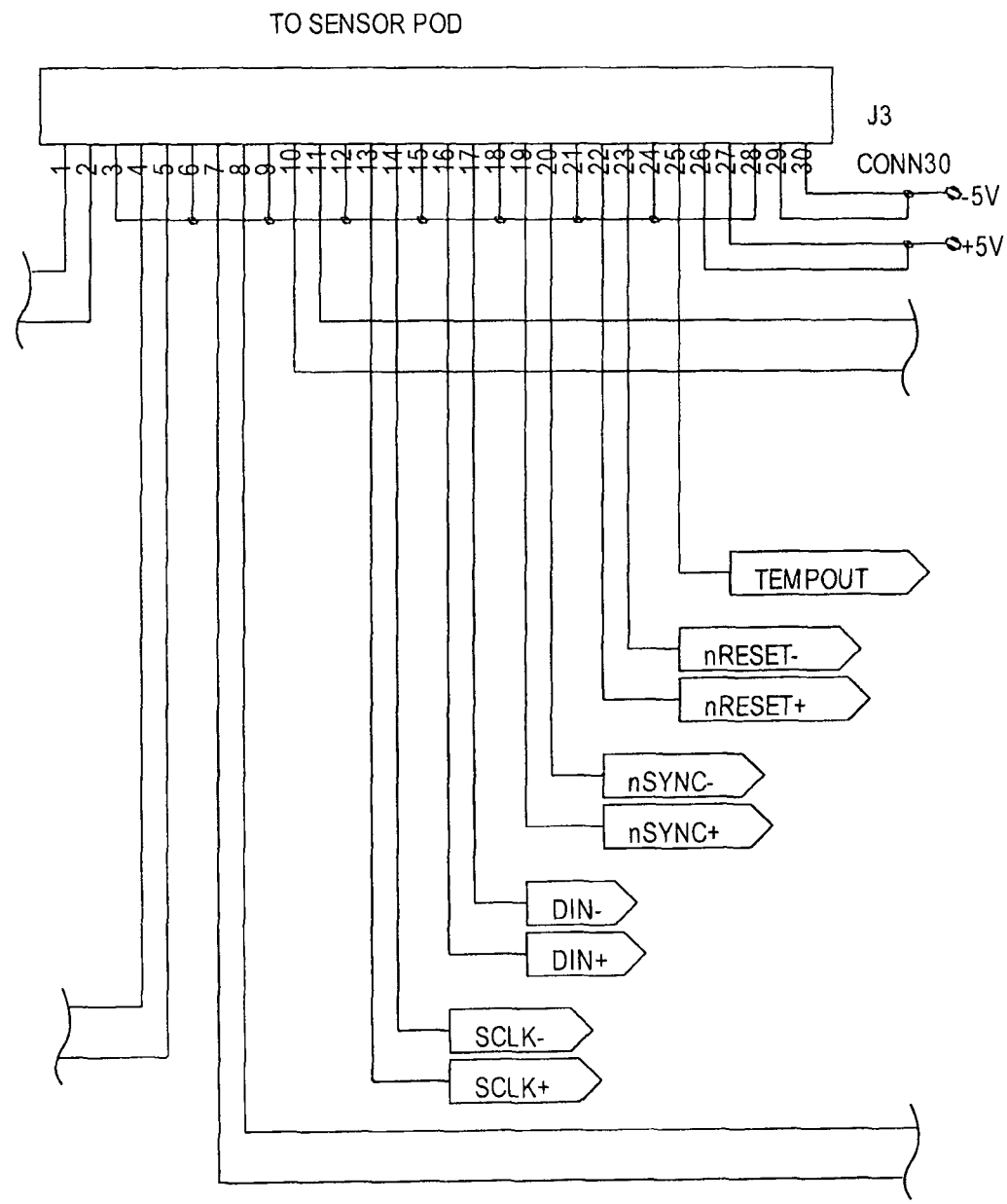
Figure 3:
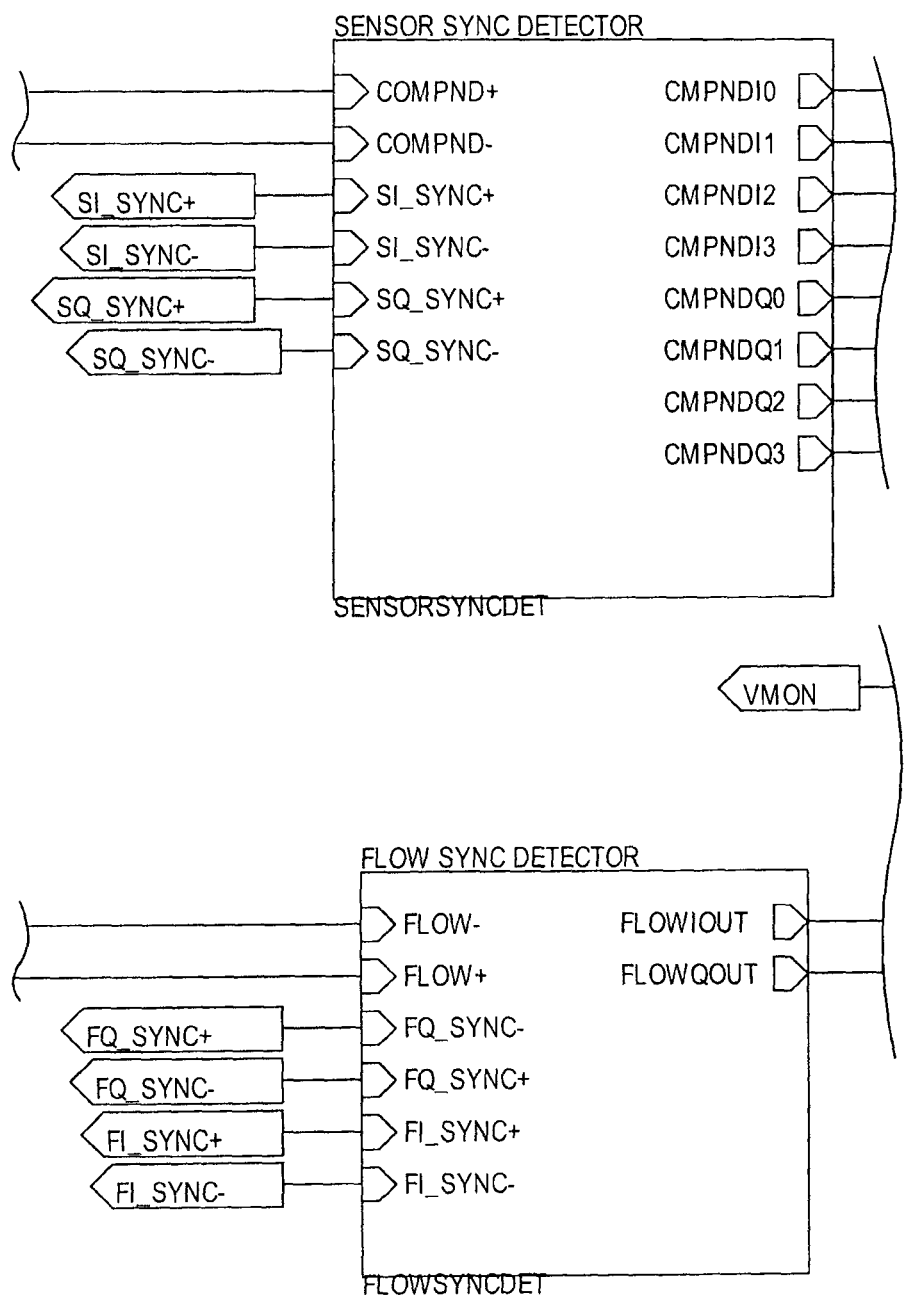
Figure 3:
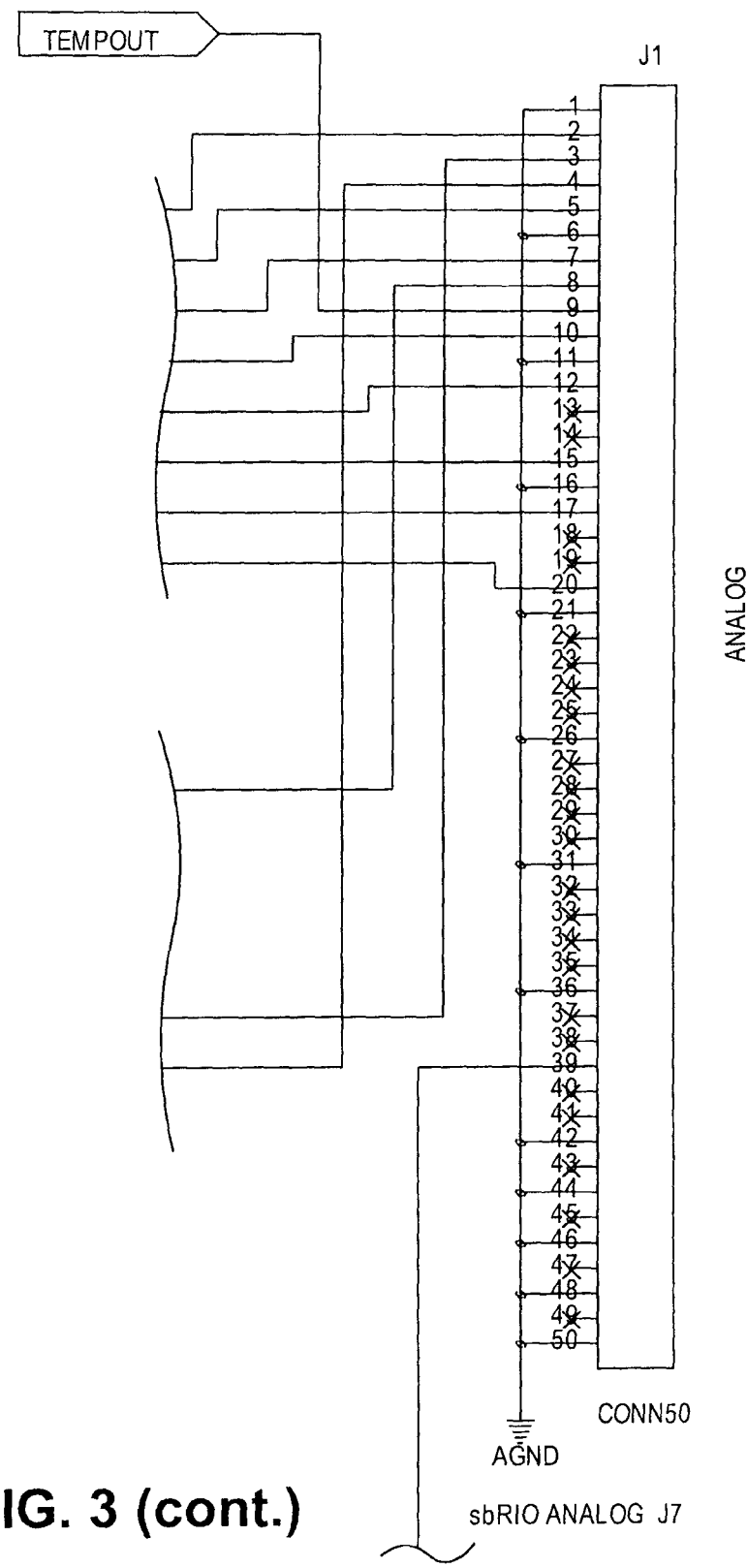
Figure 3:
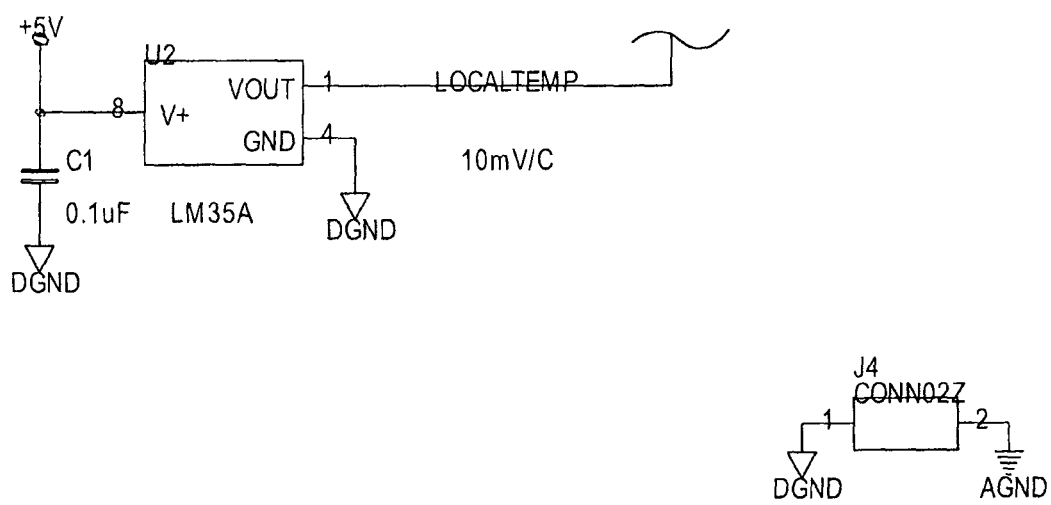
Figure 4:
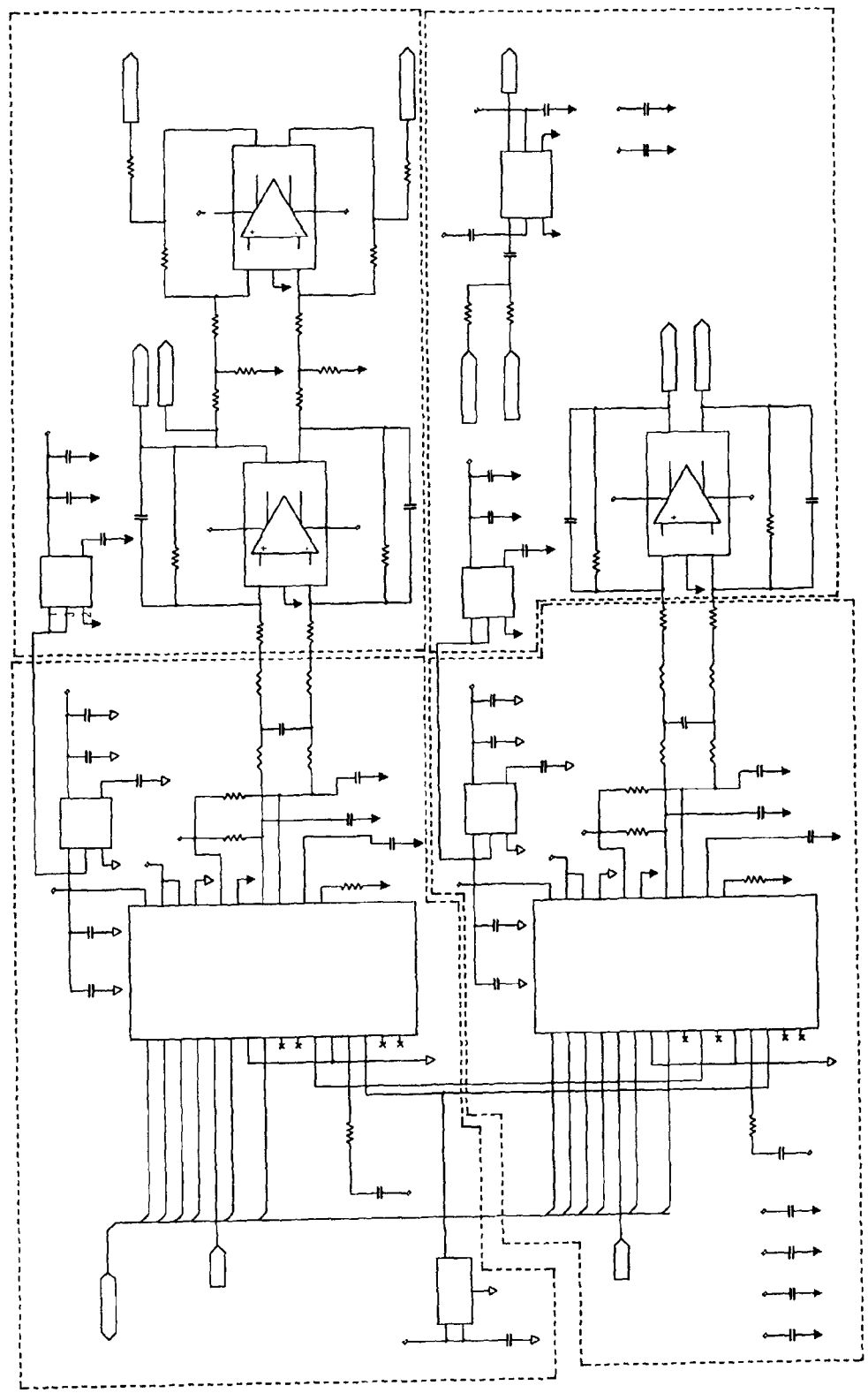
Figure 4:
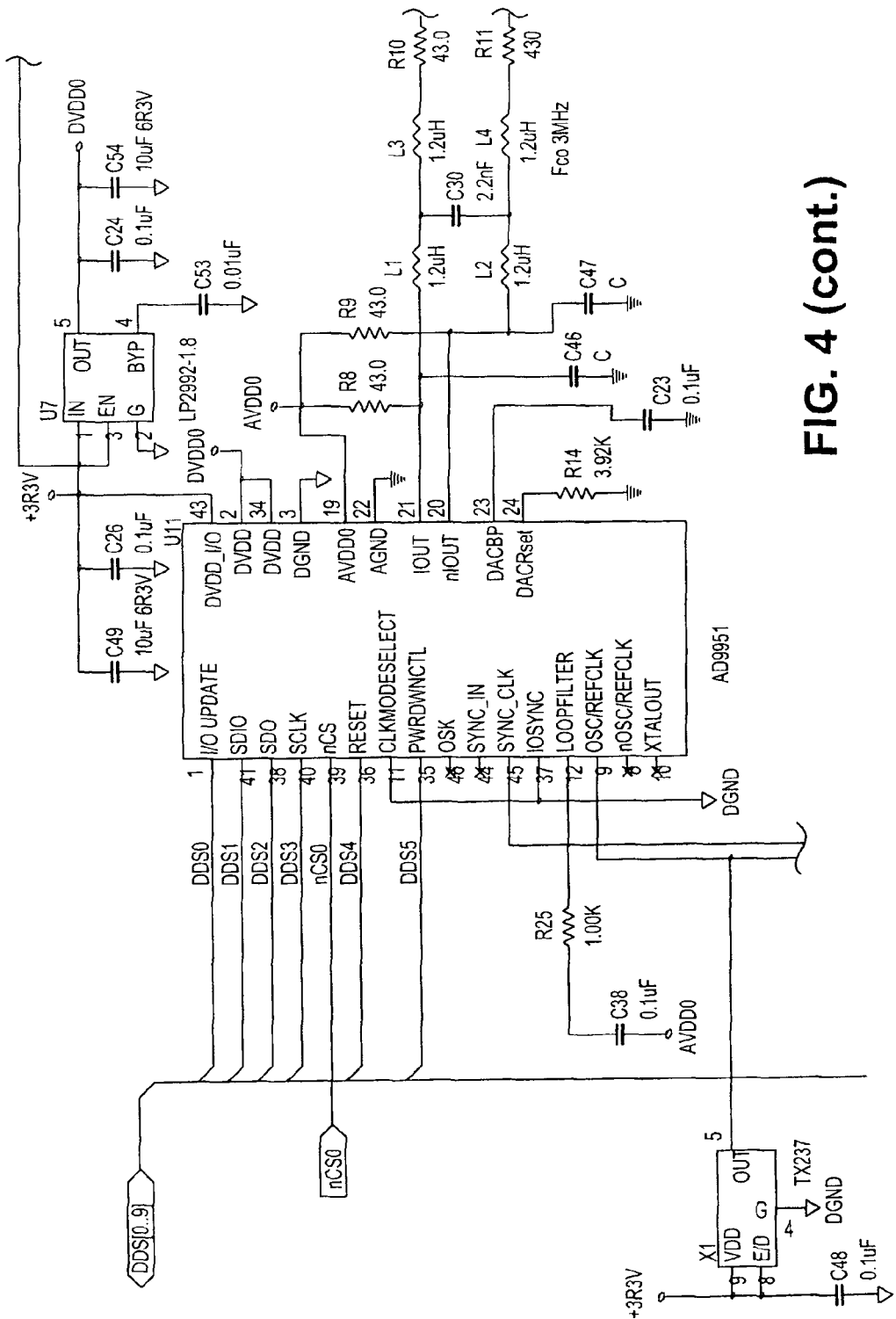
Figure 4:
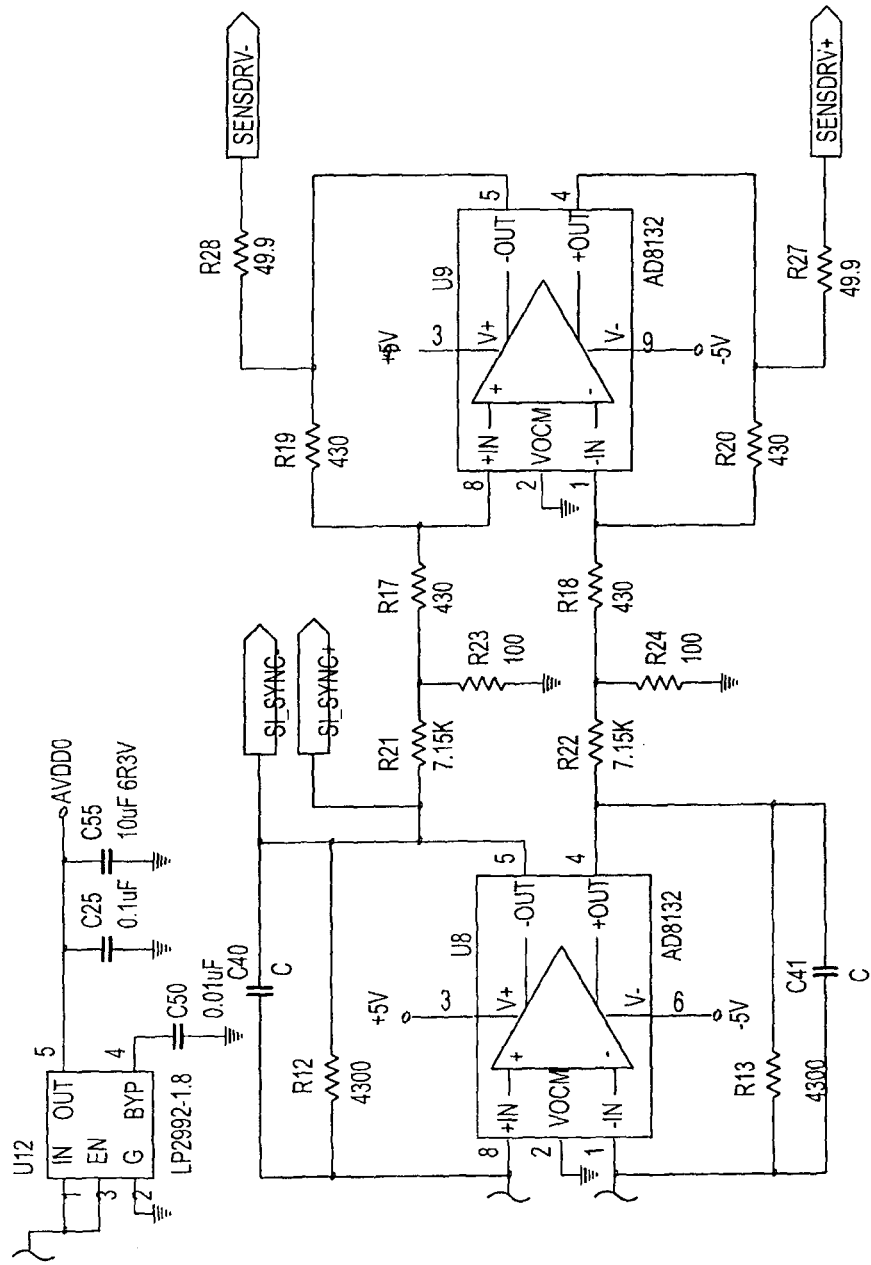
Figure 4:
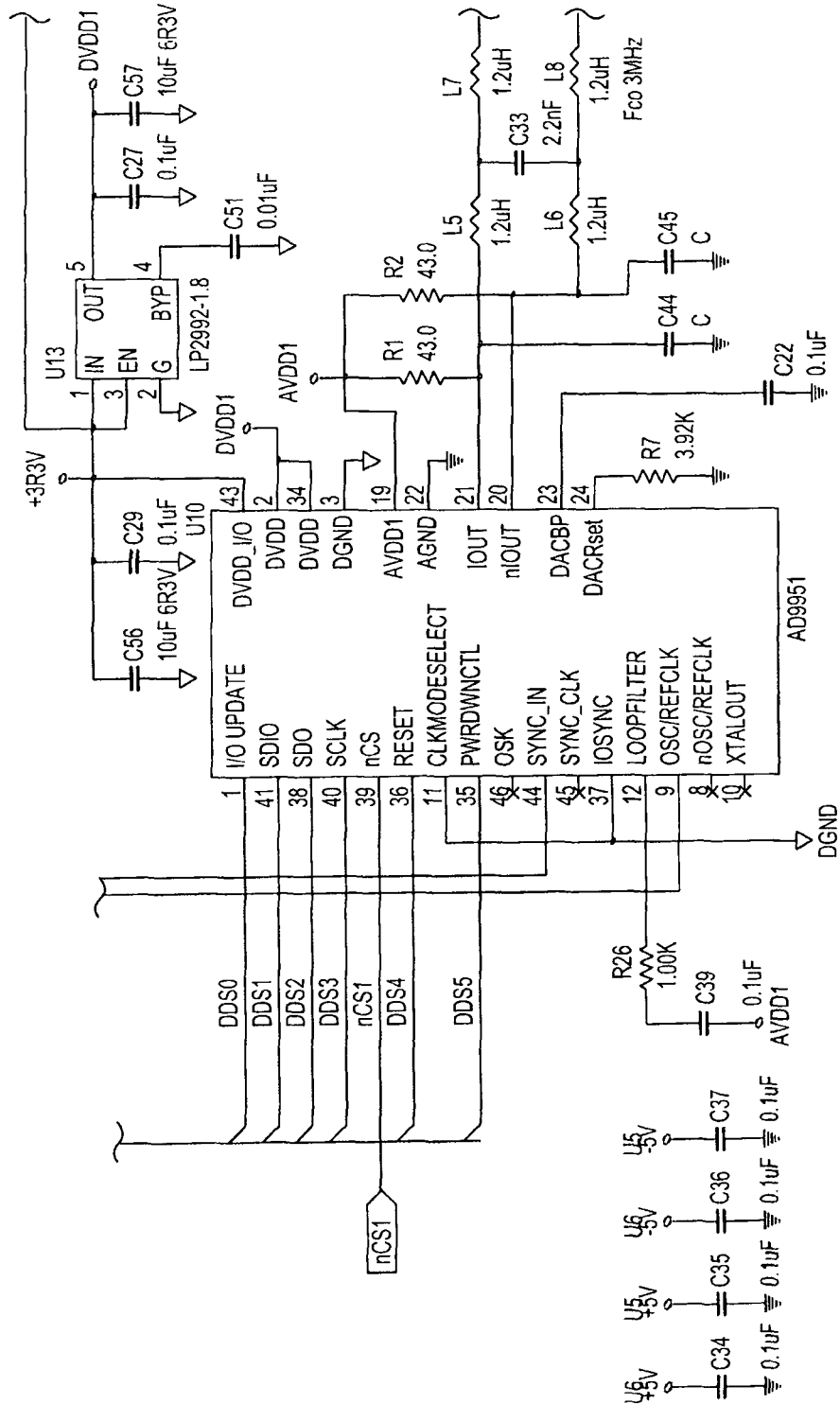
Figure 4:
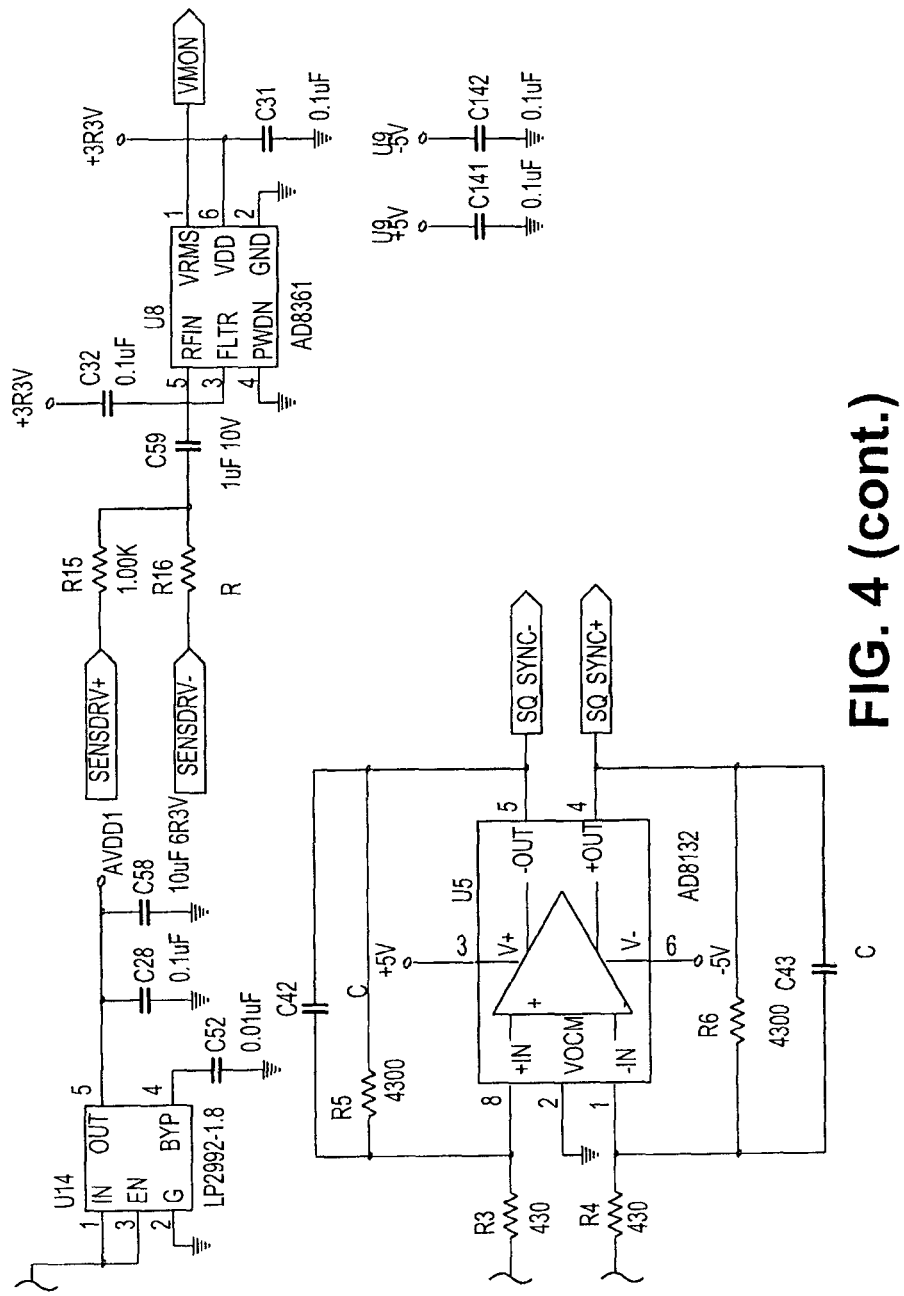
Figure 5:
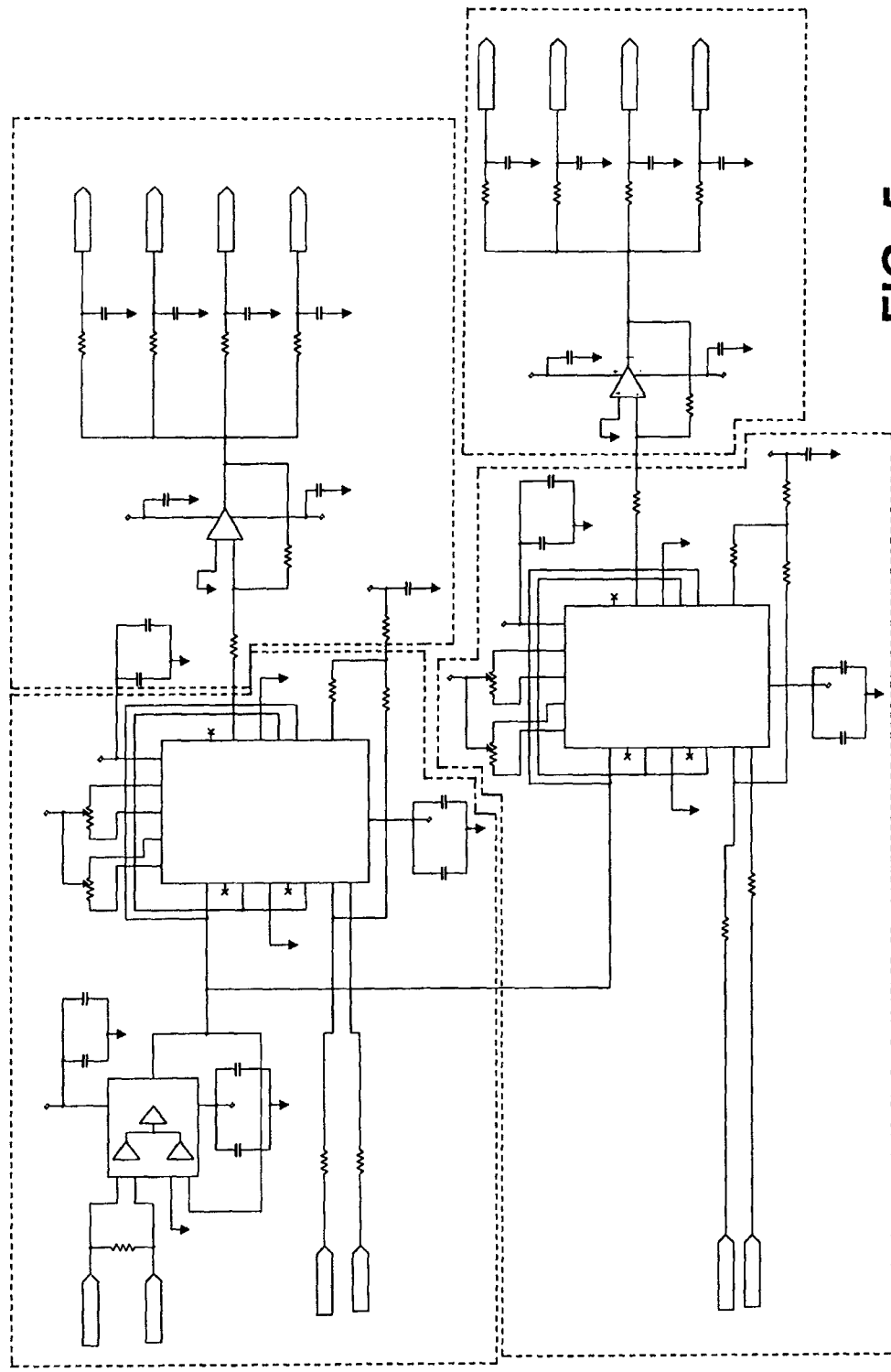
Figure 5:
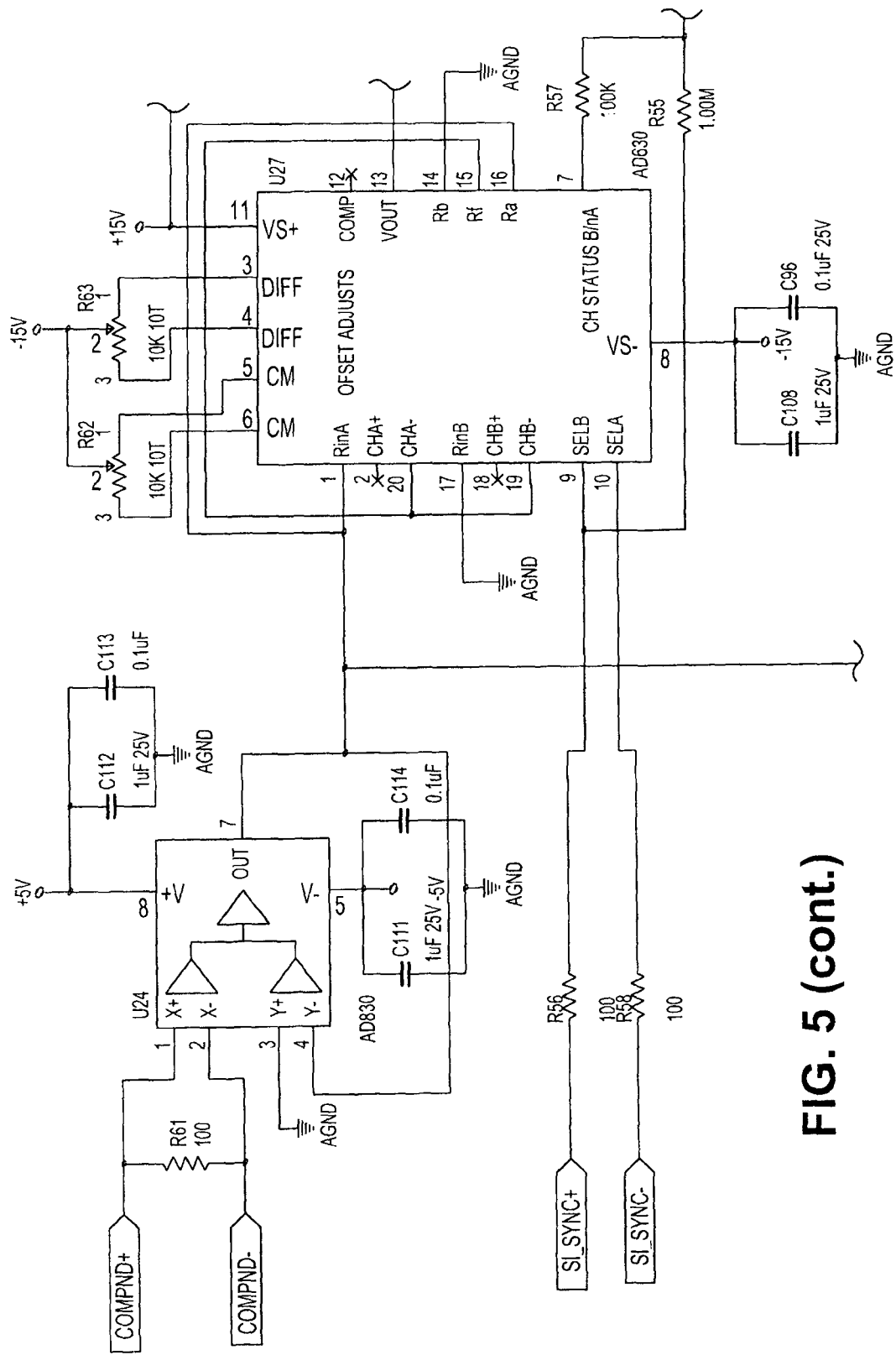
Figure 5:
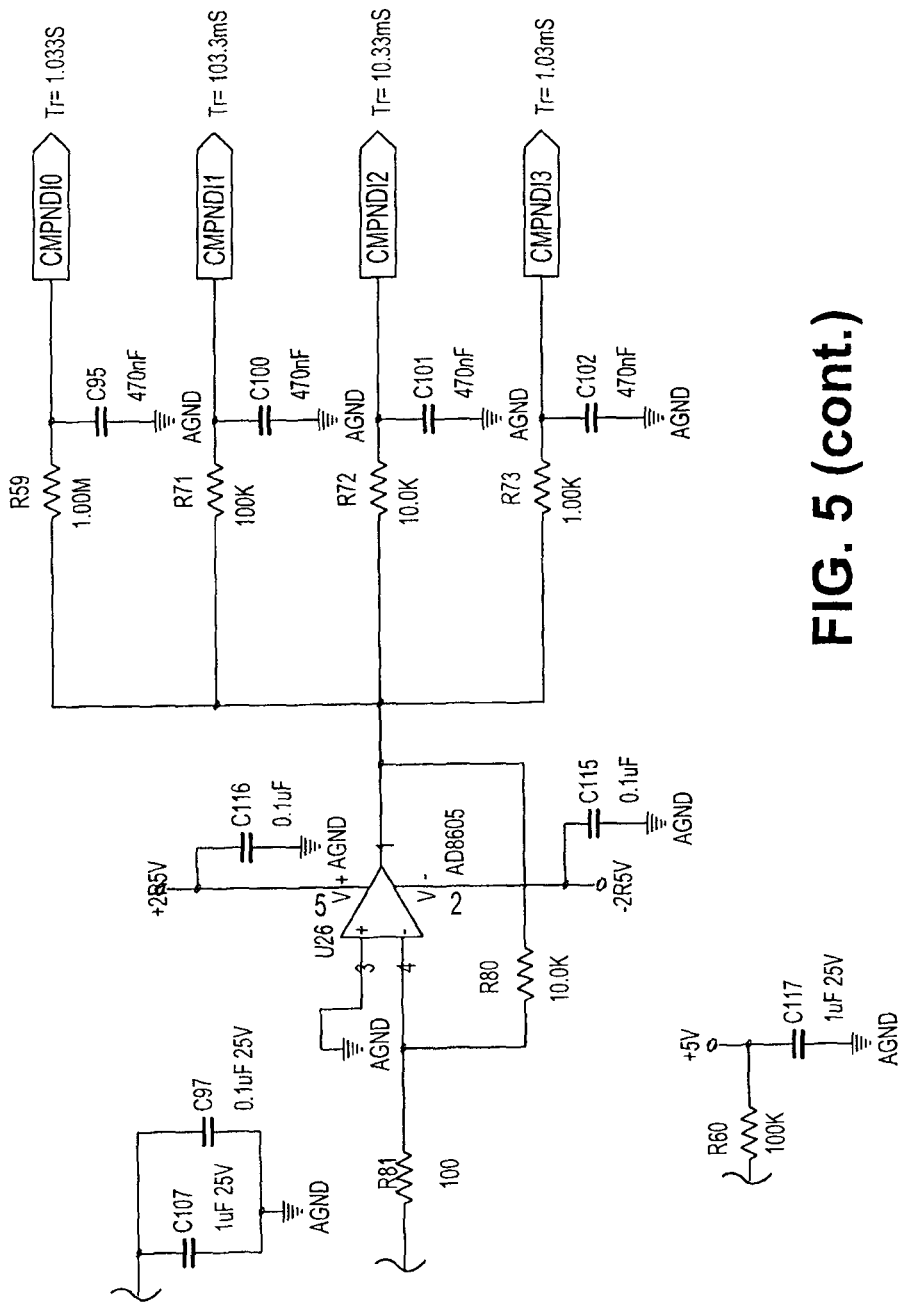
Figure 5:
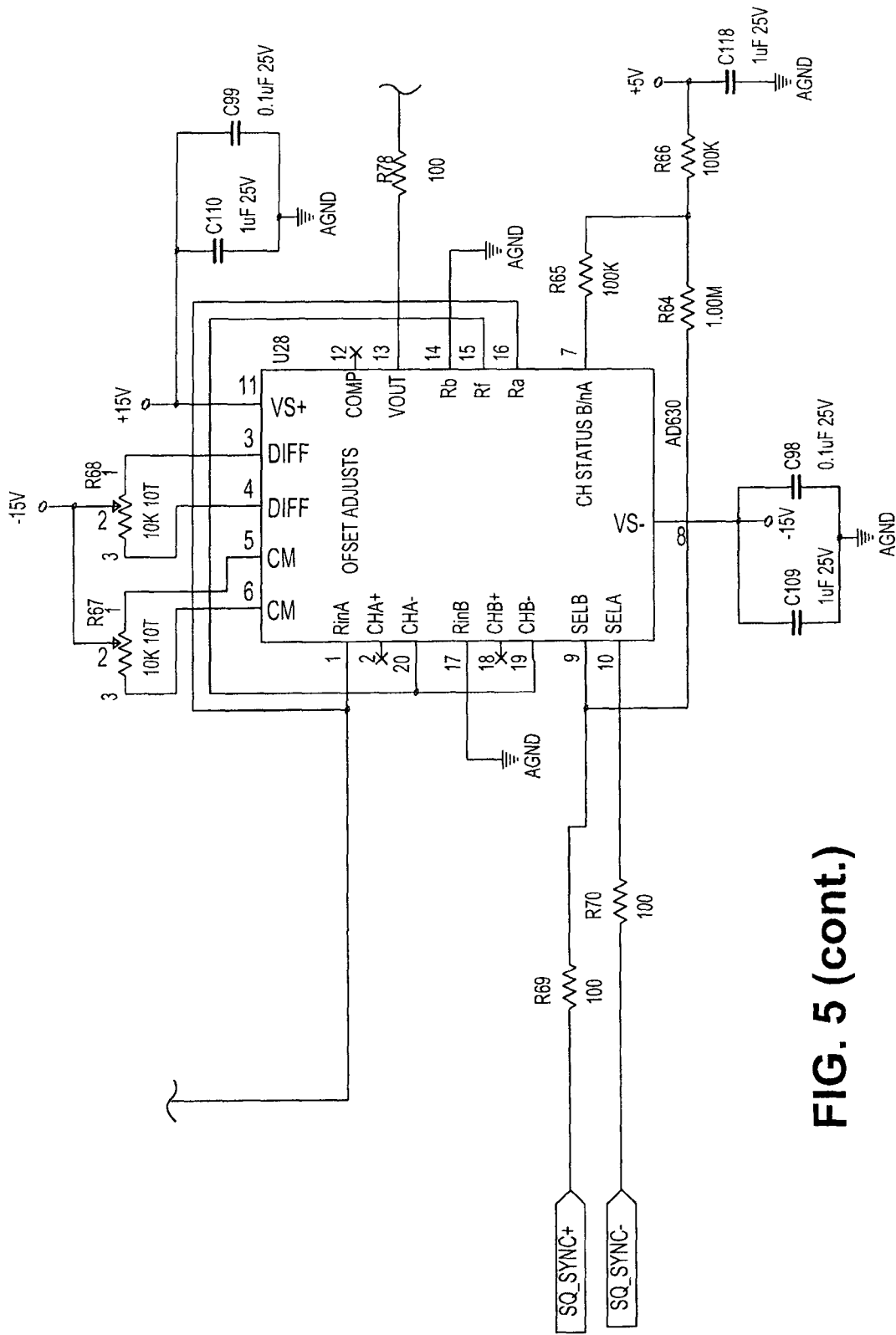
Figure 5:
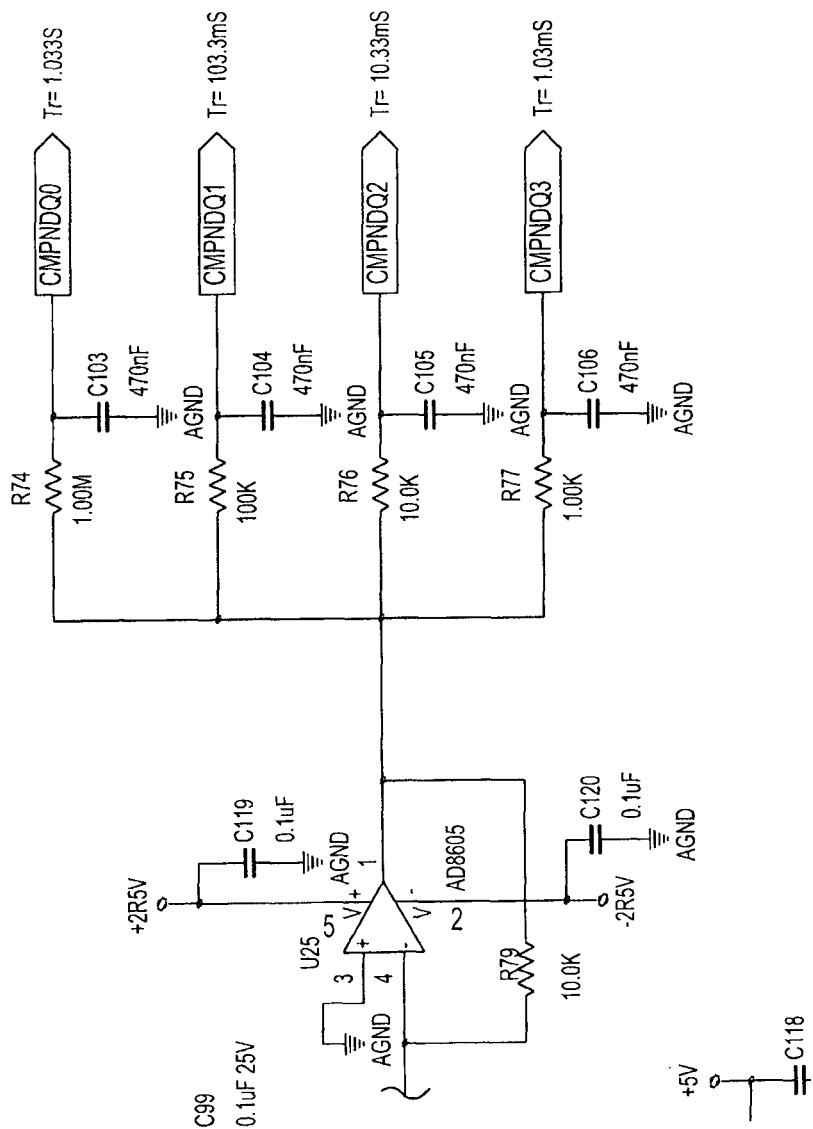
Figure 6:
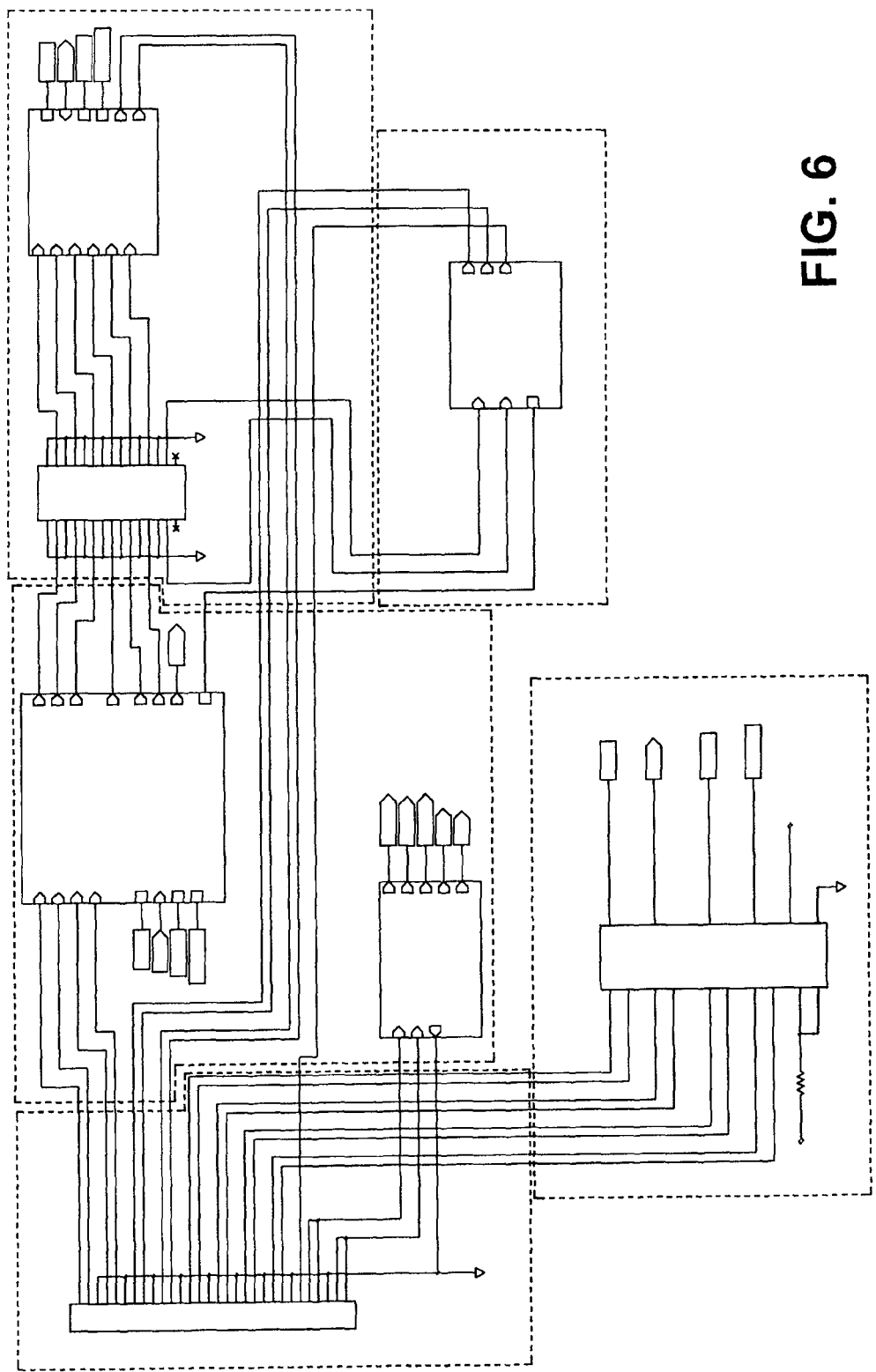
Figure 6:
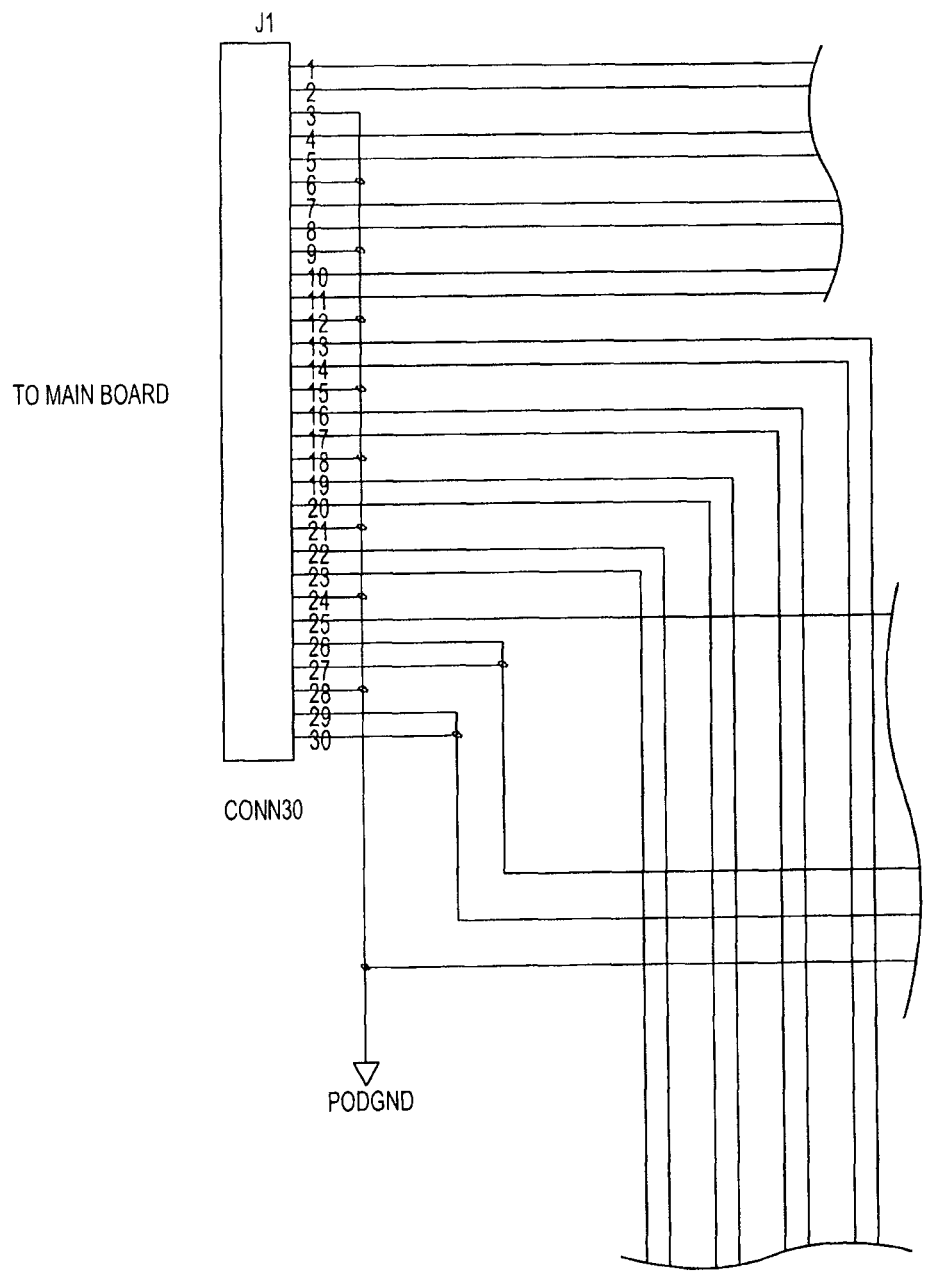
Figure 6:
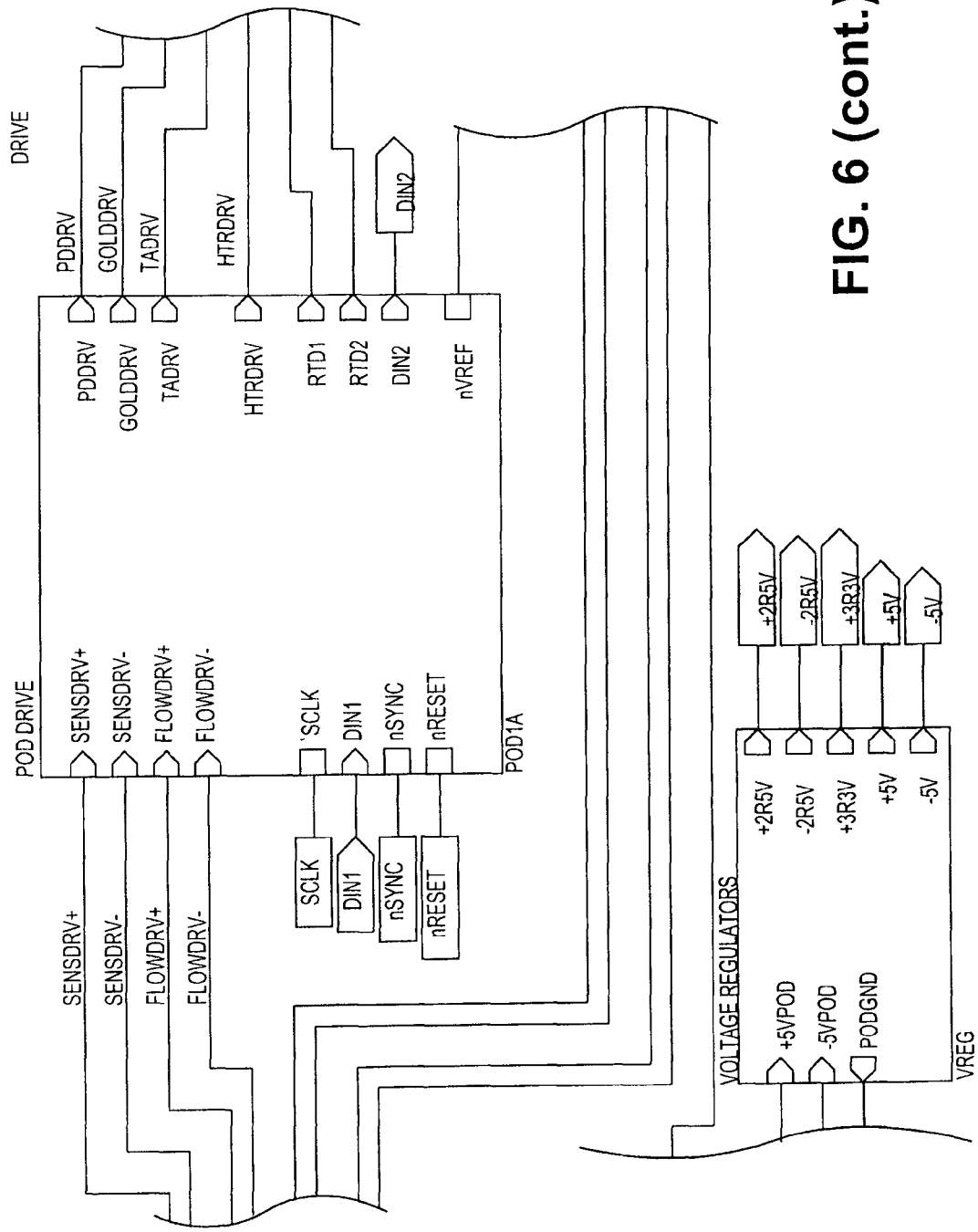
Figure 6:
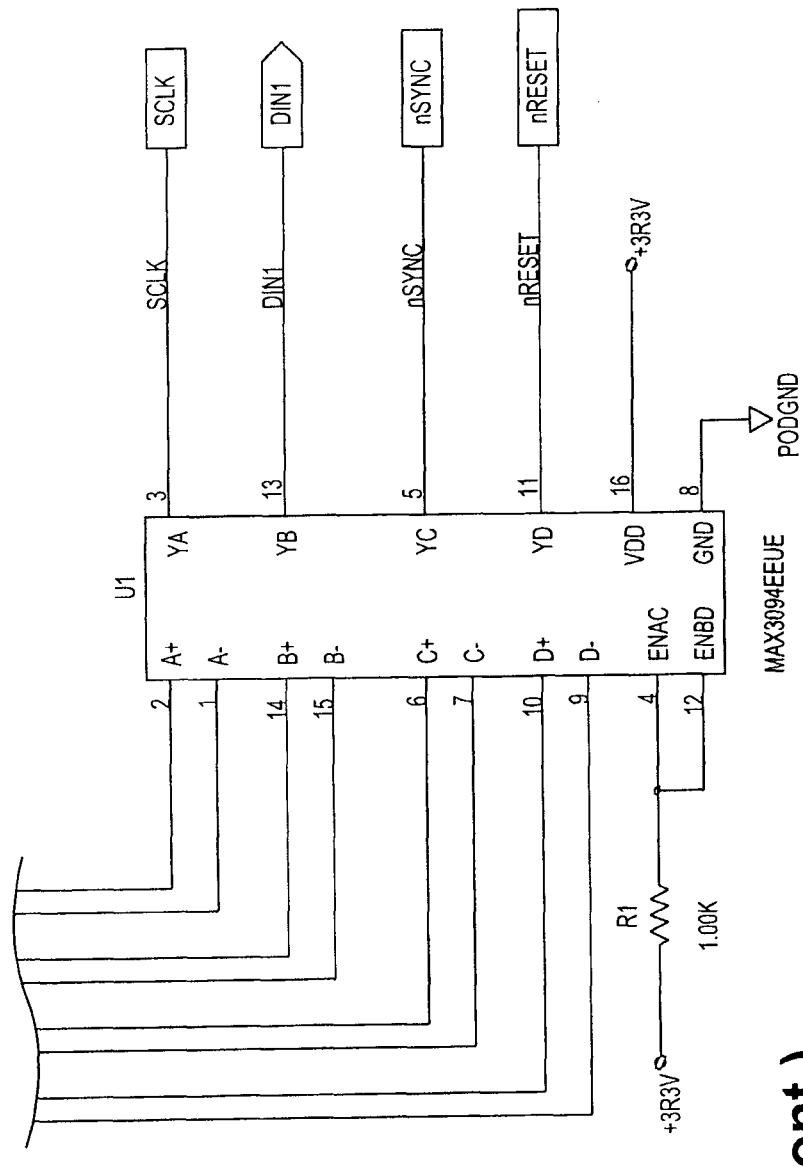
Figure 6:
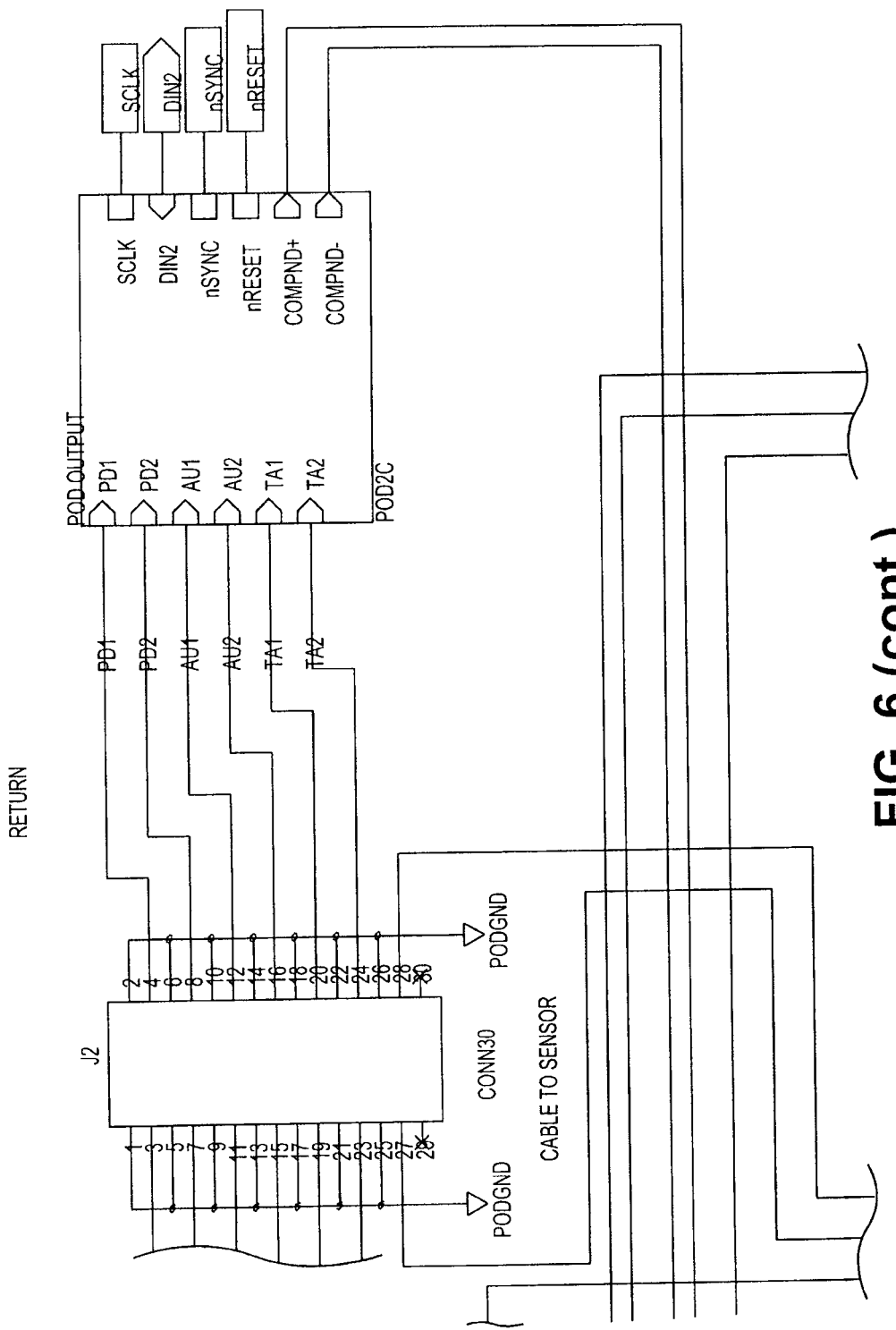
Figure 6:
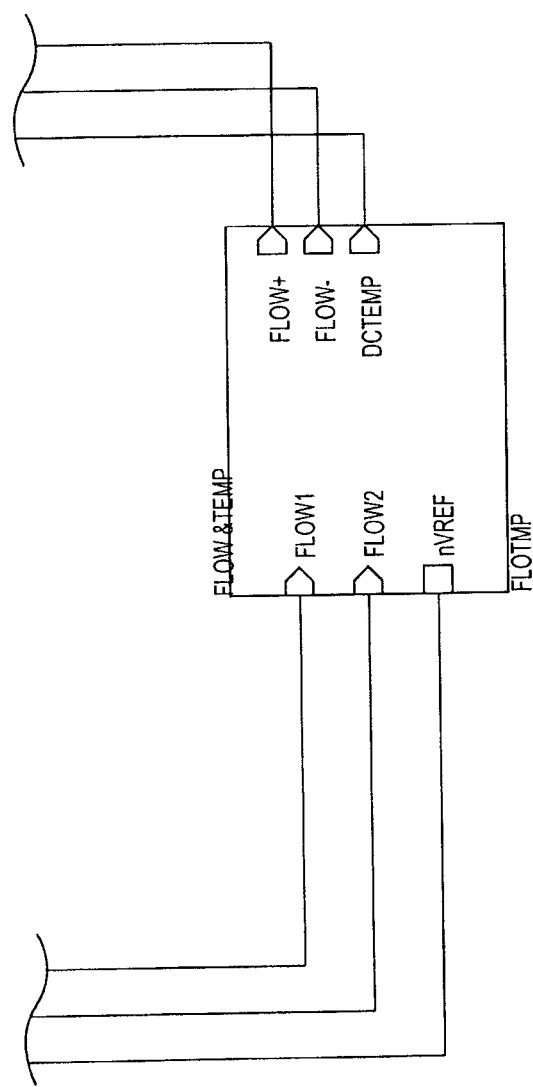
Figure 7:
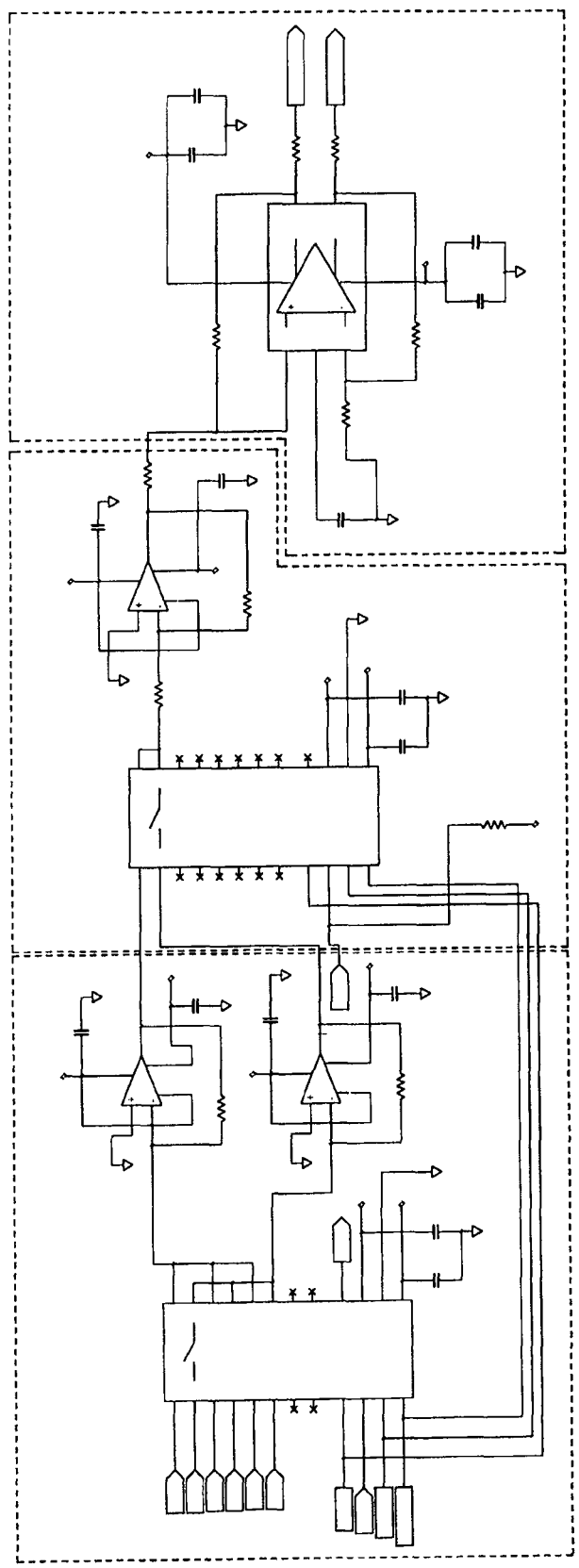
Figure 7:
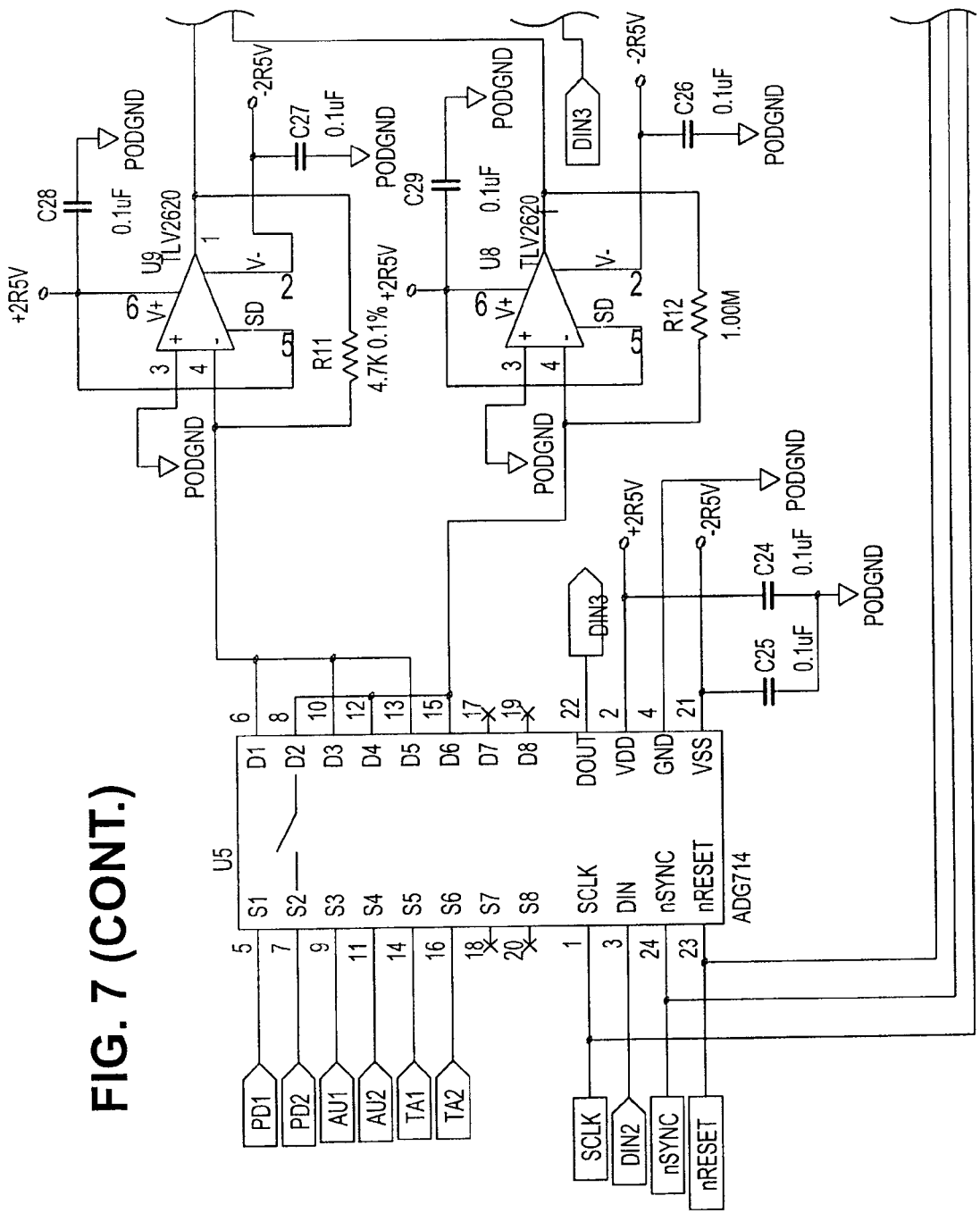
Figure 7:
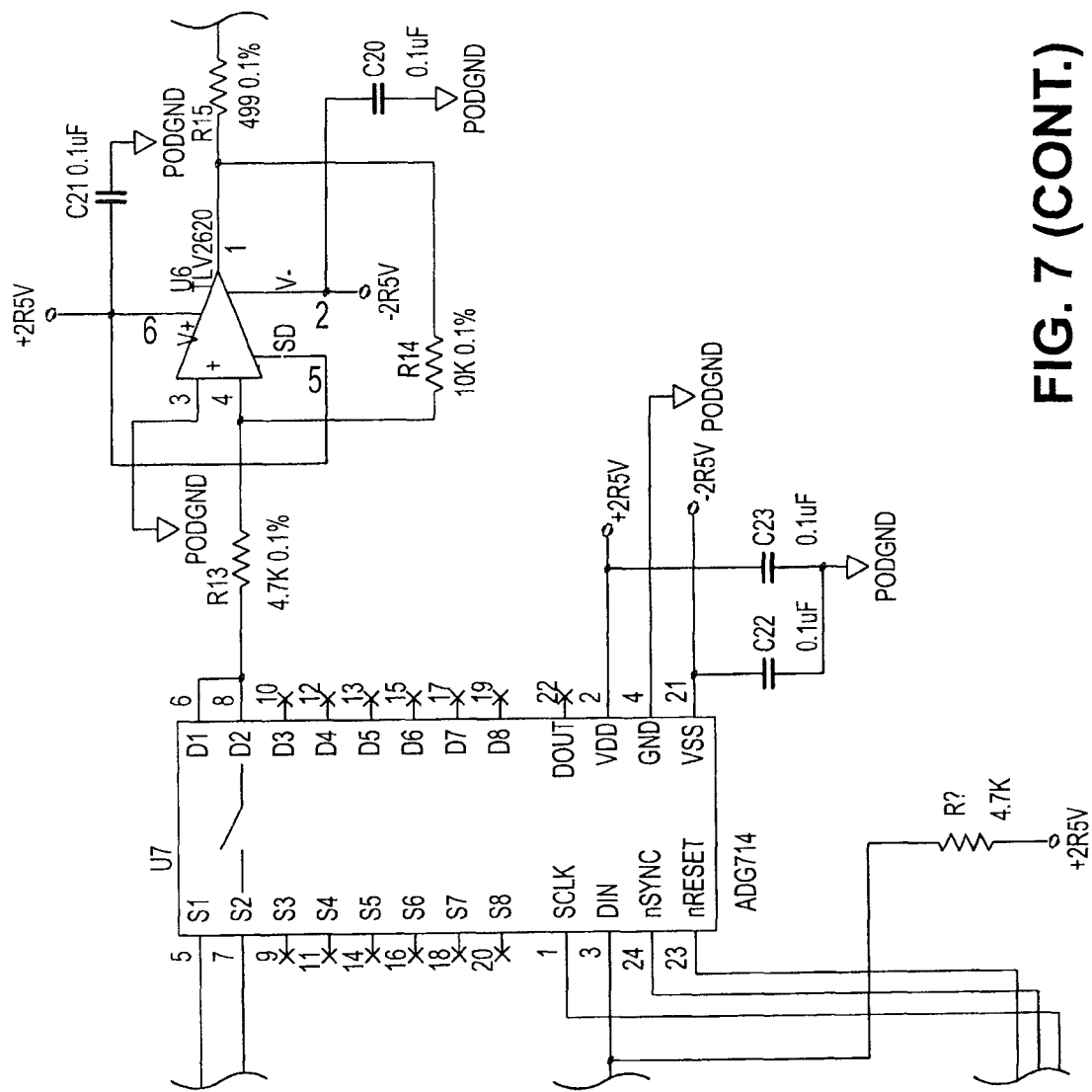
Figure 7:
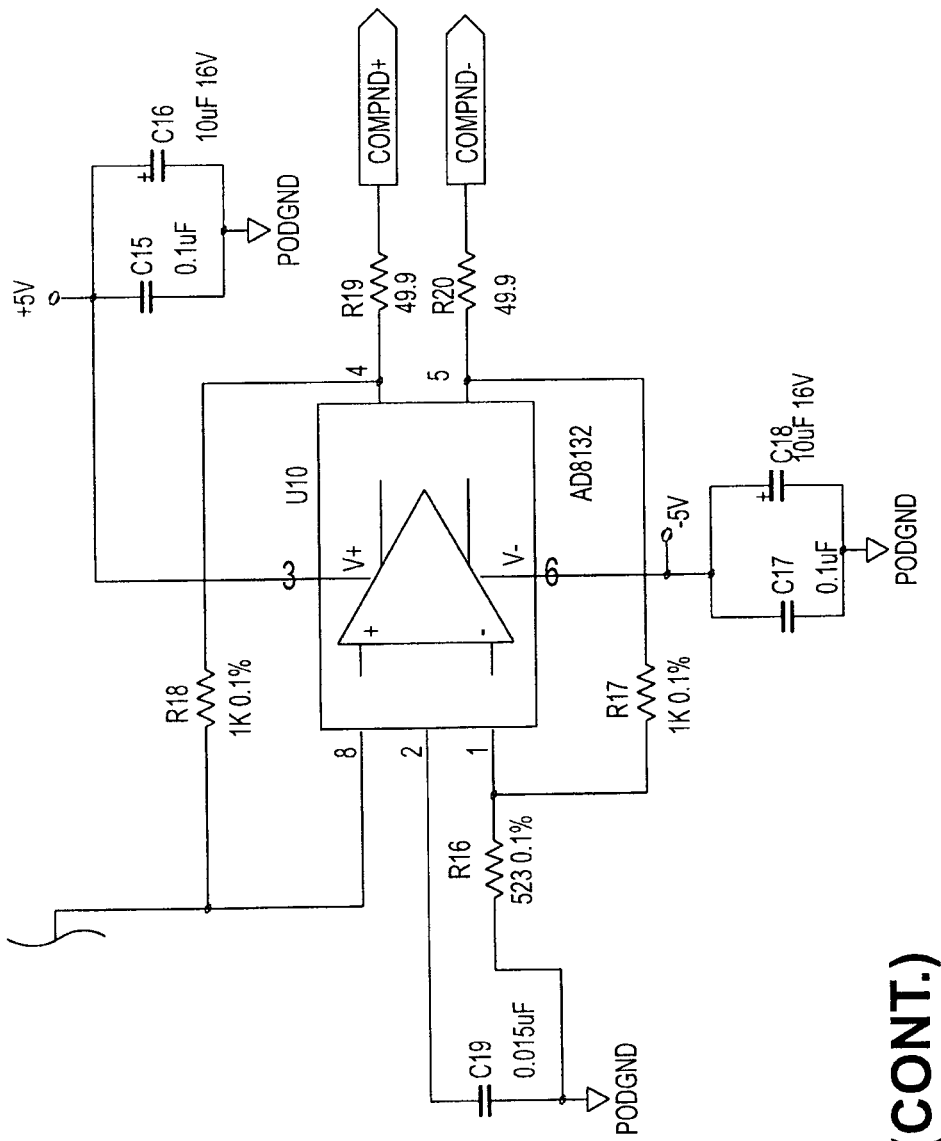
Figure 8:
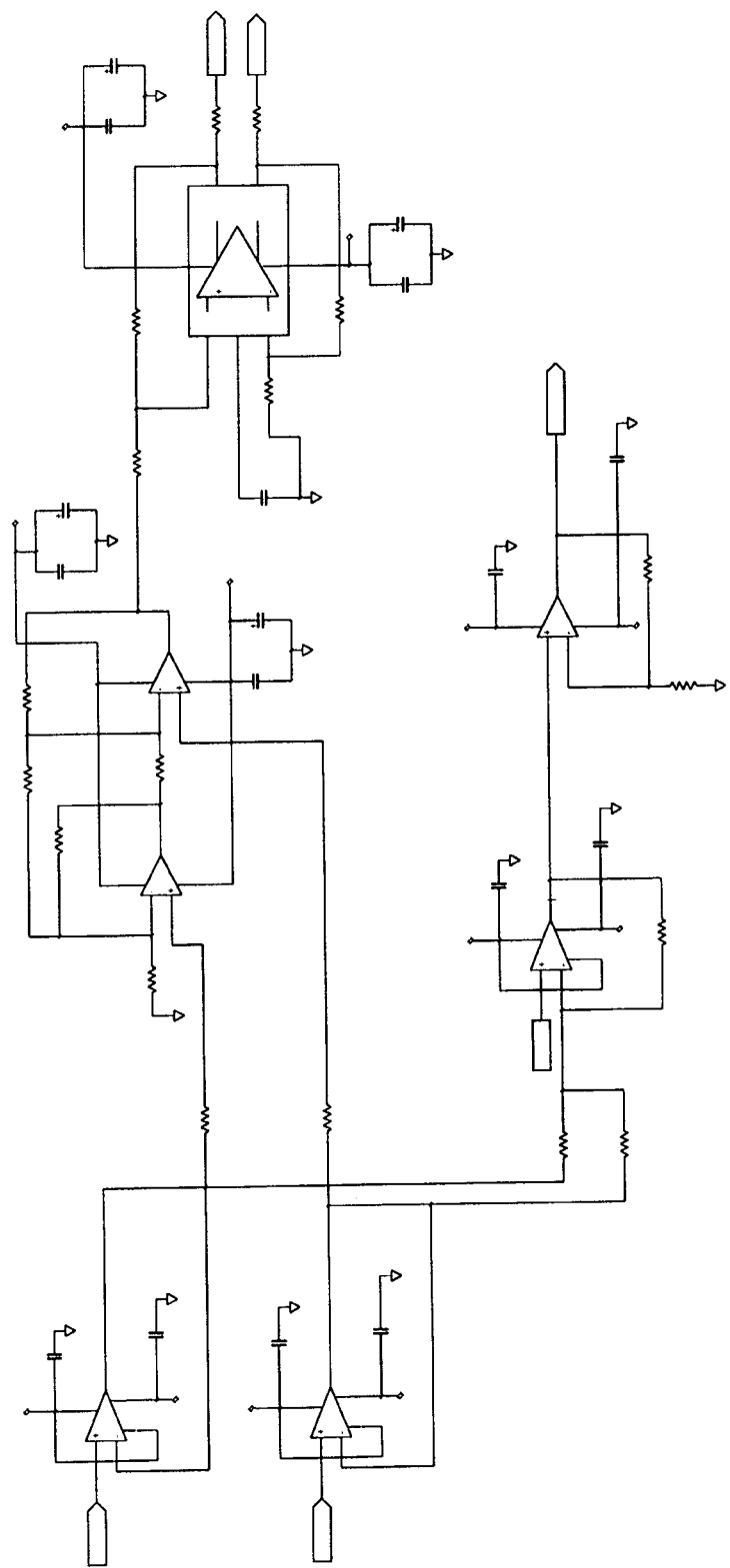
Figure 8:
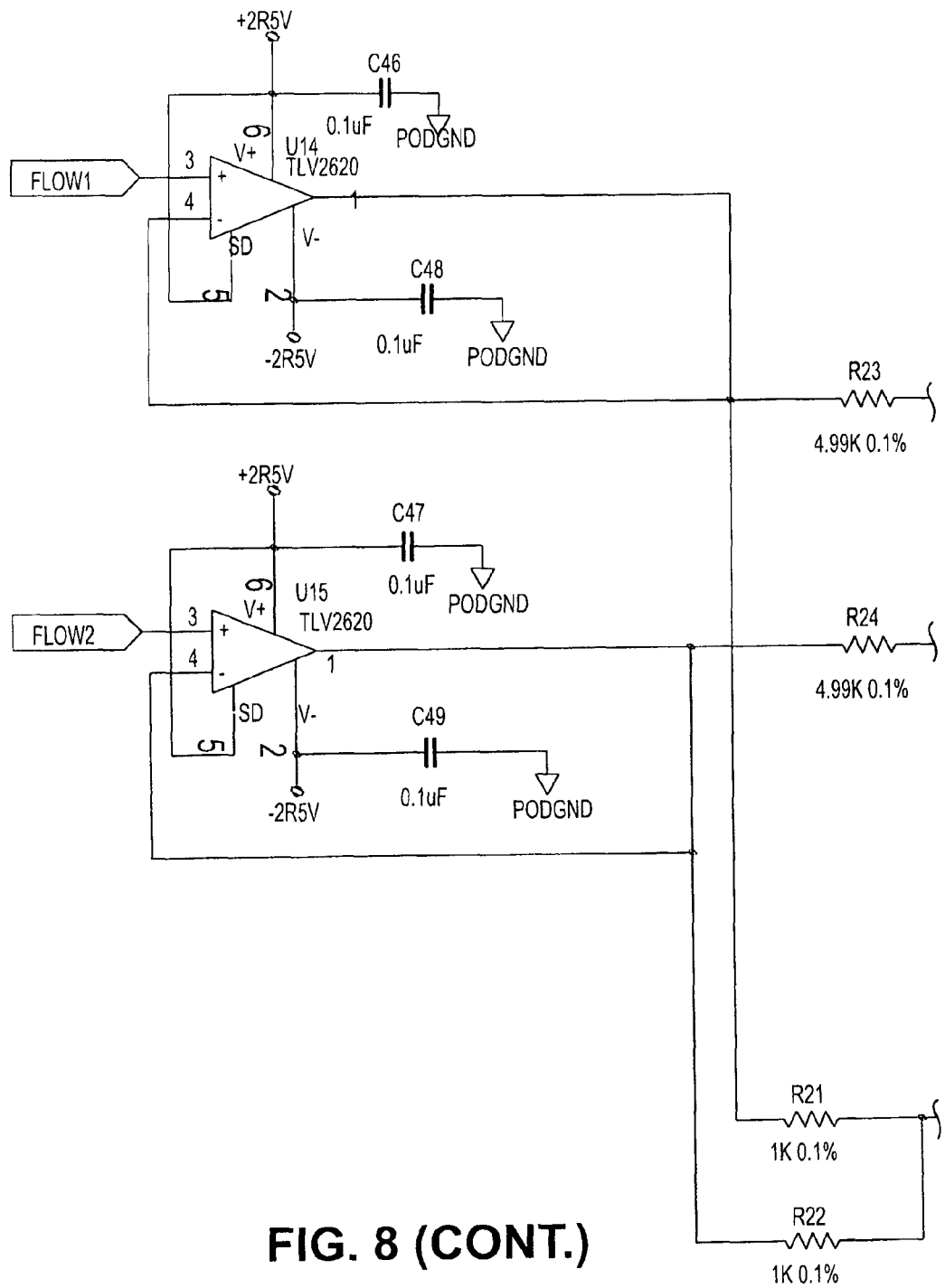
Figure 8:
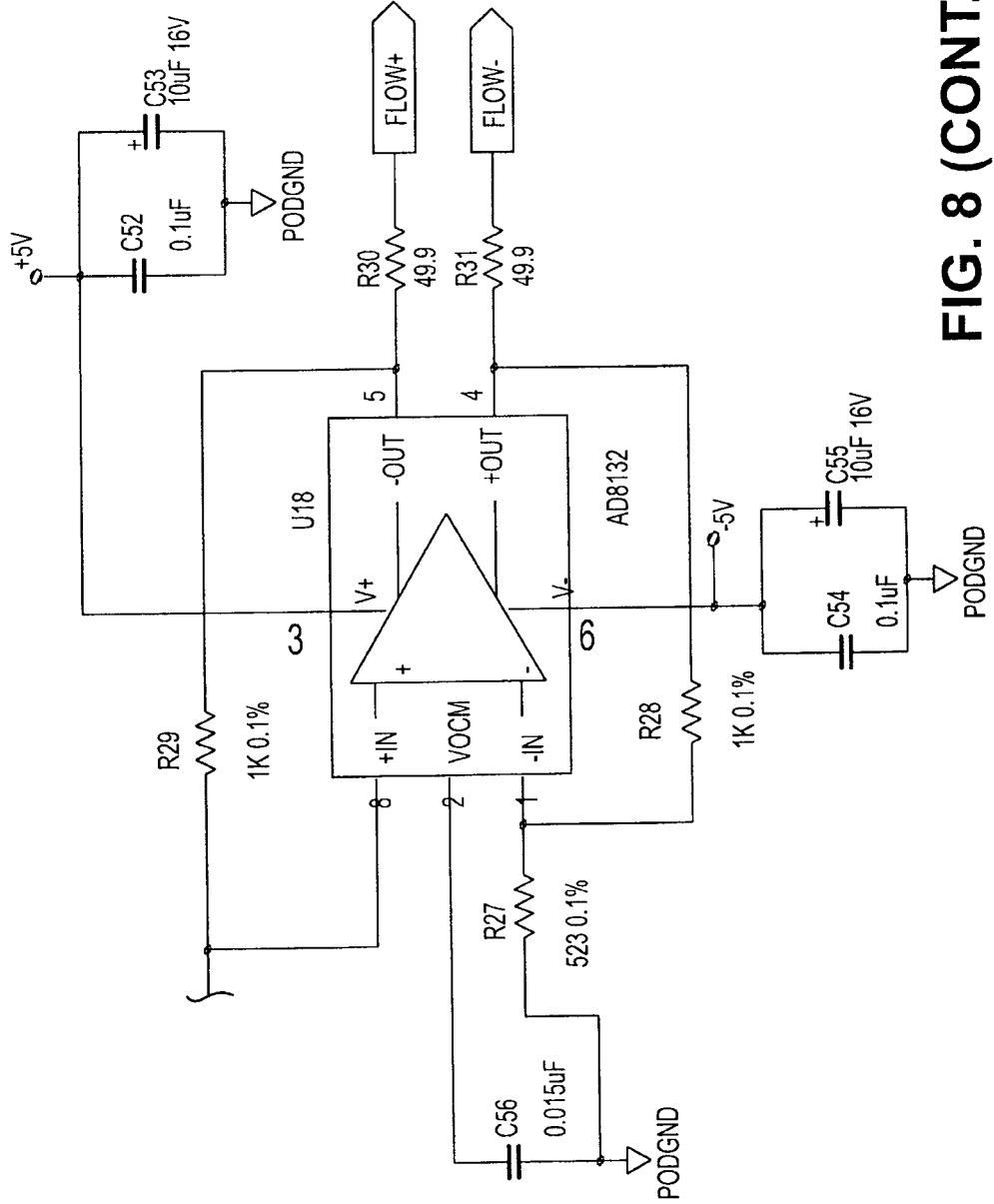

For example, FIG. 3 shows an example of a main electronic board circuit diagram. FIG. 4 is a circuit diagram of one variation of a signal synthesis circuit, and FIG. 5 is an example of a synchronous detector circuit with four filter output. An example of the inline POD board circuit is shown in FIG. 6, and FIG. 7 shows an example of a POD board signal switching system. A POD Flow sensor circuit example is shown in FIG. 8.

Figure 9:
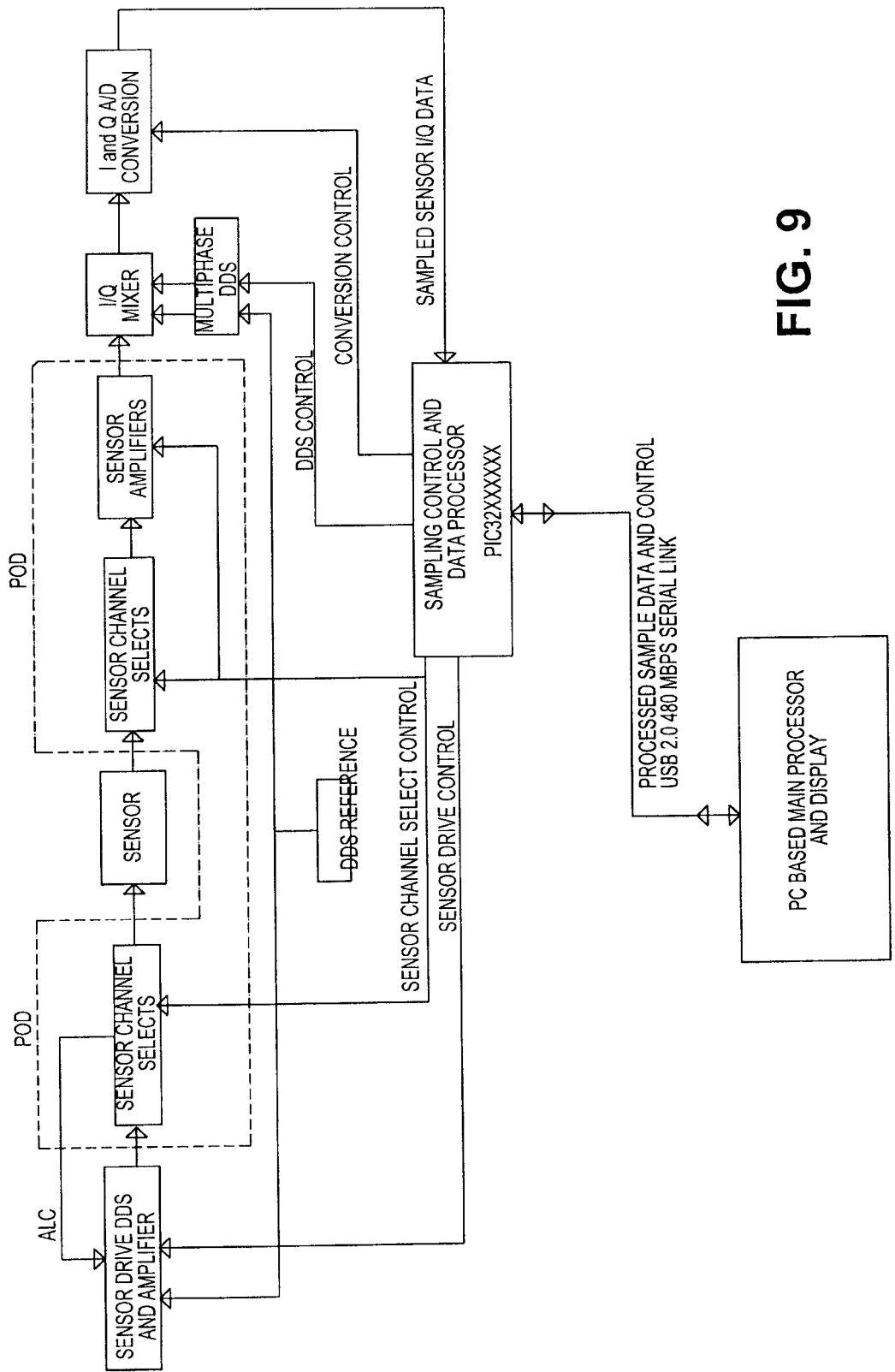
FIG. 9 shows an alternative variation of a system architecture in which the main processor is remote from the rest of the system.

An alternative variation of the system architecture is shown in FIG. 9, in which the main processor is not integrated with the rest of the system but is connected by a network connection from an external location. For example, direct digitization of the sensor output in an I-Q configuration may be followed by processing in a local processor to generate the pattern data, and the data can be passed over a high speed serial connection to a PC based main processor (e.g., running either Windows® or Linux) that does the data storage and pattern recognition. The main processor communicates with the outside world as needed over a network connection. This configuration may offer improvements in performance and may reduce electronics cost.

Any of the systems described herein may be configured to operate with low ionic strength liquids (e.g., diluents).

Systems and Devices for Use with Low Ionic Strength Liquids

An immittance spectroscopy system may be adapted to operate with low ionic strength liquids or with both low and high ionic strength liquids by adapting the sensor to include electrode pairs configured to operate a low ionic strength; the system may also be configured to provide very low frequency (e.g., miliHz range) electrical energy for immittance measurement. Such adaptations may improve the sensitivity to low ionic strength solutions.

The systems described in the U.S. patent application Ser. No. 12/920,203 (titled "INTRAVENOUS FLUID MONITORING") and U.S. patent application Ser. No. 12/796,567 (titled "SYSTEMS AND METHODS FOR THE IDENTIFICATION OF COMPOUNDS IN MEDICAL FLUIDS USING ADMITTANCE SPECTROSCOPY") assumed that most fluids for IV delivery are ionic and may be salts or contain ionic formulation components. Thus, the initial 31 high alert drugs and drug combinations described in those applications typically produced unique fingerprints in ionic solutions ("normal" ionic strength solutions, which may also be referred to as "high" ionic strength fluids to contrast with low ionic strength fluids).

However in some variations it may be desirable to use complex immittance to determine the composition of low ionic strength solutions, particularly in a hospital pharmacy setting. Many drugs are prepared in the hospital pharmacy in low ionic strength fluids such as 5% dextrose in sterile water (D5W) or other non-ionic solutions. In low ionic strength solutions, the previously described systems and sensors generated immittance profiles that had a very low magnitude, particularly compared to those generated in high ionic strength solutions.

For example, nine high alert drugs were formulated in D5W or sterile water and examined using the previously described system. These compositions generated unique fingerprints, however, the magnitude of some fingerprints was very small compared to those of drugs in ionic solutions, and the signal to noise ratio was greater.

In low or non-ionic fluids, the values for the real and imaginary components of the alternating current (ac) response of electrodes immersed in a fluid to applied electrical current at a particular frequency is small. Fingerprints for such fluids show a response caused by the presence of one or more drug(s). The drugs and/or their formulation components supply ions which create the signature. Despite the fact that some drug signals were small, all drug signals observed were different and significantly above the noise. Some drug signals are only positive in the real component (x-axis) of AC Admittance and are in the range of the noise in the imaginary component (y-axis) causing the loss of some of the multi-dimensionality of the fingerprints.

Figure 10A:
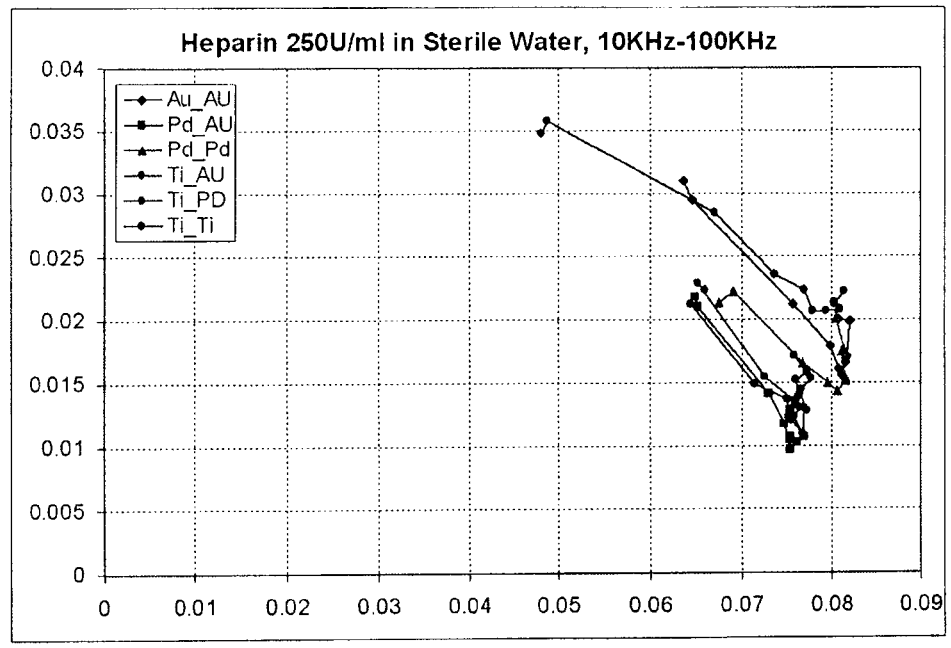
FIG. 10A shows a complex immittance pattern of Heparin in sterile distilled water for the frequency range of 10 KHz to 100 KHz.
Figure 10B:
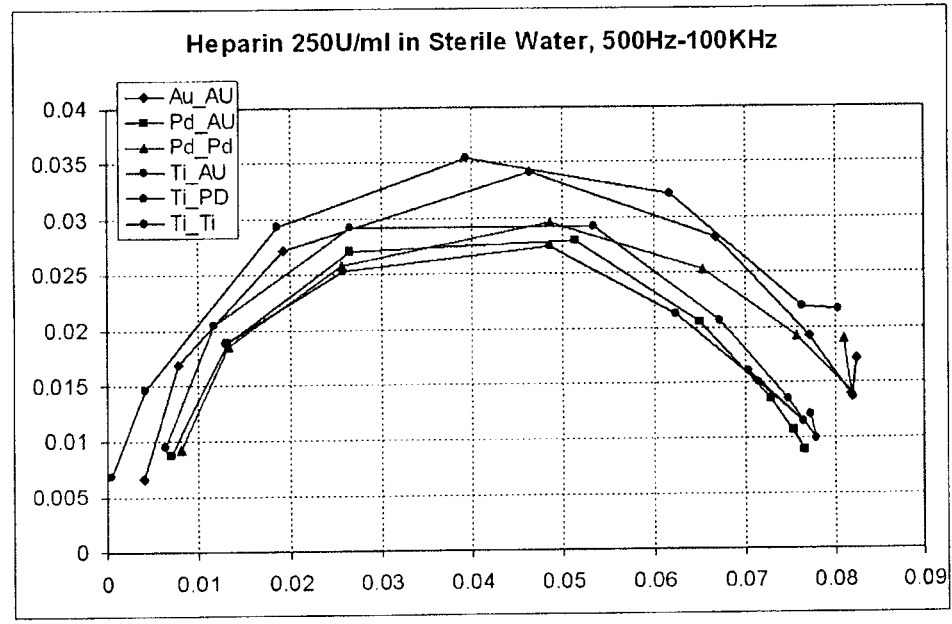
FIG. 10B shows a complex immittance pattern for the same solution of Heparin for the frequency range of 500 Hz to 100 KHz.

In order to improve the resolution of drug fingerprints in low ionic strength solutions, the frequency range at which AC Admittance (impedance) measurements were made was expanded. Previously, the typical range of frequencies used was approximately 10 KHz to 100 KHz. In order to facilitate low ionic strength measurements, the electronics was modified to allow measurements at frequencies as low as 35 miliHz (0.035 Hz). Detection of low ionic strength drugs using a frequency range that includes lower frequencies resulted in a dramatic improvement in the information and distinctiveness of the resulting fingerprints, as illustrated in FIGS. 10A and 10B. FIGS. 10 A and 10 B show partial complex impedance patterns ("fingerprints") for Heparin compounded in sterile distilled water across two different frequency ranges. FIG. 10A shows a frequency range of 10 KHz-100 KHz, which works well for high ('normal') ionic strength formulations, but not for low ionic strength ones such as in water and D5W, as shown by the low magnitude response.

In FIG. 10B the same solution is shown measured between 500 Hz and 100 KHz. The complex impedance pattern is much more robust when measured at the lower frequencies, as illustrated. In both figures, six pairs of electrodes (Au/Au, Au/Pd, Pd/Pd, Au/Ti, Ti/Ti, Pd/Ti) were used.

In addition to modifying the electronics to accommodate a lower frequency range, the systems described herein may also include a modified sensor adapted to operate with low ionic strength fluids. Previous prototype sensors for multi-parametric (immittance) sensing of drugs and doses had a geometry (size and distance apart) of the AC Admittance sensing pads that was well configured for detection of drugs in ionic fluids like saline. However, the sensor geometry may be modified to more readily detect low ionic strength fluids. For example, some sensor variations include one or more (and preferably three) pairs of low ionic strength electrodes (electrodes configured to measure complex immittance at low ionic strength). In variations of sensors configured for operation at both low and high ionic strength, in addition to the low ionic strength electrodes, electrodes for high (normal) ionic strength are also included.

Low ionic strength electrodes typically have a geometry that is configured to assist with measurement of complex immittance in low ionic strength solutions. The change in sensor geometry improves the sensitivity of drug detection in low ionic strength fluids by splitting each one of the two metal electrodes in the pair and changing the geometry of the resulting pair so that there is higher coupling with the surrounding liquid than with other electrode structures. For example, the electrodes in the electrode pair may each be formed of elongate, parallel strips of conductive material (with an exposed solution-contacting surface) that are interdigitated with the other parallel strips of the other electrode in the pair. This configuration takes into account the fact that the bulk conductivity of D5W- and water-based formulations is much lower than that of higher ionic content formulations, while the admittance of the double layer next to the electrode remains of the similar order of magnitude as in saline. Since these two admittances are connected in sequence, the response from the bulk conductivity prevails over the surface effects and thus partially disguises the surface effects caused by differences in liquid composition. An interdigitated geometry allows the electrode pair to substantially reduce the effects of the low bulk conductivity by effectively bringing the electrodes close together and providing multiple parallel passes for current to bridge the electrode fingers through liquid without considerably affecting the surface effects useful for drug identification.

Figure 11A:
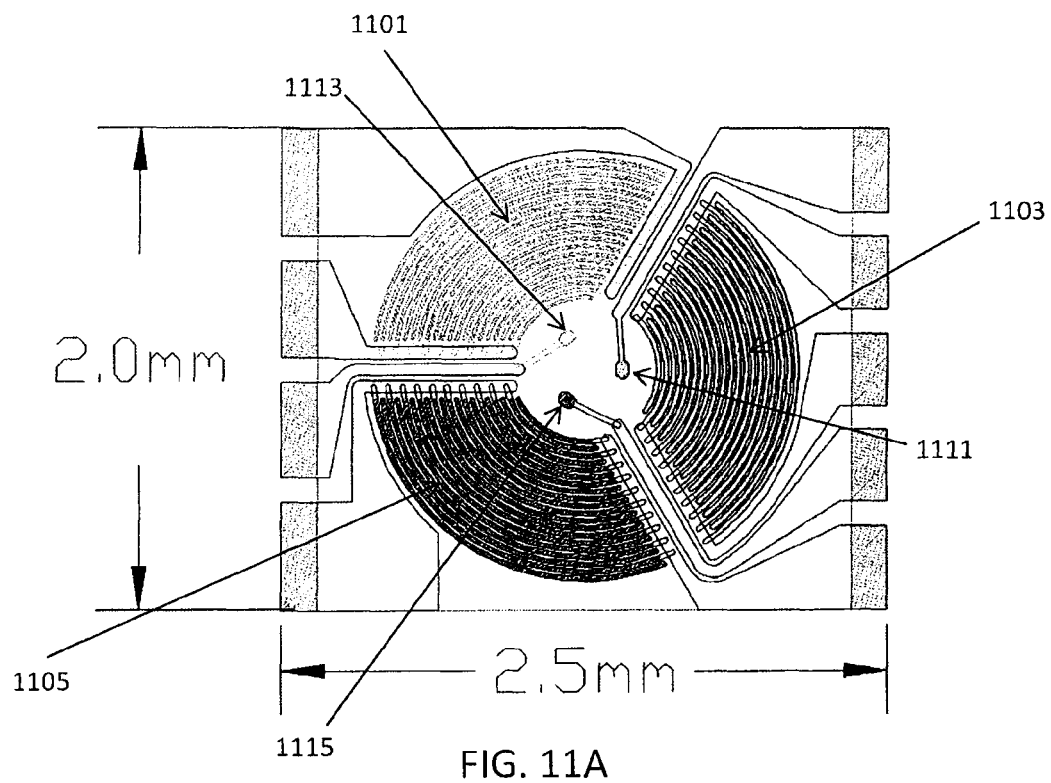
FIG. 11A shows one variation of a sensor including three pairs of low ionic strength electrodes, as well as three high ionic strength (single pad) electrodes.

A sensor geometry very sensitive to drug detection in low ionic strength fluids is described in FIG. 11A. In this example, the sensor includes three low ionic strength electrode pairs in which each electrode of the pair interdigitates the two metal electrodes and the geometry of the resulting pair provides much higher coupling with the surrounding liquid than a non-interdigitated electrode structure. As mentioned, the reason this works is that the bulk conductivity of D5W- and water-based formulations is much lower than that of higher ionic content formulations, while the admittance of the double layer next to the electrode remains of the similar order of magnitude as in saline. Since these two admittances are connected in sequence, the response from the bulk conductivity prevails over the surface effects and thus partially disguises the surface effects caused by differences in liquid composition. In FIG. 11A, the three pairs of interdigitated electrodes are indicated by the arrows; each of the pairs is made of a different electrically conductive material: Au—Au 1101, Pt—Pt 1103, and Ti—Ti 1105. In some variations the two metals are different, so that one of the electrodes is made of a first conductive material (e.g., Au) which is interdigitated with a second conductive material (e.g., Ti) forming the second electrode. Three high ionic strength electrode single pads 1111, 1113 and 1115 are also shown for reference. Each of these electrodes is formed of a different electrically conductive material, Au 1113, Pt 1111, and Ti 1115, and thus three electrode pairs (Au—Ti, Au—Pt, and Pt—Ti) may be formed; additional pad electrodes may also be included. In some variations, a single electrode for high ionic strength measurements is separated from the low-ionic strength inter-didgitated pair. In use, the same excitation electrode from the low-ionic strength interdigitated pair may be used, but the current may be measured (picked up) on the separated high ionic strength electrode. Thus, the Au—Au high ionic strength measurement may be measured between one of the Au electrodes of a low ionic strength electrode pair and the nearby high ionic strength Au electrode.

In some variations the low ionic strength electrodes are interdigitated and separated from each other by less than about 100 micrometers for low ionic strength formulations such as in D5W. The high ionic strength electrodes (pads) are typically separated from each other by more than 0.25 mm for high ionic strength formulations such as in 0.9% normal saline. The geometry of low ionic strength electrodes also differs from high ionic strength electrodes by the pitch of the electrodes. For example, the pitch of the low ionic strength electrodes is approximately 30 micrometers and separation (edge-to-edge gap is 10 micrometers) or pitch and trace width are approximately 30 and 20 micrometers.

Figure 11B:
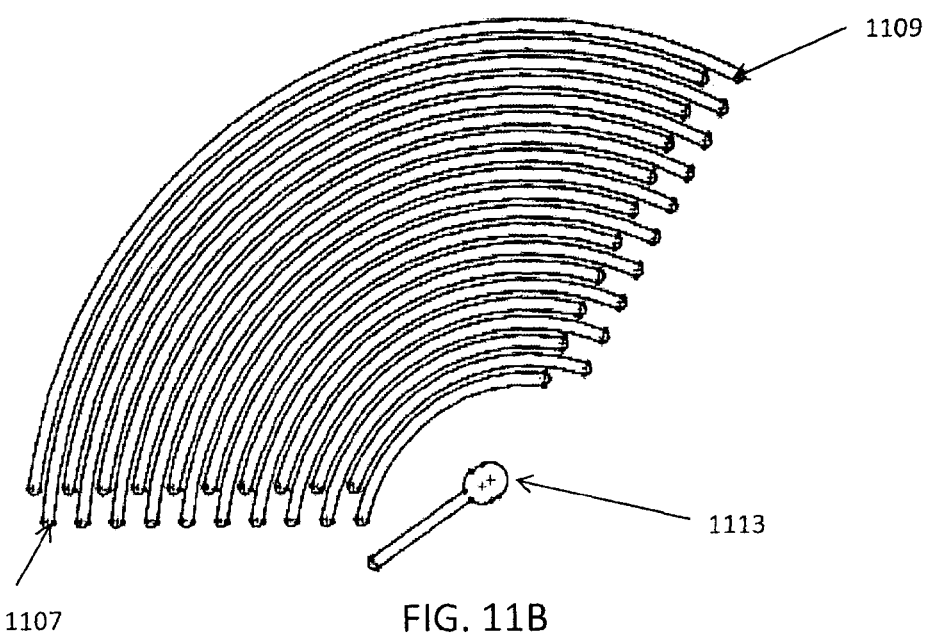
FIG. 11B shows an enlarged view of the conductive material forming the two interdigitated electrodes of one of the pairs of low ionic strength electrodes, and one of the single pad (high ionic strength) electrodes. In the figure, the white rectangular area is an insulation layer under which all of the structures are buried. The areas free from the insulation are the arcing trenches aligned with the electrodes underneath and the (grey) pads on the sides.

FIG. 11B shows an enlarged view of the fluid-contacting surface of one of the pairs of electrodes; the elongate, parallel lengths of the first electrode 1109 are shown interdigitated with the elongate parallel lengths of the second electrode 1111. All of the parallel lengths (e.g., every other length in FIG. 11B) are electrically connected in this example; the connection is not visible in FIG. 11B, which only shows the fluid-contacting surfaces of the electrode. One of the three high ionic strength electrodes (single pad 1113) is also shown for reference.

In FIG. 11B, the non-fluid contacting surfaces of the electrodes are insulated. For example in FIGS. 11A and 11B, a 2-5 micrometers thick insulation layer covers all of the structures except the liquid-contacting parts of the electrodes, including the elongate strips forming the interdigitated low ionic-strength electrodes. The insulation is removed from along the elongated lengths, forming trenches that define the geometry through which the electrodes are exposed to the fluid to be tested. The width of such trenches is approximately 10 micrometers to 30 micrometers wide. The insulation layer is not covering the pads at the perimeter of the sensor chip, to allow for external electrical connections to the sensor traces.

Low ionic strength sensors with interdigitated electrode structures may be linear and/or curved/circular; the circular configuration is shown in FIG. 11A and in more detail in 11B. The circular/curved configuration may allow better space utilization as the single-pad (non-interdigitated, "high ionic strength") electrodes can be smaller and placed in the middle of the circular pattern. In the linear (non-curved/circular) configuration, shown in FIG. 12, the single pad electrodes 1211 are stretched into a line and aligned against the linear interdigitated structure 1201.

Figure 12:
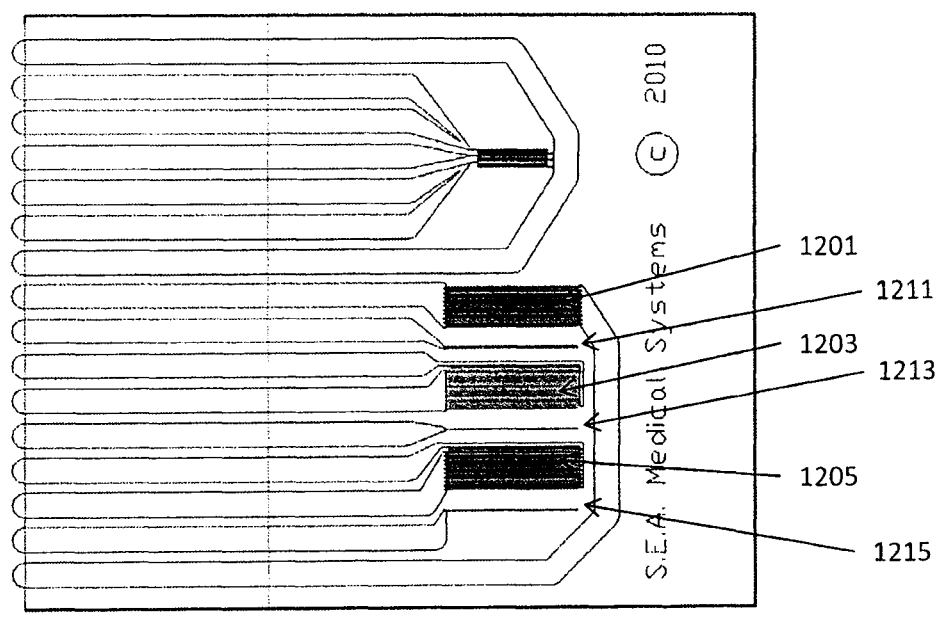
FIG. 12 shows another variation of a sensor including three pairs of low ionic strength electrodes, configured in an interdigitating linear arrangement for each and three high ionic strength electrodes.
Figure 13A:
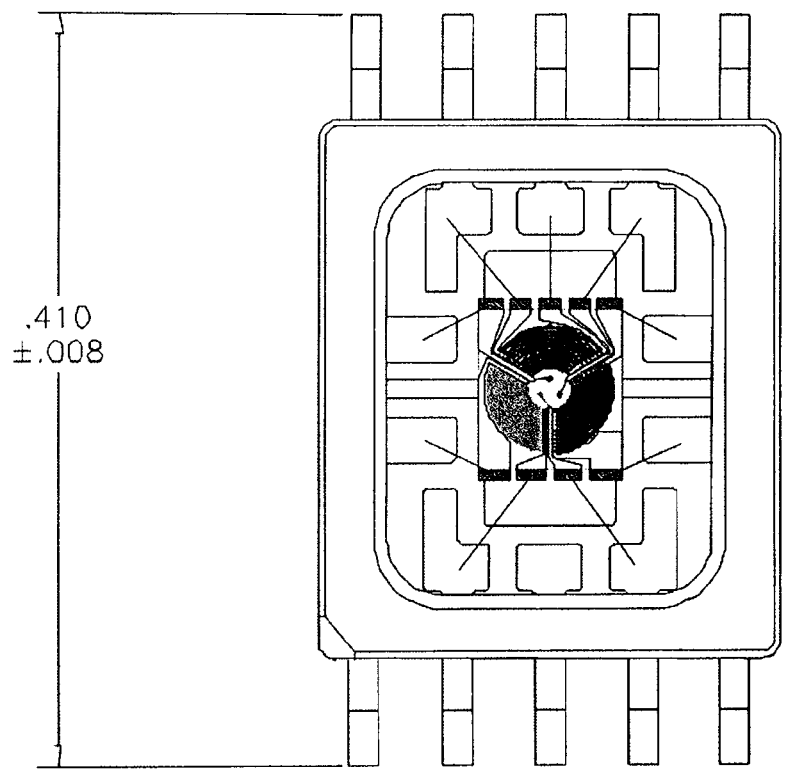
FIG. 13A shows one variation of a mount for a sensor in a standard SOIC-10 dual inline integrated circuit package such as the sensor shown in FIG. 11A.
Figure 13B:
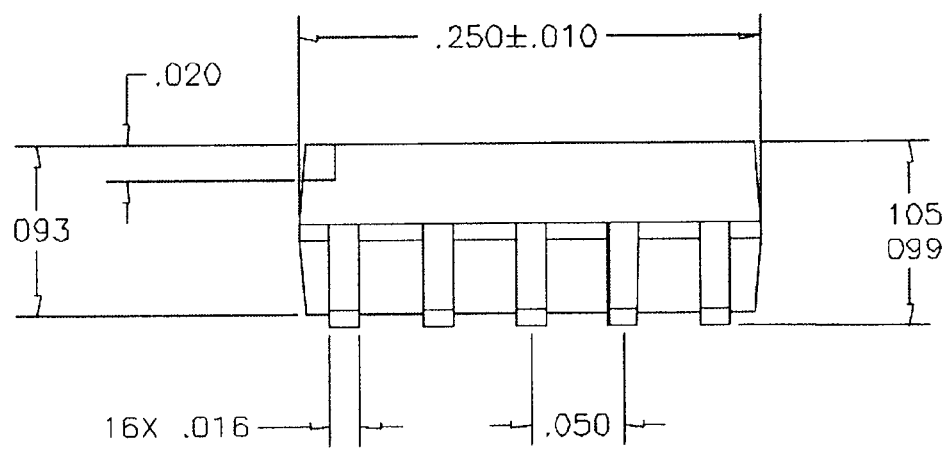
FIG. 13B shows a side view of the mount of FIG. 13A.
Figure 14:
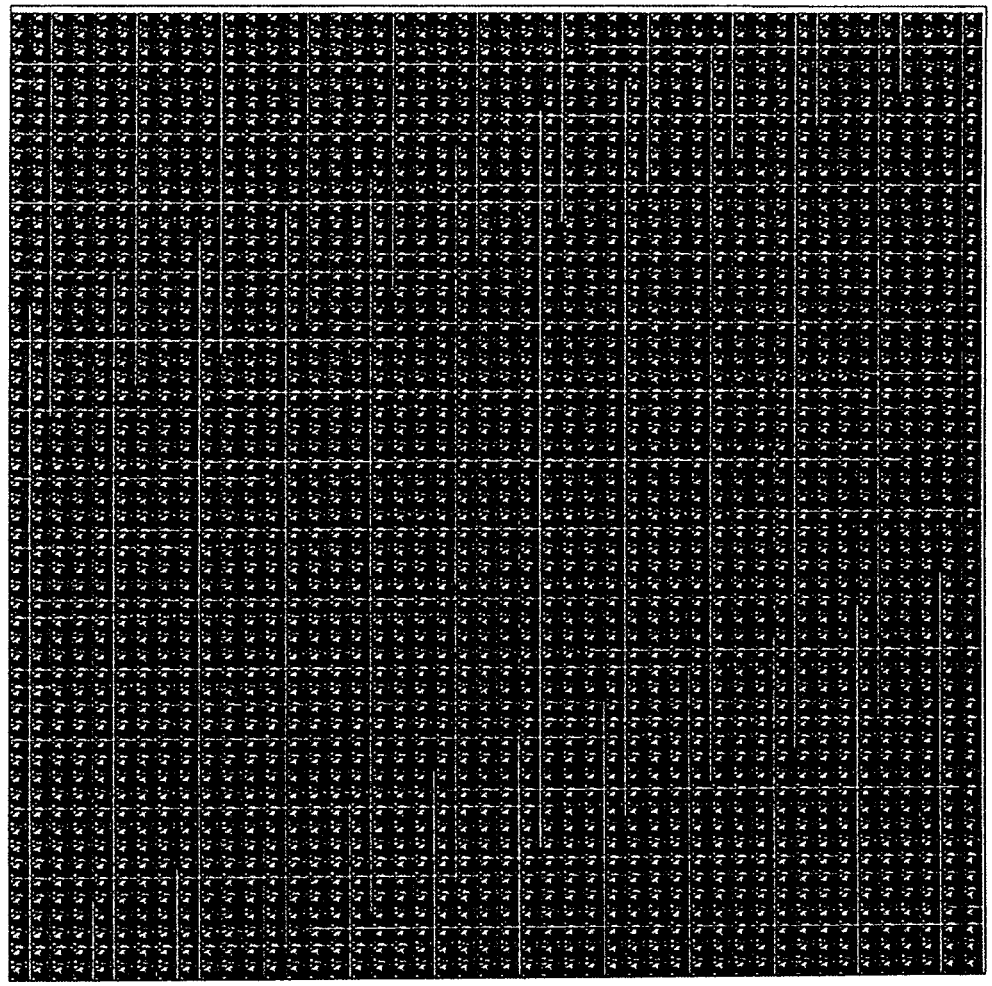
FIG. 14 is an example of a 5"×5" wafer densely patterned with sensors.

FIGS. 13A and 13B show one example of a mounting system/holder for the sensor described in FIGS. 11A and 11B. In this example, the sensor is mounted to a standard SOIC-10 package, having an opening on the top to permit fluid to contact the electrode. One possible benefit of this sensor design is the smaller footprint, primarily in variations that do not include a flow meter. Other variations may include a flow meter, as shown in FIG. 12 and FIGS. 15A and 16. As mentioned, these sensors may be mounted in small and low-cost packages with reduced lead count such as standard SOIC-10 package widely utilized in integrated circuit packaging; exemplary dimensions are shown in FIGS. 13A and 13B. In any of the figures shown herein, dimensions are for illustration only; the actual dimensions may be larger or smaller. The smaller footprint of these sensors may also allow a large number of sensors to be batch fabricated. For example, 2,576 sensors may be lithographically produced from each standard 5"×5" wafer (e.g., FIG. 14). Various alternative sensor designs are shown in FIGS. 15A-17J.

Any sensor sensing traces pattern design is the reflection of a number of compromises between performance, lithography limitations and cost of production. For example, to generate a statistically meaningful dataset that can be treated as a pattern for pattern matching or recognition, the sensor response data should be collected within a certain frequency range, that is may not be known a-priori. Frequency range can be estimated form the sensor's simplified lumped C-R equivalent circuit, where C is the equivalent capacitance of the polarization layers and R is the bulk resistance. Both of these parameters may depend on composition of fluid and geometry of the sensor traces. These two parameters can be measured in a calibration liquid such as, for example, 0.9% saline and extrapolated based on the knowledge of properties of other fluids. The sensor geometry may be chosen so that as the solution ionic content ranges from pure saline to D5W or sterile water it was experimentally found that value R ranges from about 1.5 kOhm to several megaOhms. Capacitance may not change as much; it typically changes within one order of magnitude of the 0.9% saline value of about 2.15 nF. Sensor admittance creates a characteristic 180° arc in the complex plane when frequency is swept from 0 Hz to infinity. In practice full arc is not needed, and just a section of the arc is a sufficient pattern for the following automated recognition. The simplified relationship between the angular position of the complex admittance measurement point on the arc $\phi$ as it is viewed from the arc's center, the equivalent circuit parameters R and C and the measurement frequency f is the following:

$$2\pi f = \frac{1 + \sec(\phi)}{RC \tan(\phi)}.$$

To cover the arc segment starting, for example at 10° and ending at 170° angle as it is viewed from the center of the arc one has to scan frequency range from 4.38 KHz to 572.6 KHz. To generate 16 measurement points distributed uniformly along the arc at 10° steps the measurements would have to be performed at the following frequencies: 4.38; 8.83; 13.42; 18.23; 23.36; 28.92; 35.08; 42.04; 50.1; 59.7; 71.54; 86.77; 107.43; 137.64; 186.96; 284.11 and 572.6 KHz. It is relatively straightforward working within this frequency range utilizing conventional commercially available integrated circuits.

The duration of the data set acquisition may also be adjusted to match the sensor configuration. As mentioned above, the value of the R increases drastically in D5W formulations while C remains range-bound. As can be seen from the formula above frequency goes to zero as R increases to infinity for any given angle. Very low frequency requires long detection time, which is detrimental for the device usability in clinical settings where acquisition time should not exceed several seconds. The additional interdigitated pattern addresses this issue by providing considerably higher coupling of the electric field into the low ionic strength fluid, which lowers values for R, while in fluids of higher conductivity such as normal saline the interdigitated electrodes are virtually shorted electrically. Due to these effects, the measurements in low ionic strength fluids are done between interdigitated electrodes and in higher ionic strength ones between either smaller individual electrodes or between the interdigitated electrodes and the individual ones.

Modern lithography processes are capable of producing highly accurate metallization patterns and insulation layers, but to keep the price of sensing element low the focus has been on using the low accuracy and low cost lithography, while retaining the sensing element's high reproducibility. The compromises made between the accuracy, reproducibility and cost of manufacturing may suggest keeping the size of the smallest features on the sensor at 10 μm. Improvements in technology and manufacturing may reduce this smallest feature size.

Linear interdigitated electrode structure such as that illustrated above, may address many of the factors mentioned above, but further reduction in the sensing element area can be achieved by designing a circular interdigitated pattern, as illustrated in FIG. 11A. The straight individual electrodes used in high ionic strength fluids can be reduced in size and placed closer to the rest of the electrode pattern, keeping the resulting values R and C for the equivalent circuit virtually the same and wrapping the interdigitated pattern around, without compromising the electrical coupling with fluids of low ionic strength. The resulting reduction in size allows for nearly doubling the number of sensor elements per wafer.

The sensing elements described herein may include an integrated lead frame to facilitate easy access to the sensing pattern and interconnect with the lab equipment and a variation in the number of interdigitated pairs and finger-to-finger distance within the pattern, as illustrated in FIGS. 15B and 15C (and previously in FIGS. 13A and 13B). In general, any appropriate mount, holder or other interface for securing the sensor so that it may communicate with the fluid to be tested may be used. Numerous examples of such mounts/connectors that may be used in any of the various systems are described and discussed in greater detail below.

The modifications to improve sensitivity of the system to drugs in low ionic strength solutions (including both modifications of the electronics and the sensors) described herein may also have the additional advantage of reducing the drug recognition time from seconds to milliseconds.

Sensor Mounts

As mentioned with reference to FIGS. 13A and 13B, the sensing element may be mounted to a standard open-cavity SOIC-10 package. Other sensor variations may reduce the area of the sensor die and implement low-cost packaging technologies such as a "flip chip". In general, the sensors described herein can be used with integrated circuit packaging systems for mounting sensor with wire bonding for electrical connections and overmolding to form package and liquid containment. For example, structures similar to commercial packages for laser diodes and integrated circuits may be applicable for mounting a sensor and providing liquid containment. In some cases, the package may not contain a window but may just have an opening in the top.

Figure 18A:
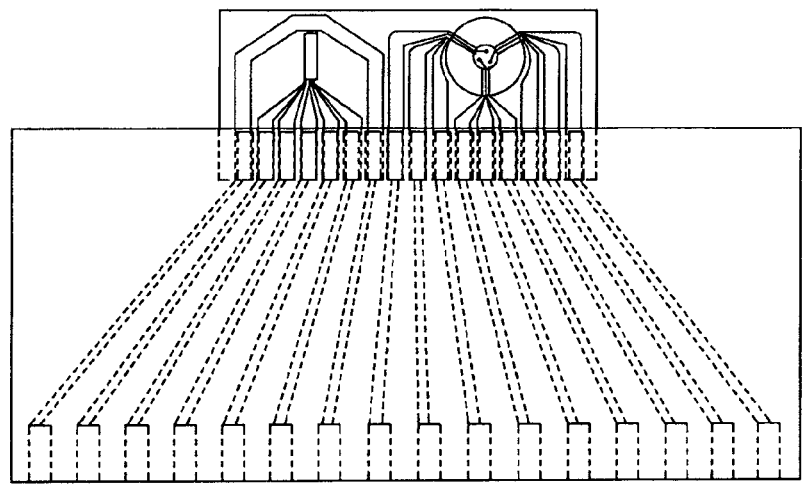
FIG. 18A shows one example of a sensor mounted to a printed circuit board (PCB).
Figure 18C:
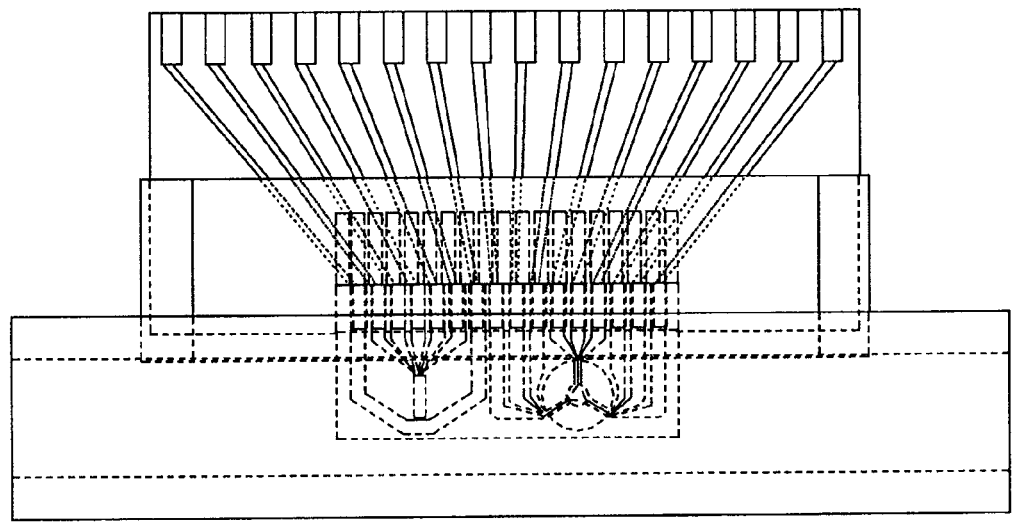
FIGS. 18B-18E illustrate the sensor and PCB of FIG. 18A coupled to a plug or tube for measuring immittance from a sensor immersed in a liquid passing into or through the plug/tube.
Figure 18B:
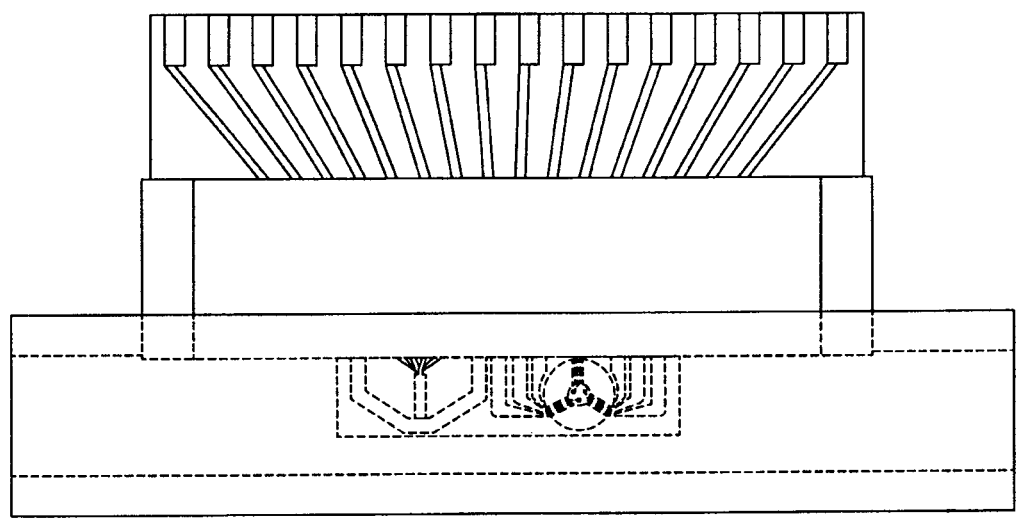
Figure 18D:
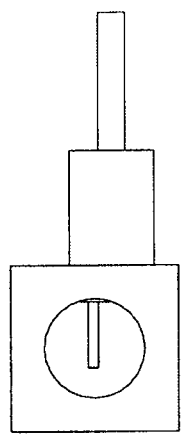
Figure 18E:
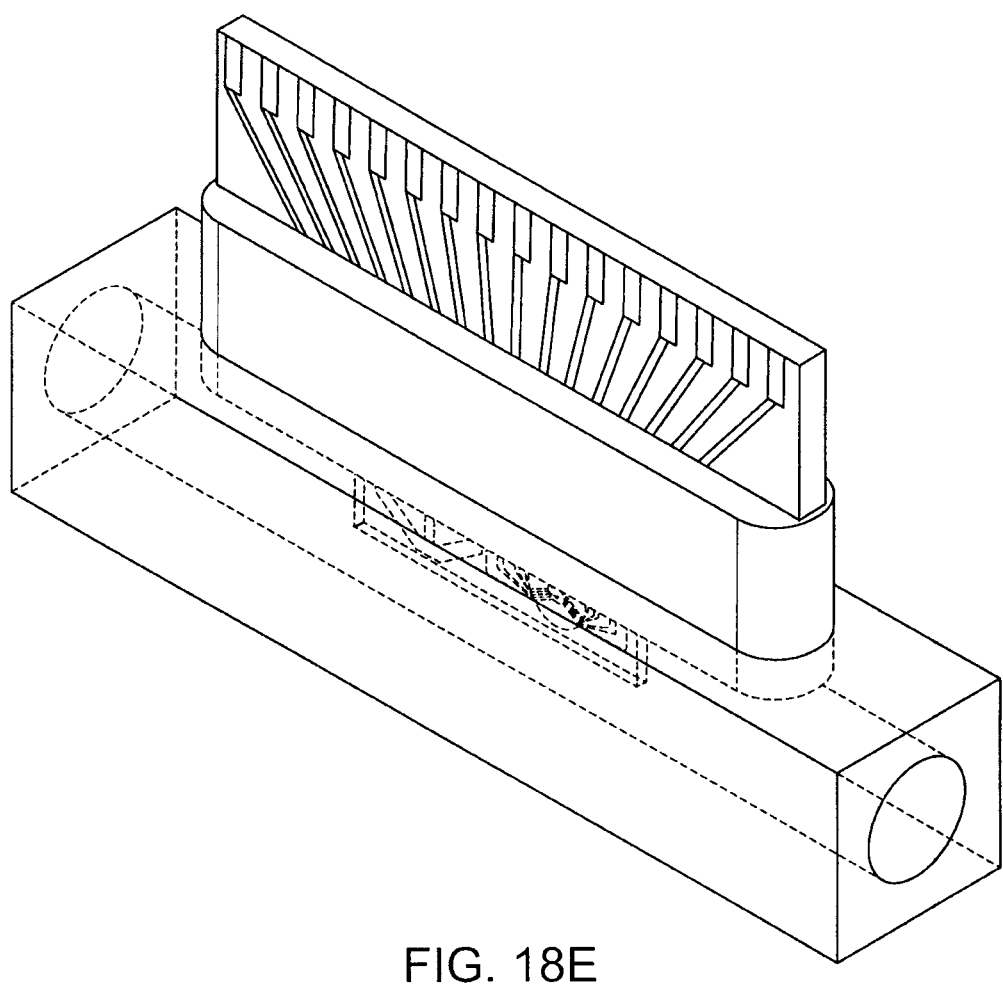
Figure 18F:
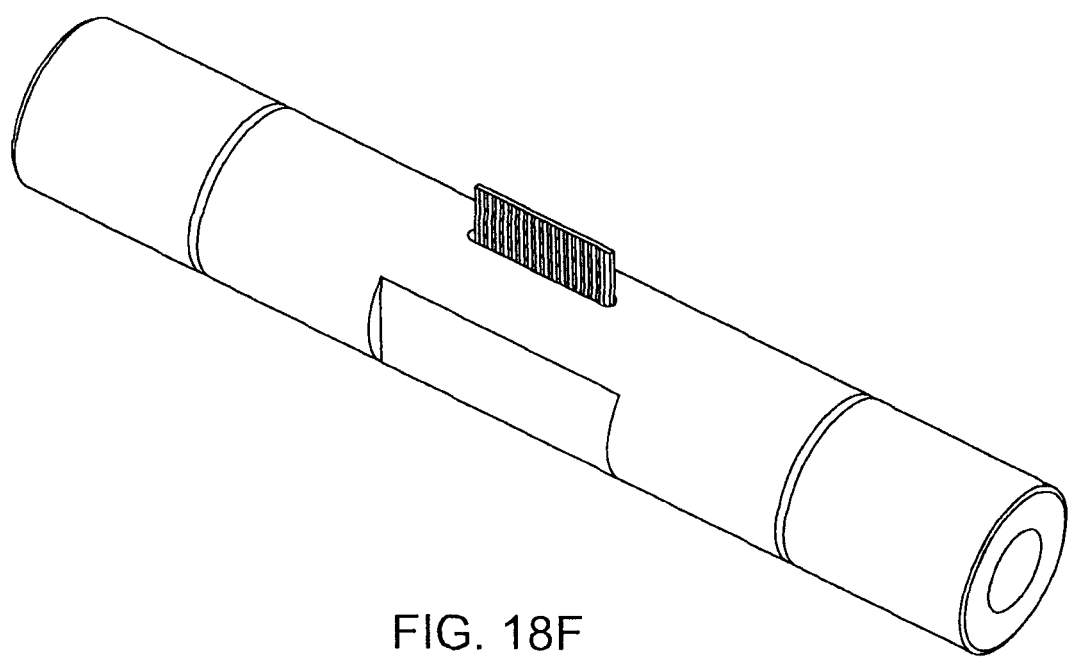
FIGS. 18F-18I illustrate other variations of sensor assemblies (e.g., sensors and mounts/housings), including flow-through configurations and static configurations.
Figure 18G:
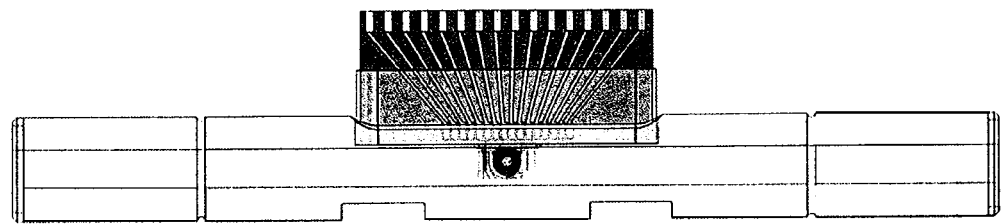
Figure 18H:
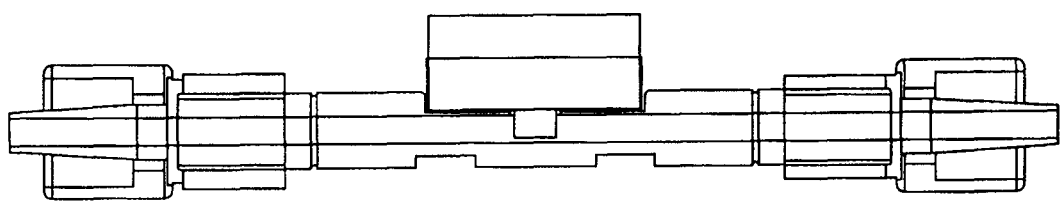
Figure 18I:
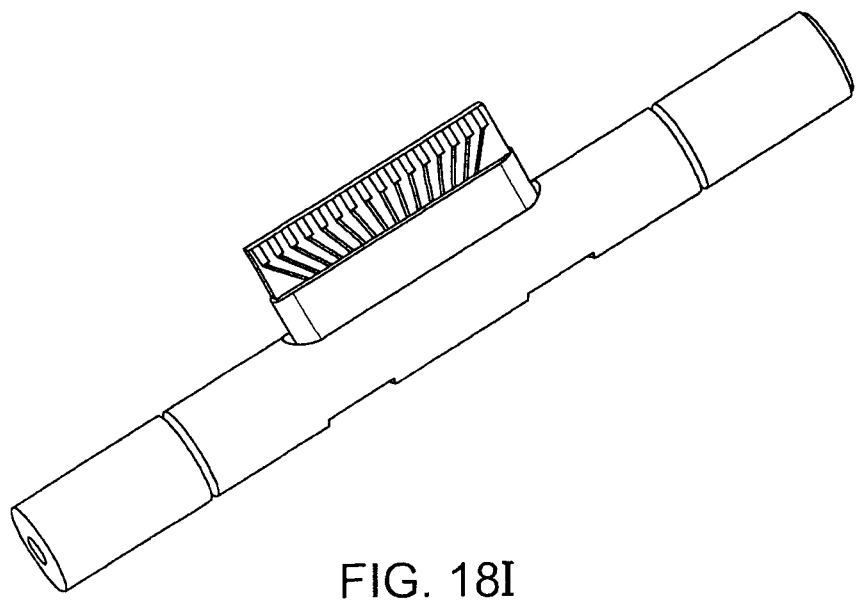

Alternatively a sensor can be attached to a small section of printed circuit board (PC) board that is patterned to provide leads for connection to an edge connector or other interface system. PC board can be rigid or flex material. The sensor and board can be molded into a plug or other assembly where the sensor is exposed to fluid and the pc board passes through the housing to connect to the measurement system. FIGS. 18A-18E illustrate one example of this configuration. For example, in FIG. 18A, the sensor "chip" is soldered to a PCB with electrical contacts. The sensor and PCB may then be coupled to a holder by molding into an oblong plug so that the sensor projects into a tube with an appropriate accepting shape, placing the sensor in the path of any fluid flowing through the tube. The tube region may then be coupled with a device for measuring the immittance of a fluid within the device to determine the composition of the fluid. FIGS. 18B and 18C show side views of this construction, while FIG. 18D shows an end view of the tube with the sensor projecting into the lumen of the tube. FIG. 18E shows a perspective view of this same variation.

The orientation and/or configuration of a sensor mount may depend upon what the sensor and system will be used for. For example, in some variations the sensor is mounted in an "in line" configuration, so that fluid can be monitored, and the composition, including concentration of any drug(s), as it is delivered to a patient. Other variations of mounts may be appropriate for "sample and measure" configurations, in which a small amount of the fluid to be tested is placed into a test cell containing a sensor. Additional examples of these configurations are illustrated below.

Figure 20A:
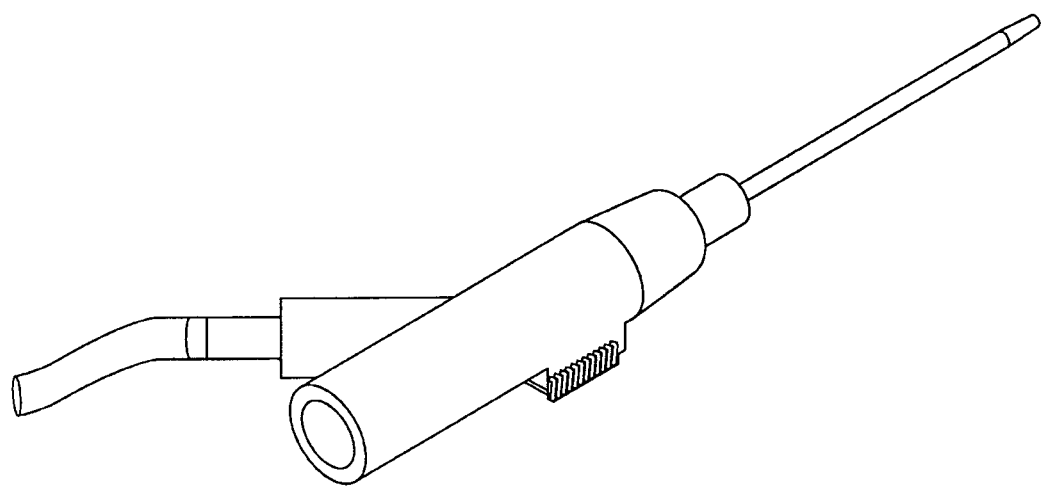
FIGS. 20A-20C show side perspective, end and side views, respectively, of another variation of a mount for a sensor.
Figure 20B:
Figure 20C:
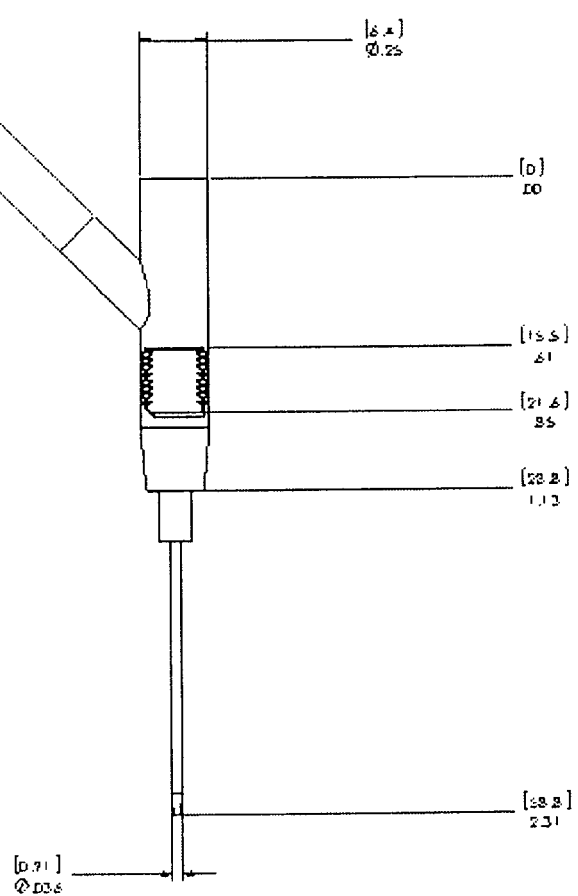
Figure 20D:
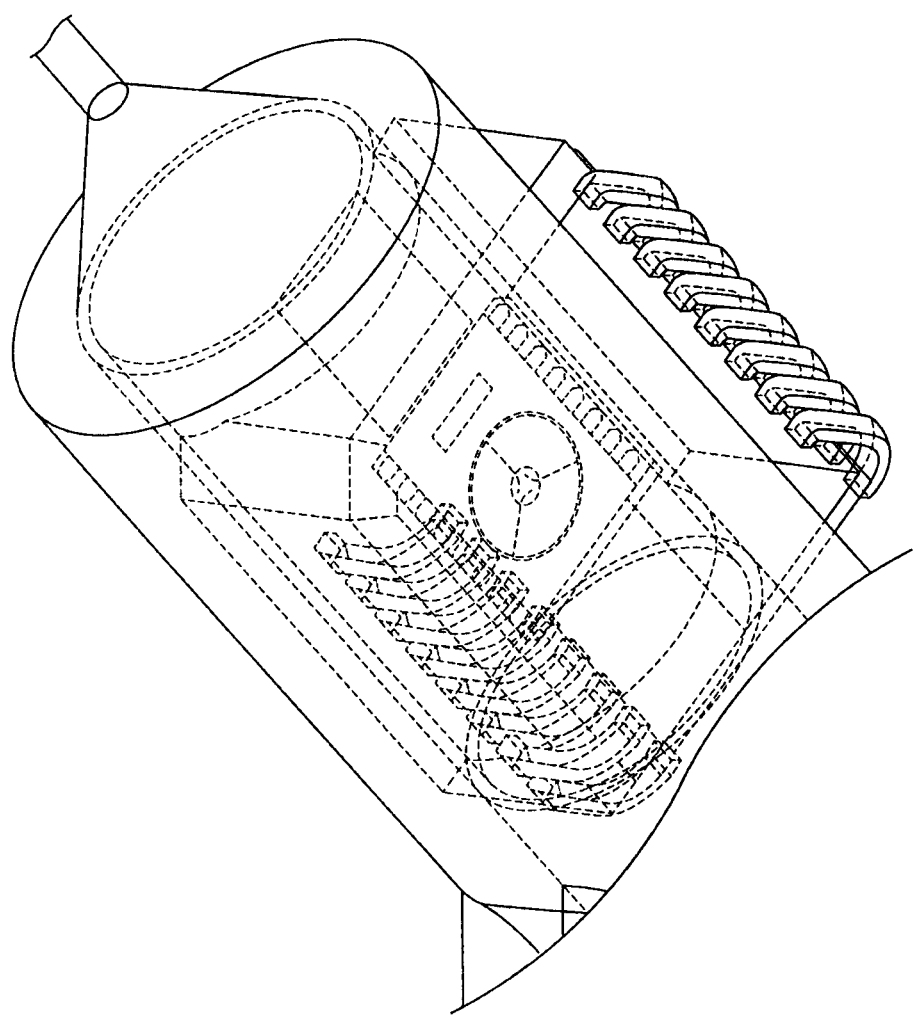
FIG. 20D shows an enlarged, transparent view of the mount region of the adapter/mount of FIG. 20A.

For example, FIG. 19A-19B shows one variation of an inline catheter including a sensor in a chip lead frame. In this example, the sensor 1901 is bonded or molded to a catheter body. A cable 1903 extends from the sensor to a connector, and the end of the mount includes a Y-molded/bonded to the connector. The entire unit is disposable. FIGS. 20A-20D illustrate a similar variation of an in-line connector holding a sensor. The sensor in this example is incorporated into a catheter that may be placed in-line with an IV fluid line. The sensor projects into the fluid pathway, and may include a flow sensor. FIG. 20A shows a side perspective view, FIG. 20B shows an end view, and FIG. 20C shows a side view. An enlarged transparent view is shown in FIG. 20D.

Figure 21A:
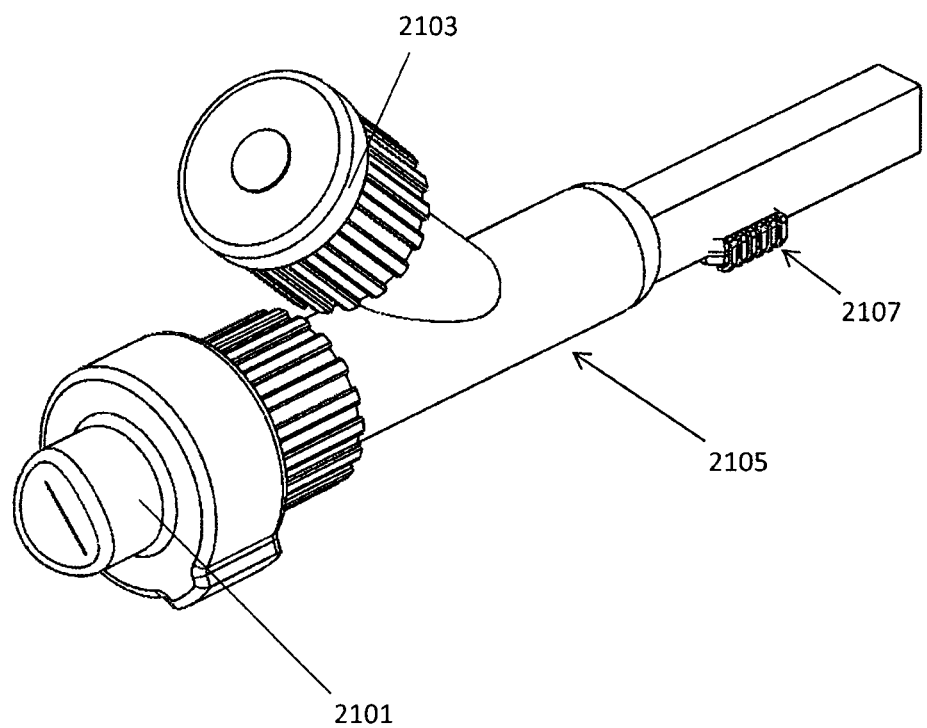
FIGS. 21A and 21B show side perspective and side views, respectively, of a mount for a sensor having a septum for static measurement of liquid characteristics by immittance spectroscopy.
Figure 21B:
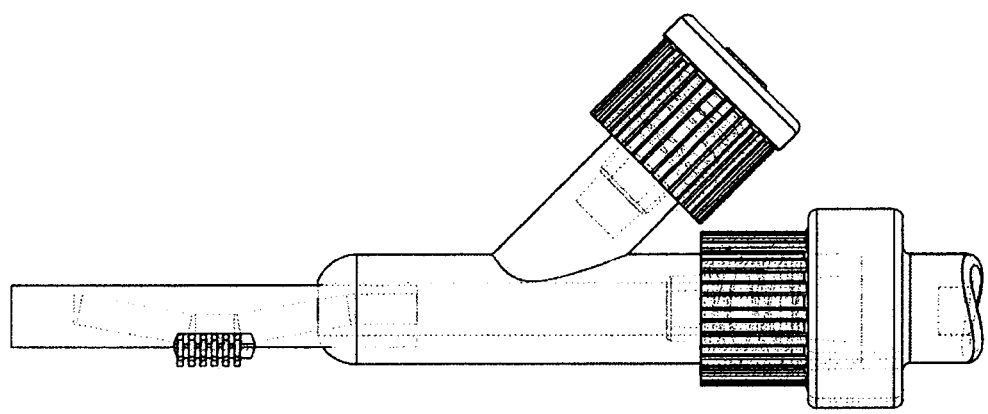

FIG. 21A illustrates another variation of a sensor and mount, including a septum or other sealing mechanism. In this example, a septum or seal will contain fluid and prevent sensor contamination before usage. The assembly is configured for single use, as fluid may be difficult to remove from the sensing chamber/sensor. The septum 2101 and valve capping system allows for containment of dangerous fluids. The assembly can relieve the internal air pressure through the one-way valve 2103 caused by the reduced air volume during the addition of fluid into the assembly. The lower sensor assembly 2105 consists of an injection molded tube with a sensor element 2107 attached to it via adhesive or other means. This end of the connector may be closed. The y-assembly can be attached to the lower sensor module assembly. FIG. 21B show a side perspective view.

Figure 22A:
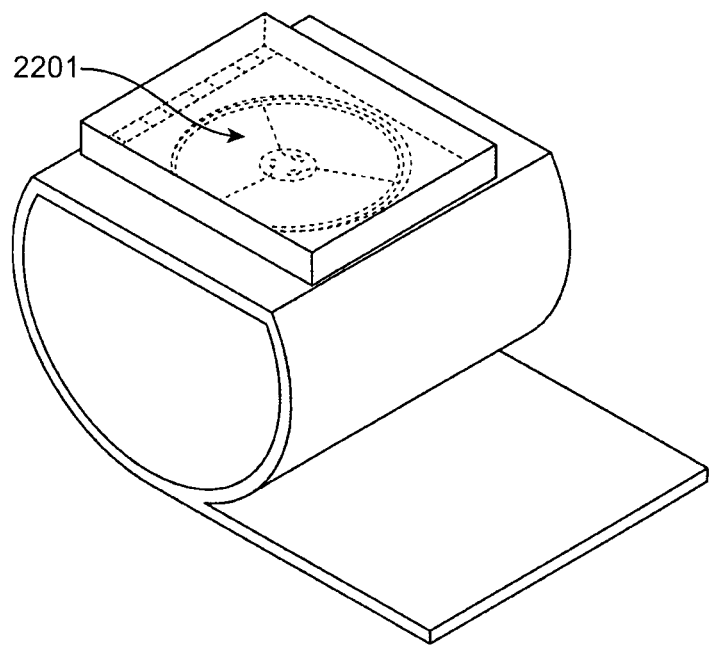
FIGS. 22A and 22B show another variation of a mount for holding a sensor so that the sensor can communicate with a liquid sample to be examined by immittance spectroscopy.
Figure 22B:
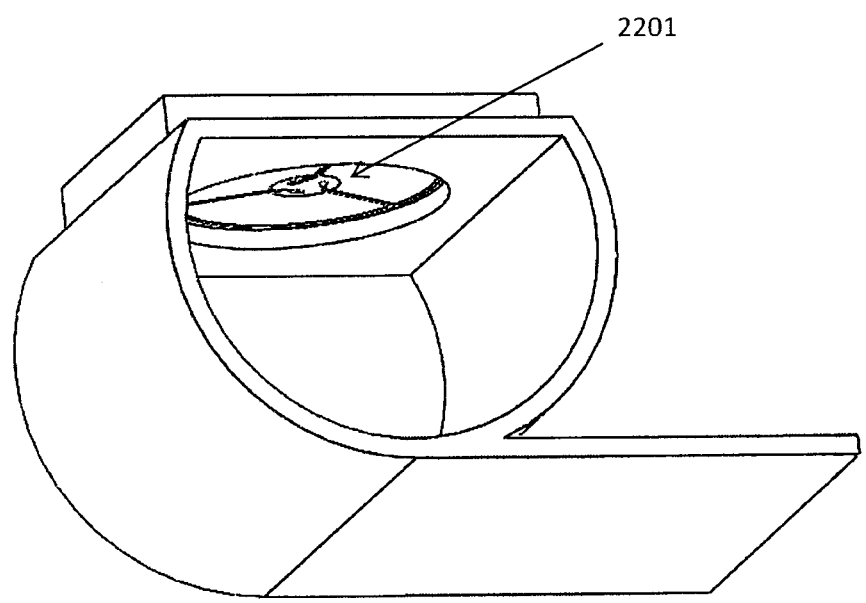

Another variation of a sensor mount is shown in FIGS. 22A-22B. This mount is configured as a circular tube with the sensor on the wall of the mount. The tube structure can be formed from the sensor element 2201 and either a rigid or flexible PC board that is bonded to it, with conductive adhesive or solder pads. The PC board will have an opening over which the sensor is attached to allow exposure to fluids of the sensor face. In this example, if the board is made from flex material, it can be rolled into a tube containing the attached sensor and the tube structure over molded with polymer to create a tube section with the sensor inside the wall and contacts on the outside. The tube can also be rolled into a cylinder and the ends attached to the sensor element. Either of these configurations can be wrapped around a support tube with an opening to expose the sensor and then over molded to form a tube assembly having exposed contacts around the outer circumference of the tube.

Figure 23A:
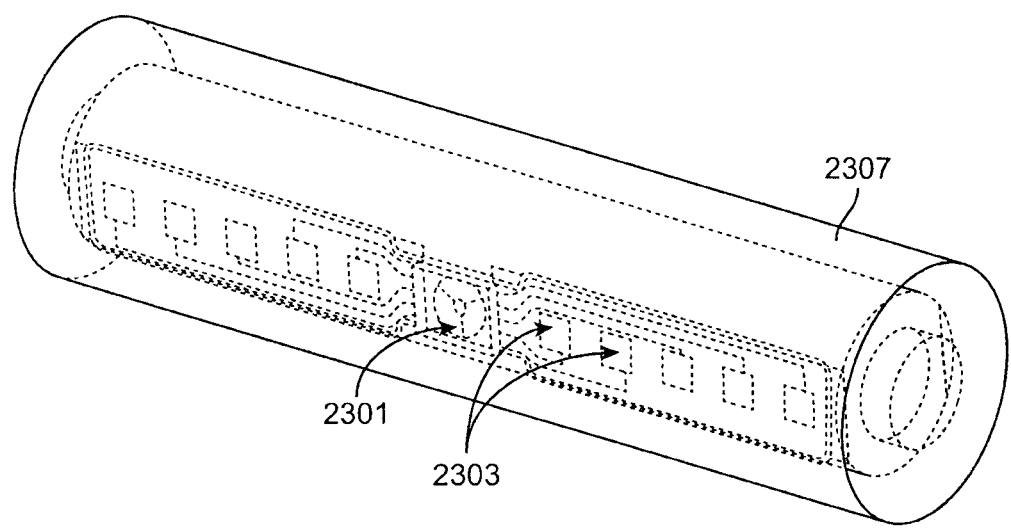
FIGS. 23A and 23B show a cylindrical mount.
Figure 23B:
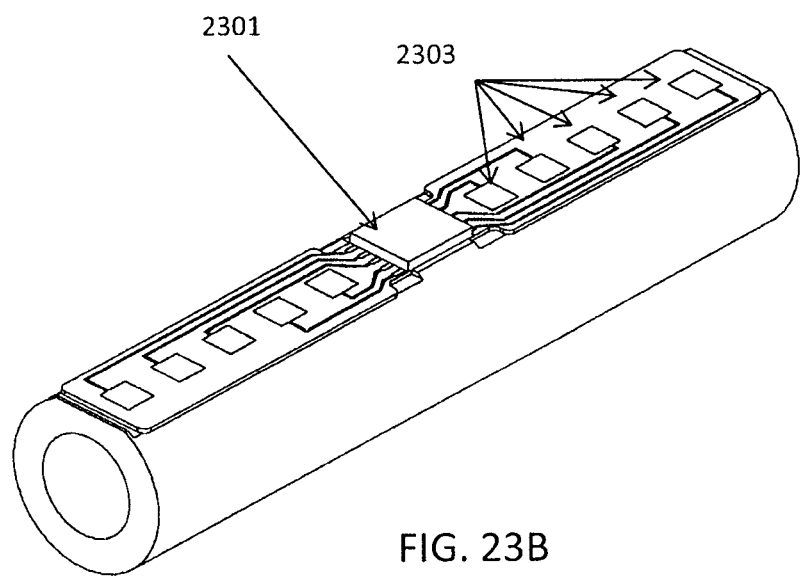

FIGS. 22A and 22B illustrate another variation of a tubular mount that may be used in-line or static (if one end is closed off). The sensor of this example includes both a low ionic strength electrode region 2201 and high ionic strength single pads 2203. If designed with symmetric ring or other symmetric structure contacts, the sensor tube assembly can be installed into a system without requiring rotational alignment. FIGS. 23A and 23B illustrate another variation of a cylindrical mount for one or more sensors 2301, 2303 that may be used with an over molded outer sleeve or housing 2307. In this example the sensor includes both low ionic strength electrode pair sensors 2301 and high ionic strength (single pad) sensors 2303.

Figure 23C:
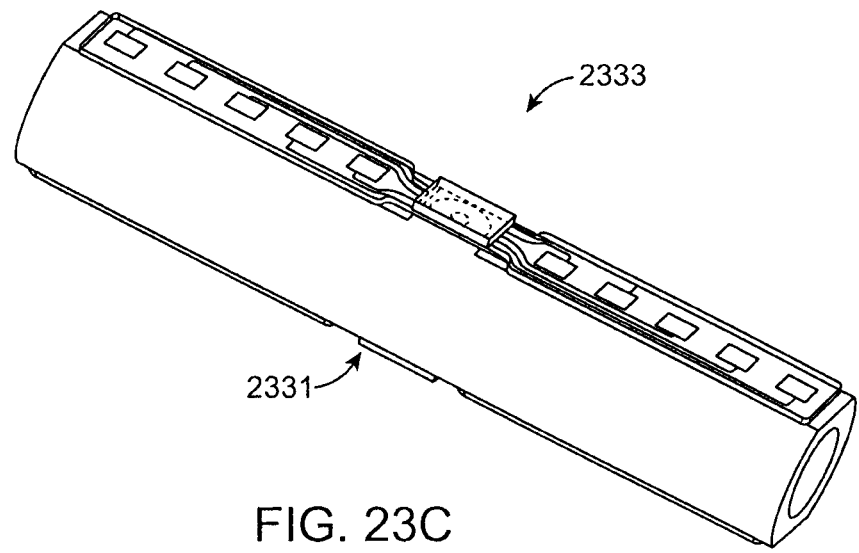
FIG. 23C shows another variation of a cylindrical mount having multiple sensors (on opposite sides).

In any of the systems described herein, multiple sensors may be used. Thus the mount may be configured to hold multiple sensors, as illustrated in FIG. 23C. Using multiple sensors 2331, 2333 may improve reliability. For example, multiple sensor elements may be used in a given system to improve reliability by comparing responses of the multiple sensors against one another and if different, likely inaccurate measurements may be rejected.

Figure 24A:
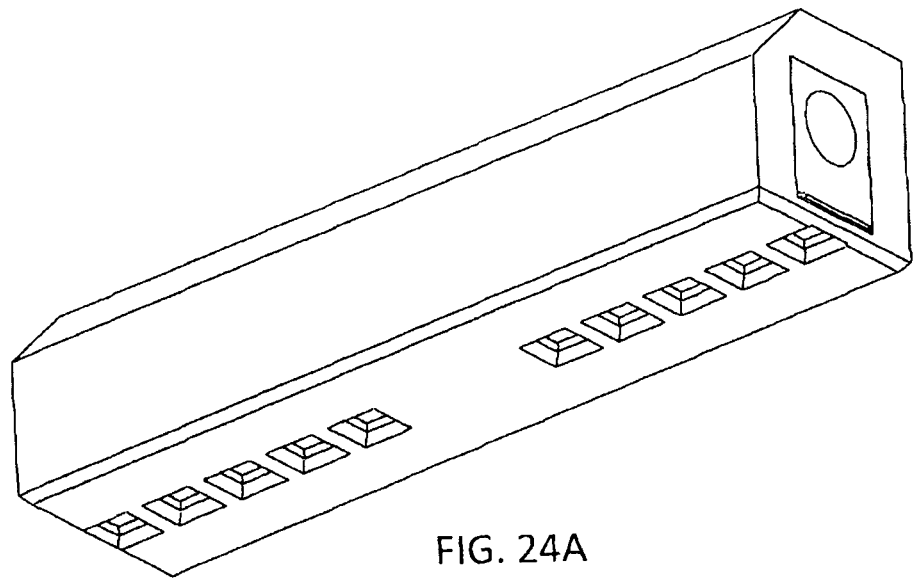
FIG. 24A shows another variation of a mount including an over molded holder.
Figure 24B:
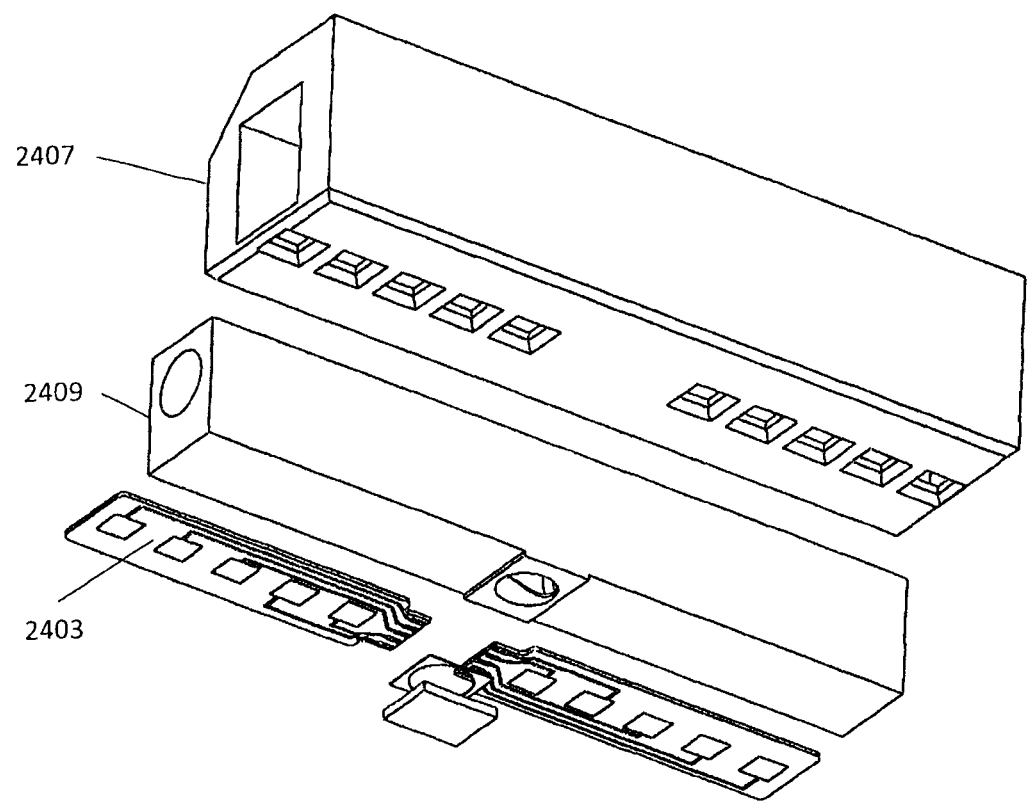
FIG. 24B shows an exploded view of the mount of FIG. 24A.

As mentioned, such tubular mount designs can either be sealed on one end or used as a liquid chamber, or open for flow through applications. Another embodiment (FIGS. 24A-24C) uses square or rectangular sections with circular bores 2409 through them to transport liquid with an opening in the bore to access the sensor elements. The sensor 2403 can be soldered to flexible cables and then adhered to the square tube. This assembly may then be over molded 2407 to encapsulate the sensor and cables while leaving access to the leads on the flex cable. The overmolding can be keyed to mate with the rest of the system, confirming that the sensor is in position.

Figure 25A:
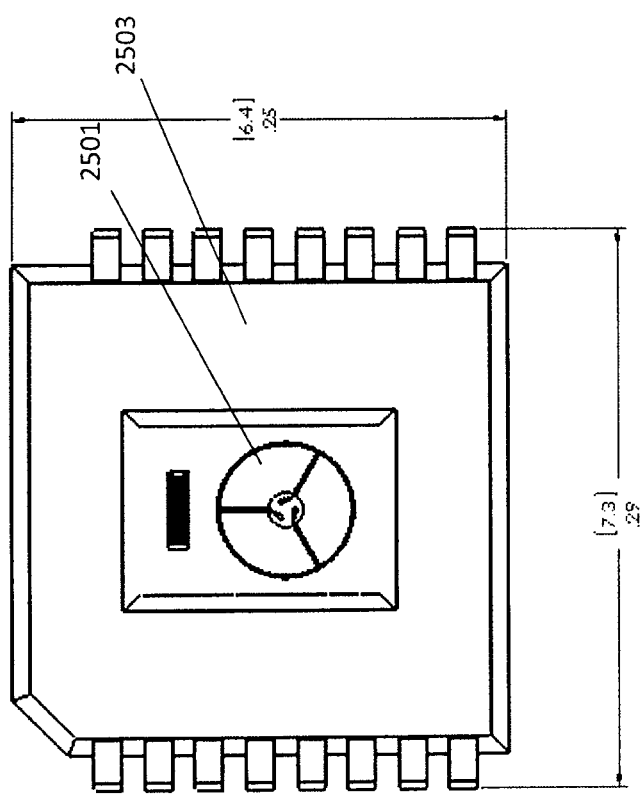
FIGS. 25A-25C illustrate another variation of a sensor mount configured as a lead frame.
Figure 25B:
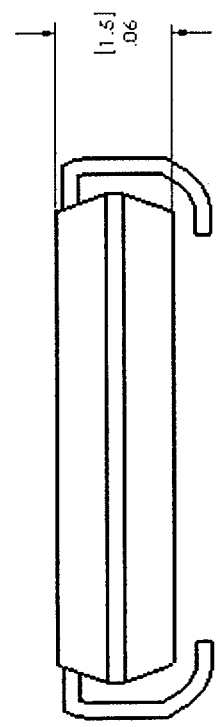
Figure 25C:
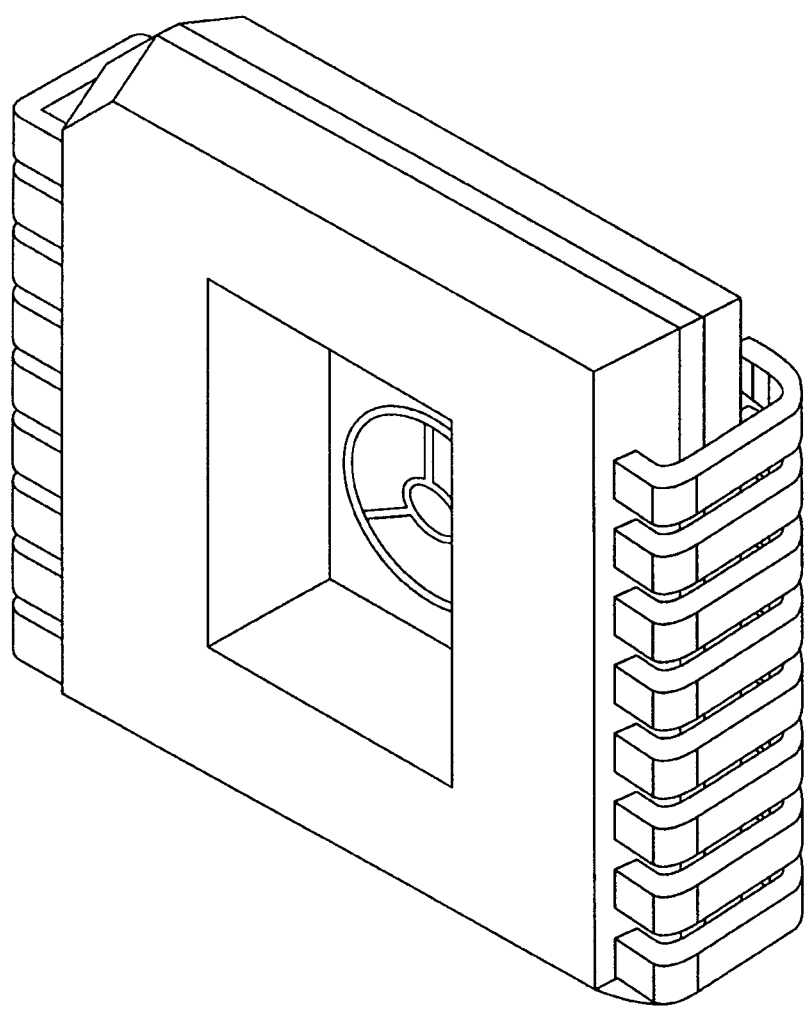
Figure 26A:
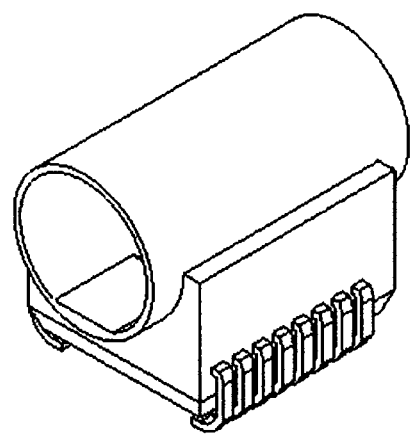
FIGS. 26A-26C show another variation of a sensor mount or holder configured as part of a frame.
Figure 26B:
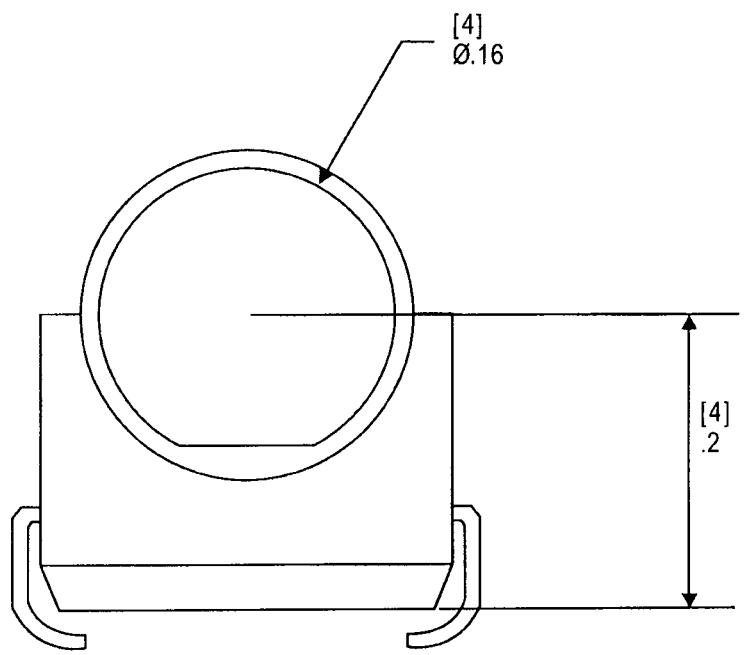
Figure 26C:
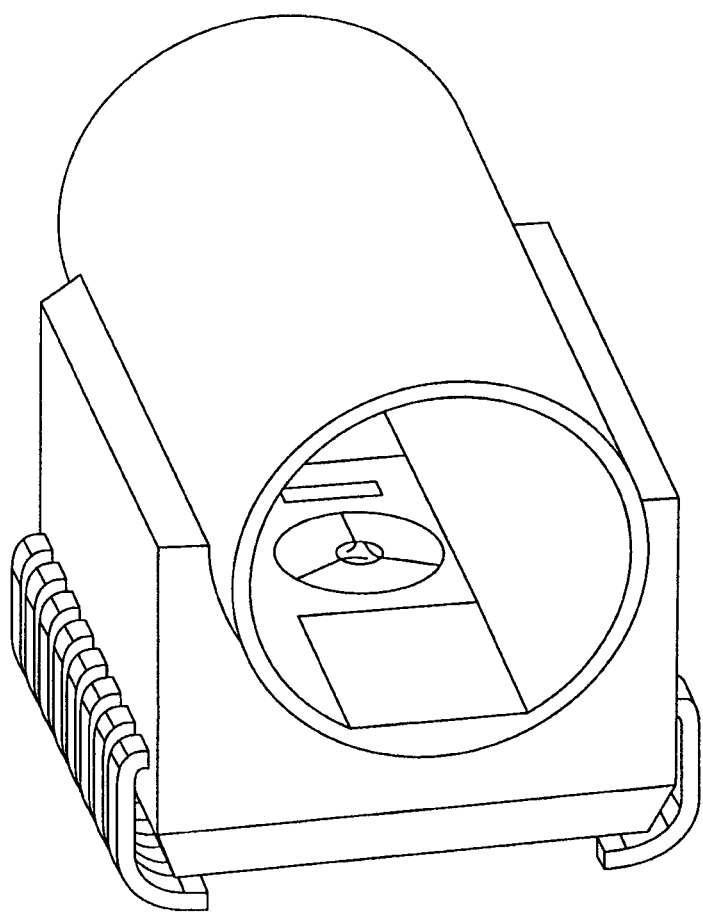

FIGS. 25A-C shows another example of a sensor packaged in a lead frame, similar to that illustrated above in FIGS. 13A-13B and 16B-16C. In this example, the sensor 2501 is packaged in a lead frame 2503 and wire bonded to lead frame and molded/formed top. Fluid may be directly applied to the open cavity for static measurements. A similar lead frame technique with an enclosed tubular structure attached may be used for in-line dynamic measurements (or static measurements with one end closed). An example of this is illustrated in FIGS. 26A-26C.

Figures 27A, 27B:
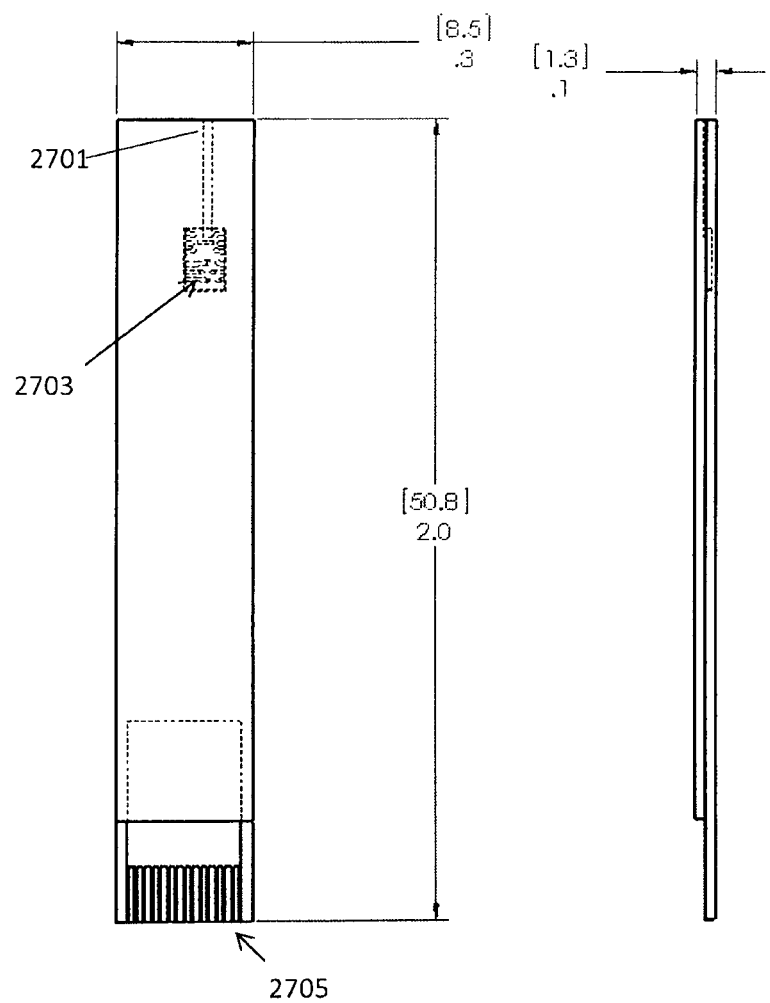
FIGS. 27A-27C show front, side and side perspective views, respectively, of a capillary strip mount for a sensor, allowing the sensor to sample fluid via capillary action within a disposable strip.
Figure 27C:
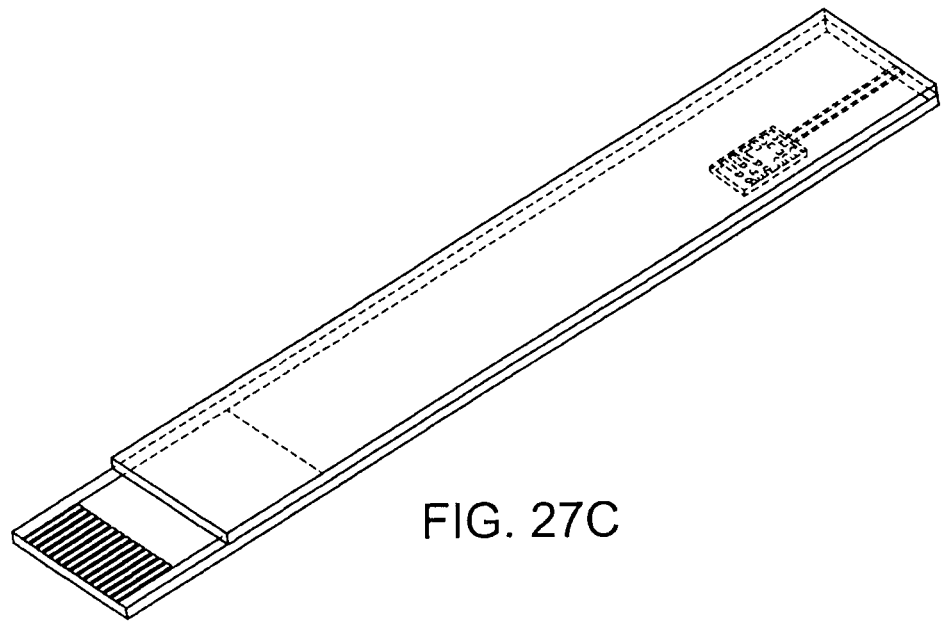

In some variations the sensor is configured (with the appropriate mount/holder) as a capillary strip. FIGS. 27A-27C illustrate one variation of this embodiment. In this variation, the sensor can be laminated/fit/sealed between layers of material with a small port 2701 open to fluid; the port 2701 will be designed to facilitate capillary action that will wick the fluid onto the sensor 2703. The sensor leads may be continuous from the sensor to the back of the strip to contacts 2705 that will interface to the electronics. These traces may be built into the laminating strips. FIG. 27A shows a front view and FIG. 27B shows a side view; the capillary strip may be thin, and similar in design to single-use insulin monitoring strips.

Figure 28A:
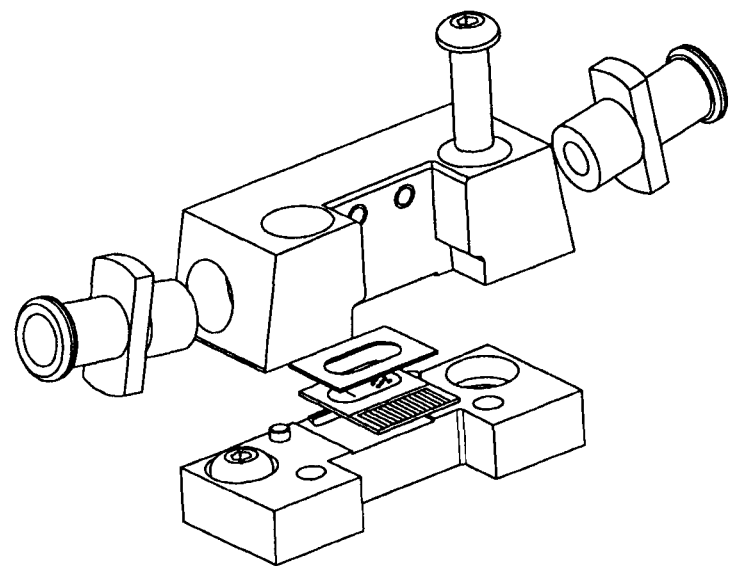
FIG. 28A shows an exploded view of one variation of a clamping mount for a sensor.
Figure 28D:
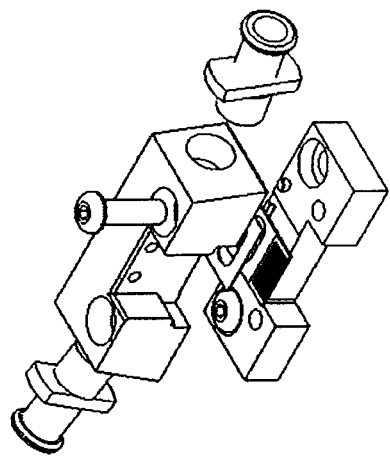
FIGS. 28B-28D show side, end and side perspective views, respectively, of the assembled mount of FIG. 28A.
Figure 28C:
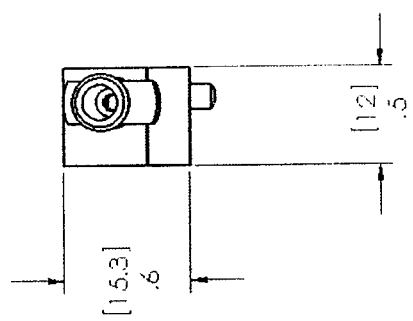
Figure 28B:
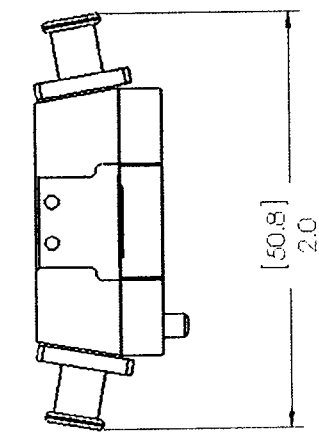
Figure 29:
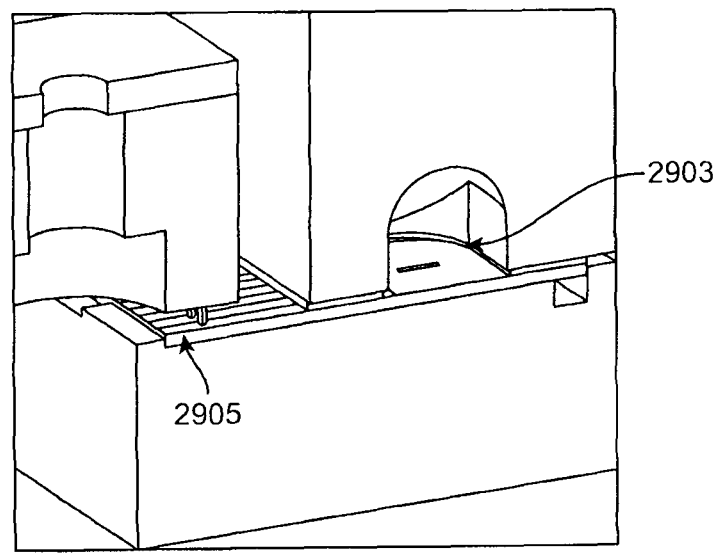
FIG. 29 illustrates one method of attaching contact pins to output pads of a sensor held in a clamping mount such as the mount shown in FIG. 28A.

In some variations the sensor can be configured for contact with a fluid by clamping and thereby sealing the sensor in communication with the fluid. For example the chamber may be configured to interface with a sealing gasket to form a flow cell. A flow cell may be particularly helpful for larger versions of the sensor that can be interfaced with flowing or static liquid by being clamped between two pieces of material and with a sealing gasket. A gasket may allow the sensor to be more easily reusable or easily replaced. The sensor can be connected to the rest of the system with either a cable or a specialized contact probe that can be mounted to the flow cell or mounted on a robotic arm that can access the contacts. FIGS. 28A-28A illustrate one variation of a flow cell and sensor. For example, in FIG. 28A, the flow cell is formed by clamping the upper housing 2801 to the lower housing 2803 to seal a sensor 2803 and gasket 2805 between the upper and lower housings, while leaving the connector (in this example, shown as an attached PCB) exposed for connection to the rest of the system. An inlet 2811 and outlet 2812 port and connector(s) may be used to couple the assembled flow cell with a fluid source. In some variations the outlet is closed off or blockable to allow static measurement. FIGS. 28B, 28C and 28D show front, side and side perspective views, respectively, of the assembled flow cell. FIG. 29 illustrates one variation of a contact probe coupling to the PCB connector for the flow cell of FIG. 28A-28D. In this example, the contact probe includes pins 2905 that interface with the contacts on the PCT. FIG. 29 shows a cross-section through the flow cell, showing the sensor 2903 within the flow cell.

In some variations, a fluid cell with a sensor can be formed by an open chamber, rather than one that is sealed shut. For example, the fluid cell may be a tubular chamber formed by securing one end of a tube to a substrate including the sensor(s); a tube can be adhered to a sensor and a small aliquot of liquid added for a static measurement.

Although many of the device variations described above include sensors that are fabricated in a batch and cut into individual sensors for coupling with a mount or holder, in some variations an array of sensors (e.g., uncut from a sheet, or cut into strips with multiple sensors, etc.) may be used and a mount or holder may be adapted for use with the array or sensors, either in parallel or sequentially. For example, the sensors can be manufactured in long un-diced strips and tubes or other fluid containment elements can be coupled to each sensor so that the sensor is exposed to fluid within the formed fluid cell (formed by the tube and sensor). In some variations the "walls" of the fluid cell (e.g., tube) may be moved to different sensors on the sheet or strip, so that a new sensor can be used. Multiple parallel fluid cells may be formed at the same time. For example, a strip of sensors could be loaded into a device and indexed to a set of contacts so that when the strip is in the proper position the system actuates and forms the fluid cell while connecting the sensor contacts.

Figure 30A:
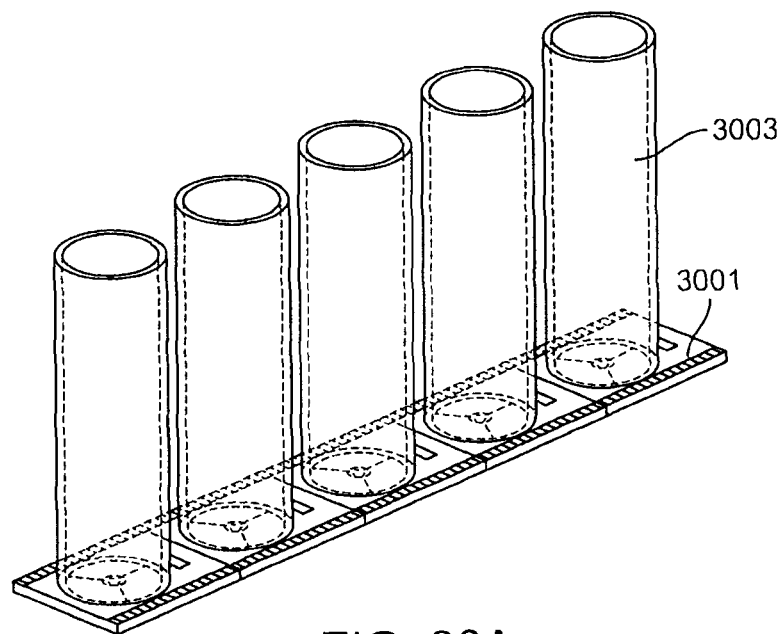
FIGS. 30A-30C show one example of a plurality of sample chambers formed by coupling an array of sensors (shown in a strip) to a plurality of cylinders.
Figure 30B:
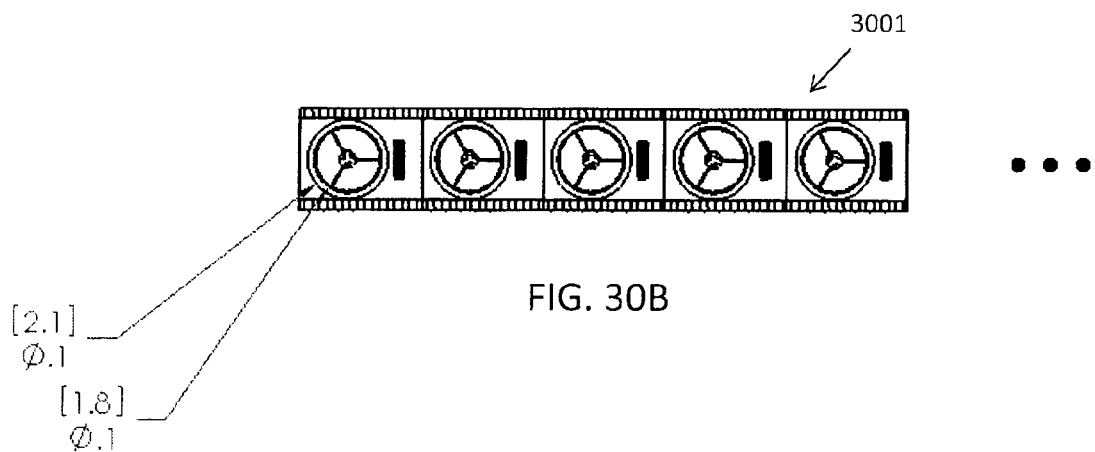
Figure 30C:
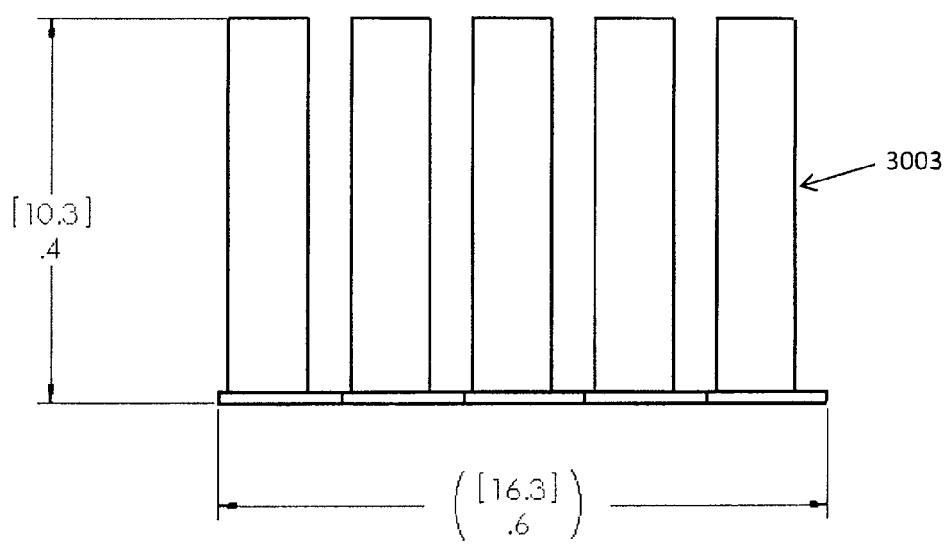

FIGS. 30A-30C illustrate one variation of a system configured to form fluid cells (five parallel cells are shown) by placing tubes 3003 over a strip of sensors 3001. FIG. 30A shows a side perspective view of the assembled chambers, configured as five open chambers formed of five tubes that are sealed onto a strip of sensors; the sensor may be locked down onto the strip so that the connectors are either exposed or connected to a coupler/connector to be attached to the rest of the system. FIG. 30B shows a portion of a strip of sensors that may be used with the tubes shown in FIG. 30C and assembled as shown in FIG. 30A.

Figure 31A:
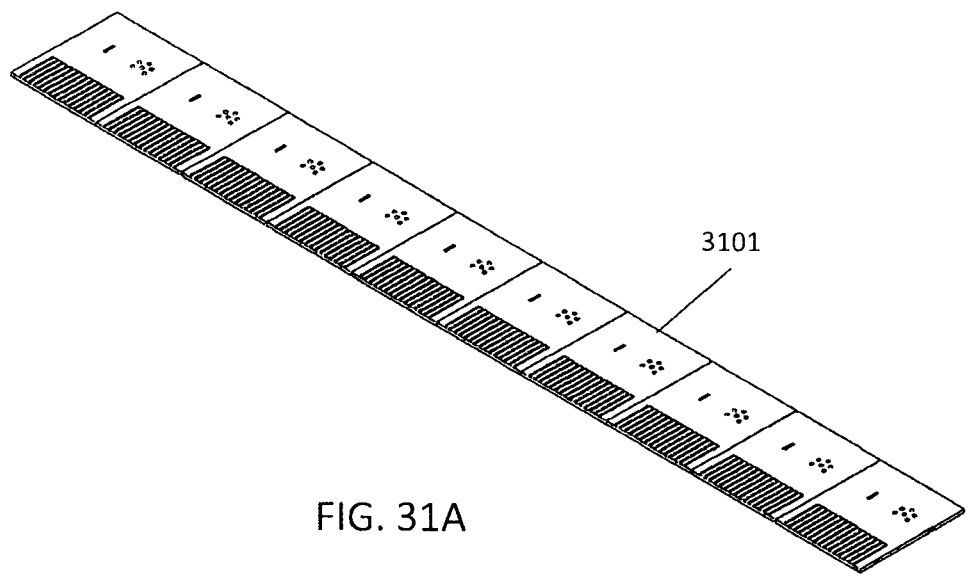
FIGS. 31A-31C illustrate the formation of a well by integrating a layer include one or more holes over the sensor that can hold fluid. The well-forming layer may be adhesive.
Figure 31B:
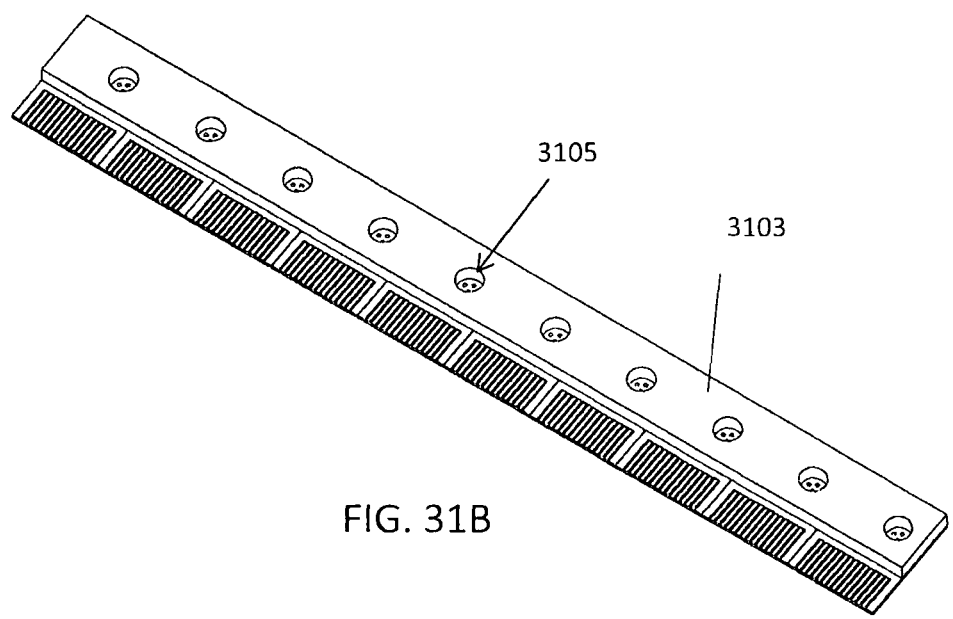
Figure 31C:
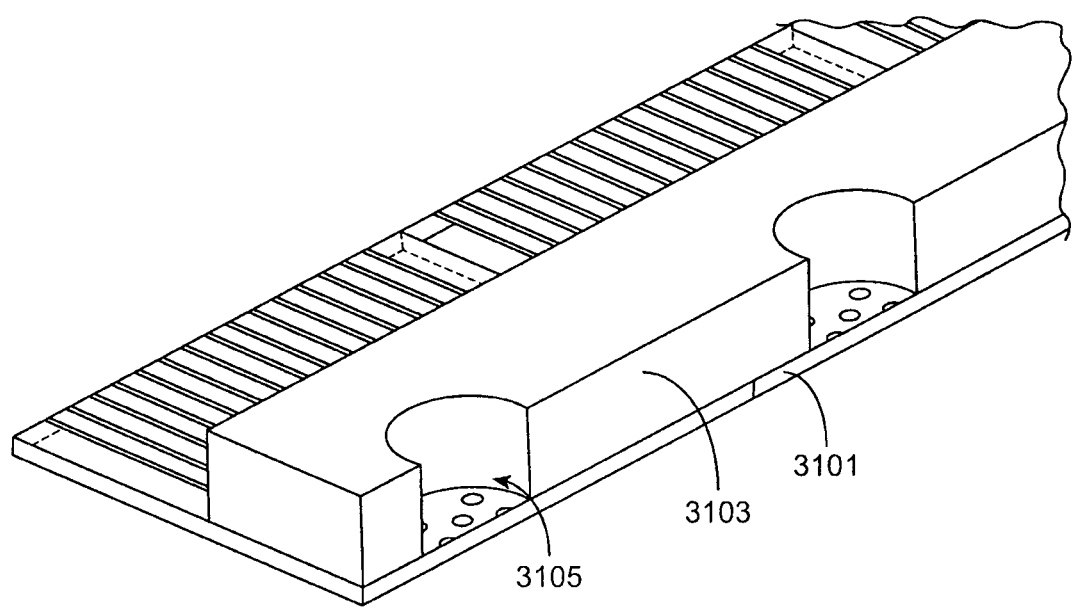

In some variations the sensors (e.g. a strip or sheet of sensors) may be attached to a material that forms wells or other fluid cells, including open fluid cells so that fluid can be applied directly to the sensor(s). For example, FIG. 31A shows strip of sensors 3101 onto which chamber or cells 3105 for fluid can be formed, as shown in FIG. 31B. In FIG. 31B, an applied strip of thick tape 3103 has been drilled, die cut or punched to form holes (chambers) over the active area of the sensor. In this case, the fluid well is formed by these holes in the thick added layer 3103.

Figure 32A:
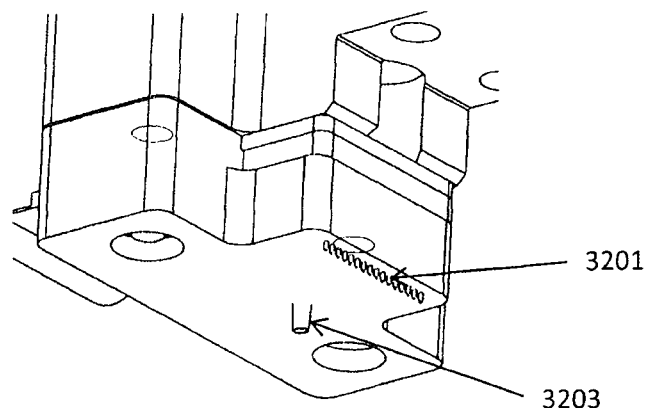
FIGS. 32A and 32B illustrate a system including a reading/dispensing head that is positionable above the sensor or an array of sensors.
Figure 32B:
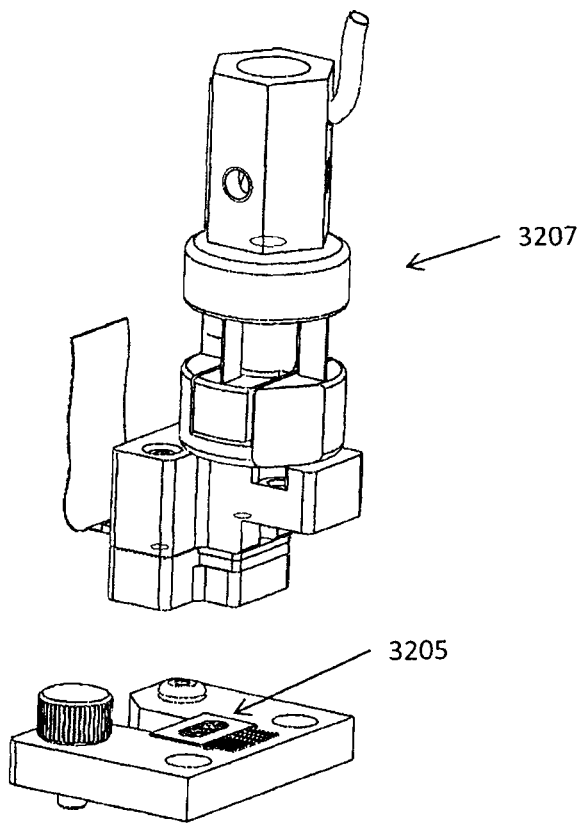

Any of the systems described herein may be configured to automatically measure complex immittance to determine the composition of a solution. For example, a system may include a moving or robotic arm/sensor to read one or more sensors. This configuration may be particularly helpful for reading arrays of sensors. For example, a system may include a "flying head" read sub-system. A movable test head and/or movable sensor holder for moving a sensor, sensor array or wafer of sensors, could be used. In some variations a movable head containing contacts (e.g., pogo pins) makes contact with the sensors; the movable head could also include a liquid cartridge filled with a test fluid. The head could then deliver a drop of fluid to be tested onto a sensor (e.g., as a small droplet) when the probe head touches down on the sensor. FIGS. 32A-32C illustrate one variation of such a system. FIG. 32A shows the underside of a movable head 3207 that includes pins 3201 for contacting a sensor and a droplet dispenser 3203 for delivering drop of liquid to be tested onto a sensor. FIG. 32B shows the movable head 3207 positioned over a stage holding a sensor 3205. This is one example of a system that may be adapted to provide high-throughput screening or processing of liquid samples to determine the composition of the liquid.

Figure 33:
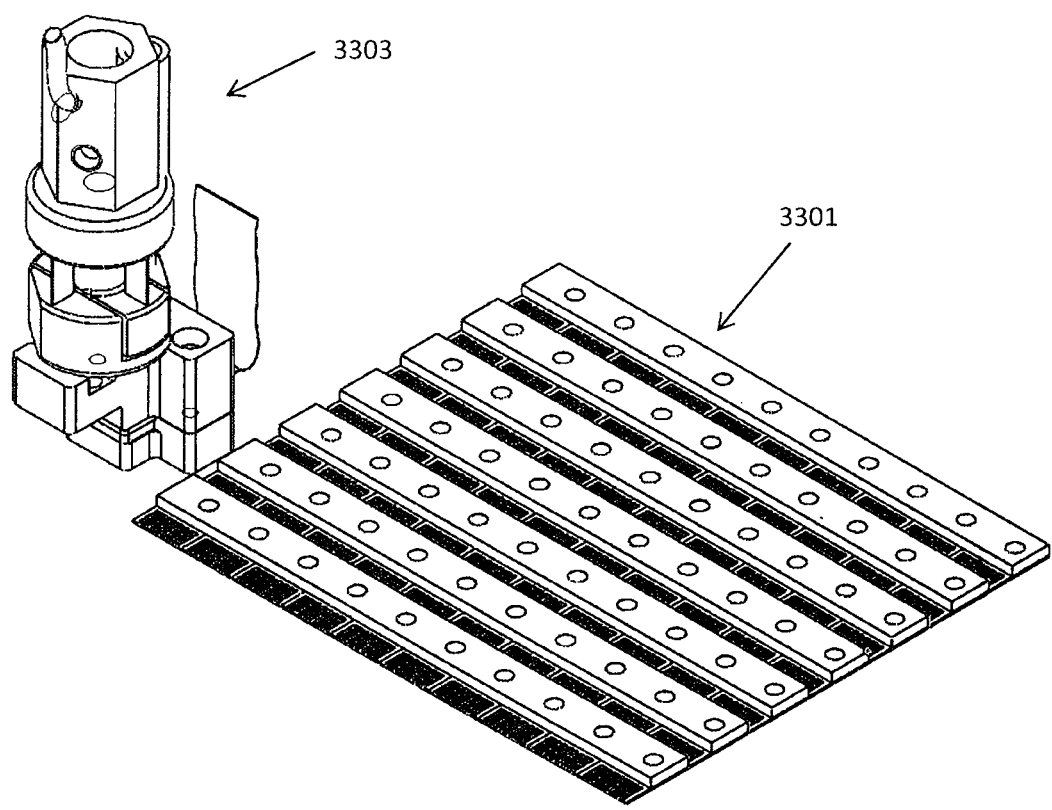
FIG. 33 shows an array of sensor (similar to those of FIG. 31C) having wells formed directly on the sensors being sampled by a reading head as shown in FIG. 32A.
Figure 34A:
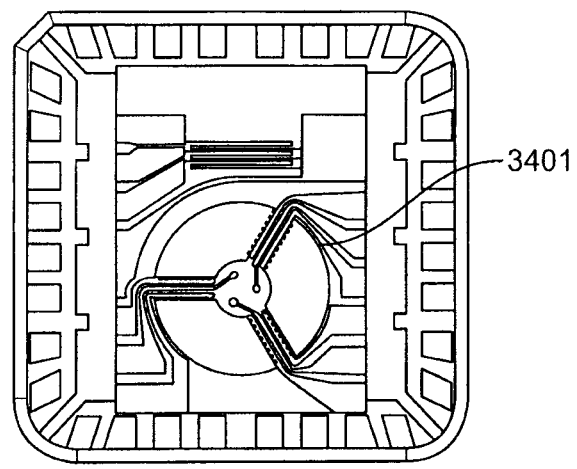
FIGS. 34A and 34B illustrate one variation of a mount using a lead frame.
Figure 34B:
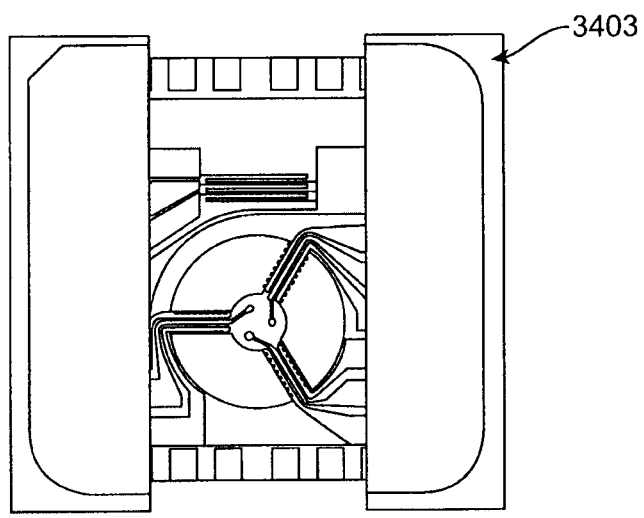

Another variation of the system may include a full wafer of sensors that could be adapted for use with a flying head, probe assembly or edge contacts. For example, as shown in FIG. 33, a flying head (movable head) may be used to read sequentially from a sheet 3301 or strip of wavers. Thus, the sensors can be manufactured in wafer form and not diced. The sensors could be accessed by a probe system 3303 via a robot (or human) for taking measurements. The array of un-diced sensors can be linear, circular or other geometries. The probe can take the appropriate shape to access the contacts of the sensor. Furthermore the probe can access the sensors automatically or manually. As mentioned above, in some variations the sensors could also include a well, and thus fabrication of the array of sensors could include a manufacturing step to add a well to each sensor element.

Although the methods for manufacturing sensors described here include primarily lithographic methods (e.g., fabricating the sensors by photolithographic methods to form precise arrangements of electrodes), in some variations, the sensors are produced from wires that are embedded into a nonconductive material and cut to form the conductive surface. For example, sensors may be produced by embedding wires into insulating materials and either cutting, polishing or drilling the material to expose the ends of the wires. These wire ends become the sensor elements and the wires themselves provide the leads for connection to measurement systems.

FIGS. 34A to 35B show another variation of a sensor mount in which the sensor 3401 is packaged in MLP style lead frame 3403 with a configurable fluid path. In this embodiment, the sensor can be adhered to an MLP style lead frame device like the SEMPAC MLP5×5-32-OP-01 with a thin layer of adhesive, then wire bonded to the contacts on the left and right sides of the package. Then a dam and fill process can cover/encase the wire bonds. This leaves a clear path across the center of the sensor for mounting a fluid path assembly.

The fluid path assembly may consist of an injection molded plastic with a specific external geometry that allows it to be bonded with adhesive to the sensor face and the MPL package. The mount may include a groove on the side that creates a snapping locking feature for a connector to the MPL package and a shape on either end of the path to attach fittings to the sensor. The external geometry of the mount can also include a series of rack gears or tabs along one of the long sides to be used for actuating the sensor connection in a system for receiving information from the sensor.

Figure 35A:
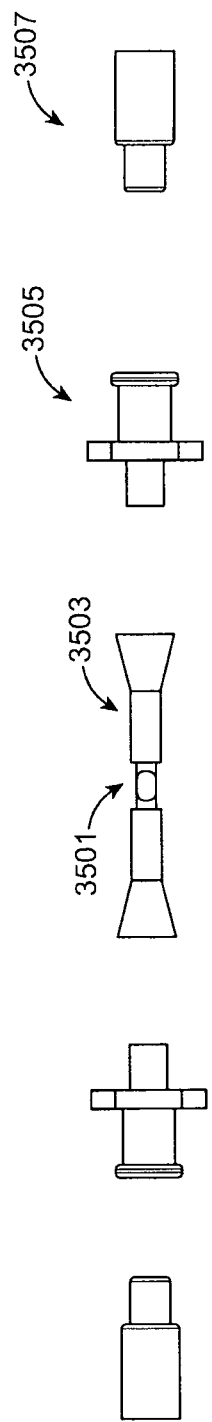
FIGS. 35A-35D show one variation of a connector/mount for use as part of an in-line sensing assembly.
Figure 35B:
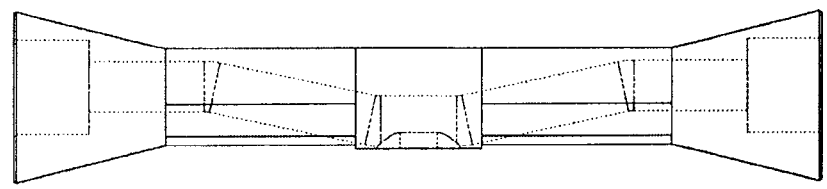
Figure 35C:
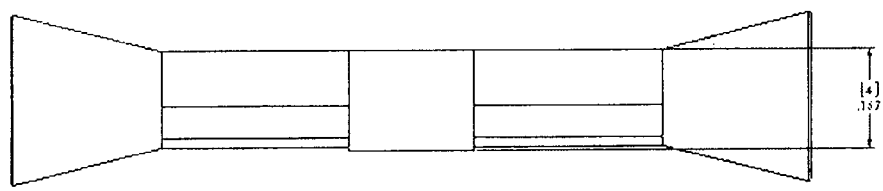
Figure 35D:
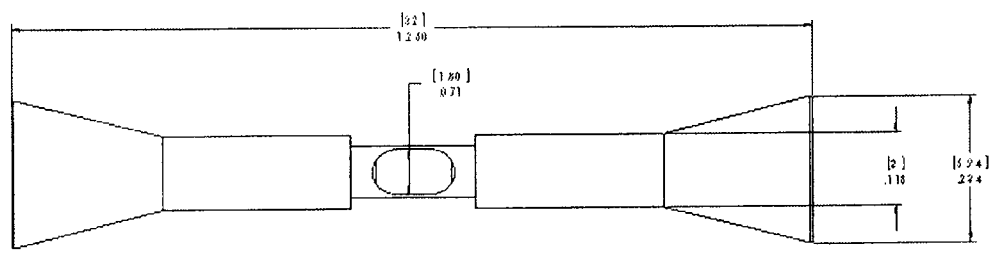

The fittings may be designed to interface with the rest of the system as needed. For example, in some variations the holder may include fittings for connecting the sensor in-line with the fluid path to a patient. Thus, the holder may include luer fittings, plugs, and/or dimensional transitions to help in adapting to IV tubing and to help improve the fluid dynamics of transitions to assure a smooth flow across the sensor. In some variations the internal geometry of the fitting/holder will be configured to allow the fluid access to the sensor element and provide a smooth fluid path, preventing turbulent flow within any tubing or fitting. An example of a connector configured to integrate into a fluid path is shown in FIGS. 35A-35D. In this example, the holder 3503 for holding the sensor 3501 is configured as a tubular (in-line) mount which holds the electrodes of the sensor in contact with fluid flowing through the connector. The ends of the connector are configured to connect to a luer fitting 3505 and via the luer fitting to the end of a piece of tubing (e.g., IV line) 3507. The luer may lock the mount to the tubing in some variations. FIG. 35B shows a partially transparent view of the mount/holder of FIG. 35A, showing the fluid pathway through the mount and past the sensor region in the center. FIG. 35C shows a non-transparent view of the mount/holder, and FIG. 35D shows a top view of the mount.

Figure 36A:
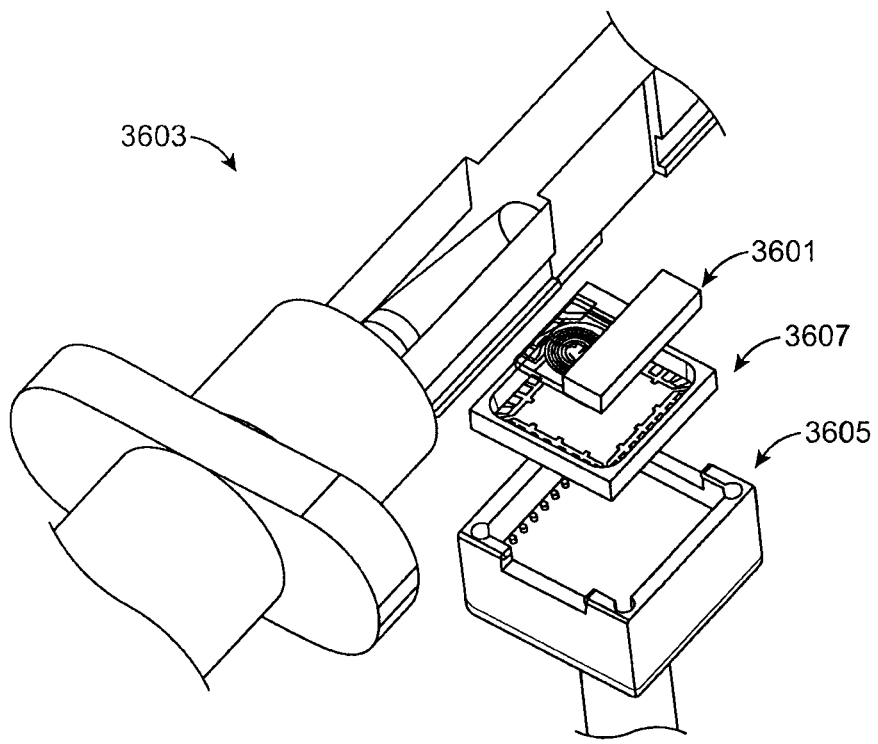
FIGS. 36A and 36B illustrate connection of a sensor to the housing/mount shown in FIG. 35A-35D as well as a connector and locking mechanism for coupling the sensor to the rest of a system for determining liquid composition.
Figure 36B:
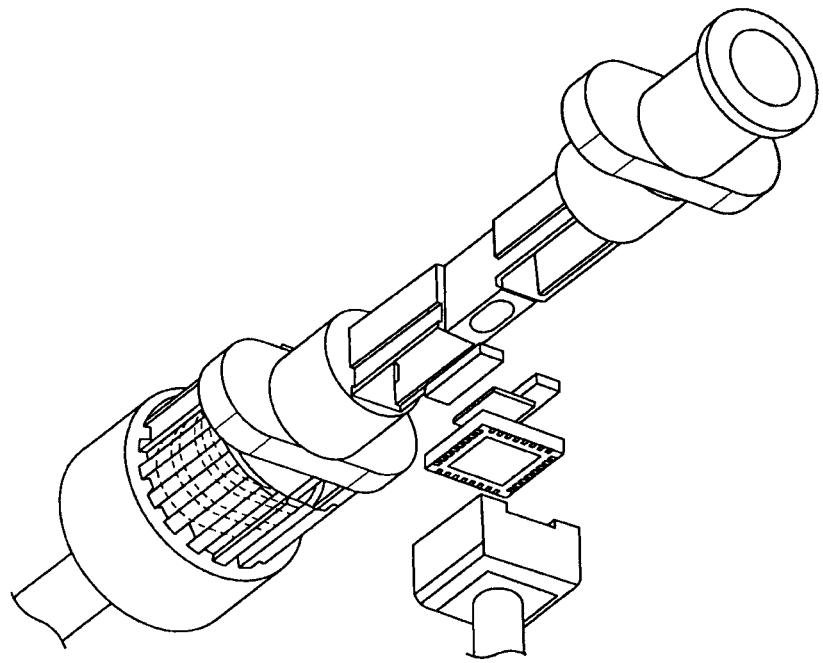

FIGS. 36A and 36B illustrate attachment of the sensor to the mount/holder. A connector 3605 that has a series of pogo style pins can be used to interface to the mounted sensor/fluid interface assembly shown in FIGS. 35A-35D. A locking mechanism 3607 may be included that allows the connector 3605 to locked firmly to the sensor package 3601 and be flexible enough to be removable after use.

Figure 37:
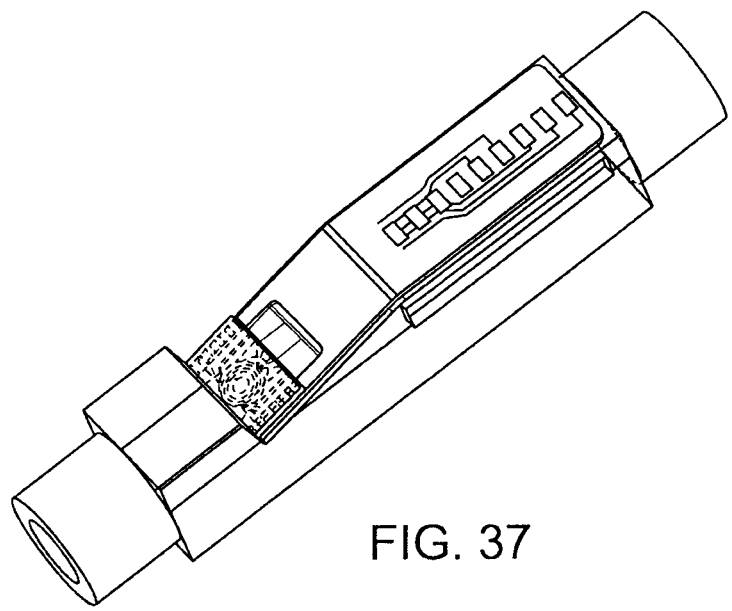
FIG. 37 is another variation of a sensor mount.

FIG. 37 shows another variation of an in-line mount or holder for a sensor to be used as part of a system for determining liquid composition by immittance spectroscopy. In this example, the sensor(s) are held by the mount directly into the fluid path. As in the MLP style mounts described above, direct mounting may be achieved by a central injection molded plastic component that holds the sensor in position. The end interfaces can include an extruded boss of some appropriate diameter and length, rather than just a bore. In general, any appropriate end interface may be used, to allow maximum flexibility when interfacing to any of the various configurations of systems for determining composition and/or IV systems or fluid management devices.

Figure 38:
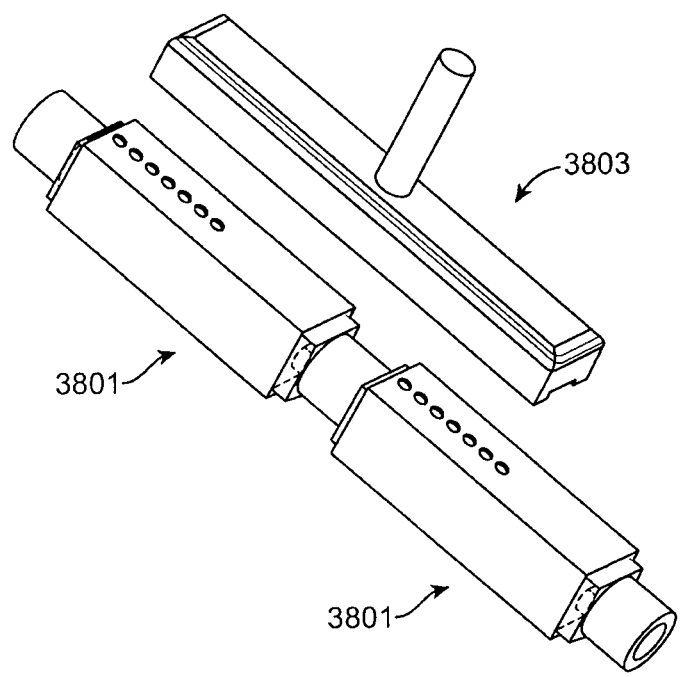
FIG. 38 shows two sensor mounts connected in tandem and an overmolding that may be positioned over the sensor mounts.

In this example, the sensor can be a liquid sensing and/or flow sensing, or both. In some variations, multiple sensors can be used in parallel or in series ("stacked" together). The example show in FIG. 37 may include an overmolding to finalize the liquid seal between the sensor and the fluid path; this overmolding (sleeve, housing, etc.) may also provide contacts and connectors to other system components, and may include added geometry for actuation or sensing purposes. FIG. 38 illustrates one variation of two sensors, each coupled to a connector 3801, and an overmolding 3803 that will couple to both of them; the sensor and holder may snap onto the overmolding to seal the sensors in fluid connection with the internal lumen of the connectors.

Figure 39D:
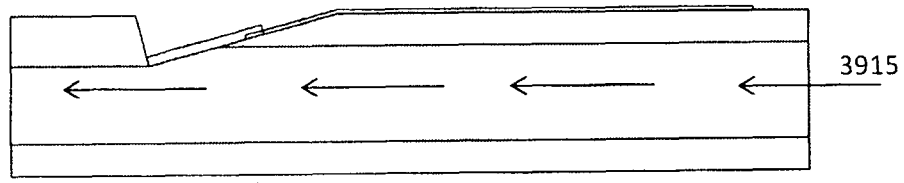
Figure 39E:
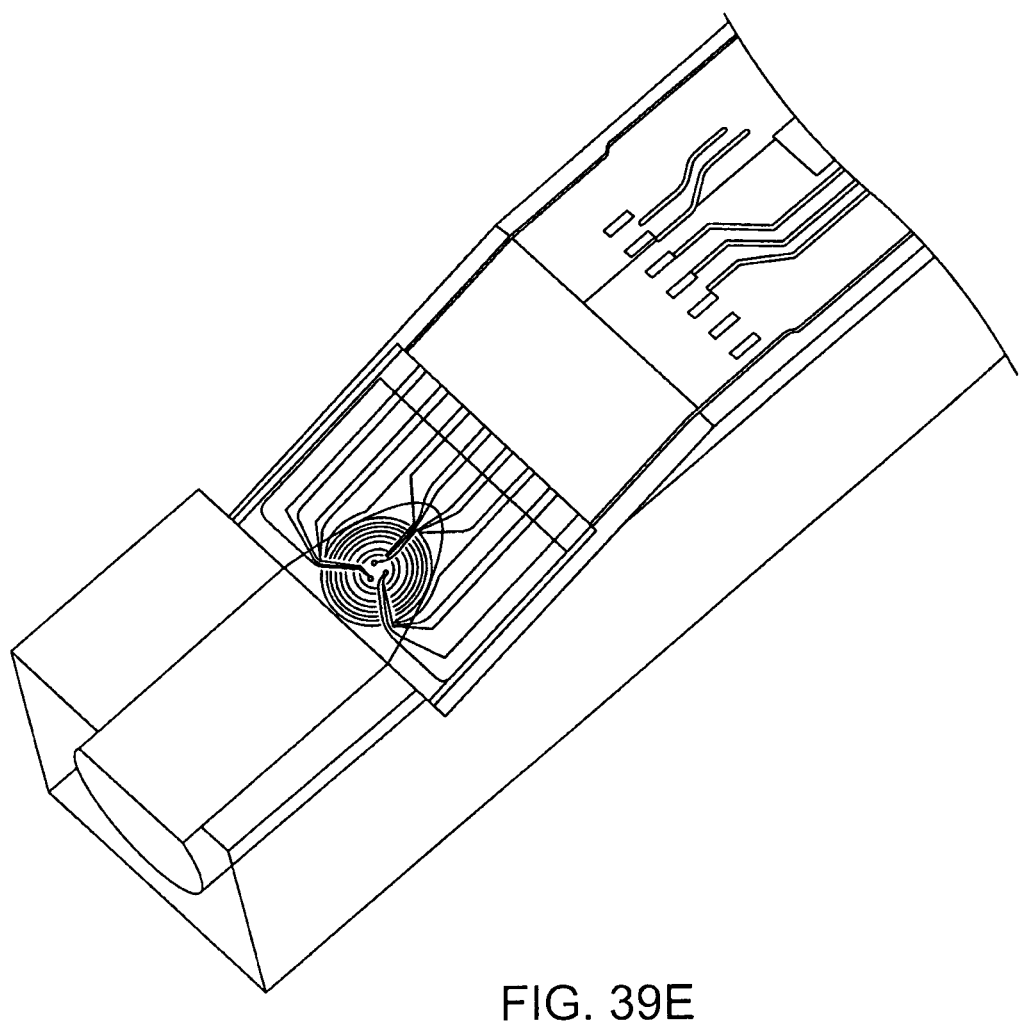
Figure 40:
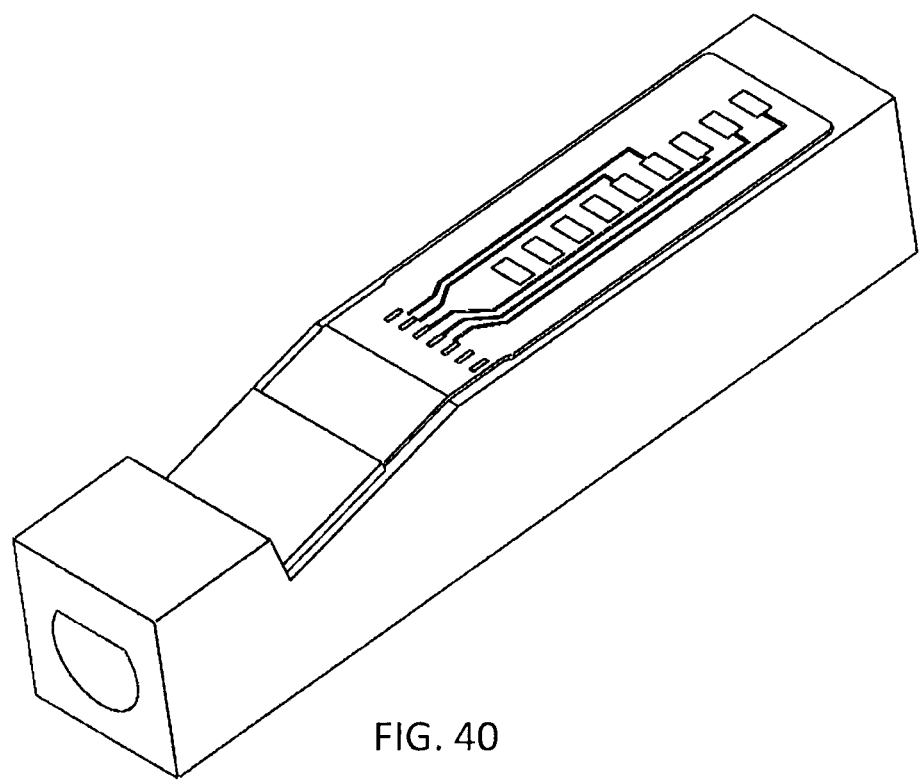
FIG. 40 is another example of a sensor mount.
Figure 41:
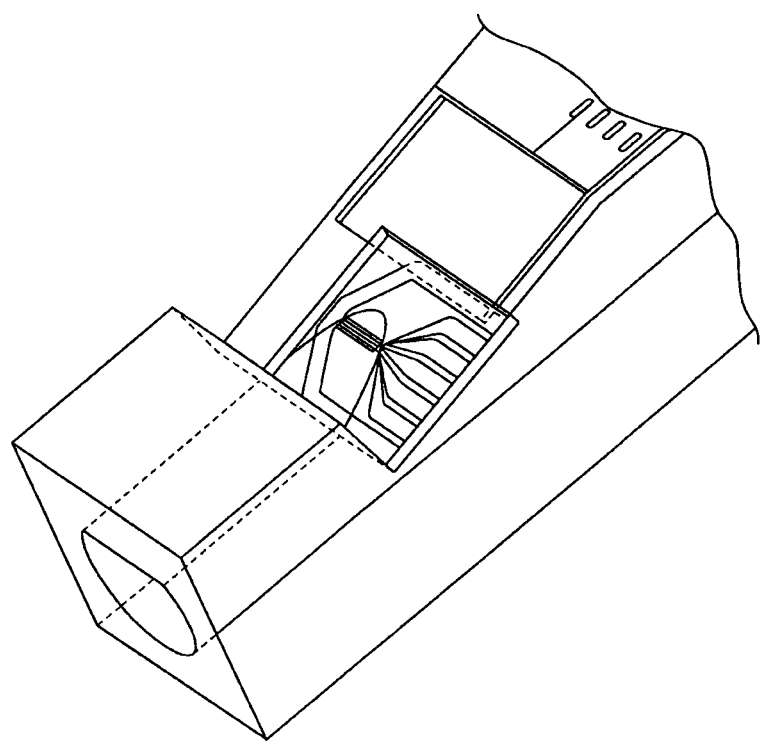
FIG. 41 is an example of a sensor mount and a fluid flow sensor.

A similar example is shown in FIG. 39A-39E. In this embodiment, the sensor can be adhered directly to an injection molded tube (mount) that has the appropriate geometry, face down so that fluid flowing in the lumen of the mount/tube contacts the sensor, similar to the configuration shown in FIG. 37. An adhesive seal around the sensor could create a liquid barrier between the sensor and the tube. FIG. 39D illustrates the direction fluid flow 3915 within the lumen of the mount/tube so that fluid contacts the sensor. Any additional flexible circuits could be coupled (soldered) to the sensor and routed along the long axis of the tube, as shown in FIG. 39E. An overmolding (not shown) can then be applied to this inner assembly to encapsulate the flex circuit and the sensor, and create the final liquid seal allowing fluid flowing in the mount (tube) to contact the sensor. The overmolding and/or mount could also be structured to create keying features for engagement with a reader unit or other system components. This sensor module can then be adhered to or assembled to other instruments to facilitate other fluid dynamic configurations (i.e. a plug on one end for static measurements, tubes on each ends for flow measurements, a spike for IV bag penetrations, etc.). Any appropriate sensor (including low and/or high ionic strength sensors, flow sensors, etc.) may be used with this or any of the mounts described herein. For example, FIG. 41 shows an example of a mounted flow sensor 4103. As mentioned, multiple sensors (including different types of flow sensors) can be attached together to provide fluid ID and flow measurement or be used separately for individual flow or fluid ID measurements.

Figure 42A:
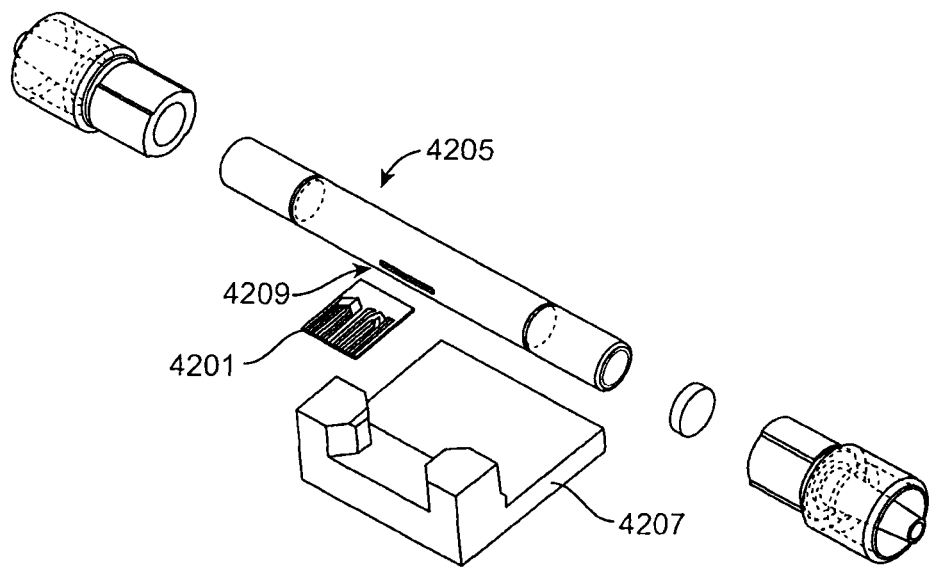
FIGS. 42A-42C illustrate one variation of a sensor mount.
Figure 42B:
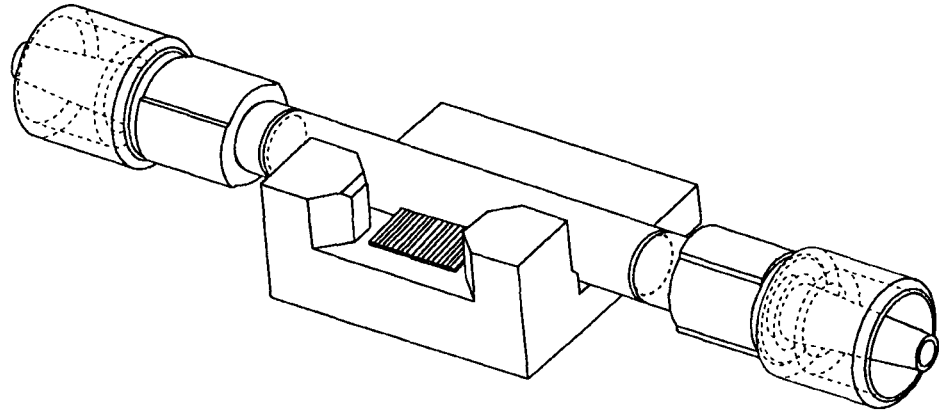
Figure 42C:
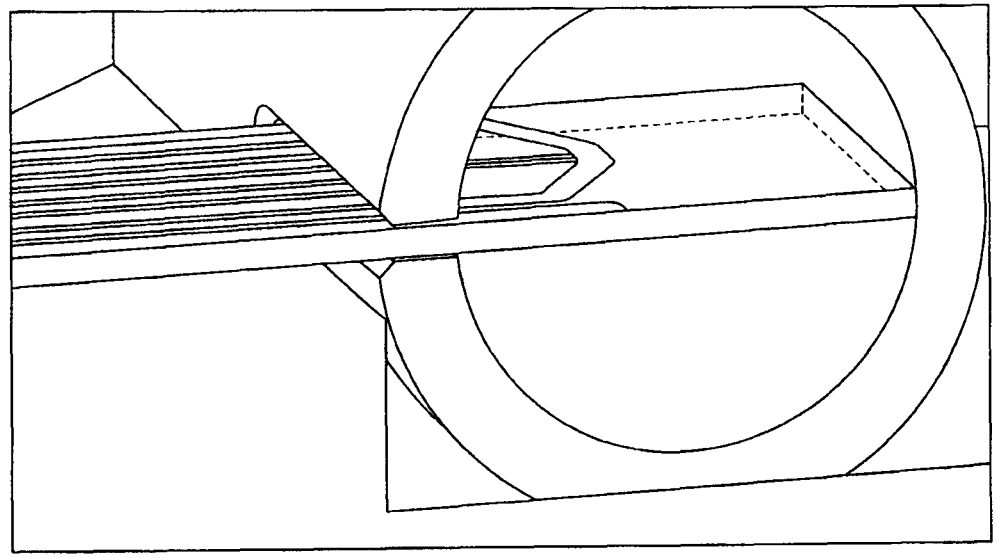
Figure 43A:
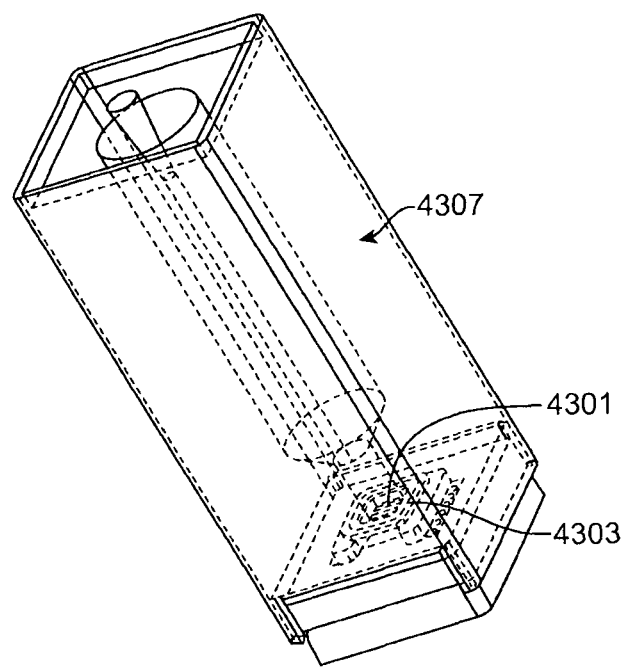
FIGS. 43A-43E show another variation of a sensor mount.
Figure 43B:
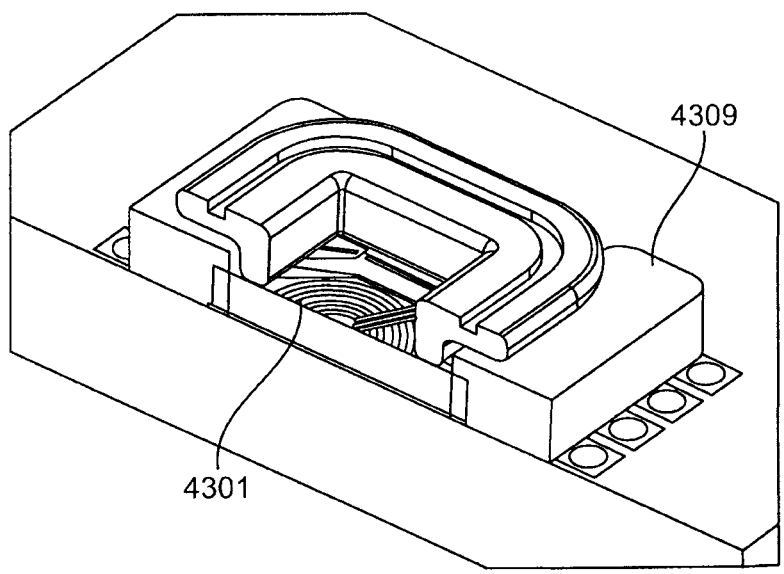
Figure 43C:
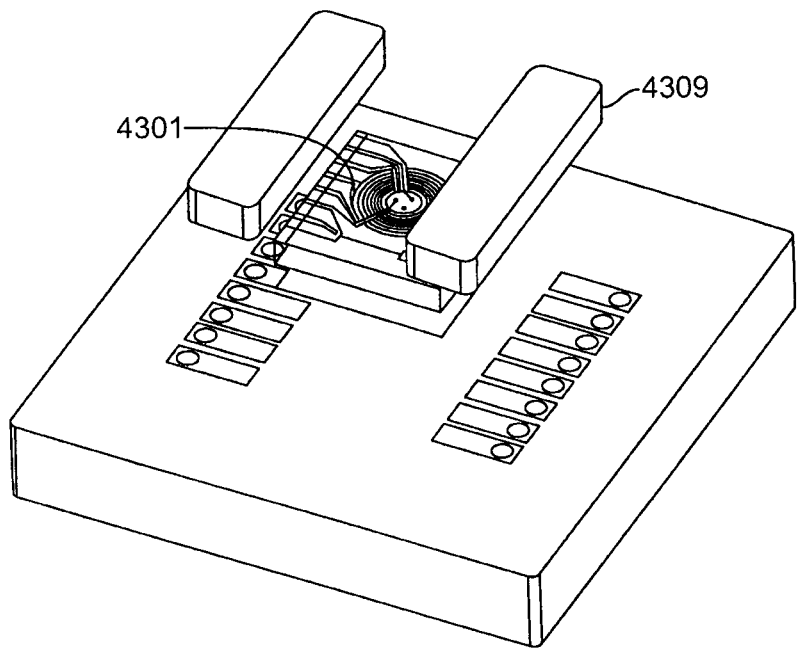
Figure 43D:
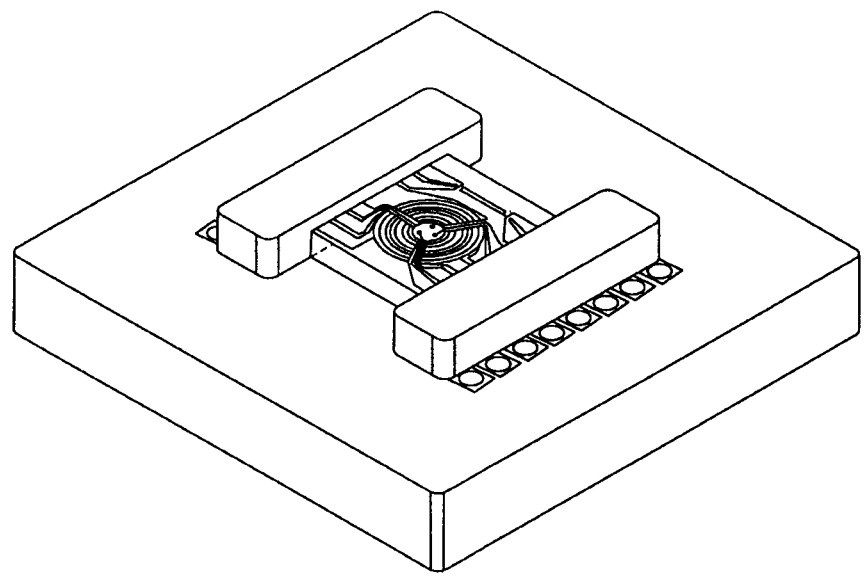
Figure 43E:
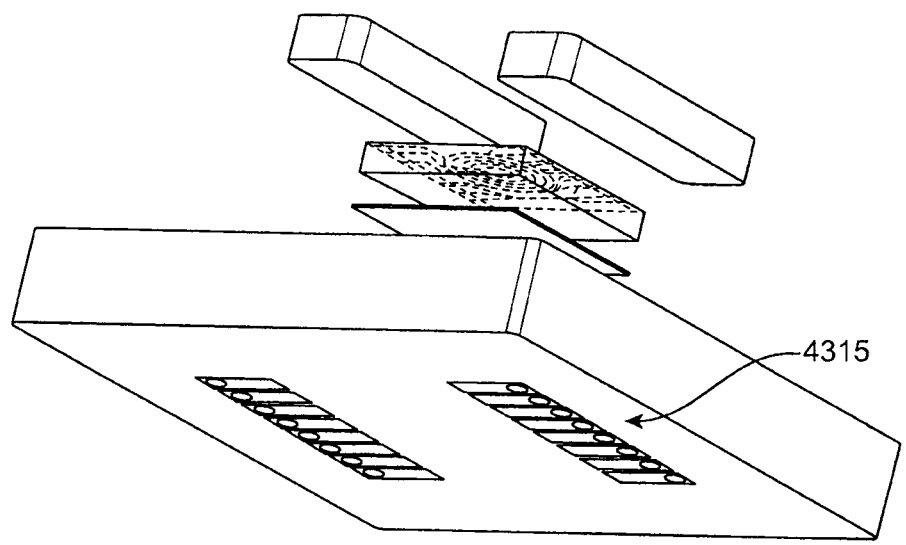

FIGS. 42A-42C show another variation of a sensor and mount configured as a flow cell. In this variation a sensor may be included in a tube for static or flowing measurements. The tube 4205 can be a polypropylene or other appropriate material and (in this example) has a 1/64" slot 4209 machined in the tube extending the length of the sensor 4201 to allow access to the inner diameter. On the outer diameter of the tube and around the slot, a chamfer is machined in with a ball end mill to create a lead in for the sensor 4201 and to provide a small volume for adding adhesive between the sensor and the tube. The ID of the tube in this example is 0.093" and the OD is 0.250". The ends of the tube are threaded with 1/4-28 threads. This threaded connection can adapt to fit many other types of fittings. In one instance, one can attach a luer fitting with the same ID to adapt to a variety of luer fittings all the while minimizing any change in ID during the transition to the tube. In inlet length of the tube can be optimized to allow for turbulent flow to settle in to a more stable flow pattern. The sensor is located in the center of the flow. The sensor is located by carefully inserting the sensor body into the 1/64" slot until it bottoms out on the bottom of the ID. The test sensor is then sealed in place with small "bead" of VAX or UV cured adhesive. A 10-100 μm stainless steel frit can be placed on the inlet of the tube to assist in preventing bubbles and breaking up turbulent flow. A base is included to support the sensor lead frame and provide positioning for use in automation. The exploded view of FIG. 42A is shown assembled in FIG. 42B.

FIG. 42C shows the sensor projecting into the inner diameter of the tube, placing the sensor in contact with the liquid.

Another variation of a sensor mount is shown in FIGS. 43A-43E. This variation is configured as a static fluid sensing element (holder and sensor) that includes a snap-on reservoir and chip-on-board sensor packaging. This configuration is particularly useful for loading of fluid via a needle. In this design, shown assembled in FIG. 43A, the sensor 4301 is attached to a PCB with a slightly elastic die 4309 attach material to allow for mismatched CTE's and geometric imperfections. The die is wire bonded from the contacts on the sensor to Au pads on the PCB. The pads are electrically conductive to corresponding pads 4315 on the back of the PCB through plated vias. The wire bonds are encapsulated with an epoxy or thermoset or other encapsulating material. This assembly can be mounted on to a reservoir 4307 that has an elastomeric seal 4303 co-molded into a body that has a snapping feature. When the sensor package snaps in place, the seal crushes down on to the sensor face creating a liquid tight interface. The reservoir can have a side injection port that will prevent a needle from damaging the sensor. This port can be tapered to allow for a lead in for the needle and taper down to a certain diameter to prevent large needle sizes from extending too far into the body. The post can turn into the central reservoir to deliver the liquid just above the seal and sensor. Air that is displaced by the liquid can be vented through the central reservoir bore. The top can be designed to prevent any spilling while allowing venting of displaced air by addition of frits, one-way valves or small geometries. The top injection port surface may have a small lip to prevent a needle from slipping off. FIGS. 43B-43E illustrate various views showing the assembly of the sensor and mount.

Figure 44A:
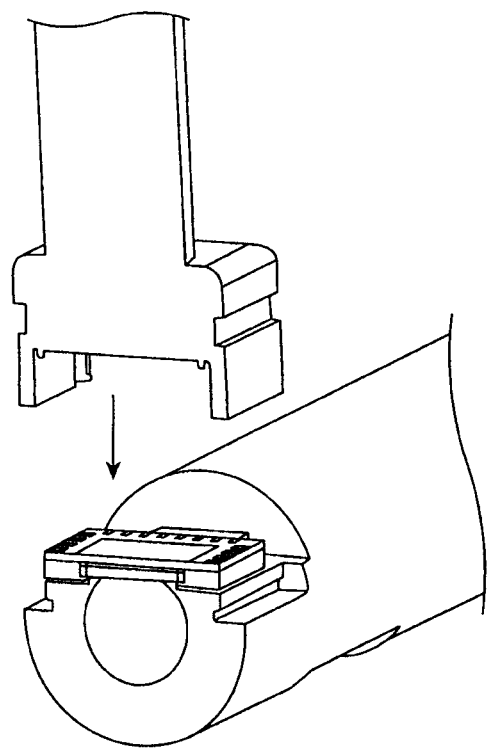
FIGS. 44A-44C show another variation of a sensor mount.
Figure 44B:
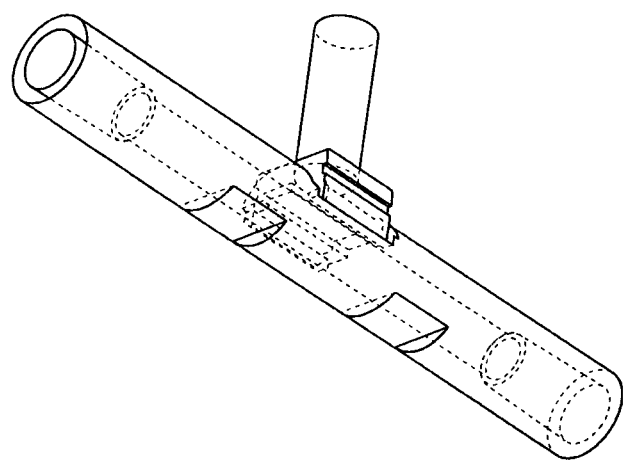
Figure 44C:
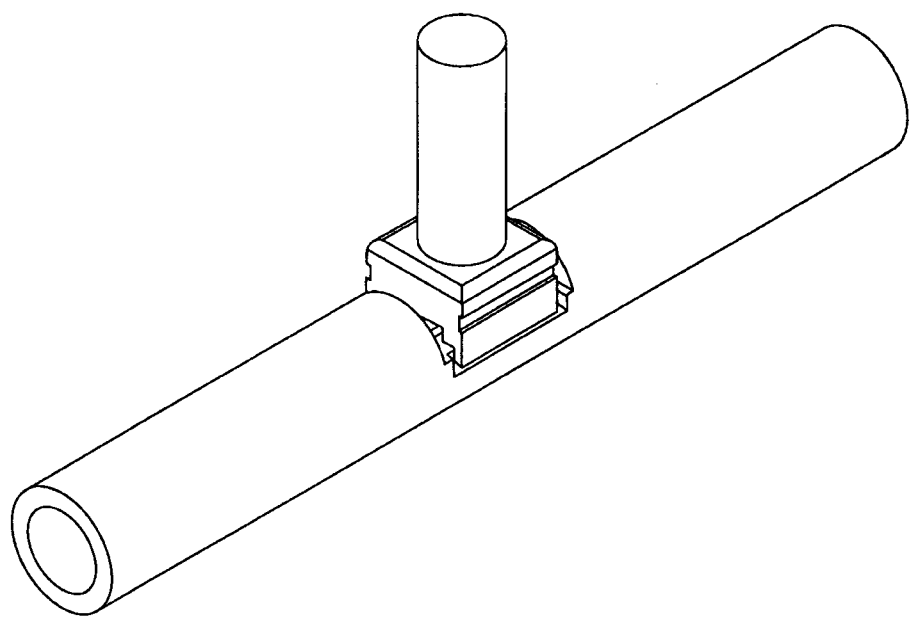

Another example of a sensor configured for use with an IV line or other fluid handling system is illustrated in FIGS. 44A-44C. A flow path made of an appropriate resin for use in health care, injection molding, and bonding to a glass sensor substrate may be used as a mount to attach to a sensor assembly, as illustrated in FIGS. 44A and 44B. In this example, the flow path through the assembly is 1/4" OD with a 3 mm ID. The ends of the tube assembly can have internal female slip luer geometry to accept off-the-shelf fittings that can be attached with adhesive. The 1/4" OD can accept fittings that are made for 1/4" OD tubing. Additionally the 1/4"' OD can have threads that will allow it to adapt to other types of equipment (i.e. 1/4-28 threads in flat bottom ports). The design of the tube may also include external features that will allow for robotic manipulation as well as act as finger holds for users. There may be an opening in the "top" of the tube that will allow the sensor to be oriented horizontally to the flow path. There may also be an adhesive-type of seal to seal against fluid from escaping the fluid path. In some variations the mount assembly may also include a bond of adhesive between the sensor packaging and the tube that is robust to allow the on and off cycle(s) of the connector. If a C-30-10 sensor is used (such as shown on FIGS. 11A, 15A and 17A), one of the dimensions of the sensor may be equal or greater than 3 mm in length to allow for the packaged sensor to span the opening in the tube. The opening may be just large enough to expose the sensor elements to the fluid. The opening can have different opening sizes to accommodate different sensor designs.

The connector can have multiple configurations that allow it to be used with a variety of systems. In one instance, the connector housing may have snap tabs that allow it to attach to a fluid path tube (e.g., IV line). Inside of the connector housing a PCB board may be included that has a series of pogo pins that can be connected to and provide the interface to a cable. In another variation, the internal configuration can have the same PCB and pogo pins, and an interface to another PCB or flex circuit or connector and housing with or without snap tabs. The housing can have external features that allow for robotic or automation manipulation, including coupling sites for robotic manipulators. For example, there may be some non-symmetric geometry in the tube to allow only one way to make a connection. There can be a connector design that allows for easy manipulation by human hands.

The flow characteristics of fluid in this variation is expected to be smooth over the sensor elements for the ranges of 50 to 2000 ml/hr but could perform well in higher and lower flow rates. This is illustrated in FIGS. 45A and 45B, showing the CFD at 50 (top) and 2000 ml/hr (bottom).

FIGS. 18F-18I illustrate other variations of sensor housings which may be used for in-line fluid sensing, similar to those shown in FIGS. 18A-18E. For packaging the sensor into a flow or static cell, a sensor can be incorporated into a mount/housing and provide contact pads to connect the sensor to an external connector of a device. The housing can be a two part injection molded that snaps together with an appropriate sealing material or adhesive between them. Alternatively the housing can be molded to have square or rectangular or circular or another geometric shape that will allow the sensor elements to become wetted and provide a non-turbulent flow across them. The inlet and outlet can have any number of configurations to facilitate connection to common fittings. One configuration may have 1/4"-28 threads on either end of the chamber to adapt to various pump housings, common fittings and other devices.

For example, a sensor could be placed into a machined tube of ~3/16" ID with similar input and output ports as discussed earlier. A 1/64" slot can be cut into the center bore with a countersink chamfer machined at the top of the slot with a ball endmill. The sensor can be placed into the slot and the countersink provides a reservoir to apply an adhesive. The adhesive can be of a certain viscosity to not drip down onto the sensor elements and be a UV cured type appropriate for medical use and can be set quickly. There can be a flat cut into the outside of the tube parallel to the sensor to mount a support bracket to stabilize the sensor, prevent fracture and provide geometry to attach a connector to the sensor leads.

Another version similar to this concept may further reduce the sensor size and allow for greater tolerances of both the flow vessel and sensor assembly. For example, a sensor can be configured to be any of the desired configurations which would be adhered to a corresponding appropriate PBC then wire bonded or ball soldered to contacts on the PCB. This assembly could then be over molded to encapsulate the connections but expose the outgoing contacts on the PCB. The overmolding can have features that would allow for a connector to snap to it to make the connection. This now over molded assembly can be placed into the vessel and bonded in place with a reservoir similar to the above design or sonically welded or other forms of attachment that will hold the two together and create a liquid tight seal. The ID of this design can be 0.093" and have a length to the sensor element from either of the two ends of ~35-40 mm to allow the flow to stabilize and become less turbulent. Less turbulent flow generally creates more robust flow rate measurements. Additionally the fittings attached to both ends can have the same ID to minimize turbulence and jetting of the inlet stream. Smooth transitions between the inlet and outlet fittings create more laminar flow patterns. Additionally, filter elements in the form of frits, filters, fibers, mixers, static mixers and the like can be built into or added to the inlet to break up turbulent flow patterns before coming to the sensing element. Pressure capabilities of this design can be upwards of 50 psi.

Figure 46:
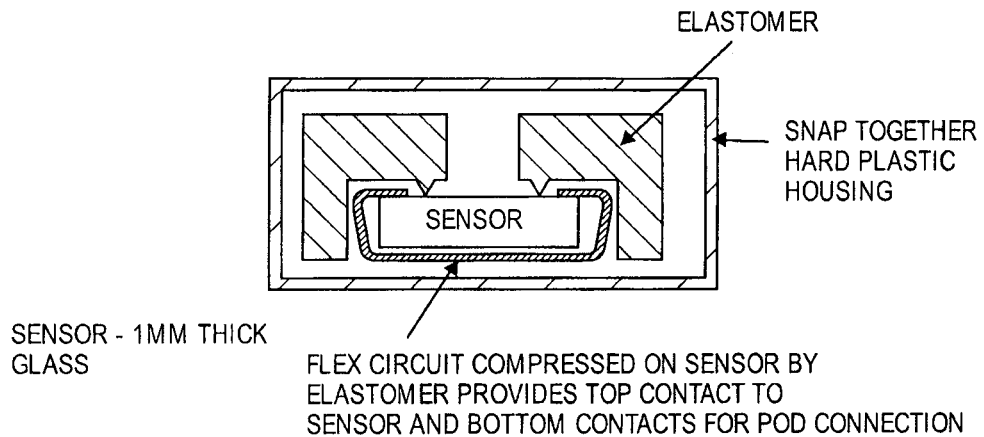
FIG. 46 is another variation of a sensor mount assembly, including an enclosed chamber for loading liquid to be tested.

In some variations, the sensor and a mount may include an elastomeric seal into which fluid may be injected or loaded to take a measurement. In this variation, a needle may be used to inject fluid to be sampled into a chamber or well to contact the sensor. This concept may be particularly useful for static liquid measurement. In one variation a flexible circuit is wrapped around a die and soldered to the contact pads. The bottom of the flexible circuit may have exposed external contact pads. An elastomeric sealing element can be placed on top of the die/flex circuit assembly and then a two-part plastic housing can be snapped together to crush the elastomeric seal against the die and hold the assembly together. The bottom of the plastic can have through holes that expose the contacts. The top of the assembly may have a port for a needle that is off center of the sensor elements. An example of this is illustrated in FIG. 46. Thus, in this example an internal chamber above the sensor may be surrounded by an elastomer and liquid to be sampled may be injected therein.

Figure 47:
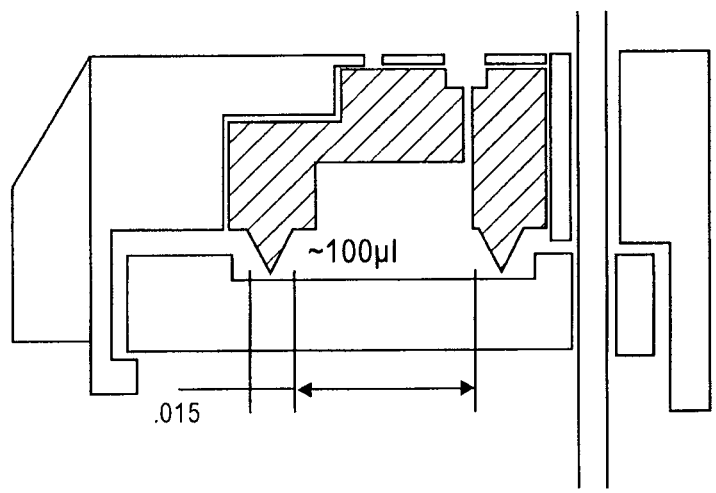
FIG. 47 is another variation of a sensor mount assembly.

FIG. 47 shows another example of a loadable internal chamber, configured as an over molded static cell. In this example, the cell design includes an over molded elastomeric element with polypropylene outer shell. The design may work with a 5×5 mm DLP sensor package as illustrated above, with the dimensions shown in the diagram for the single circular C-30-10 sensor. The elastomer can be a sanoprene or EPDM material or equivalent type of material. The example shown in FIGS. 46 and 47 may utilize the C-30-10 sensor, may have a polyimide or $SiO_2$ dielectric and insulating layer, use the 5×5 DFN constructed using film assisted transfer molding. The elastomeric element can be extended upwards to be used for the septum membrane with the injection port off center to protect the sensor element. There can be a vent hold built into the elastomeric element to vent off trapped air that will become displaced upon injecting the liquid sample. The top of this vent can be a little larger in size and accept a separate porous material that will allow air to escape but retain the sample liquid if tipped over. The datums of the sensor sides will locate the package in the top housing. The sensor package and the top housing can be pushed together and will snap together crushing the seal against the die face and held in place by a locking tab design. The volume of liquid the design can hold in a min of 100 µl and max 1 ml. An alternate to this design is to only have the elastomeric seal be on the bottom and can be simply an o-ring and the septum can be an off-the-shelf type that can be adhered to the housing. A vent for this device may or may not be used. Liquid will fall in a vertical direction upon entry into the vessel and if the vent is not present, the air trapped inside will achieve a higher pressure. This higher pressure may increase the wetting rate of the sensor element. Another variation on this design is to incorporate an existing off-the-shelf design of an elastomeric seal/septum combination like the MERLIN MICROSEAL. If a device like this is used it could be incorporated into an injection molded housing and assembled as described.

Figure 48:
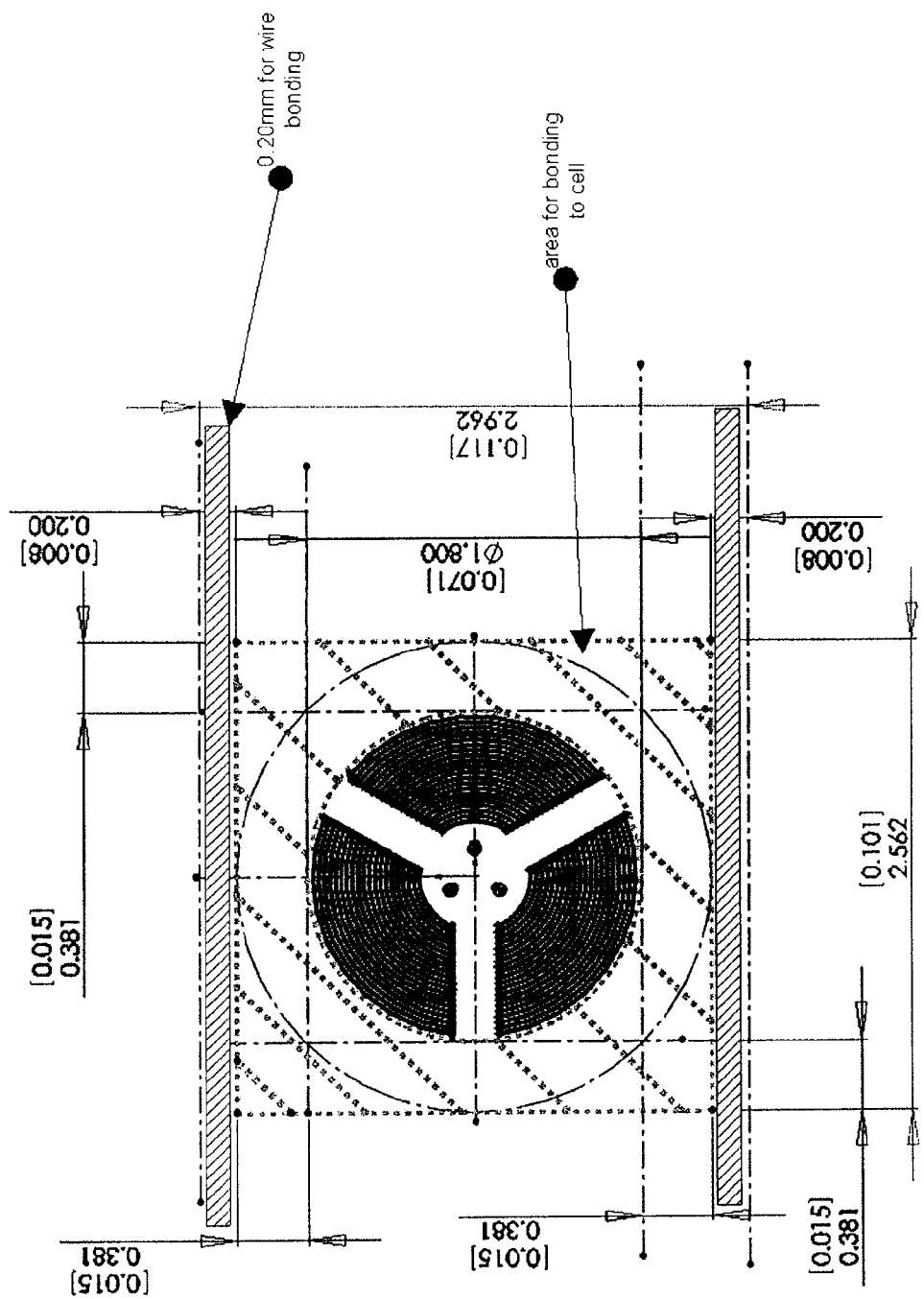
FIG. 48 is a schematic of one variation of a sensor.

FIG. 48 is a schematic of one variation of a sensor that may be used with some of the cells and mounts described herein.

Figure 49A:
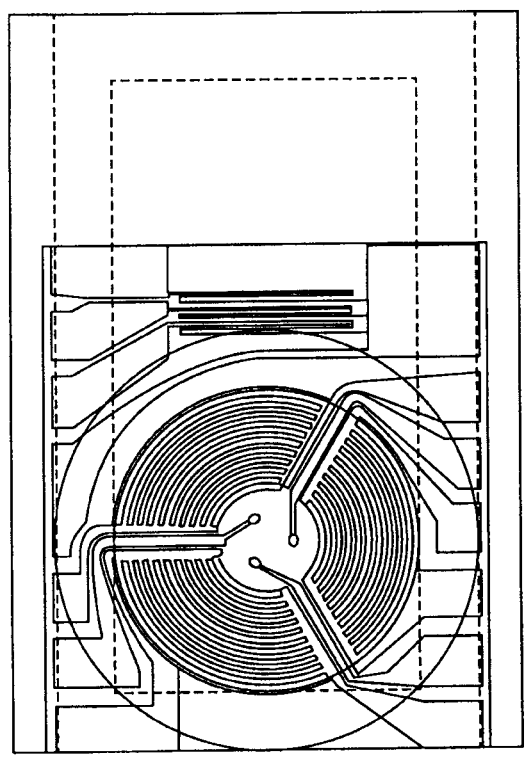
FIGS. 49A and 49B are front and side views, respectively, of one variation of a sensor.
Figure 49B:

In some variations a sealed elastomere chamber may be adapted for use as a flow cell. Thus, the same concepts illustrated in FIGS. 46 and 47 for the static cell above can be translated into a flow cell. The sensor die can be larger (see, e.g., FIGS. 49A and 49B), the same DFN package can be used, and the flow cell may have an angled flow path with a max step height of 0.005" on the inlet and outlet step down to the die from the cell. The elastomeric seal can be an over molded design or an o-ring.

Figure 49C:
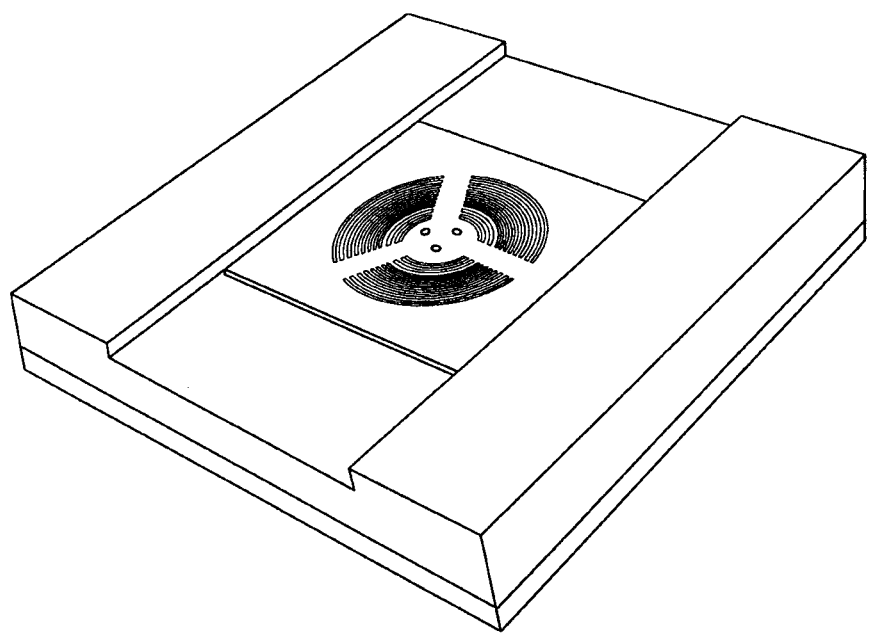
FIG. 49C shows another variation of a sensor mount assembly.

Any of the sensors described herein may also be coupled to a mount or holder (including those described above) and referred to as a sensor "package." The package may give the sensor additional support or protection. For example, FIG. 49 shows one variation of a sensor package. In this example, a static SEA C-30-10 sensor can be packaged on a 5×5 mm DFN design. The die is attached to an etched lead frame, wire bonded and then transfer molded to expose the sensor element (s). The molding in the center of the package is flush with the top of the die and extended upwards on the edges to allow for the wire bonds. The process will be such that the sensor element(s) are not damaged or compromised.

In some variations the sensors are configured as microfluidic cells, similar to the capillary-fed variation shown in FIGS. 27A-27C. In one variation, the sensor and/or mount is configured to provide capillary loading and active heating. In general, any of the sensors described herein may include one or more temperature control elements (including heating elements) for controlling the temperature of the sample. For example, in one variation, a consumable (e.g., disposable) sensor for static fluid measurements can be constructed having a top cup or reservoir, a lower capillary flow path, and the sensor package. Fluid of various temperatures can be added manually or automatically to the reservoir, and then the consumable is placed into a system or device for measuring the composition of the fluid. When placed in position, a heating element may heat the sample to a known temperature and then the fluid identification measurement is taken. The heating system will control temperature and heat the sample to a stable temperature in an appropriate amount of time consistent with the workflow (e.g., within a few seconds or less). The heating element may be an electrical resistive heating element, the temperature of which may be regulated by feedback control.

In one example of a sensor element, an IC packaged sensor can be used in conjunction with a surface (e.g., glass slide) to create capillary action to wet the elements for static measurements. This configuration can fit into the elastomeric sealed static flow cell as described above. For example, a slide may be etched or machined to have a shallow boss on the bottom that will fit into the center of the C-30-10 sensor element or some other configuration that does not interfere with the sensor elements. It can be held in place by a force exerted from the top of the housing and would be inside of the crushed seal. As liquid is added to the cell, it will pool above and on the sides of the slide then and eventually wick underneath the slide to wet the sensor elements.

Figure 50A:
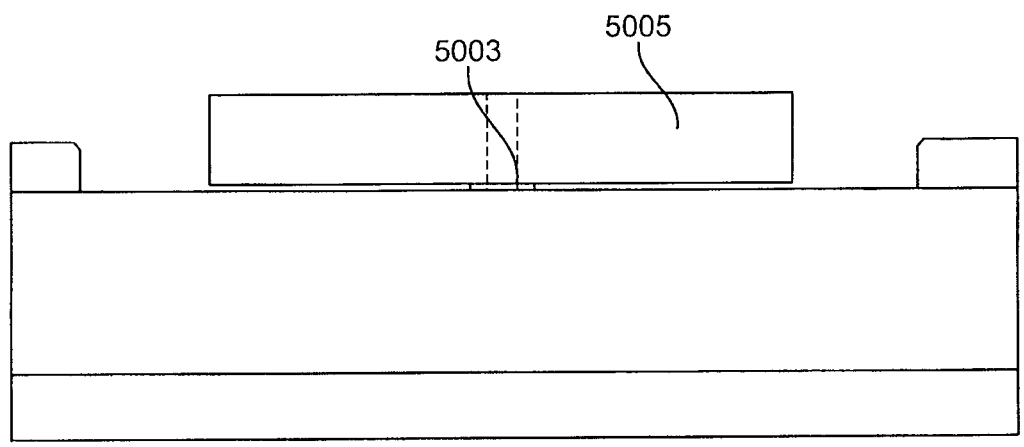
FIGS. 50A and 50B illustrate one variation of a sensor including a protective cover over the electrodes.
Figure 50B:
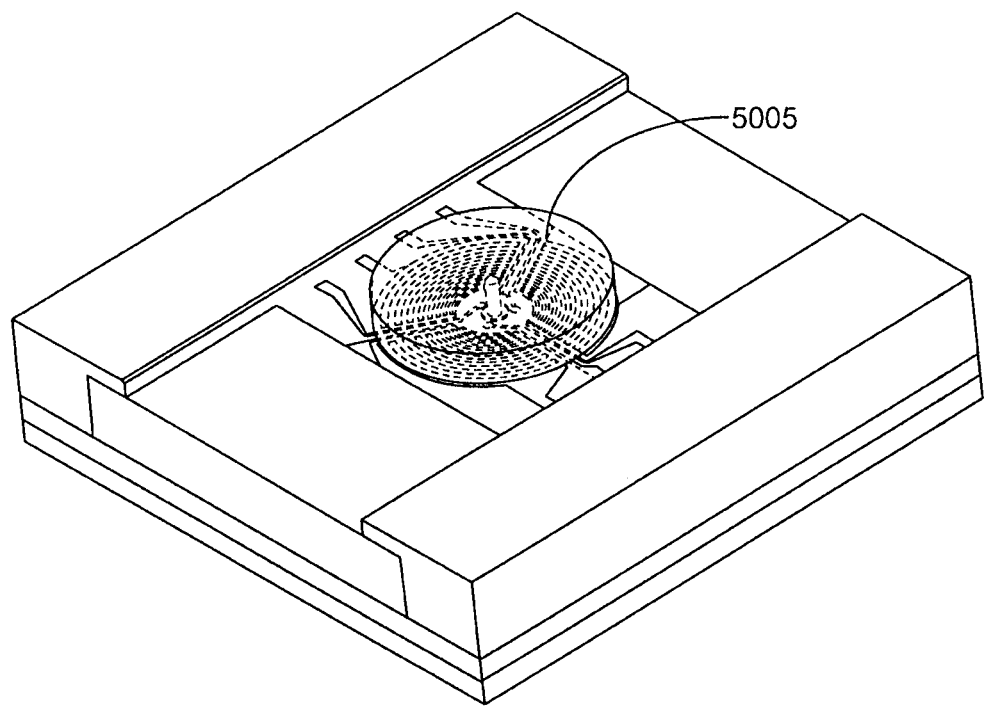
Figure 51:
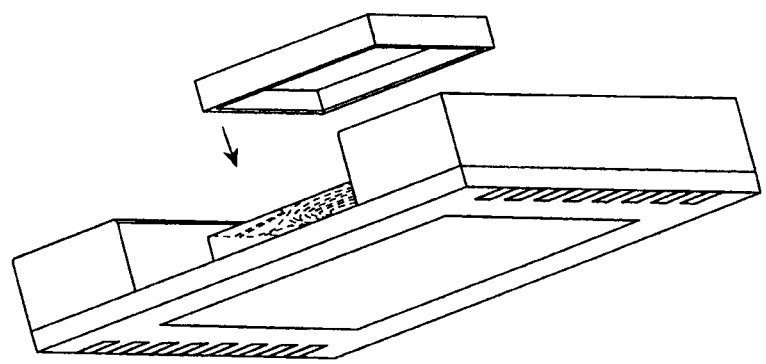
FIG. 51 is another variation of a sensor including a protective covering.

In any of the variations described herein a protective cover may be used over the sensor, including during fabrication. During the manufacturing process, the sensor may become contaminated by the dicing, wire bonding, transfer molding, transportation, storage, etc. In some variations the device is installed with a protective "cap". An example of this configuration is shown in FIGS. 50A-50B. A protective cover or cap 5005 may be made of a low outgassing plastic and be adhered with a temporary water soluble adhesive. An exemplary adhesive such as Aquabond Technologies ABS-55 or equivalent may be used. At the end of the sensor packaging process and just before combining the sensor (package) with a cell, the adhesive can be removed and cleaned off. The same idea can be implemented with sheets of material like Kapton that can be adhered to the wafer before processing.

Any of the systems described herein may be automated. For example, a modular automation platform may consist of a lower support frame and table top, a top frame, and a hood on top of the top frame. The lower support frame can house automation equipment, power supplies, liquid handling equipment, data acquisition, computers and the like. The tabletop can sit on top of the lower frame and can support the automation robots. The upper frame can have either sealed doors, windows, gloved ports, sliding doors or a combination of these. Insulation can also be added to the interior of the upper frame to stabilize temperatures. The upper hood can provide an ISO 5 (Class 100) environment and provide temperature control by taking air in from the environment, pushing it through a series of HEX units and/or heating elements and then through a series of HEPA filters. This makes a self-contained, clean, temperature controlled environment for library generation.

One variation of a sensor and housing is a stand-alone, pogo pin static cell. For example, a cell can be built that consists of a clam shell that can clamp against the sensor and create a seal with a small amount of adhesive or gasket material at the bottom of the sensor and be held together with bolts or by other fastening means. The sensor would be vertical in the cavity or cup that would face upward. One side of the cell would create a backing to the integrated lead frame. A pogo pin style connector can be mounted perpendicular to the cell on a linear slide or linear guide. When a measurement is needed to be made, liquid is added to the cup and the connector pushed in to contact the cell.

The sensors described herein are described using polyimide as part of the materials for fabrication the electrodes. In some variations one or more $SiO_2$ layers may be used instead or in addition. An alternate design to construct the sensor may include a layer of $SiO_2$ that can be utilized for a dielectric and protective layer instead of polyimide. The design would include the same geometry and features as any of the designs previous to this date. The differences would be etching down an appropriate distance into the substrate (glass, Si, etc.) to create the channels. Then a layer of $SiO_2$ can be applied next. Next, the metals can be deposited in the appropriate thicknesses and locations in the channels. The contact pads can be different thicknesses to accommodate wire bonding.

As mentioned, in some variations the sensors include a RTD or temperature sensor. For example, a sensor with a liquid sensing pattern can be built with an RTD or temperature sensor right next to it on the die to sense the liquid temperature. When the measurement is taken, the drug, drug concentration, diluent and temperature can be compared against the appropriate library.

In general, any of the devices, systems and sensor packages described herein may include or be operated with multiple sensors. For example, a sensor design can incorporate single or multiple sensor types and configurations. All of the supporting equipment (cables, connectors, electronics, software, etc.) can be configured to support the sensor designs.

Exemplary Systems

This technology has been shown to identify fluids based on a pattern formed by the response of a set of electrodes of different metals and geometries measured over a range of frequencies. This technology provides the ability to generate a pattern for a given fluid and to later recognize that pattern, and it can be applied to all areas in which Intravenous fluids and drugs are prepared and utilized. Applications of this technology to IV fluid management include all areas where IV drugs are produced, mixed, validated, dispensed and disposed of.

Thus, a system for performing immittance spectroscopy to determine the composition of a liquid may be used at virtually any stage of preparing, storing, using and disposing of liquid compositions, and particularly IV drug solutions. For example, during the preparation of an IV drug solution, a system using immittance spectroscopy to determine the composition of a liquid may be used to confirm or test that a prepared drug solution actually corresponds to what was intended to be prepared; both the identity of any drugs as well as their concentrations may be determined. Systems for confirming or checking the composition of prepared IV drugs may be referred to herein as "IV check systems." Preparation of IV drug solutions may be monitored continuously during the manufacture process, or IV drug preparation solutions may be monitored discretely.

During the delivery of a drug, the IV drug solution may be checked or monitored to confirm that it corresponds to an actual prescribed drug for a particular patient. Such systems may be referred to as "IV delivery systems". In some variations the IV delivery system may control the delivery to turn on, off, or control the rate of delivery of the IV drug solution. Thus, in some variations the system may be part of or may otherwise control the actual delivery of the IV, for example by being connected to an IV pump. In some variations the system is configured to simply sample and report (including giving warnings) on the composition of the drug being delivered.

Finally, a system for determining the composition of a liquid may be used for managing and regulating drug storage and/or waste handling, and may be referred to as "IV waste/diversion detection" systems.

Descriptions, variations and modification of each of these systems are described in greater detail below. As previously mentioned, any of these systems may include any of the features or elements described herein, including elements described with reference to other systems. In particular, the sensors, including low ionic strength sensors and combined low/high ionic strength sensors, sensor mount/housings, and the pattern recognition methods, devices and systems described herein may be used with any of these system variations.

A. IV Check Systems

IV check systems to confirm that a pharmacist, automated (robotic) system or other drug preparer is compounding the correct IV drugs may generally include one or more sensors including a plurality of electrode pairs for generating an immittance spectrographic 'fingerprint' for the solution being sampled, and compare the fingerprint to a library of known drugs (at various concentrations) to determine/confirm the identity of the solution. Any of these system may identify the compound in solution or may indicate that it was not able to identify it (i.e., that it was not among the list of drugs/compositions that the system can recognize). In some variations the system also indicates the concentration.

Pharmacy operators are continuing to automate and the trend in the coming years will be for more automated counting and dispensing devices, more robotics, more central fulfillment facilities and the addition of automated workflow systems. All these systems are greatly dependent on manual data entry and thus prone to operator errors, potentially automatically replicating, multiplying and propagating an error upstream of the automation, for example an erroneous or mislabeled stock supply.

Automated Workflow Systems and Automation Pharmacy Management Systems rely on IT technologies and when it comes to IV medications have no capability to verify that the tracked drug is actually present in the solution. The immittance sensing systems described herein may provide an objective empirical way of identifying drugs as they are moved through the pharmacy and the rest of the hospital. The example of systems that would greatly benefit from this sensor technology include but are not limited to AutoMed, Innovation Associates, McKesson, DoseEdge, ScriptPro, BDProtect, Omnicell, Infosys, MedAnalytics Service® and Pyxis® MedStation® System by CareFusion and others.

The principle deficiency in Automated Robotic Systems is that they cannot identify stock solutions and composition of the fluid in the compounded bags. The immittance sensing systems described herein may provide an objective empirical way of identifying stock solutions and checking the compounded products. The example of systems that would greatly benefit from this sensor technology include but are not limited to AutoMed, Innovation Associates, Parata Systems, McKesson APS, ScriptPro, Vanguard Medical Systems, Riva, Health Robotics, Gri-fill 3.0 by Grifols and others.

The immittance sensing systems described herein may also be applicable to various dispensing systems, particularly in anesthesia where drug diversion as well as precise dosage is particularly problematic and independent verification would be crucial. Examples of systems which could benefit from this sensor technology include but are not limited to Omnicell's Anesthesia Workstation™ and Anesthesia Tabletop™, Pyxis® Anesthesia System, Pyxis® CIISafe™ System by CareFusion and others.

Figure 52:
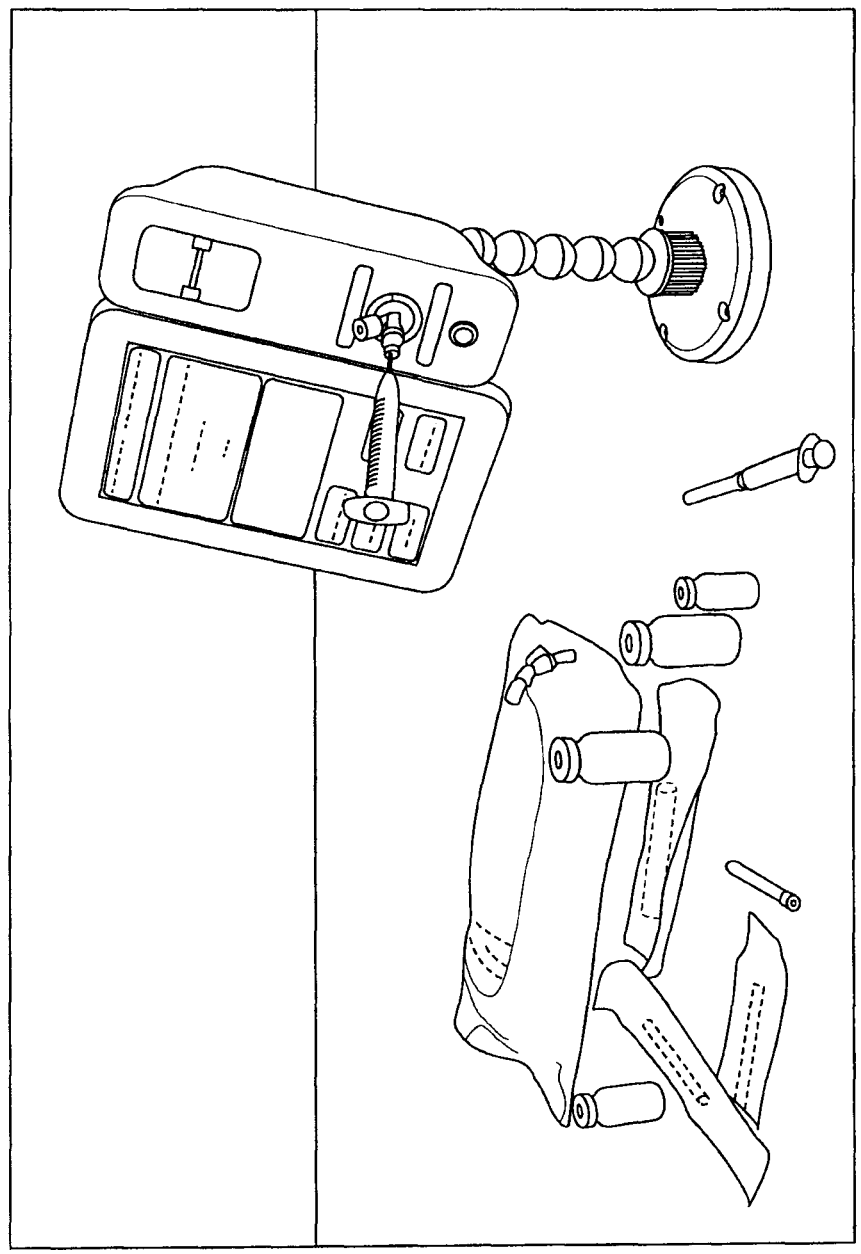
FIGS. 52, 53 and 54 illustrate one variation of an IV check system, as described herein.
Figure 53:
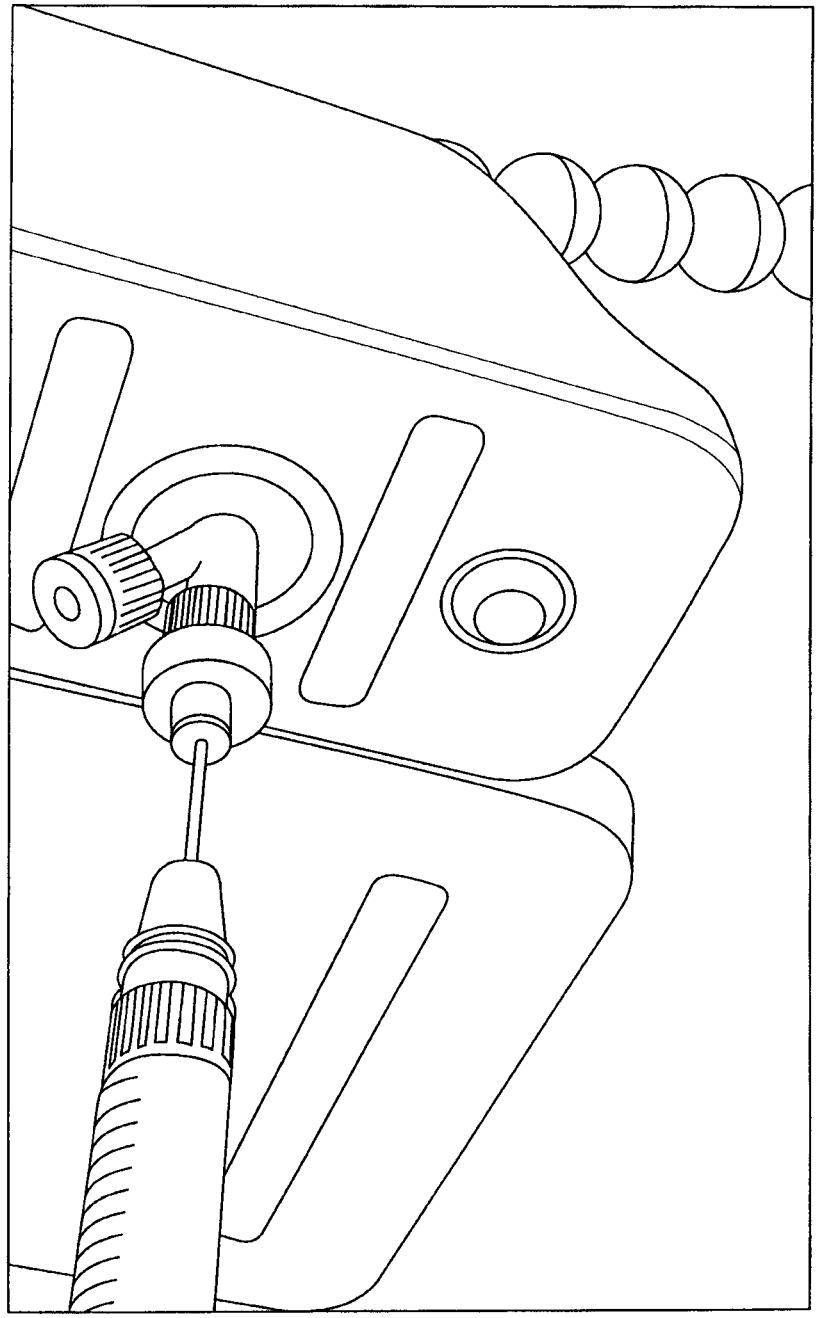
Figure 54:
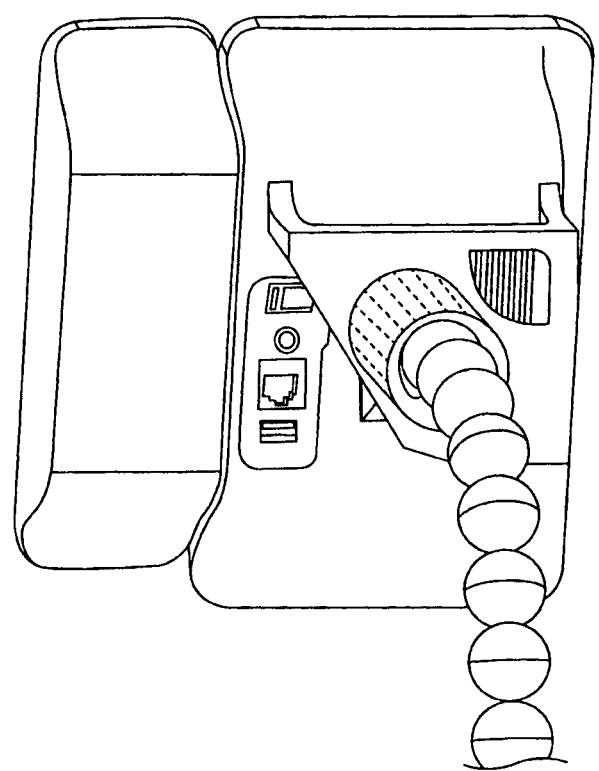

FIGS. 52-54 illustrate one variation of an IV Check system. In this example, the system is configured to receive samples injected into a sample port (see, e.g., FIG. 53), and includes a biometic ID system to confirm the user identity. A touch screen provides immediate feedback as samples are tested. The sample port may feed into a sensor and housing/holder, and particularly the static sample holders (sensor mount, assemblies or packaging) described above. The sensor element may be reusable or disposable, or semi-disposable. The device may be configured to stand or mount onto a desktop or bench top, and may communicate with a remote system including the processor for comparing the sampled immittance fingerprint with the library of known compounds (including identity and concentrations).

Figures 55A, 55B:
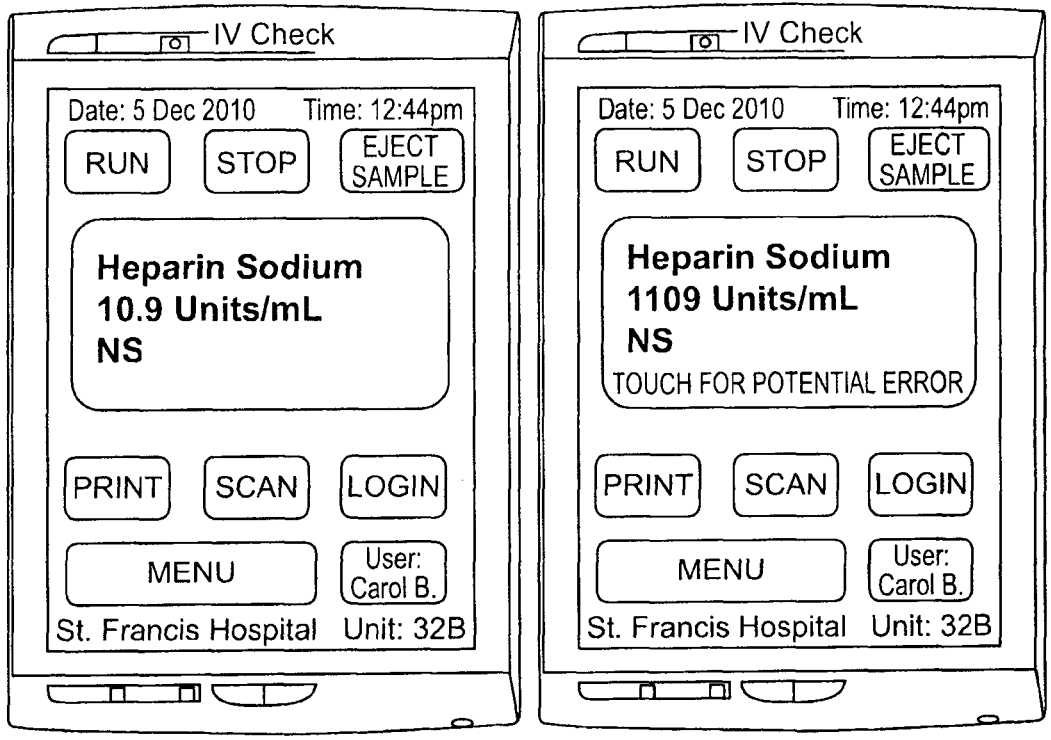
FIGS. 55A-C show exemplary screens for an IV check system.
Figure 55C:
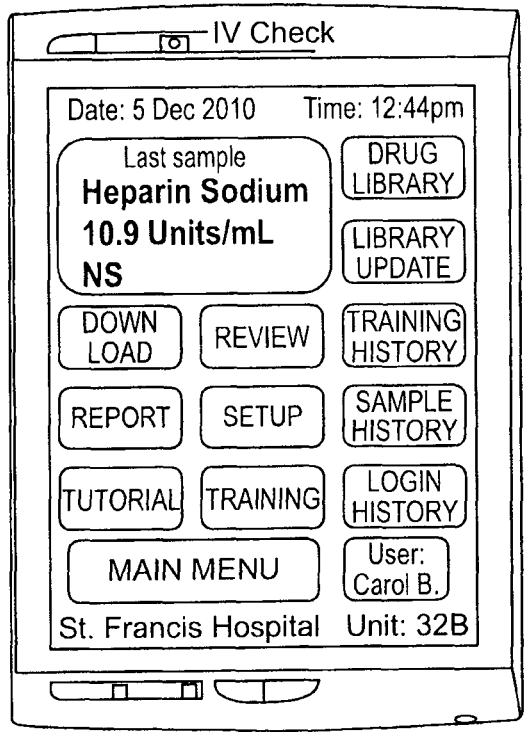

The user interface may include a number of user-driven and interactive screens, as illustrated in FIGS. 55A-C and 56. For example, FIG. 55A shows a main screen indicating the date/time, user, and other identifying information, including an immediate identification screen showing the identified composition of the sample. If the detected concentration for a particular composition is outside of a presumed safety range, the system may indicate this with a "potential error screen" as illustrated in FIG. 55B. Additional menu screens, including those shown in FIG. 55C, may indicate system controls and history of use.

Figure 56:
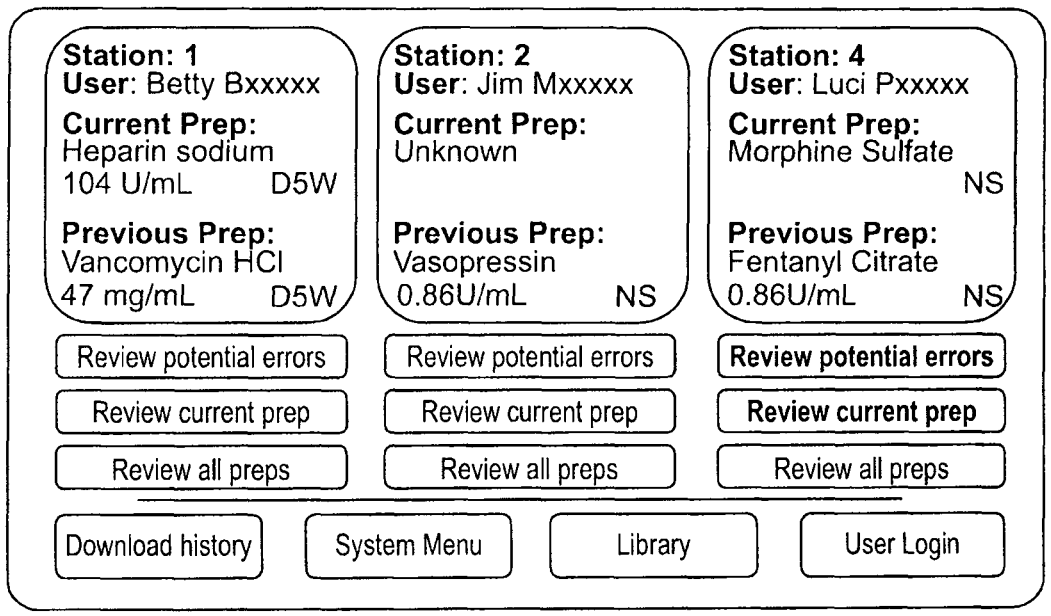
FIG. 56 is another exemplary screen for an IV check system.

The system may also receive and/or coordinate information for a number of different users and/or different units; different units may be slaved to a master controller, or may each act as a master, and coordinate information between them. For example, FIG. 56 shows an exemplary "dashboard" screen allowing a user (or "super user") to check the activity and/or history of a number of different units and/or users.

Figure 66A:
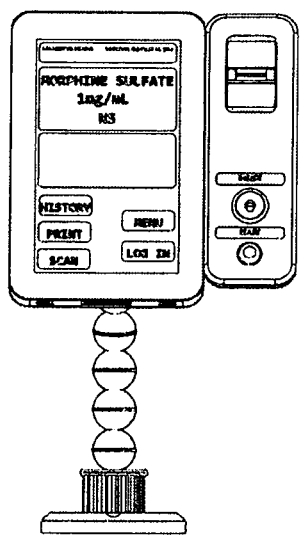
FIGS. 66A to 66C show front, side perspective and side views, respectively, of another variation of an IV check system.
Figure 66B:
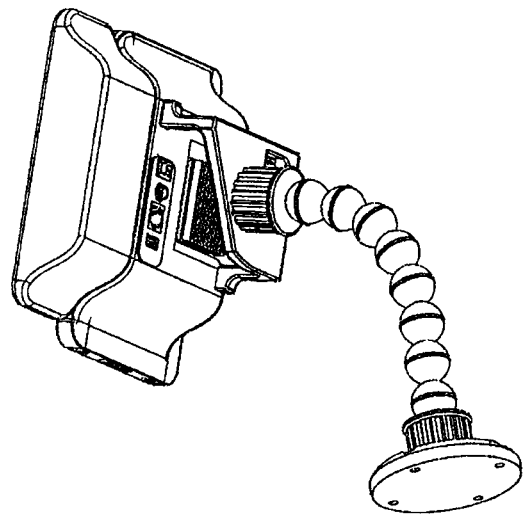
Figure 66C:
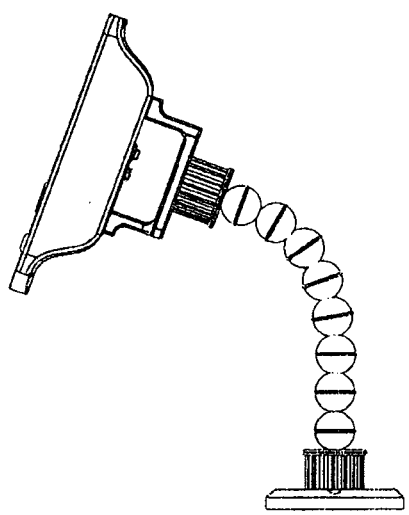

As illustrated in FIGS. 66A-66C, an IV check system may include a main touchscreen (like a Samsung Galaxy Tab), a back case that houses the main electronics, heat sinks and power and signal interfaces, a side module that housed the sensor interface mechanism(s), signal conditioning electronics, and some user interfaces (like the sensor insertion port, the start button and a biometric id device or a scroll/menu button) and a flexible stand and mounting brackets. The side module is configurable to allow for automation of the disposable sensor elements or for single use manually loaded sensors. It can also be left or right handed for user comfort. The flexible stand is also configurable and can be mounted on table tops, walls or ceilings.

Figure 57:
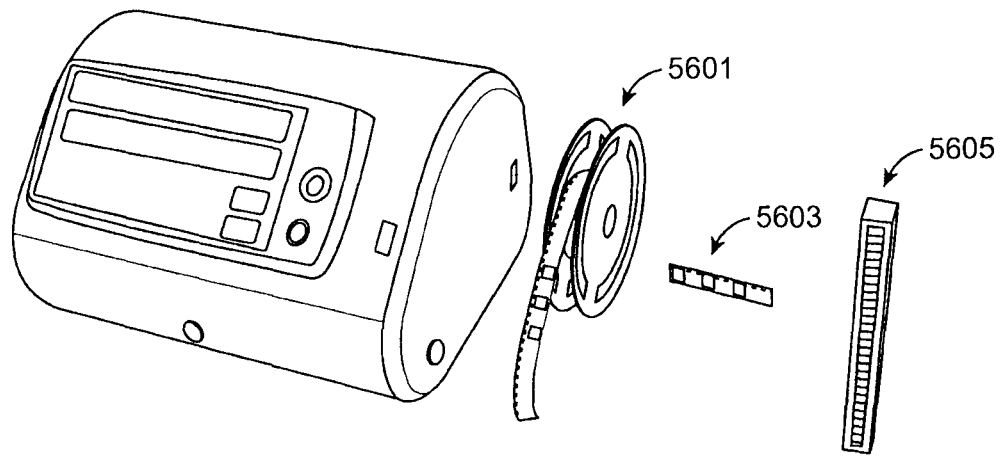
Figure 60:
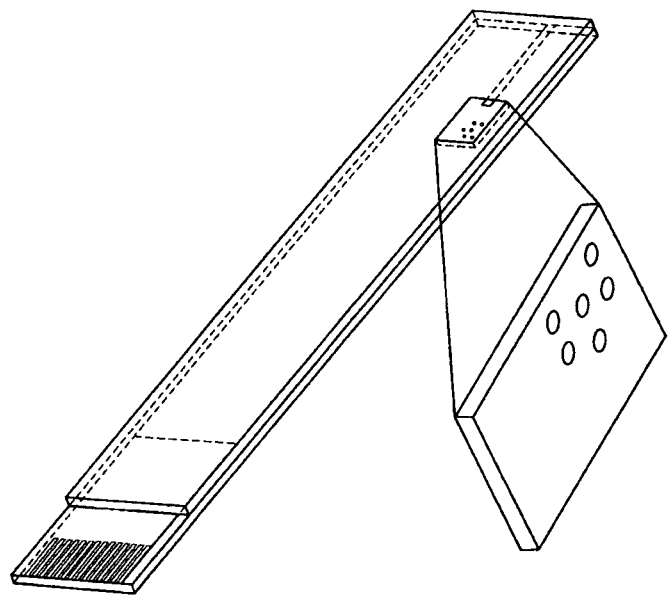
FIG. 60 illustrates a sensor strip for use with the system of FIG. 59.

Other configurations of IV Check systems may also be used. For example, an economical and easy to use device for insuring safe IV preparation may have a sample interface that fits in the pharmacy work flow and is inexpensive the manufacture. Thus, an IV check device concepts may be configured similarly to IC packaging (e.g., FIGS. 57-58) and glucose monitoring (FIGS. 59-60). Both of these concepts are currently in use for very high volume products that provide a low cost package and a low cost disposable. Devices and configurations for either basic approach were also modeled.

For example, an IC-based system may include a sensor roll 5601, sensor strip 5603, or sensor cartridge 5605 for use in the system base. An alternative embodiment is shown in FIG. 58, which was previously described for a static sampling sensor showing a sensor and housing/mount forming a well 5803 and sensor pads 5805 within the well.

Figure 61:
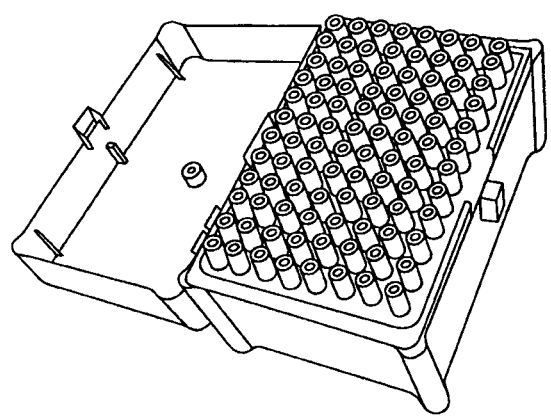
FIG. 61 shows a package of sensor tips for use with an IV check system as described herein.

FIGS. 59 and 60 illustrate alternative variations including the use of a sensor strip that can be dipped into a prepared solution, or that may include a needle or other sharp tip for puncturing a sampling chamber of a bag (e.g., IV bag) to draw a sample into the sensor chamber for testing when the sensor housing (e.g., sensor strip 5901 in FIG. 59) is inserted into the base unit 5903 in the appropriate slot 5905. The sensor strip may be a capillary strip as previously described, and shown in FIG. 61. The system shown in FIGS. 59 and 60 are utilizing capillary effects for loading the sample with a probe remote from the processor box on a short cable as a small hand held (even pen size) probe. This could include a probe the size of lab pipettor or smaller connected by a short cable. The sensor elements (which could include a small needle or other method to sample the bag) could be in a holder similar to how pipettor tips are sold, as shown in FIG. 61. The handheld device would just snap a tip on from a holder array, puncture the bag access point to draw in a sample and then after reading, eject the tip into a waste container just as is done with pipettor tips. This way, there is less issue with needle sticks and the entire set of sensor tips can be sterilized and will not be exposed until loaded.

The sensor elements can include a means of accessing fluid in an IV bag (small needle, etc.) which can include a retracting cover mechanism like those used on some needles, catheters and syringes to make it safer for the user.

As mentioned above, any of these variations may include temperature sensing and/or control to allow compensation for variations in fluid temperature.

Figure 62:
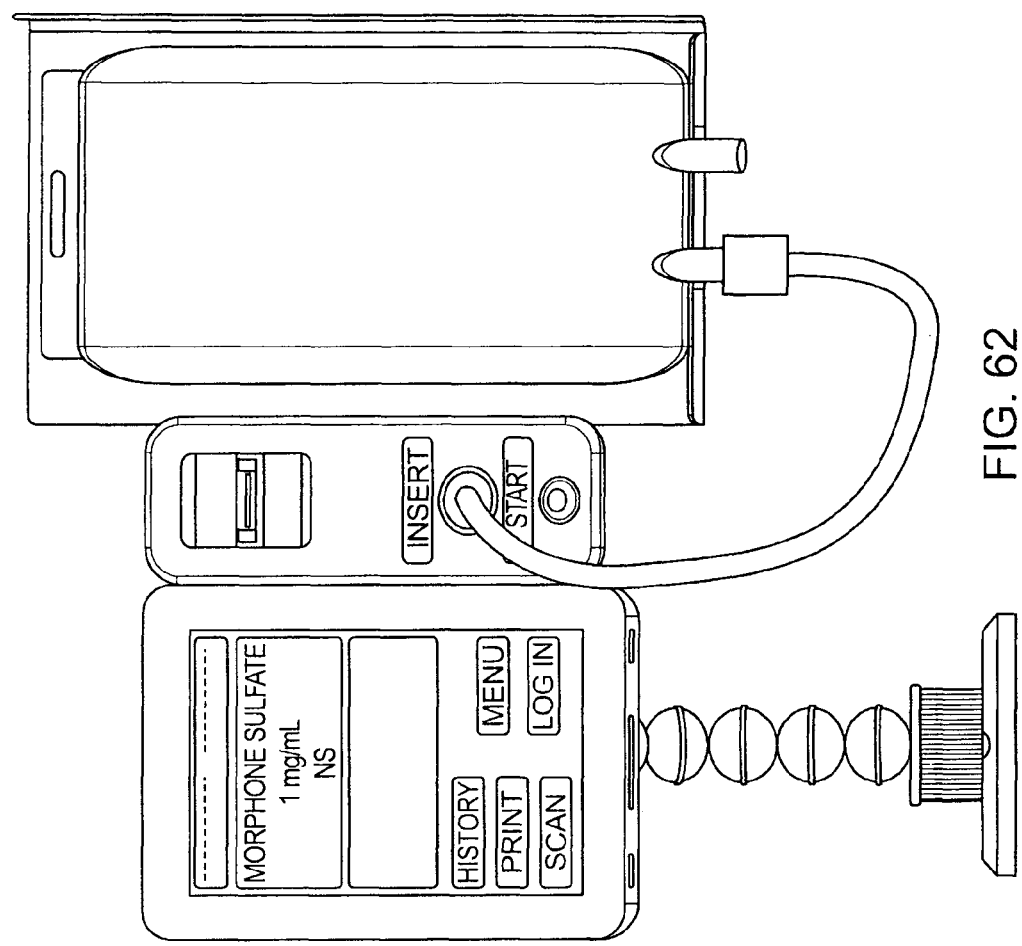
FIGS. 62 and 63 are another variation of an IV check system as described.
Figure 63:
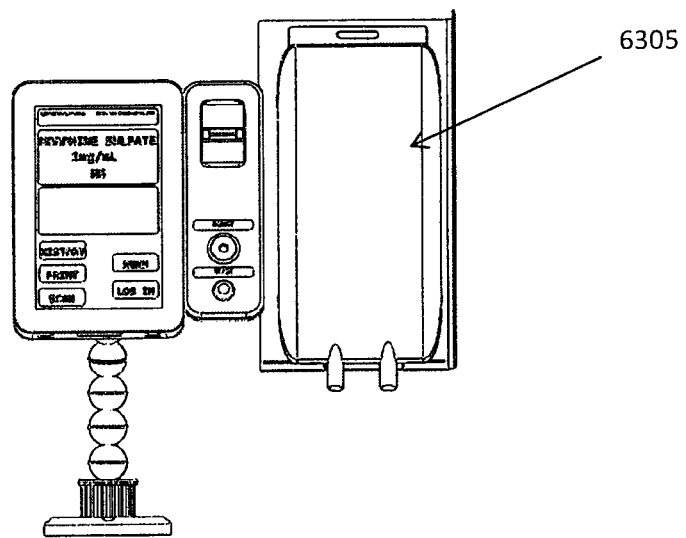

The IV check systems described herein may reduce error by ensuring that the IV bag that needs a measurement is essentially "held" in place until the measurement is taken and some sort of approval or status is given. An approval may be a printed bar code label that is to be applied to the bag or digital signature or a biometric measurement. Thus the system may include a holder for securely holding the IV bag until checking is complete, and/or a marker or identification generator (printer, etc.) for generating a marker or other label for the bag indicating that it was tested, and what the results were. For example, the IV bag 6305 in question can be placed next to the IV Check machine on a bracket. The operator could then attach a disposable sensor element to a tethered cable and then insert it into the bag through the septum. This device can include a sealed reservoir where the sensor resides and the volume of the reservoir has a pressure differential between the static pressure of the IV bag and the reservoir itself to create a flow of liquid into the reservoir. This device can be like an IV "spike" to puncture the septum of the IV bag and make the fluid contact. Next the operator pushes "start" and the measurement is taken. The approval is performed and now the cable/sample can be removed. The disposable is removed from the cable and disposed of. A new sensor element can be attached to the cable and a new IV bag loaded onto the bracket. The system is now ready for the next sample. This is illustrated in FIGS. 62 and 63.

Figure 64:
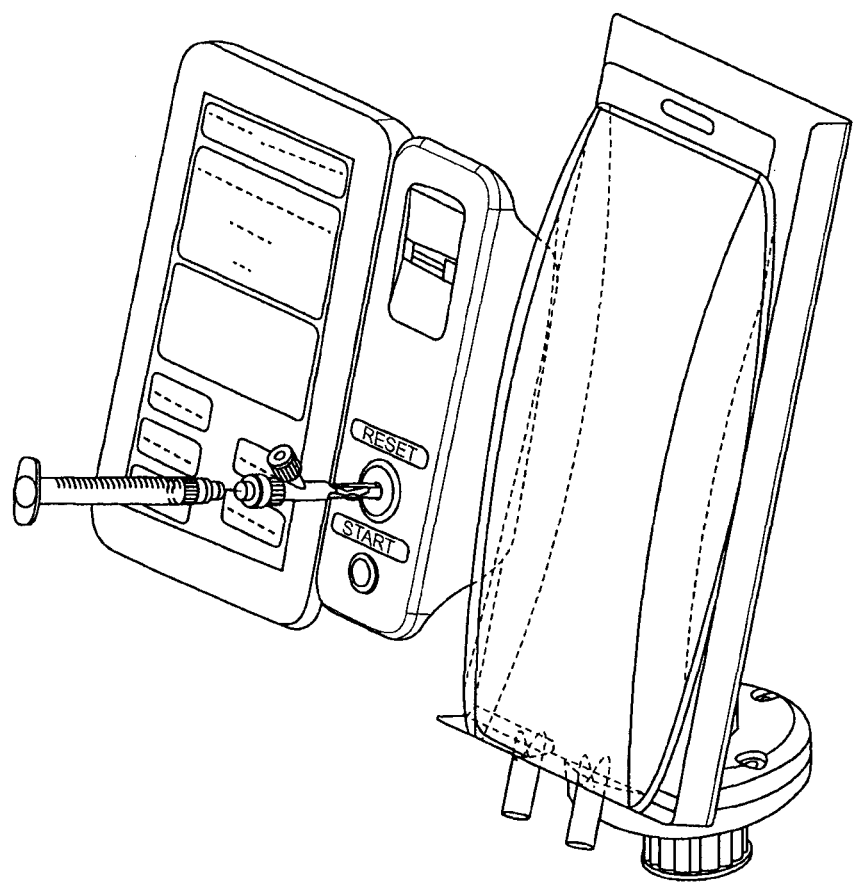
FIGS. 64 and 65 are another variation of an IV check system.
Figure 65:
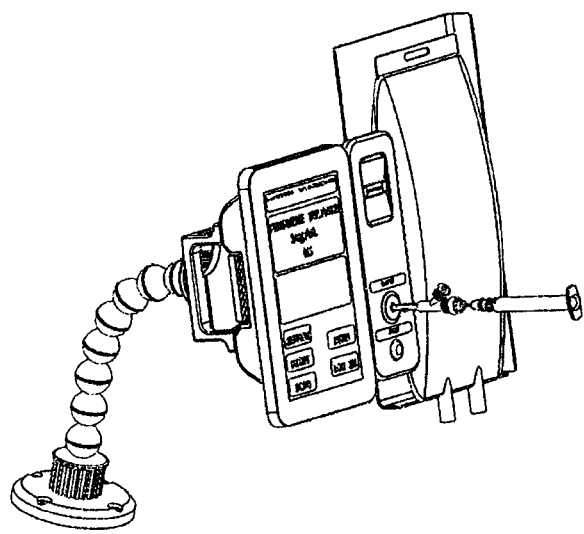

A disposable sensor element with a septum seal can be used in conjunction with a standard syringe. The operator can load the bag on the shelf and there can be a locking mechanism that holds the bag in place until the approval is given. This locking mechanism may or may not be necessary and if it is used can be overridden by a "release" button. Now the operator takes a sample of the mixture and injects it into the septum seal sensor element. The measurement is taken and approval given. The sensor element is now removed from the machine and disposed of. The bag is removed and the system is now ready for the next measurement. This variation is illustrated in FIGS. 64 and 65.

Any of the IV check systems may be used with or incorporated into portable bar code scanners used in hospitals, clinics, etc. As the sample is not returned to the IV bag or other container, it is possible to consider destructive fluid measurements where the fluid is altered or destroyed during measurement. For example, measurement in electrochemical regime with active electrodes or measurement under high temperature or electrical arcing conditions that would break down the fluid.

Any of the systems described herein, including the IV check systems, may be configured as high-throughput or high speed sampling and responding systems. For example, an IV Check type of system may be configured to accept an automated input of samples for measurements. This interface can be a sealed injection port or a series of sippers and associated tubing and valving systems. The system may allow for the sample to be measured and then a flushing solvent would clean the sensor and path for the subsequent measurements. The system can house the appropriate amounts and types of flushing solvents. A semi-reusable sensor cartridge may have a finite life and will be replaceable.

In one variation of a high-throughput configuration, the system works in conjunction with an autosampling device, such as the Agilent 1260 autosampler, which has side plate feeder, manual plate loading, and assumes vials are filled at another station via human or robot. The autosampler takes an aliquot from each of the vials and introduces it to the IV check system via a system of tubes, switching valves and pumps.

In this example, sample containers may be 2 ml with individual barcodes. An image of the entire array can be imaged and processed either on the autosampler side plate feeder or at another station. For example, an array may be 8×6-48 samples/plate, and may include a sterile spike to extract sample from bag. There may be a unique barcode on each sample holder. Throughput may be anywhere from ~250-950 samples per 8 hour shift per system (assuming 2 min vs. 30 sec "method").

A side IVC module side mounted with sensor cartridge design may be good for "x" measurements or "y" time, depending on the configuration. The sensor cartridge design may determine this, as well as the presence of rinsing by the system. A liquid waste assembly can be floor mounted or flange mounted to bottom of bench top or can be plumbed into waste line. If waste (e.g., rinsate) is stored, it can be stored in waste bottles (e.g., square 1 liter bottles w/liquid level sensors). The system may include liquid level tracking capability that can be incorporated into main electronics (or conversely another "box" if this is a required feature). Finally, the system may provide reports of data to a pharmacy IT server.

Some variations of the IV check systems described herein may include a cap element or device that allows communication of the IV fluid to the recognition sensor while maintaining containment and sterility of the IV fluid. The cap may be placed on an IV bag or syringe, and can be sampled repeatedly; it may communicate via a plug or dedicated port with a rest of the system. One configuration of this cap element connects directly to the IV bag or syringe with compatible fittings (e.g., threaded or luer connectors) and contains a spike which penetrates the IV bag septum and, through a channel, communicates IV fluid from the bag to the sensing surface. Another configuration of the cap may use the IV check sample holder and adds a connector with a spike for obtaining fluid from the IV bag and delivering to this sample holder, adapting it for use with IV bags. The connector may consist of a threaded or luer fitting at one end and a luer fitting with a bag spike at the other end. A channel through the connector would transfer a small amount of IV fluid to the sensor surface. The connector would be attached to the IV check sample holder during a manufacturing step or by the user immediately prior to use. Attaching it during manufacturing will allow subsequent sterilization of the assembly and therefore less chance of contamination of the IV fluid.

The IV check system or device itself may engage the sample sensor in such a way that this can remain attached to the bag or syringe during measurements. Preferred configurations include those which orient the bag or syringe vertically, such as a hanging bag, or those which allow the syringe or bag to rest on a table or bench top while the measurement is made. Thus a vertically oriented sample insertion and engagement or a horizontal engagement at the side of the device may be used.

B. IV Delivery Systems

An IV delivery system may refer to variations of the liquid monitoring systems described herein that determine the composition of a medical liquid as it is delivered to a patient. The system may be passive (e.g., monitoring delivery of the IV fluid and providing informational/alert outputs), or active (e.g., controlling delivery of the IV fluid based on the monitored composition of the IV fluid) or some combination of the two (e.g., intervening to stop IV drug delivery if an adverse event is likely based on monitoring of the drug delivery).

These systems may reduce IV medication errors, and improve documentation/recordation of IV drug delivery.

Although these devices may be referred to as "IV" systems, the same systems may be adapted for use with any other liquid drug delivery systems, including Epidural, PCA, dialysis, etc.

One example of an IV delivery system for monitoring the composition (including identity and in some variations concentration) of IV fluids is shown in FIGS. 67A, 67B and 68. For example, an IV delivery system may include a sensor coupled to a mount for connecting the sensor in-line with the IV fluid delivery source (e.g., tubing, bag, needle, etc.). As mentioned above, the mount may be incorporated into a housing, a connector, a tube, a drip chamber, a needle, or other component that may interface with a standard IV delivery system. The sensor may be connected to the other components of the system, including a controller and/or processor for acquiring and/or analyzing immittance spectrographic data from the sensor and/or flow information to determine the composition of the IV fluid. The system may also determine the total amount of drug delivered. As illustrated in the figures, the entire system may be connected near, on, or adjacent to the IV fluid being monitored. For example, the system may be mounted or hung from the pole holding the IV. In the example shown in FIG. 69, the controller and processor are integrated with a monitor, shown as a touchscreen. In some variations the processor and/or controller may communicate with a remote processor for data storage and/or analysis, though in some variation it may be beneficial to have a local processor analyzing the data collected.

Figure 69:
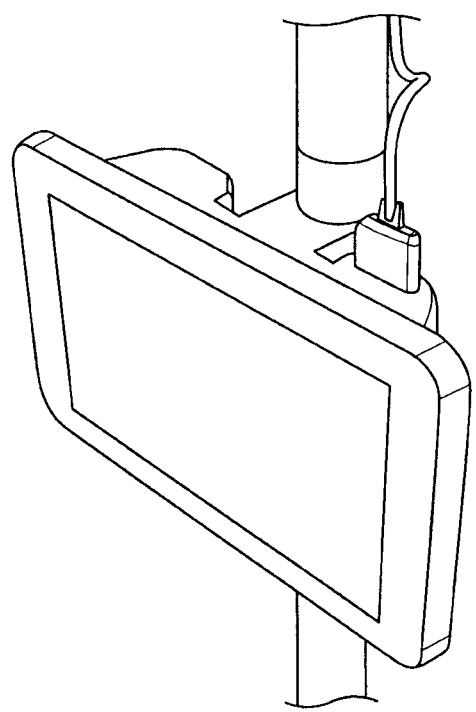
FIG. 69 illustrates one variation of a controller and monitor for an IV delivery system configured to monitor and determine the composition (including concentration) of an IV fluid) as described herein.
Figure 70:
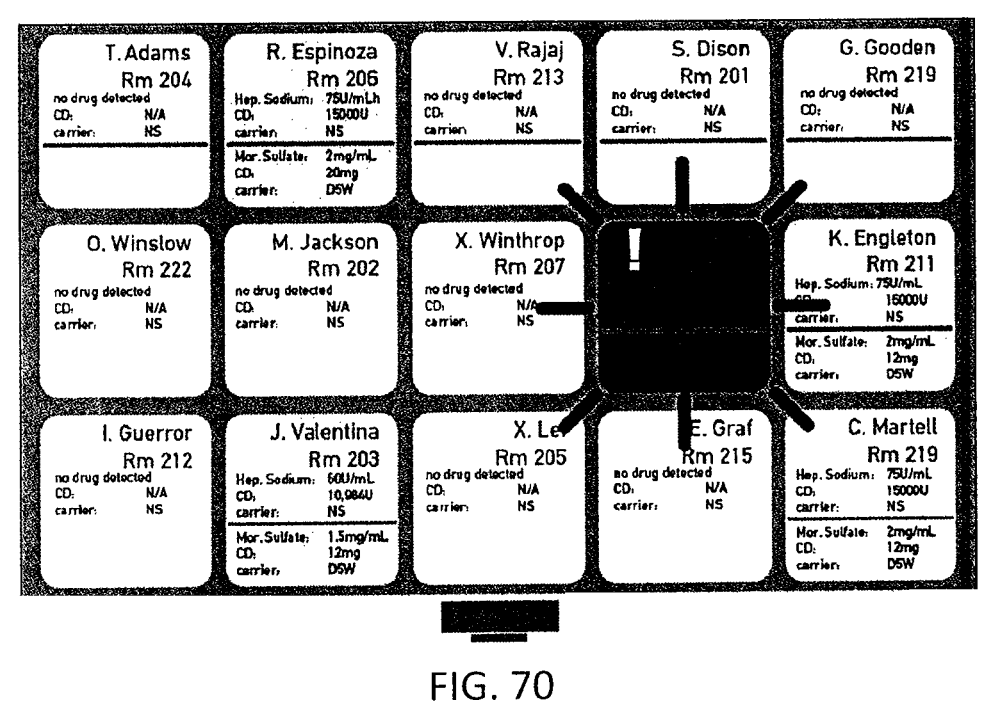

In addition to the system monitor shown in FIG. 69 that is directly connected to the sensor, in some variations a central receiving/logging/controlling station may be used. Such a station may be, for example, a nurse's station monitor that receives information on multiple IV monitoring systems. Such a station may be client software running on a standard processor (e.g., laptop, desktop, PDA or other computer). In some variations any individual IV delivery system may be competent to act as a monitoring station reviewing and/or controlling other IV delivery systems that it is in communication with. FIG. 70 illustrates one variation of a screen for a nursing station "dashboard" showing the status of multiple IV delivery systems monitoring patients.

The variation shown in FIGS. 67A-69 has the POD electronics mounted in the main electronics case. As shown in FIG. 69, the main case may include a touch screen or tablet computer with a back case mounted to it and a clamp for mounting to a standard IV stand. The case houses the all of the electronics needed to run the system, as well as a battery back-up sub-system. One cable that makes the connection from the main unit to the sensor element(s). The cable can be twisted/shielded pairs and have an overall shield incorporated into the cable and connector system. A heat transfer element may also be included to help eliminate heat from the case (e.g., by transferring to the clamp/pole). The clamp may have a pivot clamp that will allow it to change angle for better viewing. The front and sides of the unit can have a rubberized case to protect it from shock. A handle can be incorporated which could also provide an electrical path from the tablet to the electronics, in addition to being useful for portability/adjustment.

Figure 71:
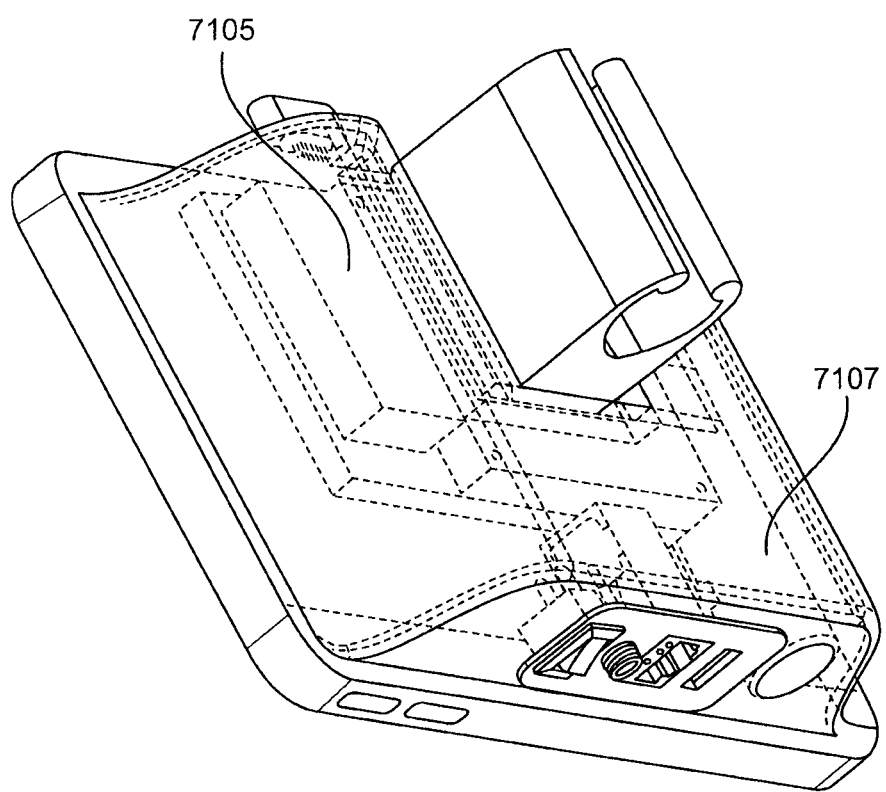
FIG. 71 is a back perspective view of a controller for an IV delivery system similar to the variation shown in FIG. 69.

FIG. 71 shows an image of the back of the controller/processor portion of the system described above. In this example the case houses the electronics 7105 as well as a backup battery 7107.

An IV delivery system may be configured as a "smart pump" that actively controls the delivery of the IV to the patient. For example, the IV delivery system may include an integrated IV pump. For example, an active IV delivery system may be configured as a fully automated smart pump that independently and automatically recognizes IV fluid (drugs, drug concentrations, and diluent). The system may set the dosing rate and time base on programming, medical records, or the like (e.g., EMR). The system may therefore administer IV drugs at the proper dose and time without requiring intervention. As mentioned above, the system may be configured to connect to an IV bag, IV syringe, IV tubing, etc. Feedback may be provided to control the delivery based at least in part on the analysis of complex immittance from the sensor (as well as flow rate). In some variations the system is configured as an insulin pump that may be coupled with a glucose monitor for closed-loop, continuous delivery.

In operation, an active IV delivery system may first be provided the patient ID. For example, a bar code reader or biometric information may be provided to confirm/identify the patient. An individual pump (active IV delivery system) may be assigned to a specific patient for IV delivery. Once the patient is assigned, the pump can automatically interrogate the patient records for appropriate IV administration conditions, which can be done once per patient or reconfirmed periodically. The IV may then be set up (e.g., by hanging the bottle or bag and attaching the IV line to the bottle/bag); depending on the pump mechanism, a syringe may be loaded onto the pump and the IV line attached to the syringe. The sensor line/cartridge including the sensor may then be engaged. For example, the IV line may be placed into the pump and secured in position. The pump can engage the IV line so that fluid is pumped appropriately and the sensor is engaged with the device to detect drug identity and concentration (and diluent identity). The pump may automatically interrogate the patient prescription records to set up the delivery time and rate, and/or to set alerts.

Figure 72:
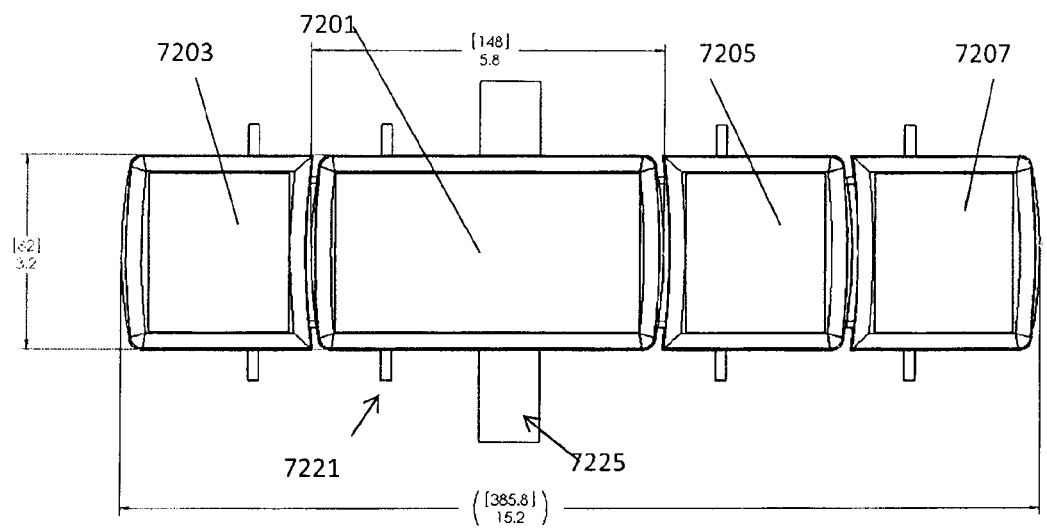
FIG. 72 shows a front view of one variation of an active IV delivery system including multiple monitoring and pumping modules.
Figure 73:
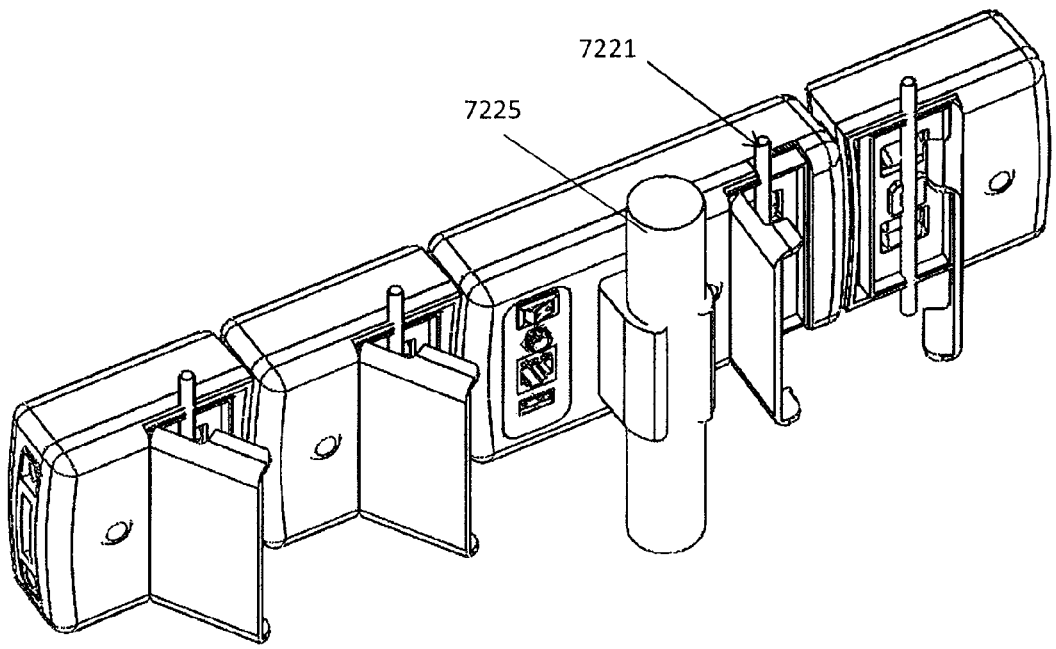
FIG. 73 is a back view of the system of FIG. 72.
Figure 74:
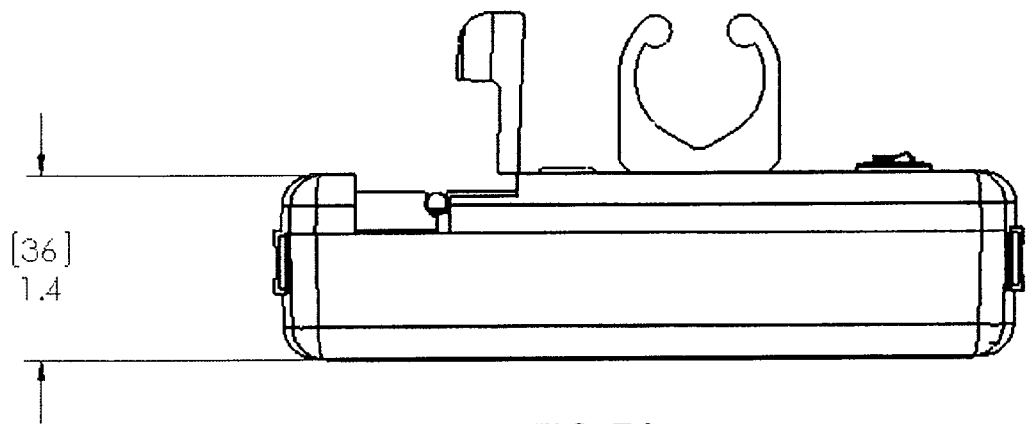
FIG. 74 shows a top view of an IV delivery system including a pump configured to be controlled at least partially based on the detected composition of the IV fluid.
Figure 75:
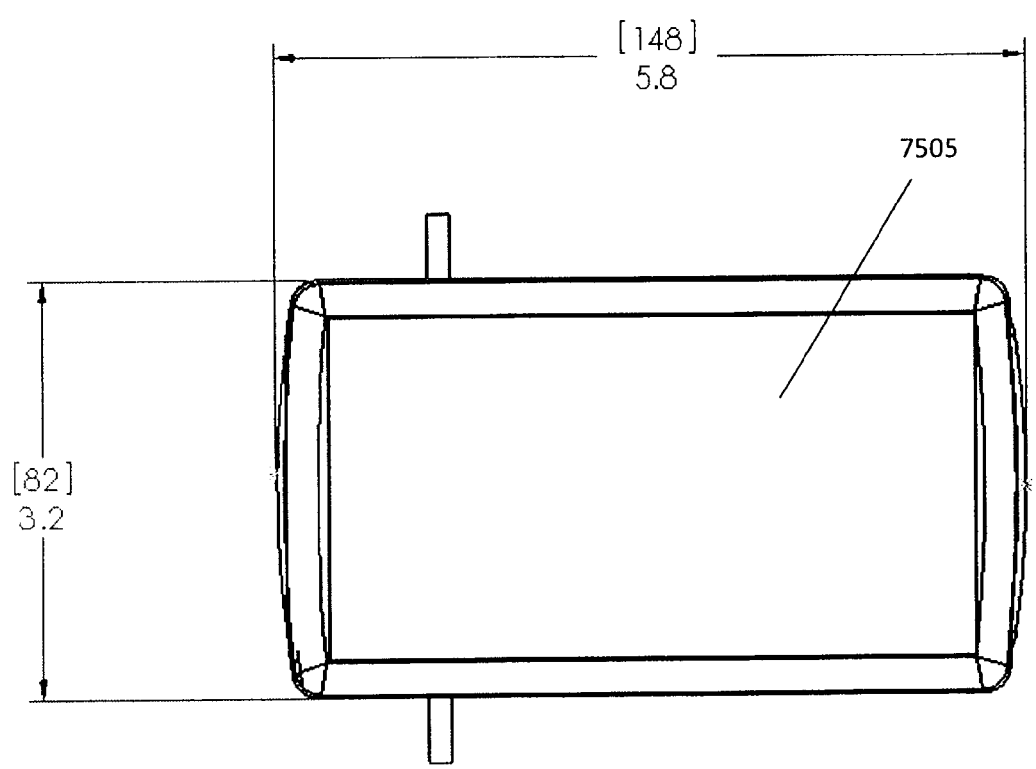
FIG. 75 is a front view of the IV delivery system of FIG. 74.
Figure 76:
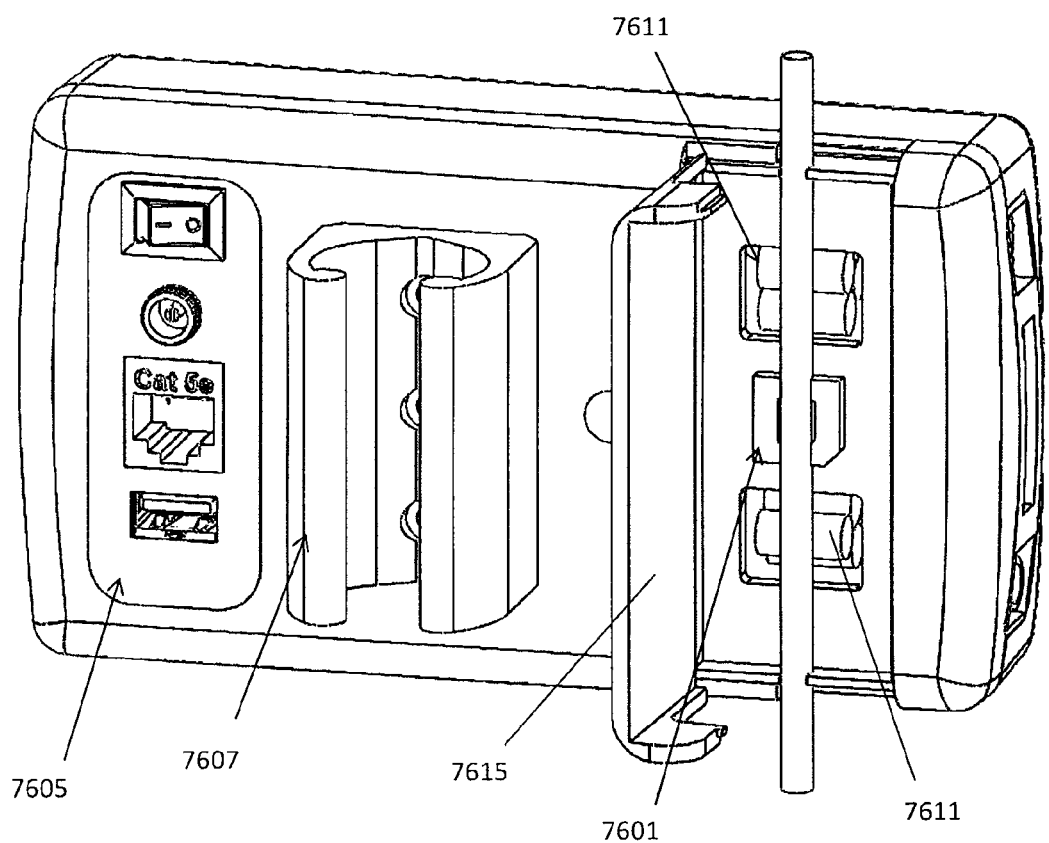
FIG. 76 is a back view of the IV delivery system of FIG. 74.
Figure 77:
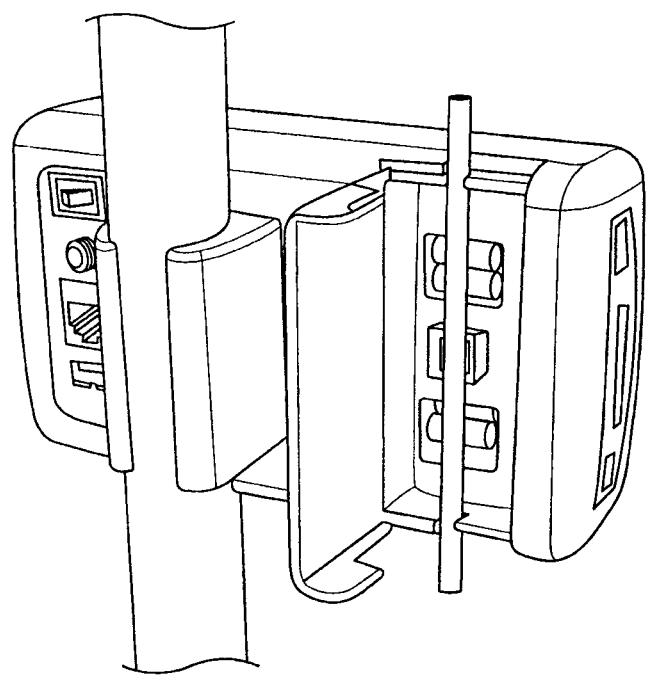
FIG. 77 is another view of the back of an IV delivery system.
Figure 78:
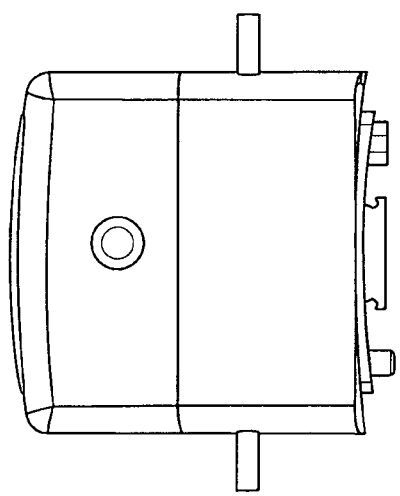
FIG. 78 is a side view of the same variation.

FIGS. 72 and 73 illustrate one variation of a smart pump system as described herein, shown with multiple pump modules for monitoring and controlling the delivery of multiple IV lines. For example, in FIG. 72 a main controller/processor unit with a touchscreen 7201 is connected on either side to three other pump modules 7203, 7205, 7207. For each module, tubing 7221 from an IV tubing set passes through and couples with the pump. As shown in FIG. 73, each tubing 7221 may be snapped into the back of the device. The entire assembly is mounted to a pole 7225. FIGS. 74 and 75 show top and front views, respectively, of the main unit of the pump system, which may house the controller and/or processor. FIG. 76 shows a view of the back of the main unit. A control panel 7605 with the on/off switch, power jack, and network connection(s) (e.g., USB) is located on the back of the device, as is a pole clamp 7607 and the entrance into the pump housing in which the tubing may be placed. Two pump mechanisms 7611 and the sensor interface are also located in the pump housing. A door 7615 may be shut once the tubing is positioned therein. FIG. 77 shows a back perspective view of this embodiment. FIG. 78 shows a back views of this variation in which the door to the pump housing has been shut.

Figure 79:
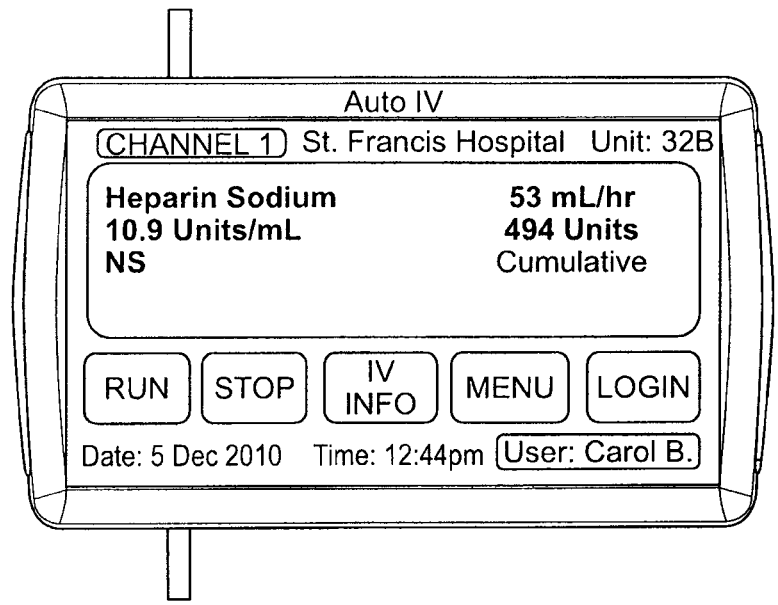
FIG. 79 is an exemplary display for an active IV delivery system such as the one shown in FIG. 74-76.
Figure 80:
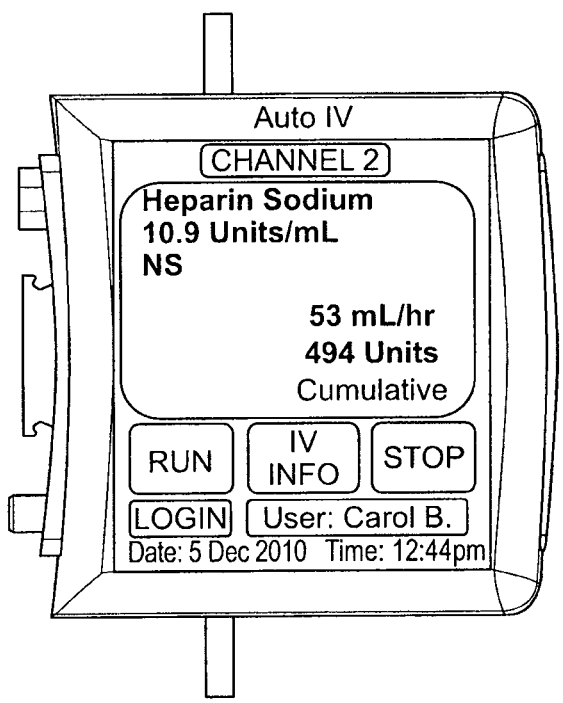
FIG. 80 is an exemplary display for a pump module of an active IV delivery system that may be used with the main pump module shown in FIG. 79.

FIGS. 79 and 80 illustrate exemplary screens for a smart pump. In FIG. 79, the main unit of the smart pump is shown with the touchscreen indicating the currently read IV delivery information. In this variation, the screen includes information on the detected drug (Heparin), concentration (10.9 U/ml) flow rate (59 ml/hr) and total cumulative drug delivered to the patient (494 Units) by the pump. Time/date, user, patient, and other information may also be displayed, and key controls (buttons) may also be shown and enabled. Additional controls (not shown) may allow manual interface and control of the system, including saving and/or sending data remotely, and programming the device, as well as entering user information.

Figure 81A:
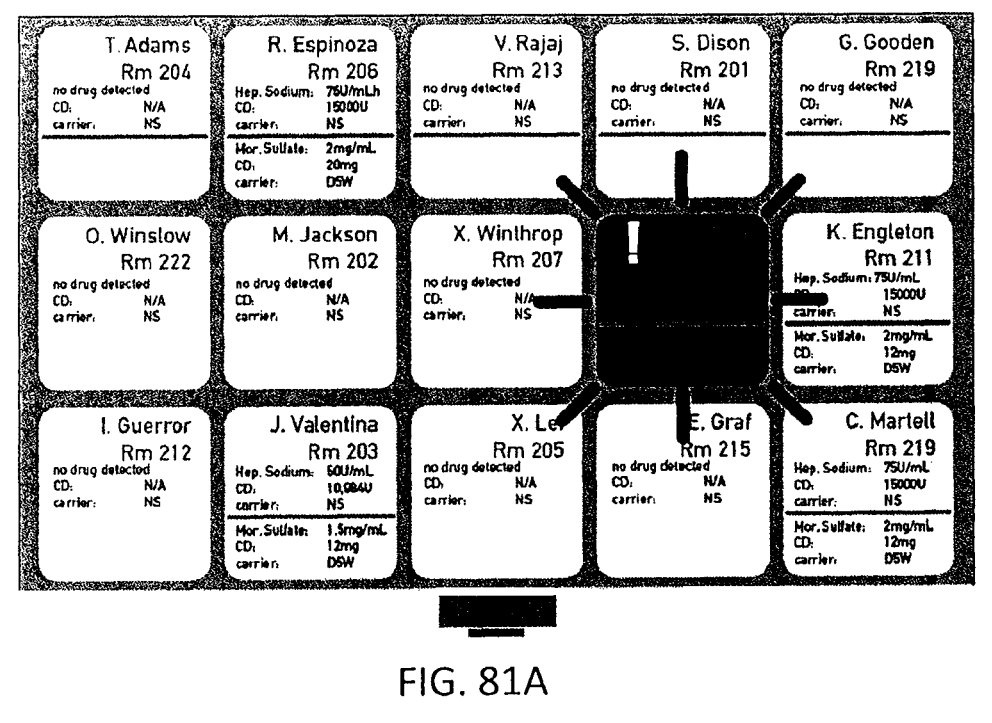

Similarly, FIG. 80 shows an example of a pump module that may be attached to a main unit as shown in FIG. 79. A pump module may be a dedicated pump controlled by the main unit to which it is attached. The screen displays the channel assigned to the pump module, the drug identity, diluent identity, flow rate, concentration, and total dose. Buttons on the screen (touch screen) enable running the pump once the setting are confirmed, or individual manual control of the pump and/or transfer of data. Control and monitoring of this smart pump may be sent or coordinated with a central station, which may be located at a nursing station, for example. Hardware, software or firmware may be configured to control the system or multiple systems, which may be spread out across multiple beds (patients). For example, FIG. 81A shows an exemplary screen ("dashboard") for a controller. The user interface shows different patients receiving different IV drugs. Alerts may be indicated relative to a particular patient. The monitor may also indicate those patients receiving watched substances, which may be more closely monitored.

The most frequent sequence for utilizing barcode technology (e.g., BCMA) is the following: scan self/obtain medication/check medication/scan medication/enter patient's room/scan patient ID band/administer medication/document administration. The last two steps are interchangeable in most cases. Currently, there is no independent verification that the medication has been indeed administered, in right time, the medication has correct composition, concentration and prescribed cumulative dose has been achieved. This information can be automatically provided utilizing proposed technology, properly stored and disseminated by the hardware throughout the information carriers or though the hospital network. If any of the above information is automatically found by the device in contradiction with the conventional practices the device can produce alerts of various degrees according to the perceived seriousness of the mistake and severity of potential consequences to the patient as pre-programmed in the device database.

Figure 81B:
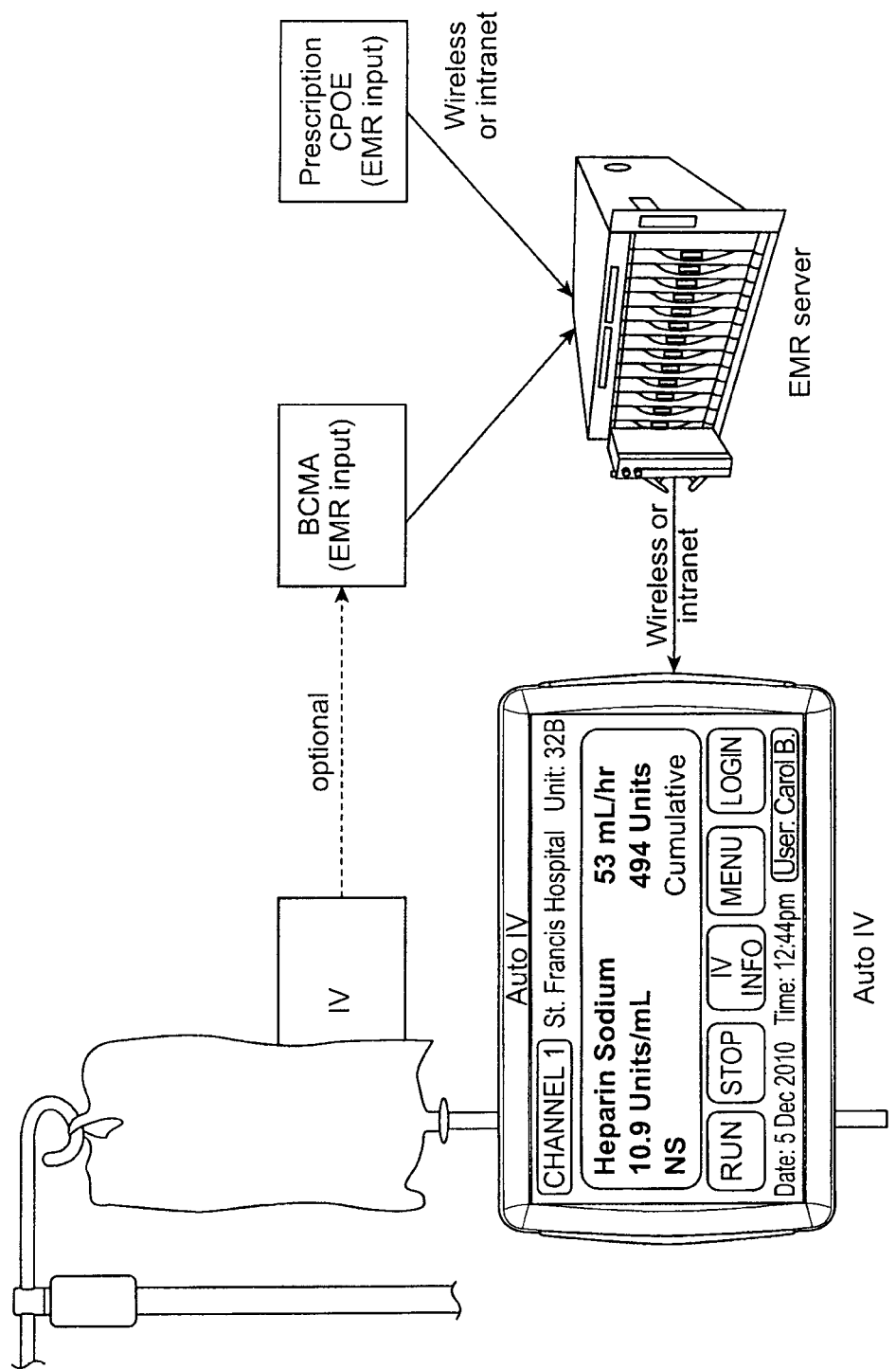
FIG. 81B shows one variation of a system for automatically administering IV drug solutions to a patient.

In addition, the systems described herein, including the IV delivery systems, could be used to automatically deliver IV drug solutions to a patient; in some variations the systems could also automatically compound the drug solution based on data from the patient's electronic record(s) and/or from physician/pharmacy instructions and/or directly from one or more patient monitors indicating the patient's physiological condition. FIG. 81B shows one variation of a system for automatically confirming and administering with confirmation an IV drug solution ("autoIV") based on information from the patient's electronic records. In FIG. 81B, the automatic IV delivery system includes a valve and/or pump for connecting to one or more IV drug solutions and delivering them to the patient. The system may receive information from a patient's electronic medical record ("EMR server"). Based on the EMR information, the IV system may determine what dosage (e.g., amount, concentration, etc.) of what drug is to be delivered to the patient, and may automatically deliver it by (1) directly sampling the IV drug solution to confirm the composition of the drug solution and (2) deliver and monitor the delivery of the drug to be certain that the patient is receiving the correct drug and dosage. This system may be a closed-loop system which may run with minimal required interaction from the healthcare professional.

In general, directly sampling the drug solutions as described herein provides of the advantages mentioned above. For example, errors in marking (even barcode marking) may be avoided, user error (misreading or mislabeling IV bags, for example), etc. Systems that both directly sample the drugs to be compounded for and/or delivered to a particular patient that can access a patient's medical records may be of even greater value in preventing error and harm to patients. Such systems may cross reference prescribed medications with the patient's existing physiological status, including drug allergies, cross-reactivity with other current medications, and the like. Any of these systems may also be configured to directly confirm patient identity. For example, biometric information (including face recognition, fingerprint recognition, etc.) may be used to confirm patient identity.

Thus, a fully automated smart pump as described herein may independently and automatically recognize the IV fluid introduced in the IV line including drug/drugs, dose, and diluent, set dosing rate and time based on EMR (Electronic medical records including physician orders and pharmacy records), and administer IV drugs at the right dose and time without the need for intervention. It may require minimal setup and running steps and provides unprecedented safety in IV drug delivery. Automated smart pump may include standard pump and a syringe pump variations.

The smart pumps described herein may include a mechanism for pumping a fluid through a tube, fluid sensing (immittance) electronics and a drug database (library) with IV drug/dose/diluent fingerprints and safe infusion conditions, a monitor for displaying drug, dose, diluent, and pumping conditions (flow rate, etc.), and a touch screen and/or buttons for interacting with the device and connections (wireless or wired) for interacting as part of a hospital computer network. The system or device may also have a power cord and a backup rechargeable battery power supply in case power is interrupted. This variation of a fully automated smart pump detects and reports drug, dose, diluent, flow rate and cumulative dose and sets infusion conditions and limits automatically based on the drug detected. It also automatically alerts the healthcare provider if they attempt to set up conditions that are not typically safe for patients, such as delivering a dose of drug too quickly.

In facilities appropriately equipped, the pump will communicate wirelessly or through a wired connection, with hospital CPOE (Computerized Physician Order Entry), BCMA (Bar Code Medication Administration) and electronic medical records systems to automatically confirm the drug and dose ordered is consistent with the drug and dose detected and set the delivery parameters automatically according to the medical orders. This includes the delivery rate, time of initiation and time of cessation. In fully automated mode, once an IV is successfully loaded into the pump, the device would prime to detect drug, drug concentration and diluent, check medical records and bar code scan results for a match, and when a match is found, set the delivery condition (rate, time) according to the orders.

In some variations, the device can be used manually in STAT conditions where orders have not been placed on the computer.

Patient assignment to a pump can be performed by reading the patient bar code or by entering the patient ID. The smart pump system may access the patient's hospital record and confirm the patient's name as well as age and weight to insure the right patient has been assigned. This may only need to be done once per patient, but the pump may confirm that it is still assigned to that patient each time a new IV is set up, or more often.

IV drug solutions may be prepared and hung from a pole or loaded in a syringe pump version as per standard practice. An IV line containing a built-in sensor and pump cassette may be loaded or threaded into the fully automated smart pump device in a manner that can only be engaged in the correct orientation. The IV line is engaged by the device, automatically engaging both the pumping mechanism and the sensor. Once engaged, the device can run an automated diagnostic confirming correct engagement and sensor signals.

The device may pump a small bolus of fluid from the bag or syringe sufficient to fill the IV line past the location of the sensor imbedded in the IV line "cartridge". Pumping may momentarily stop while drug, concentration and diluent are detected, reported on the device monitor, and the patient's medical record is accessed to confirm that this drug order is appropriate for this patient at this time. Using the administration information in the drug prescription, the pump can automatically set the proper dosing rate from the drug and concentration information. The pump can delay administration until the proper time for drugs presented early.

Once the device is loaded, the administration would take place automatically unless a potential error is detected. In the event that a potential error is detected (wrong dose, wrong patient, wrong diluent, incompatibilities with other concomitant medications or conditions, such as dextrose for a diabetic patient), an alert may sound with specific information about the nature of the potential error. Healthcare provider intervention may be required.

The pump may automatically set conditions (i.e., alerts) for different size individuals, from large adults to neonates and premature infants, by means of the access to the electronic medical record. The selection of individual size would allow the device to set drug concentration and delivery rate parameters inside the database and software, to guide the delivery of the drugs identified and delivered by the device, whose database would include pre-programmed delivery conditions (concentration and dose) for all drugs in the drug library. Pediatric and/or neonatal versions of the pumps may also be created in which conditions and drug libraries are consistent with smaller bore (diameter) IV tubing and drug doses and infusion rates for pediatric and neonatal patients.

The pump may alert for occlusions, end of run and other typical functions, as well as changes in drug or diluent detected after a run is initiated.

Some variations of the smart pump configuration of the IV delivery systems described herein may be configured as multichannel automated smart pumps. In these variations, one single processor unit as described above (e.g., having a single mechanism for pumping a fluid through a tube, proprietary fluid sensing electronics and drug database (library) with IV drug/dose/diluent fingerprints and safe infusion conditions, a monitor for displaying drug, dose, diluent, and pumping conditions (flow rate, etc.), a touch screen and/or buttons for interacting with the device, a power cord and a backup rechargeable battery power supply in case power is interrupted) and a connection to a hospital IT network may be extendable by adding special pumping modules to the ends of the processor unit. Each pumping module may connect to the power source, data processing and drug database of the processor and provide pumping and drug sensing for an additional IV line. Multiple modules could be connected in series to allow one processor unit to support several (e.g., up to 7) different pumps.

For example, each pump module may contain a small screen to display which channel of data is assigned to this pump by the processor to which it is attached. The main processor unit may contain one pump and may have the default channel one. The next module added may be channel two, and so forth. The pump module may also contain a screen displaying the information of drug identity, diluent, flow rate, concentration and total dose, and buttons or a touch screen for prime and run to prime the IV and run the pump once the settings are confirmed. Alternatively the touch screen on the main unit can be used to set up the delivery conditions for each of the attached modules by selecting the appropriate module and once the drug and delivery conditions are displayed, adjusting the default delivery rate to the desired delivery rate.

In some variations, an automated IV delivery pump or other IV fluid system such as those described may base the selection and administration of IV drugs on a patient's immediate condition. In this case, the fluid delivery system in conjunction with patient condition data would determine which medicine and how much to administer. This could have applications in emergency medicine and other areas such as battlefield medicine where full medical care is not available. For example, such a system could monitor a patient, determine what IV fluids are needed, determine which pump channel or channels have those fluids, determine the fluid concentration, calculate the needed dosage and administer the dosage, all while verifying the drug identity, concentration and total dose delivered. The dosage rate and drug given can be adjusted automatically by the system based on the patient response without the need for medical personnel.

In some variations of the IV delivery systems including a pump for the administration (basic infusion) of IV solutions, a frequent task sequence is: hang IV/turn on pump/program/push start. The first two steps may be interchangeable. If the drug programmed is not the one independently identified by the sensor and/or the concentration programmed is not the one identified—the system will produce an alert and will stop pump if the mismatch can be dangerous for the patient. The system can provide the information as to whether the IV line is properly primed and if so—identify the composition of the fluid and prompt the nurse prior to or at the programming step and suggest expected safe infusion rates and set of expected drug/concentration combinations and VTBI (Volume to Be Infused) values to choose from.

In more sophisticated administration utilizing Guardrail technology, the information automatically generated by the sensor system described above can be again utilized as prompts at all steps (for example a prompt for appropriate range of a patient weight or VTBI, etc.) virtually ensuring that the programmed infusion parameters are within the limits of guardrails saving nurses the frustration of going back and reprogramming all the infusion variables nearly from the start when the guardrail alert indicates that the resulting infusion parameters are out of limits.

In yet even more sophisticated co-administration utilizing multi-channel smart pumps, the system can prevent line-crossing by identifying the drug in primed line for each of the channels prior to the channel programming of each channel thus eliminating errors in co-infusion.

Once the sensor is exposed to the drug under the flow condition (bolus push or co-infusion) and the drug is identified at the time t—the sensor response to that particular drug can be pulled out of the database and instantaneous drug concentration can be calculated: $c(t)=\vec{s}^{-1}(\vec{r}(t))$, where $\vec{r}=(c)$ is a vector response of the sensor to a concentration of that particular drug determined experimentally and stored in the database. Vector-function $\vec{s}$ is the sensitivity to the presence of that drug and depends on the nature of the drug. If the drug concentration exceeds safe limits at any time during the infusion, the system can provide an alarm.

When the drug has been identified, the response data can be traced back in time to the point $t_0$ where the sensor response first exceeded two standard deviations from the level of the signal normally found in the pure carrier (such as saline) or to the beginning of the infusion process, when the flow first started. The cumulative dose D(t) at a time t then can be estimated as:

$$D(t) = \int_{t_0}^{t} q(t)c(t)dt \text{ or } D(t) \approx q \int_{t_0}^{t} c(t)dt,$$

where q(t) or q is volumetric flow, which in most practical cases is nearly constant. The volumetric flow q(t) is measured by a built-in "hot-wire" flow meter.

Figure 82:
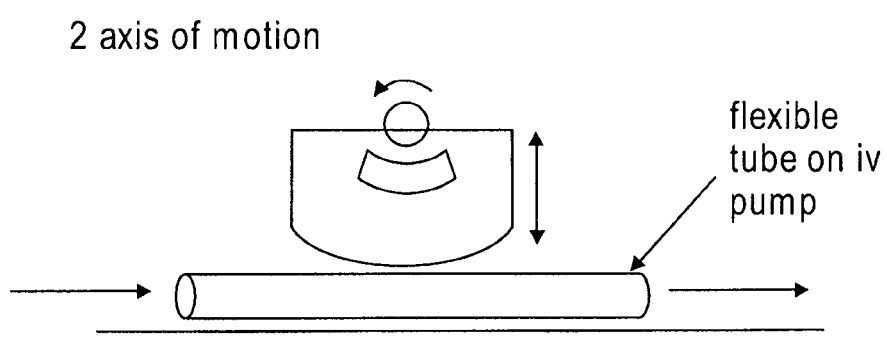
FIG. 82 illustrates one variation of a pump mechanism that may be used with IV delivery systems described herein.
Figure 83:
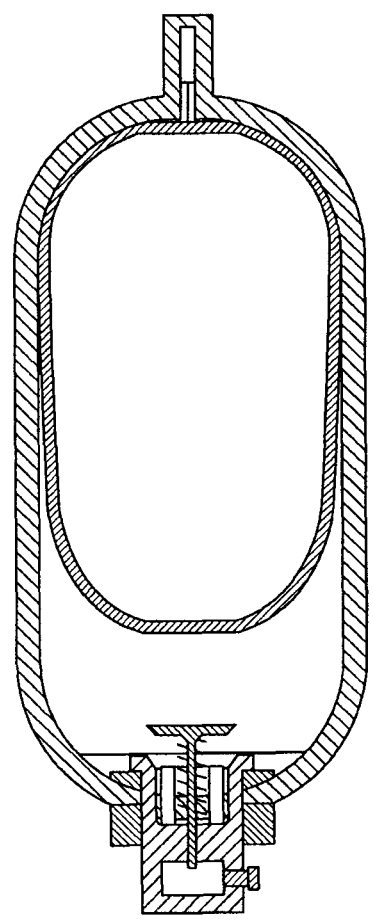
FIG. 83 illustrates another variation of a pump mechanism that may be used with IV delivery systems described herein.

As mentioned above, any appropriate pump may be used with the systems described herein. One concept to create a flow of liquid inside of a flexible tube is have a slab of material about as thick as the tubing and about as long as the length of tubing inside of the device. The edge of the slab that touches the tubing may have a curved profile. The slab may have a follower path machined out of its interior for a cam-follower actuation interaction. The slab would have two axes of automation—rotation and linear. The combination of these axes would create a wave-like motion of the curved surface on the flexible tube—this action will push the fluid along the path of the tube. This action will also be controllable in terms of the speed of the fluid. This actuation will create less fluid pressure spikes in the tubing as compared to a peristaltic pump because there is only one point of contact along the tubing and the motion can be tuned to not abruptly depress the tubing in the motion path. FIG. 82 illustrates one variation of this pump design. Another pump concept that may be used in conjunction with the smart pump systems described herein to produce a flow of liquid from an IV bag may be to control the crushing of the bag at a specific rate. One way to accomplish this is to use a pressure accumulator device in a system appropriate for IV bags. This hydraulic accumulator can be like a low pressure bladder accumulator within the bag, as illustrated in FIG. 83.

As an additional control, any of the systems described herein, and particularly the active IV delivery systems may include biometric or other confirmation of patient identity before delivering IV drugs. For example, any of the systems described herein may include facial recognition as a way of doing automated patient identification utilized in conjunction with admittance drug recognition system. The system may include a module with a camera to take a patient's picture and continue to ensure the right patient and same patient for delivery of IV drugs.

C. IV Waste/Diversion Detection

In some variations, the immittance systems for determining the composition of a liquid solution described herein may be configured to keep track of medical (e.g., IV drug) waste. Hospitals and other institutions are increasingly required to document proper disposal of environmentally sensitive waste and monitor for diversion of scheduled drugs. The IV Waste/diversion detection systems described herein, which may be referred to as "IV waste systems" for convenience, the IV waste systems may be designed to enable and automate compliance with both objectives.

In some variations, the IV waste system consists of a channel containing a proprietary sensor connected to a processor which rapidly determines drug identity and concentration. These systems or devices may also contain a flow meter to determine total volume of fluid and one or more waste containers into which the fluid can be sorted and deposited after being recognized to insure waste is in the proper containers for disposal. It can be used to identify scheduled drugs in IV bag or syringe returns, including total dose remaining, and can be used to record and segregate environmentally sensitive IV waste documenting the correct disposal into reservoirs for incineration or chemical decomposition. The device may operate empirically, independently certifying IV fluid waste for drug diversion detection and/or environmental waste disposal.

In one embodiment, the IV waste system may be operated by first attaching a bag or syringe to waste input port of device. Fluid may then be forced through a waste input port. The system/device may identify and record the identity, concentration and volume of the fluid and calculate total amount of drug discarded based on the composition. It may also divert the dose into the appropriate reservoir for disposal, segregating different classes of waste appropriately. Thereafter the empty bag or syringe may be discarded in appropriate waste.

Pharmaceuticals are considered organic wastewater contaminants by the US Geological Survey and pharmaceutical wastes are considered to be hazardous waste under EPA's Resource Conservation and Recovery Act (RCRA). Hospital pharmacists, safety, environmental services, and facility managers have difficulty applying RCRA to the complex pharmaceutical waste stream. The EPA and state environmental agencies can levy corporate fines up to $37,500 per violation per day (a violation can be defined as one item discarded into the wrong waste stream). Personal liability can be assessed from the department manager up through the chain of command to the CEO, and can include fines and prison terms.

Pharmaceutical waste is not one single waste stream, but several distinct waste streams that reflect the complexity and diversity of the chemicals that comprise pharmaceutical dosage forms. Healthcare has not typically focused on waste stream management, so there is little experience with the proper methods for segregating and disposing of pharmaceutical waste. Compounding this problem, medicinal drugs are often diverted from their intended therapeutic use for illicit use, i.e. drug abuse, by those doing the diversion or by others for whom the procurement is made. Substance abuse among nurses can range from 2% to 18% (Sullivan & Decker, 2001). The rate for prescription type drug misuse is 6.9% (Trinkoff, Storr, & Wall, 1999). The prevalence of chemical dependency is 6% to 8% (130 to 170,000) according to the ANA estimates (Smith et al., 1998). The Indiana Board of Nursing estimates that 15% nurses abuse drugs found in hospitals. The American Society of Anesthesiologists reports that 12 anesthesiologists die from overdoses of fentanyl a year and as a whole, Anesthesiologists abuse drugs at a rate three times that of the general physician population.

Among the most commonly diverted drugs are those frequently or primarily administered by IV in hospitals including fentanyl, for which there is no current technology for detecting diversion, and morphine and hydromorphone. Many oral drugs are also diverted and many hospitals use dispensing machines and diversion detection software to identify and mitigate the problem of diverting oral medications.

IV waste systems may be configured as compact devices that provide rapid and convenient identification and empirical records of any unused portions of scheduled and/or environmentally sensitive drugs that must be disposed of when not completely delivered to patients. Disposal may consist of segregation and sequestration into disposable waste containers for incineration, chemical decomposition, or other remediation approaches. Waste containers are easily accessible for quick removal and replacement with new containers, and are expected to be disposable with the waste they contain, usually by incineration.

In some variations, the immittance sensor including, if needed, any flow sensor, may be contained in a disposable cassette that would be replaced after a number of uses. The cassette would be exchanged with a new cassette and the replacement would connect the new cassette with the IV waste fluid path downstream of the port and upstream of the waste containers. The cassette may contain the port and/or fluid path so that a fresh port and/or fluid path may also be included in each sensor cassette change. The sensor cassette may also make contact with the processor to operate the sensor and interpret signals to create drug fingerprints and identify such fingerprints in the drug database.

An IV waste system or device may contain any or all of the following elements: a processor unit as described above, a mechanism for pumping a fluid through a tube (e.g., pump), fluid sensing electronics (including a sensor as described herein) and a drug database (library) with IV drug/dose/diluent fingerprints and a waste disposal compliance library, a monitor (for displaying drug, dose, diluent, and waste disposal compliance or diversion detection logging), a touch screen and/or buttons for interacting with the device, one or more waste reservoir tanks for waste disposal, a rinsate reservoir and pump or gravity feed, a power cord and a backup rechargeable battery power supply in case power is interrupted, and a connection to a hospital IT network. The battery power supply and small size insure the IV waste system or device is portable for use anywhere inside or outside a healthcare institution.

In some variations, IV fluid can be introduced into an IV waste system waste input port via user pressure, i.e. pushing a syringe connected to the waste input port, or pushing on a bag to drive out residual fluid. Such a device may include sensing flow through the IV waste channel as well as identity and concentration so that total drug dose wasted or tested for diversion can be calculated and documented. After each measurement, user may need to rinse the IV waste input port and detection channel to insure proper measurement of subsequent samples.

In some variations, IV fluid (waste) is introduced into the IV waste input port via a pump, i.e. any syringe or bag connected to the waste input port will have the residual fluid emptied automatically at a constant rate. Such a device may not need to include sensing flow through the IV waste channel since total drug dose wasted or tested for diversion can be calculated and documented using concentration and the rate of pump operation (volume of fluid per unit of time). After each measurement, user may need to rinse the IV waste input port and detection channel to insure proper measurement of subsequent samples.

Any of the systems, including the IV waste systems, described herein may also include automated rinsing of the sensor(s) and other components between sensing/testing. For example, IV fluid that remains in the IV waste input port or sensing channel after the complete wasting or diversion measurement has been made may interfere with subsequent fluids. Therefore a manual or automatic rinse of the input port and channel may be required. An automatic rinse would include a reservoir of rinsate which could include a connection to a distilled water line or an actual reservoir bottle or tank of pure diluent from sterile water to IV fluids such as D5W (5% dextrose in water) or NS (0.9% normal saline). The device may remove an aliquot of rinsate and pump it through the input port and channel using a pump, or the positive pressure of a water line or gravity from a reservoir above the device.

Figure 84:
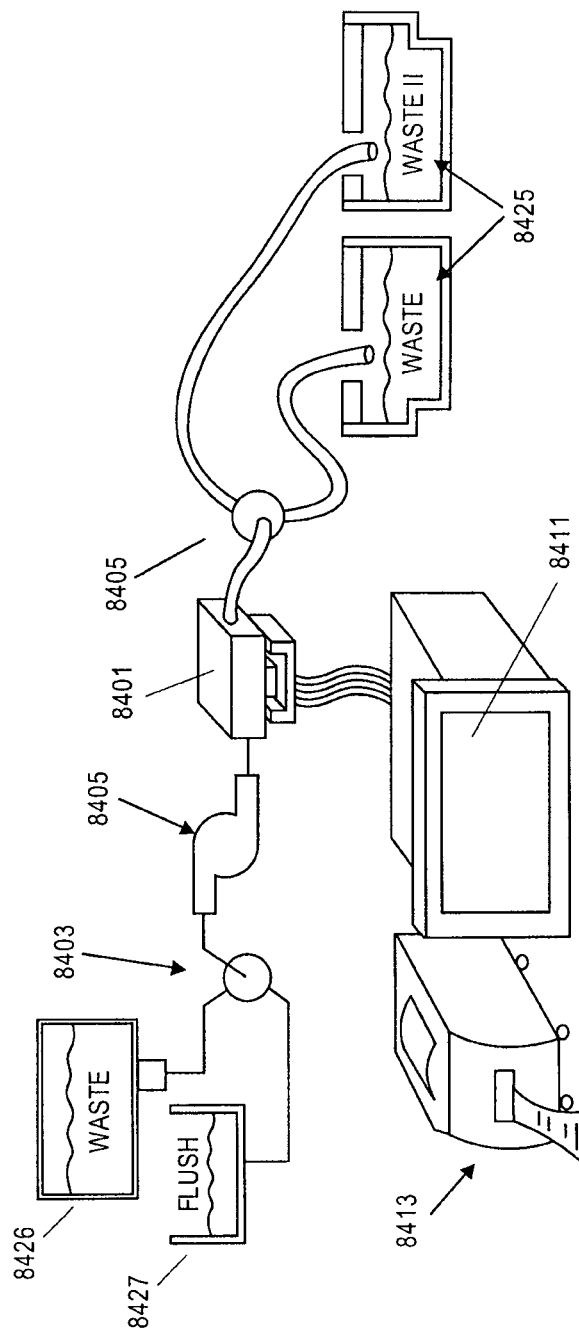
FIG. 84 shows one variation of an IV waste system.

In some variations the system also includes: 2 switching valves, a pump and the overhead for the power distribution and automation controls and plumbing. For example, FIG. 84 shows two waste destinations and one flush solvent source. The design allows for wall, ceiling or floor mounting and the liquid station can go below, on the side, etc. In general, the system can have a printer, scanner etc. for producing a hardcopy of the activity/status of the system. A mentioned above, the system may include a semi-disposable sensor cartridge and interface. The user may install and maintain the cartridge in this "side-module" and there would be a tubing interface for syringes/bags and a cable going to the main unit and placed on the deck so the work is right in front of them. This work module can also have a small status display. The liquid supply and waste containers can be placed on the side of the unit, in back, below or anywhere convenient. The system can connect to the liquid via tubing plumbed from the main unit to custom caps on the containers. There can be a structure that routs these tubes to keep them from being in the way. The containers can be installed in special racks and/or plates that keep them safe and easy and safe to use. The containers, caps trays, plates and racks can all be color coated to help the user identify the correct material. The containers can be round or square. There can be additional liquid handling equipment and sensors used to facility the correct queuing of the measurement such as valves, tubing loops, additional switching valves, etc. There may also be a liquid level system to help the user understand when the containers are full or empty. The design may include automation electronics to control the system including motor control, relays and common automation equipment.

Figure 85A:
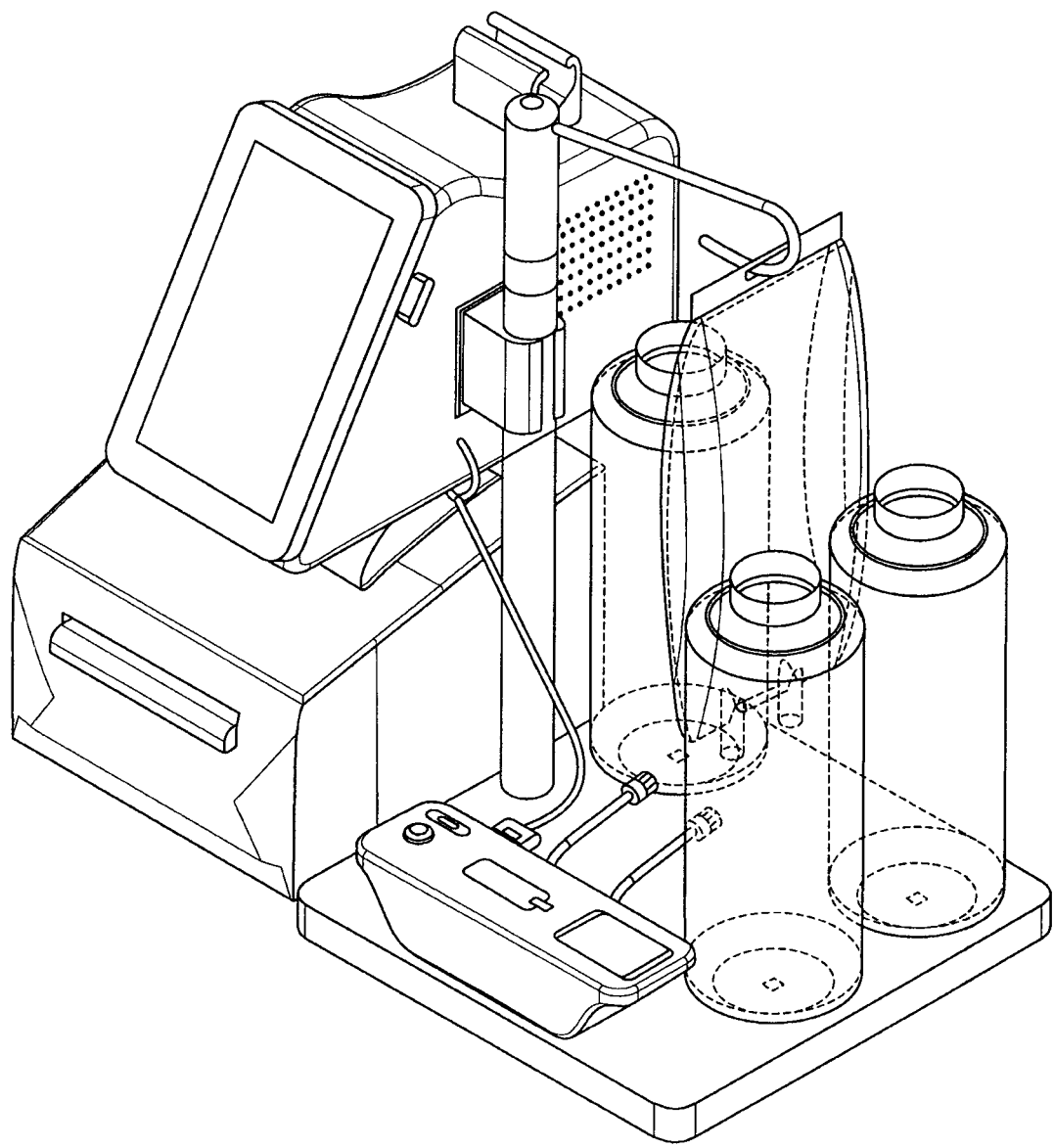
FIGS. 85A-85B show front and back perspective views, respectively, of another variation of an IV waste system.
Figure 85B:
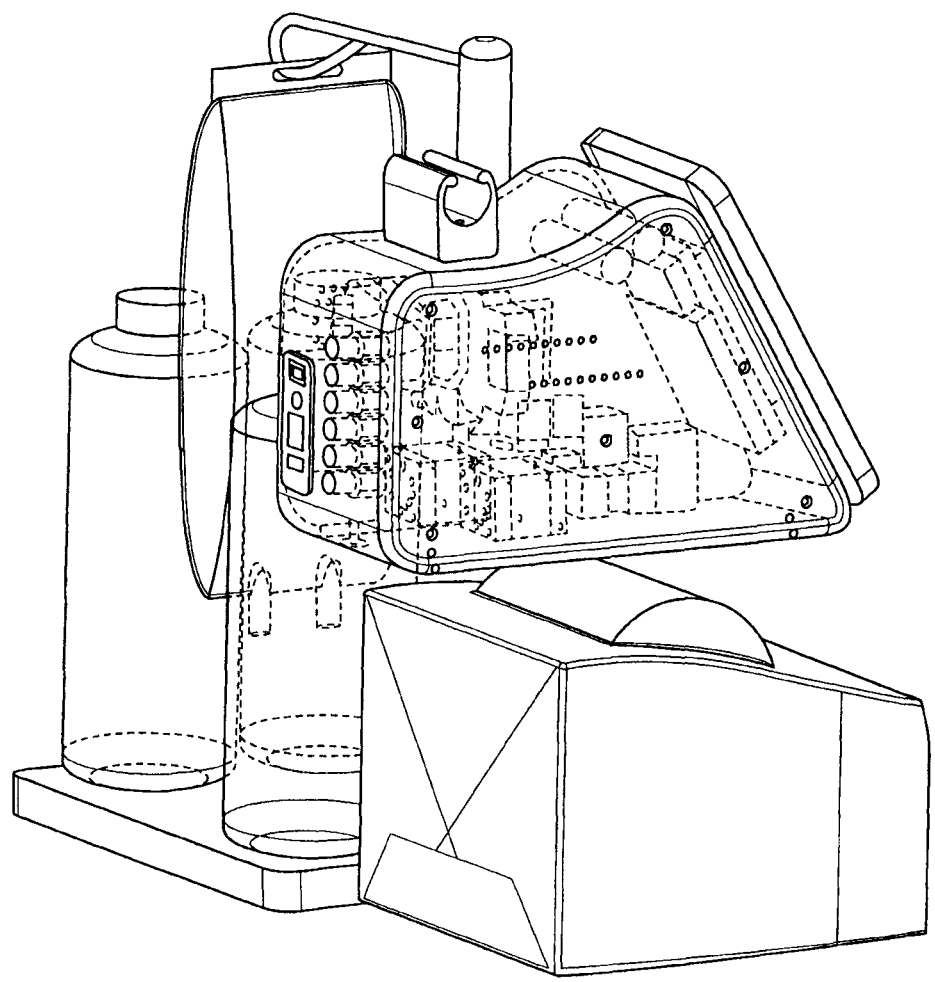

FIG. 84 shows a simplified drawing of one configuration of an IV waste system including a display 8411, printer 8413, processor 8401 (including sensor or sensor cartridge). Two waste containers are included 8425 for storing measured IV waste, and a source container for IV waste is also shown 8426, as is flushing source (e.g., rinsant) 8427. FIGS. 85A and 85B show front and back views, respectively, of another variation of an IV waste system including three waste containers, a source of IV waste (IV bag) and a housing holding the sensor cartridge, printer and electronics (e.g., controller/processor).

Figure 86:
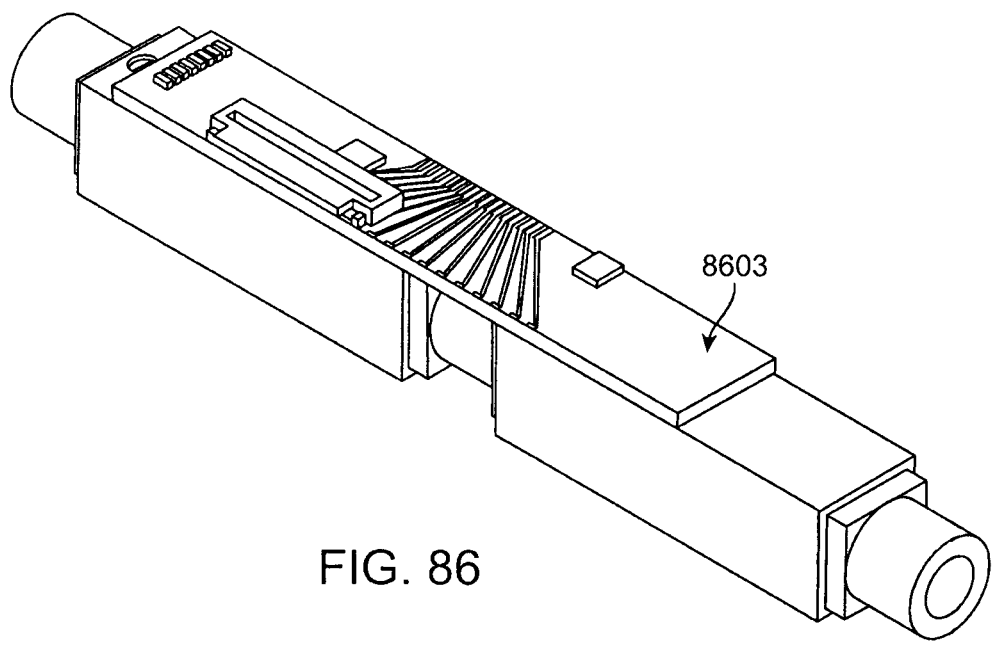
FIG. 86 shows one variation of a portion of a sensor cartridge.
Figure 87:
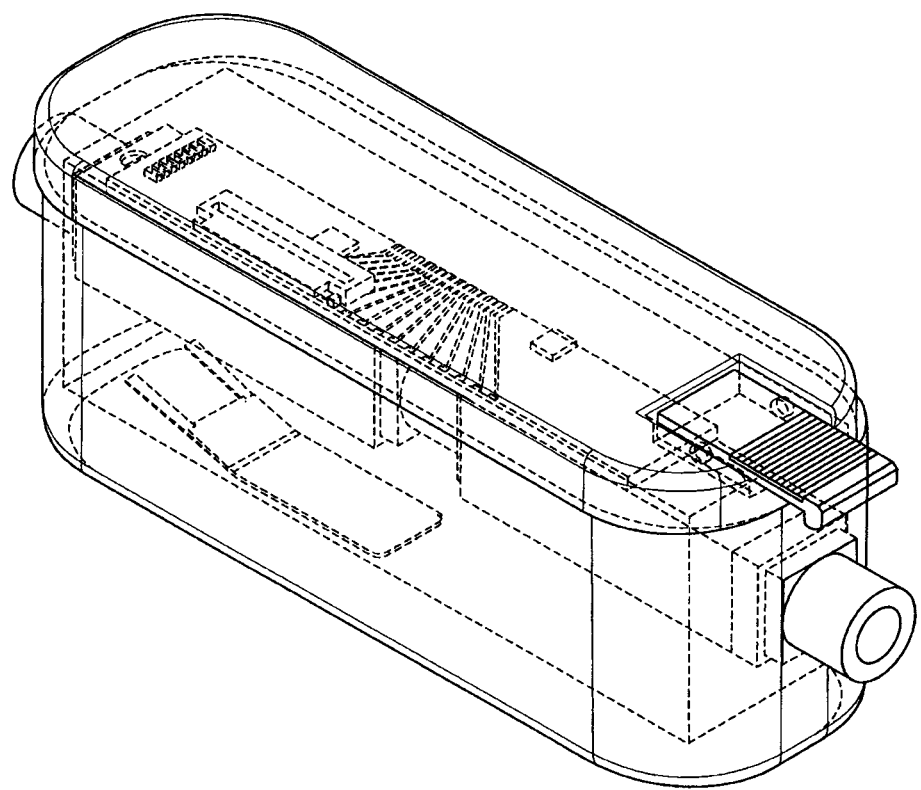
FIGS. 87 and 88 show a sensor cartridge.
Figure 88:
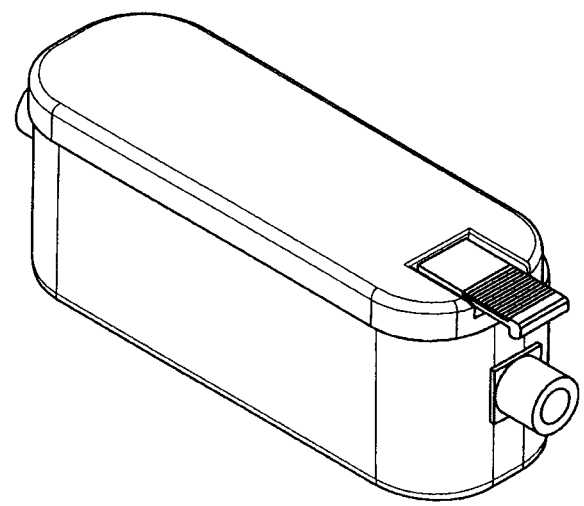
Figure 89:
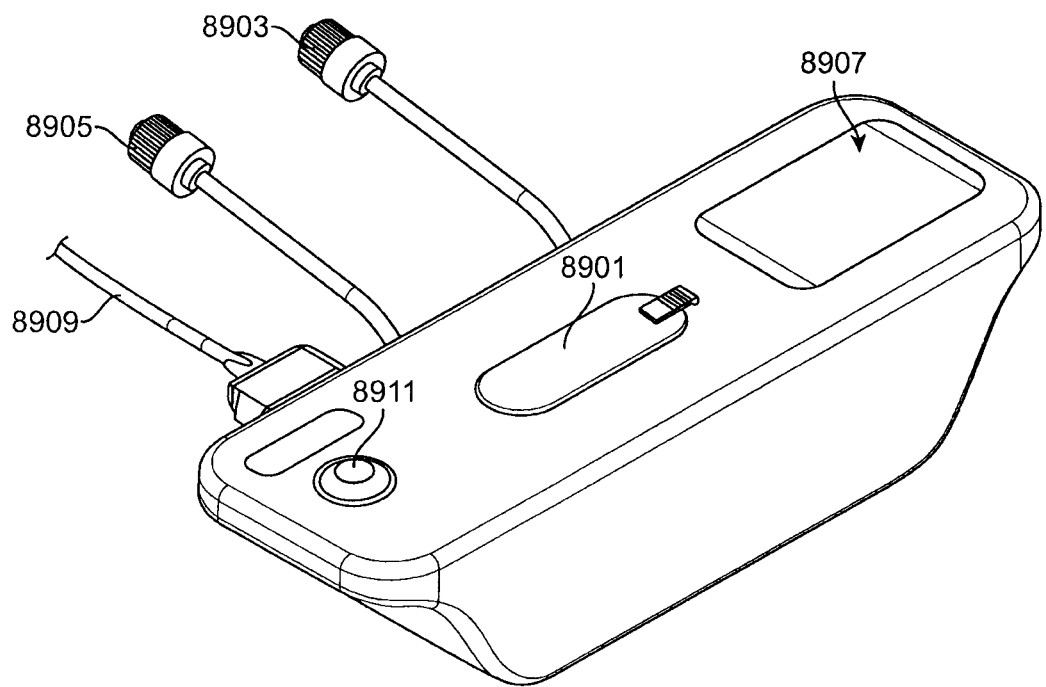
FIG. 89 is a portion of one variation of an IV waste system.

The sensing elements of the IV waste working module can be configured as a unit capable of multiple measurements with intermediate cleaning steps. It can consist of the sensor packaging in either of the both above configurations, and it can have a calibration electronics installed that are then connected to a bottom flexible circuit that can connect to the exit connector of this module. In some variations the sensing elements are removable. For example, the sensors may be configured as a semi-disposable cartridge so that after an appropriate number of uses the cartridge is removed and replaced. FIGS. 86-88 illustrates one variation of a semi-disposable cartridge, including a calibration board 8603. In these figure, the cartridge includes a cylindrical mount/housing through which fluid may pass and be placed in contact with the sensor. The cylindrical mount may itself reside in a chamber with the connectors at either end of the cylindrical mount open and exposed for connection in the system (e.g., in the system shown in FIG. 85A. Thus FIG. 88 shows one variation of a cartridge including a sensor; FIG. 87 shows a semi-transparent view of the same cartridge. FIG. 89 shows a portion of an IV waste system including an inlet 8903 an outlet 8905, a holder for the sensor cartridge 8901, a display 8907 for presenting information on the IV fluid waste processed, and a connection (cable) 8909 to the main unit. The processor and/or controller may be included in this sub-system, or they may be included in the rest of the main unit (e.g., refer to FIG. 85A).

In general, any of the features described herein as relevant to one or more embodiments may be applied to any of the other embodiments (e.g., described in the different sections of the document). The various sections described, including section headings and titles, are intended for convenience only.

System Architecture

Figure 90:
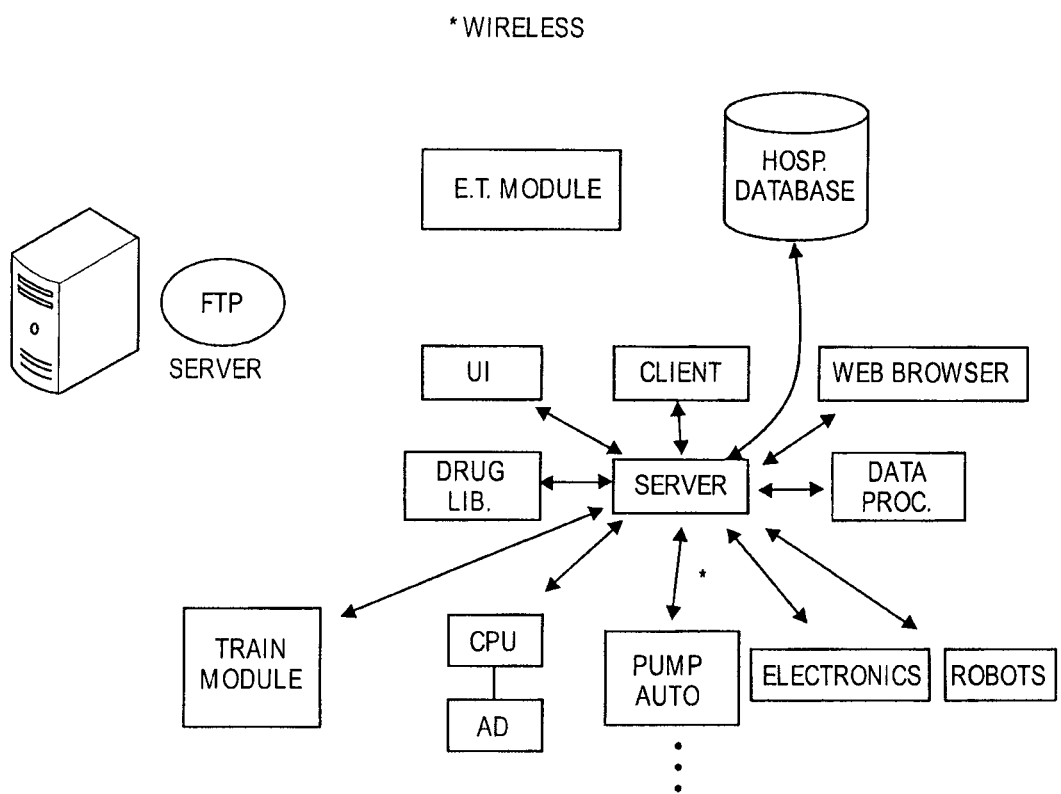
FIG. 90 illustrates one variation of a system architecture that may be used with any of the systems describe herein.

In some variations, the systems may have a system architecture that includes a remote server into which client systems (IV check systems, IV delivery systems, IV waste systems, etc.) communicate with. Each application may have its own server, or the same server may be used for multiple applications. The server may receive reports from the client systems, and may provide them (securely) to outside databases, including hospital databases. In some variations the servers are configured to be accessed by a web browser platform. FIG. 90 illustrates one variation of such a system architecture.

Figure 91:
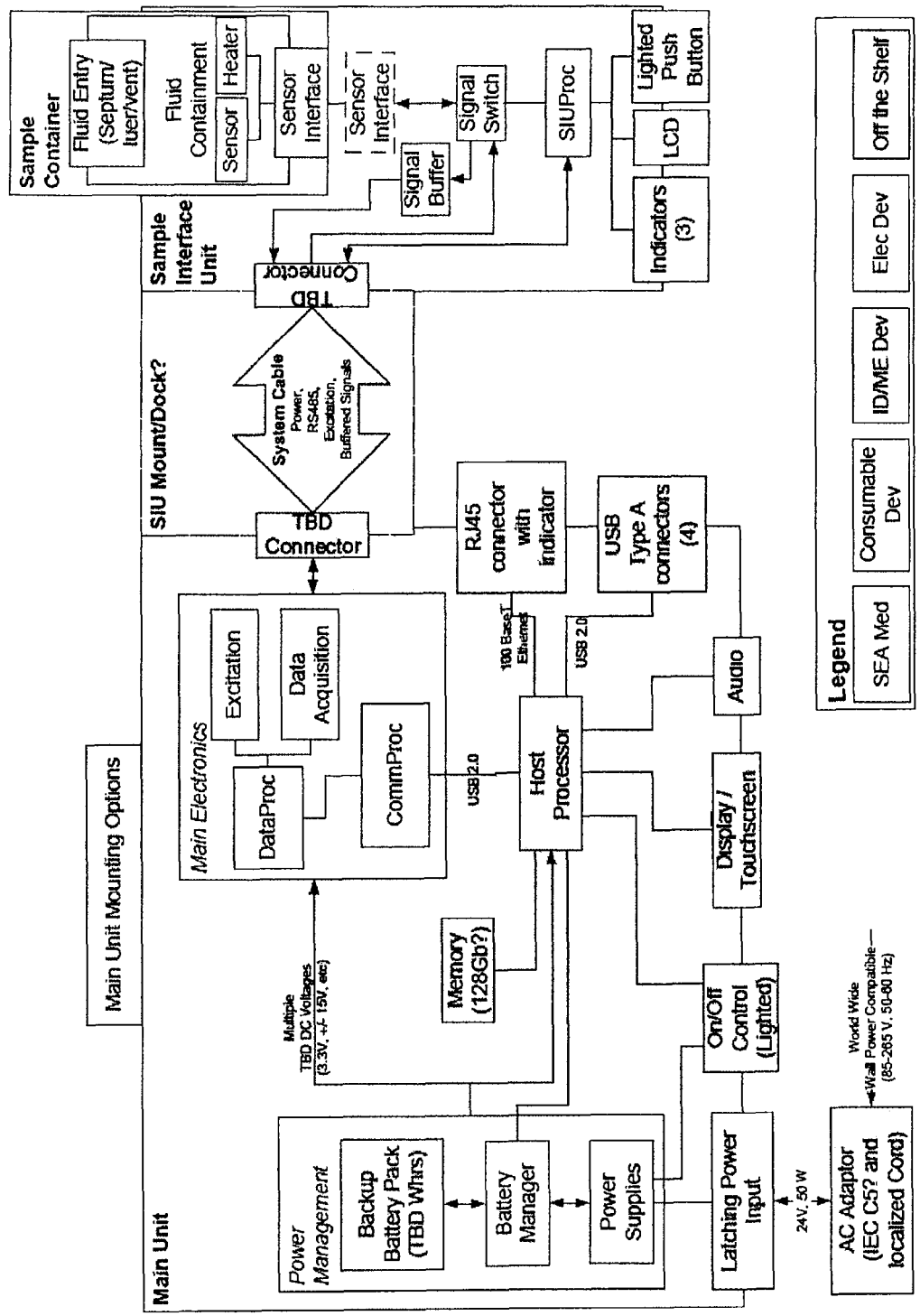
FIG. 91 shows one example of a system schematic which may be adapted for use in any of the systems described herein for immittance spectroscopy.

As mentioned, the various systems described herein may be configured in a variety of different ways, and may use different sensors. FIG. 91 illustrates one schematic of an architecture for a system of determining the composition of a fluid which may be applied in whole or in part (or with modification) as discussed above. This example is intended to illustrate how some variations of the systems described herein may be interconnected.

Many of the systems described herein may include a library of known compositions (including drug identity, dillutent, and concentration). These libraries may be generated a priori or on the fly, specific to a particular setup. For example, a system may allow a user to build a library specific to that system. Thus, the system may be configured to allow a user to make known compositions and use these known compositions to determine library/known "fingerprints" that may later be used to identify a composition of a solution.

Figure 92:
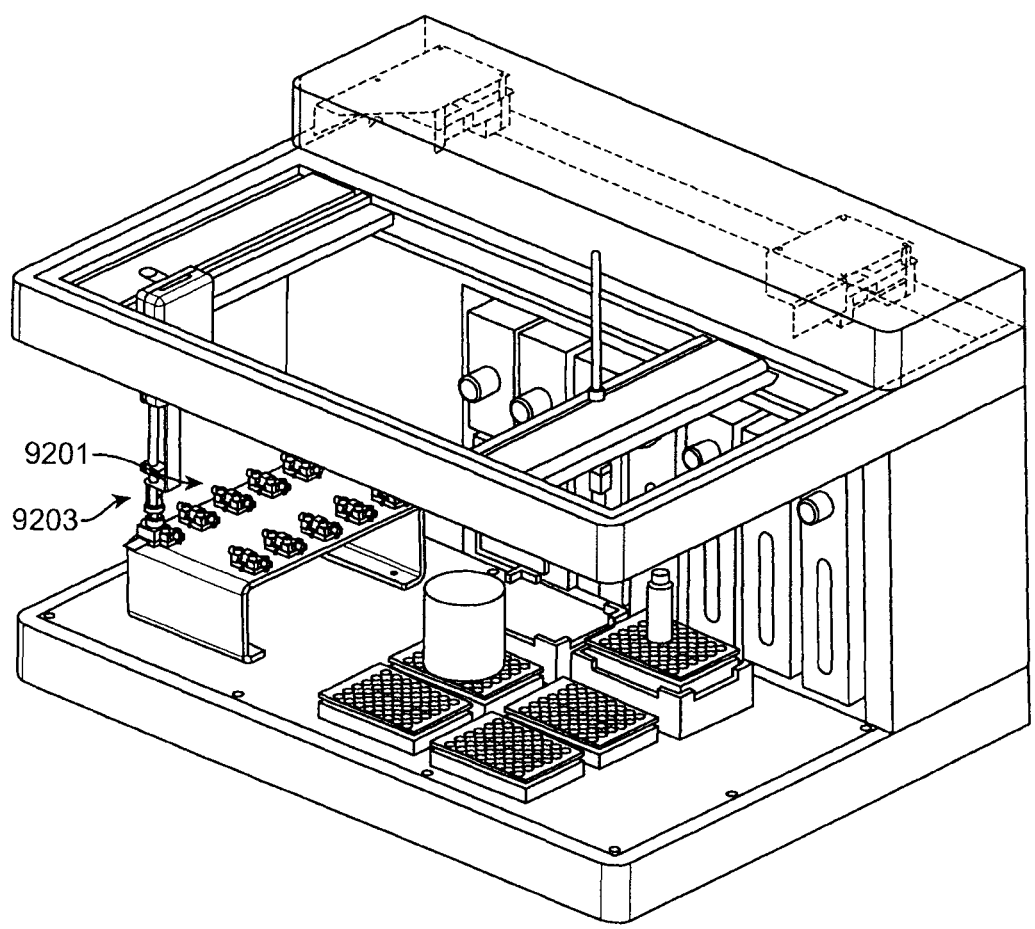
FIG. 92 shows one example of a system for generating an immittance spectrographic library.
Figure 93A:
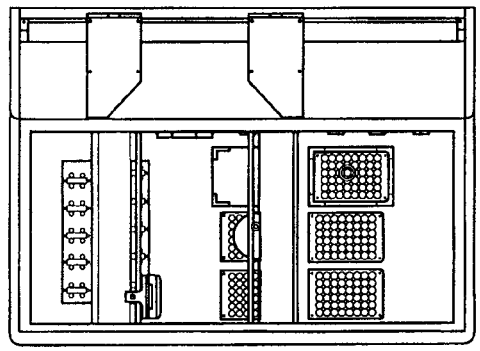
FIG. 93A-93D show enlarged detail of the system of FIG. 92.
Figure 93B:
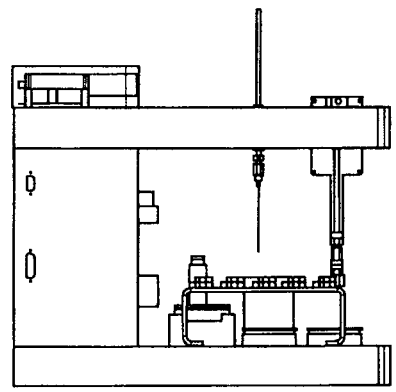
Figure 93C:
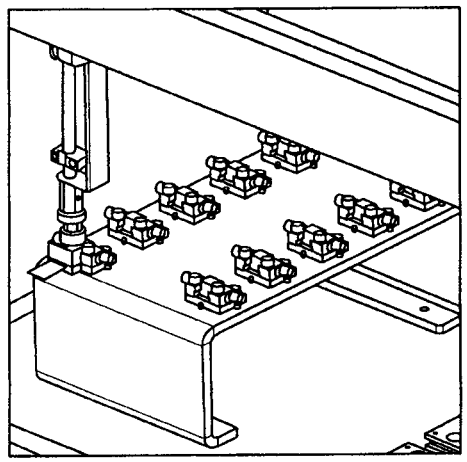
Figure 93D:
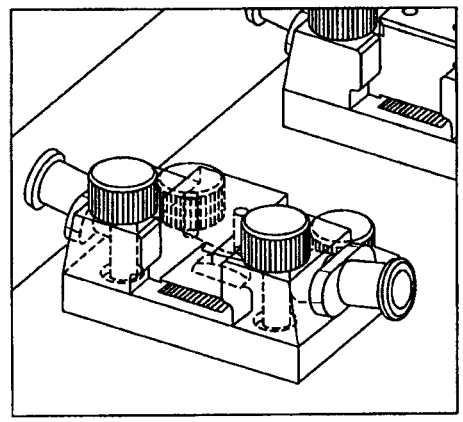

In some variations a system includes a module or mode with which known solutions may be examined to generate a library, supplement a library or correct a library. In some variations a dedicated system may be used to rapidly create a library for use by other systems. For example, FIG. 92 illustrates one system to create a library of known drugs for use with any of the systems described herein. The system shown in FIG. 92 and in additional detail in FIGS. 93A-93D includes an array of sensors 9201 having sample chambers (e.g., shown in greater detail in FIGS. 93C and 93D) that may be probed a robotic arm 9203; fluid may be added from above into each sensor chamber. In general, although the sensor holders may be different, as long as the same sensor design is used (and particularly the same geometry and material for the sensor) the library may be transferrable between different systems. Thus, multiple measurements may be made of different fluid concentrations and compositions.

Flow Sensors

Figures 16A, 16B:
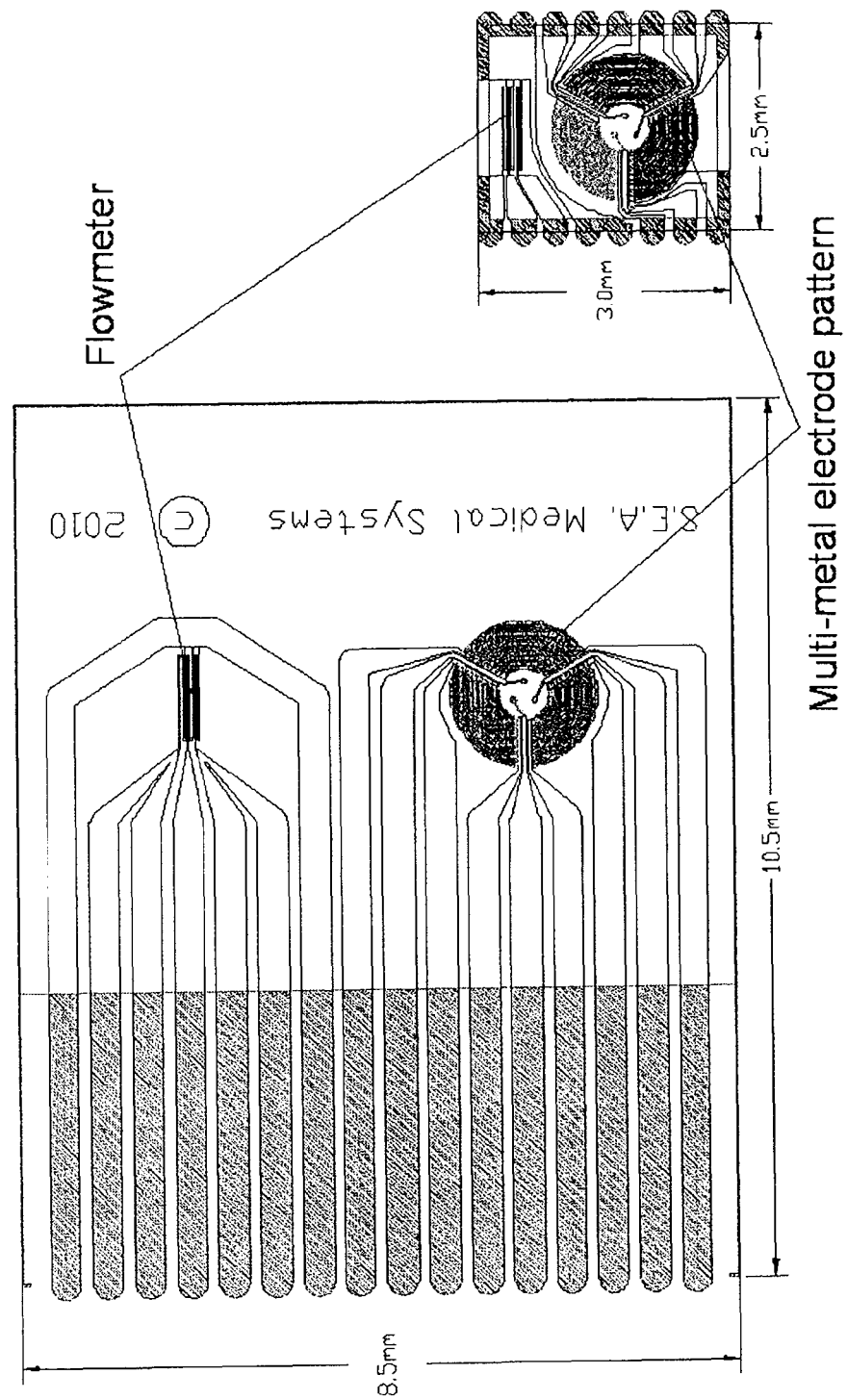
FIGS. 16A and 16B show another variation of sensor including low ionic strength electrodes and a flow meter.

As mentioned above, in some variations the system may include a flow sensor, either as a separate sensor, or integrated into the immittance spectroscopy sensor, as illustrated in FIGS. 12 and 16A.

The volumetric flow of an IV fluid can be measured by a built-in "hot-wire" flow meter or flow sensor. In some variations, the sensor comprises 3 metal film resistance temperature detectors (RTDs) placed next to each other along the direction of the flow to be measured. In a simple mode of operation, the central RTD is heated by passing current through it and resistance difference between upstream and downstream RTD is measured. This resistance difference reflects temperature difference between upstream and downstream RTDs, which is close to 0 in the absence of flow. When flow is present, heat transfer from the central RTD is more pronounced toward the downstream RTD and the temperature difference measured electronically through resistance change between downstream and upstream RTDs serves as the measure of flow. The RTD temperature typically exceeds the ambient temperature by several degrees Celsius and does not affect the temperature of fluid flowing over the sensor in any significant way. More sophisticated schemes of measurement can also be utilized.

Figure 94:
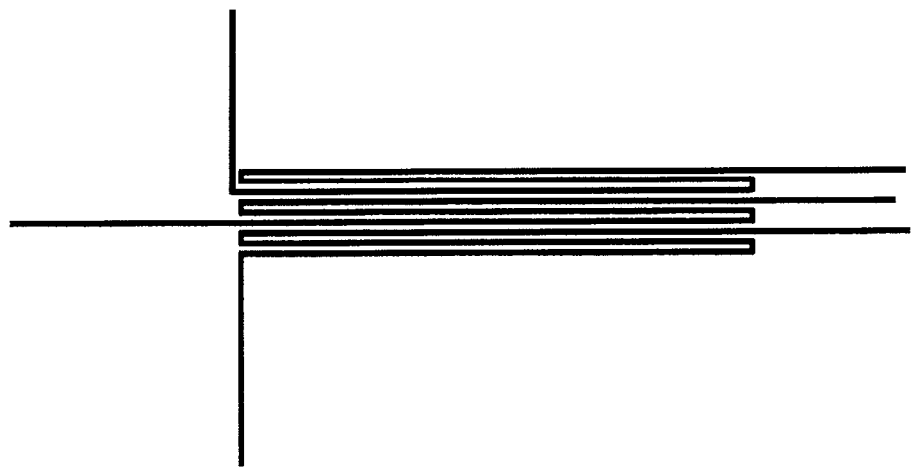
FIG. 94 illustrates one variation of a flow sensor (hot wire anemometer).
Figure 95:
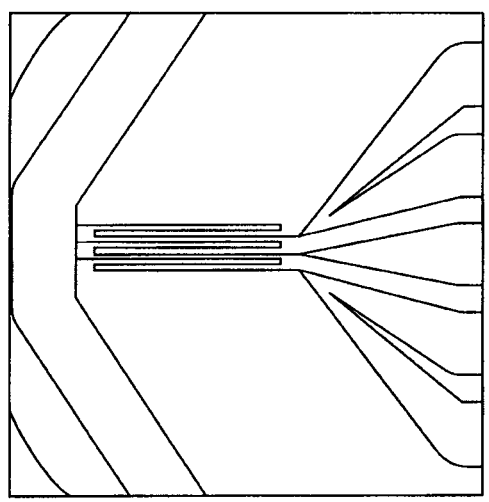
FIG. 95 shows a lithographically manufactured version of the flow sensor of FIG. 94.

Designs for a hot wire anemometer flow detector may include a thin film, hot wire anemometer as shown in the detail in FIG. 94. In this example, the sensor measures flow by applying a very small amount of heat at one point in a flow stream and from the change of temperature of a downstream sensor, the flow rate can be determined. As illustrated, thin film metal traces form 3 resistors, one upstream and one downstream of the central heated trace. This sensor may be used in a differential configuration to improve sensitivity and stability. It also has the capability of measuring the direction of the flow. The design shown in FIG. 94 is for a thin film anemometer produced by metal deposition and lithography. It includes a set of 3 traces with dimensions of 1 mm long, 10 μm trace width, 10 μm trace-to-trace clearance. These dimensions are typical and designed to fit into the sensors discussed above. FIG. 95 illustrates a lithographically produced flow sensor as just described.

A hot wire anemometer such as that shown above may be used to measure fluid flow (see, e.g., H. Bruun, Hot-wire anemometry: principles and signal analysis. Oxford University Press, USA, 1995). In addition to or alternatively, if multiple wires or traces are available, the flow rate is known, it may be used to measure changes in the fluid thermal conductivity and/or heat capacity of the fluid. The basic idea of the hot-wire technique for the simultaneous measurement of the flow and the properties of fluid is that the usual calibration based on King's law can be extended to a fluid property (such as drug concentration) so that the "calibration constants" become calibration functions of the fluid property. Accordingly, if there are two wires available for measurements, two calibration functions, for which dependence of the fluid property is different, are present in King's law for each wire. The system of two King's equations then can be solved for two unknowns—the velocity and the fluid property with the accuracy determined by the wires implementation and signal to noise ratio of the measurement system. The calibration coefficients in King's law depend strongly on the thermal conductivity of the mixture and thus are sensitive functions of a drug's nature and concentration. A similar approach has been developed for the gas mixtures (e.g., P. Libby and J. Way, "Hot-wire probes for measuring velocity and concentration in helium-air mixtures," AIAA Journal, vol. 8, no. 5, pp. 976-978, 1970).

Thus, any of the systems and devices described herein may also include one or more sensors for measuring flow. For example, a flow detector may be incorporated into a common sensor assembly. The sensor assembly in this example includes patterned electrodes that form the electrical admittance sensors and the flow meter.

In addition to the examples of sensors and systems described above, other modifications, applications and modes of use are contemplated. For example, other electrode materials including metal eutectics, alloys, amorphous metals, liquid metals, conductive oxides, metals with insulating oxide layers, inert electrodes, chemically active electrodes, etc., may be used to form the sensor(s). In some variations the admittance spectroscopy electrodes may be separated from fluid by insulating layers. Admittance spectroscopy electrodes may be separated from fluid by semi-permeable membranes. The surfaces of any of the admittance spectroscopy electrodes described herein may be chemically modified or physically modified. For example, admittance spectroscopy electrode surfaces may be physically modified by micromachining, nano-lithography, etc. In some variations, the admittance spectroscopy electrodes may have two or more different materials in two or more areas of the same electrode.

In some variations, the system includes sensor element designs incorporating leads, pads and fluid containment for interfacing with an automatic sample loader or an automated readout system. A sensor element may be enclosed in or exposed to a fluid container in which gases may dissolve. This can include a semi-permeable membrane on one or more sides to allow the gas to enter and dissolve into the fluid. Additionally, the fluid may contain additional materials that will selectively absorb specific materials from a separate fluid (gas or liquid) stream and/or react with specific materials in the stream. Both the contained fluid composition and the semi-permeable membrane can be designed to provide selectivity in the types of materials that will be absorbed. Materials that enter the fluid will be detected by admittance spectroscopy or any other applicable technique.

In some variations, a sensor element design may include a mat of absorbent material over the sensor elements such as glass fibers, polymer fibers, etc., that will absorb and hold the solution to be tested in contact with the sensor elements and provide containment for the sample as well as preventing overflow.

The systems described herein may be operated at measurement ranges outside that normally used. In particular, lower frequencies (in the miliHz range) are described above; in addition, higher and lower applied voltages, higher and lower frequencies of excitation, etc. may be used. In addition, measurement may be done in an electrochemical regime. For example, measurement of admittance above an applied potential of 0.5V. This may include high voltage measurements (kV, etc.). Measurements of complex admittance may be done in measurement modes that include cyclic voltammetry measurements. Pulsed modes for measurement may also be used. In some variations, operation of the ac admittance measurement with applied DC biases both above and below 0.5 Volts and variable DC bias voltages may be used. This may have advantages in introducing additional variability to the measurement thus adding dimensionality to the data for increased ability to distinguish drugs.

Electrode preparation and cleaning may also be used as part of the system and methods described herein. For example, pre and post assembly sensor cleaning protocols including solvent based, plasma cleaning, etc. may be used.
Identification of Compounds and Concentrations All of the systems described herein for using immittance spectroscopy to determine the composition (identity, concentration and diluent) of a liquid typically use some form of pattern recognition. In the simplest form, the system may match a pattern of the complex immittance spectroscopy (the "fingerprint") recorded to a library of known immittance spectroscopic patterns. When these, often complex, multi-dimensional patterns are the same, the composition of the liquid can be affirmatively identified. Since the complex immittance patterns determined as described herein, using multiple frequencies and a plurality of different electrodes, are characteristic to the specific components in the liquid, including the identity, concentration and diluent, this pattern recognition provide an accurate and reliable method of determining the composition of the solution.

Pattern recognition, or the process of matching the patterns of a test signal and a known library of signals, has proven difficult and complicated, at least because of the large number of dimensions (often as many as 60) collected, variability in the signals recorded, and slight variations in the concentrations of solutions being tested compared to the known standards in the library. One solution is to expand the extent and granularity of the library of known signals; the greater the number of known fingerprints, the more likely a match will be identified. Alternatively, it may be possible to use one or more methods that would allow the system to accurately match a test complex immittance fingerprint to a library of complex immittance within various ranges of accuracy that permits identification and extrapolation from library fingerprints without requiring an exact match. Thus, various pattern recognition techniques are described below that may allow identification of compositions of solutions tested by the system even when the library does not include an exact match. Further, these techniques may allow rapid pattern recognition of even high-dimension datasets of complex immittance data in a rapid (i.e., approaching real-time) manner that would not be possible even when identifying an exact match.

As applied to automated identification of drugs and IV fluids, "pattern recognition" is measuring the raw data from the sensor and either reporting unknown identity or displaying the identity and concentration of drug based on the category or "class" of the pattern. Ideally, the systems would apply a pattern recognition system capable of nearly instantaneously classifying sensor data based on a knowledge extracted from the patterns registered in the prior sets of measurements performed on the known compounds and compositions (the library). Such a system may be referred to as a performing pattern matching system, although patterns in the various applications described herein are not rigidly specified, due in part to inherent variability in composition of the IV fluids, the sensor-to-sensor differences, variability in electronic parameters and other factors including temperature.

The complex immittance data described for the systems herein are typical examples of syntactic (or structural) patterns, where the data is produced by a controlled process as opposed to statistical patterns generated by probabilistic systems. The classification or description scheme therefore is based on the structural interrelationships of features observed in the course of measurements. The data is also an example of multivariate or multidimensional data sets, which dimensions are partially correlated and can be subject to reduction to fewer orthogonal dimensions thus simplifying calculations and reducing storage requirements, defining points in an appropriate multidimensional space.

Although any appropriate pattern recognition technique suitable for comparing (or simplifying and comparing) large dimensional dataset may be used with the systems for identifying the composition of a liquid by immittance spectroscopy described herein, two general types of pattern recognition are described herein: pattern recognition by neural networks and pattern recognition by principle component analysis.
Method 1: Neural Networks In general, the neural networking methods used in the prototype systems illustrated below may match the experimental test patterns against a library of known patterns by training the network using the library. In general this method may preserve all of the dimensions of the dataset.

For example, EasyNN-plus software package was chosen as a platform for testing the applicability of the neural network algorithms to IV fluid pattern recognition. Five (5) experimental sensor traces for each of five (5) different IV fluids were formatted and placed on an EasyNN Grid—an input facility. The neural network input and output layers were created to match the grid input and output columns.

Hidden layers connecting to the input and output layers were then "grown" to hold the optimum number of nodes semi-automatically.

Once the neural networks learned the training data in the grid, data in the grid was used to self-validate the network at the same time. Fluid data utilized in these tests were for the following IV formulations: pure 0.9% Saline (SAL), Dopamine at 2 mg/ml (DOP), Furocemide at 4 mg/ml (FUR), Midazolam at 0.5 mg/ml (MID) and Vecuronium at 1 mg/ml (VEC)—all typical therapeutic concentrations formulated in pure 0.9% saline. Training for this dataset generated 60 input nodes, a one hidden layer with 14 nodes and 5 output nodes.

When training finished the neural network was used to experiment with the same data from the training set with added artificial noise to assess error rate as a function of noise amplitude. Each drug trace was "randomized" and presented to EasyNN for recognition 1000 times and instances of incorrect recognition counted. The results are presented in the Table 1 below.

TABLE 1

Error rate in % as a function of % noise.

| Noise, % | DOP | FUR | MID | SAL | VEC |
|---|---|---|---|---|---|
| 2 | 0 | 0 | 0 | 0 | 0 |
| 4 | 0 | 0 | 0.1 (VEC) | 0 | 0 |
| 6 | 0 | 0.3 (SAL) | 2.2 (VEC) | 0 | 0.6 (MID) |
| 8 | 0.3 (MID) | 0.2 (MID) 4.1 (SAL) | 7.0 (VEC) | 0.1 (DOP) | 1.7 (MID) |
| 10 | 0.4 (MID) | 0.4 (MID) 13.8 (SAL) | 10.8 (VEC) | 0.1 (DOP) | 2.7 (MID) 0.1 (VEC) |

The noise was added to both X and Y component of the experimental traces as a percent of the X and Y values by a standard random generator function that produced uniformly distributed noise in the range 0 to % indicated in the first column of Table 1. Next to the percent error rate is indicated the name of the formulation that was mistakenly identified.

Figure 96A:
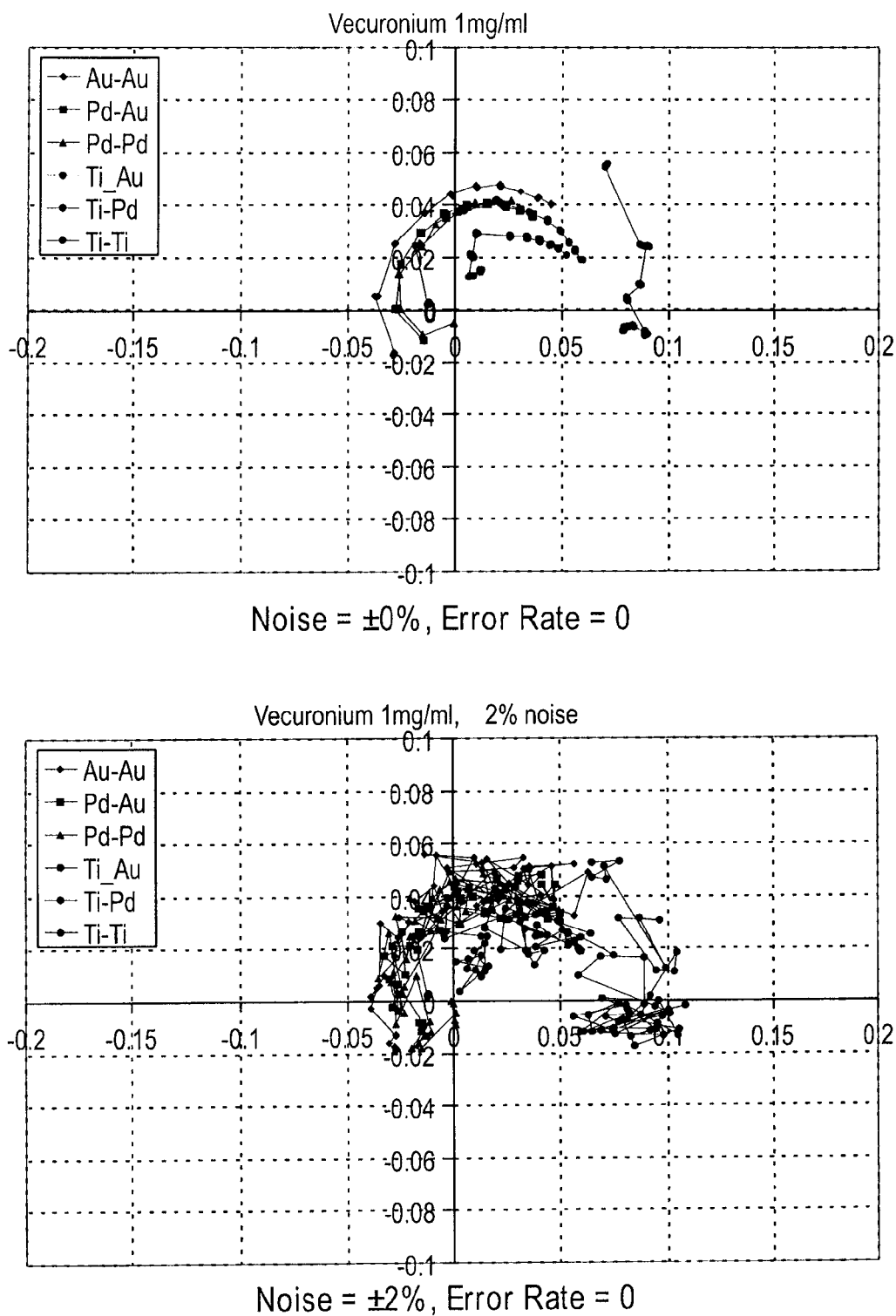
FIG. 96A shows six versions of a set of immittance spectrographic data with increasing amounts of artificial noise added for Vecuronium at 1 mg/ml (VEC)
Figure 96C:
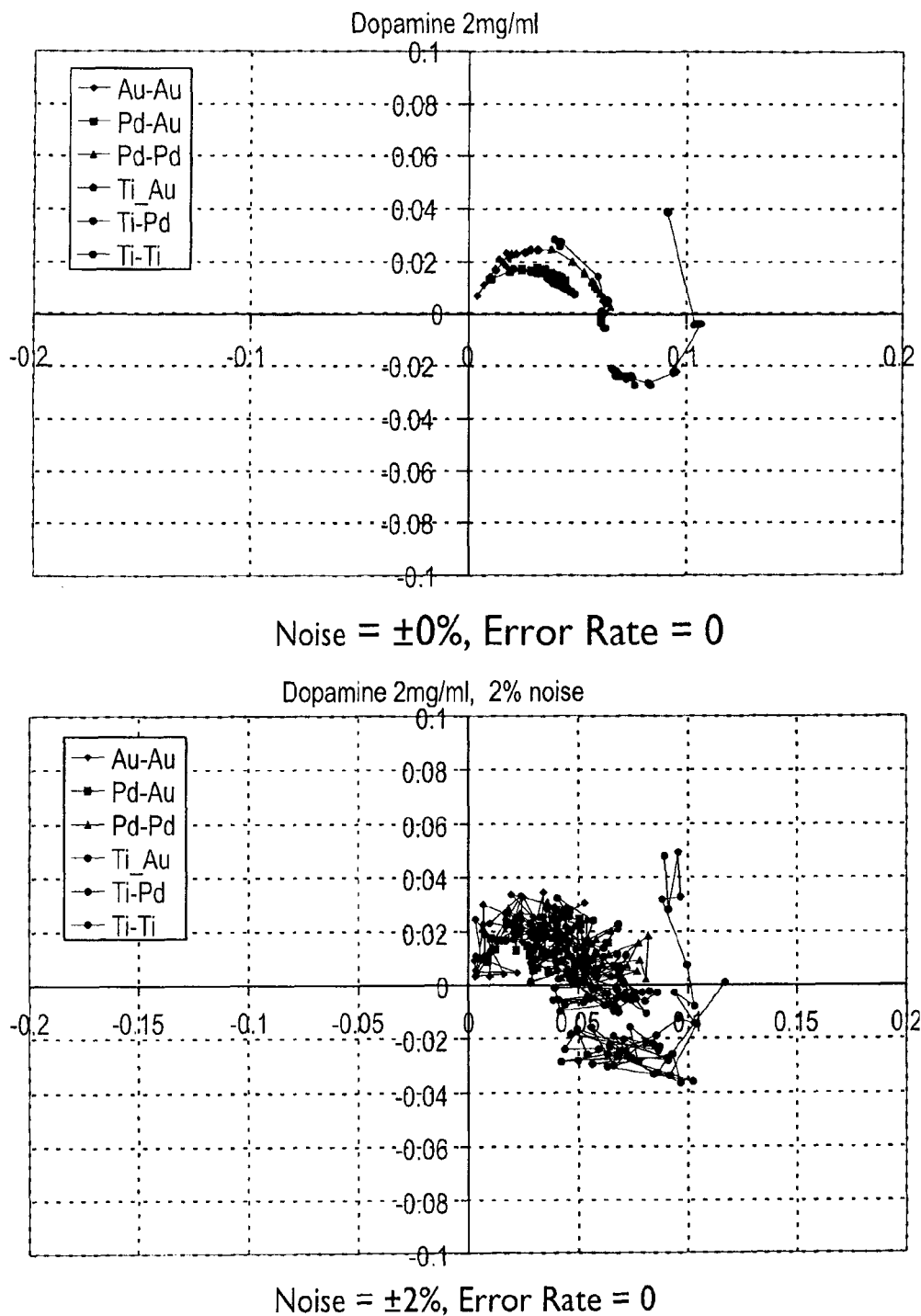
FIG. 96C shows the patterns with artificial noise added for Dopamine at 2 mg/ml (DOP)
Figure 96C:
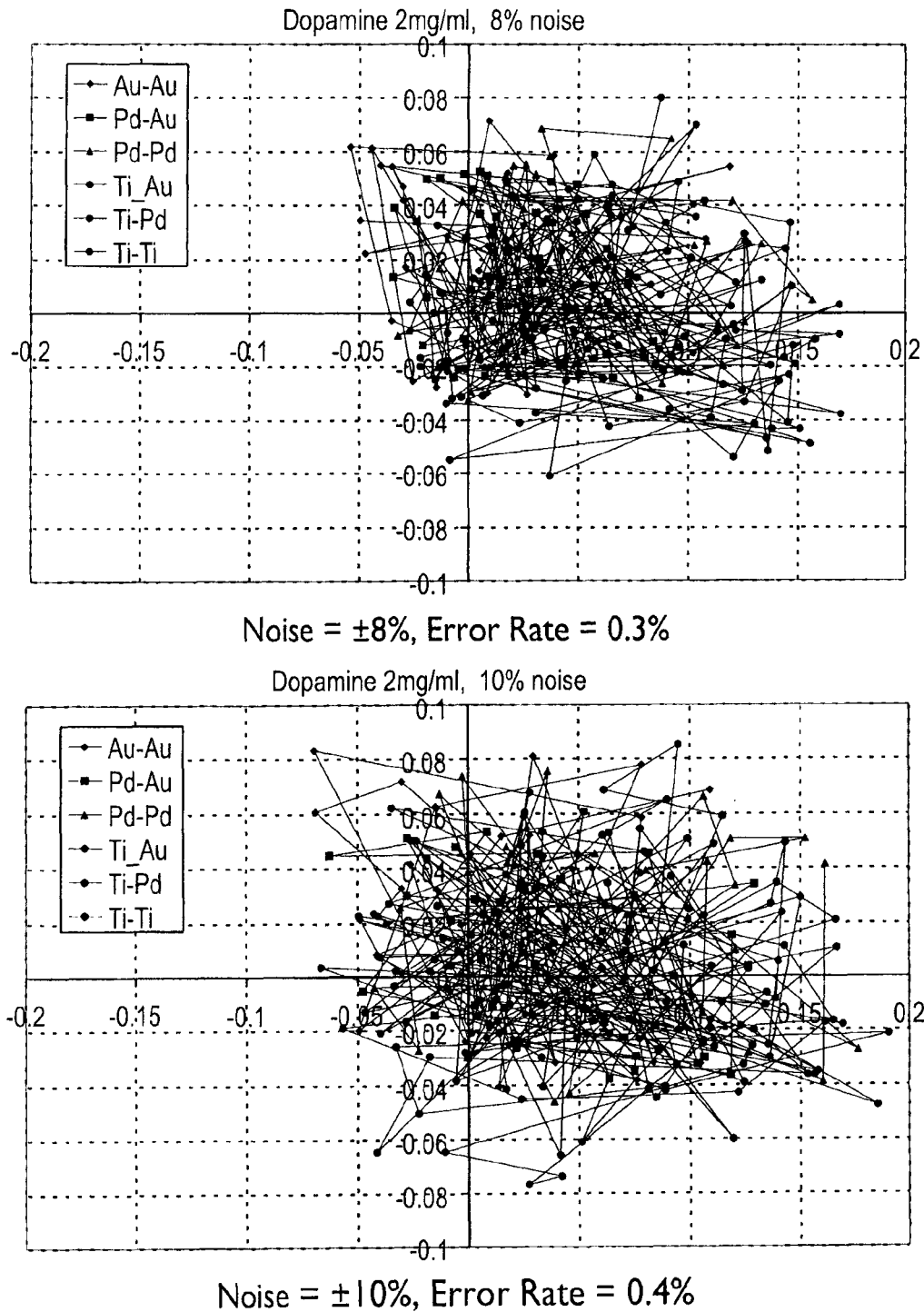
Figure 96D:
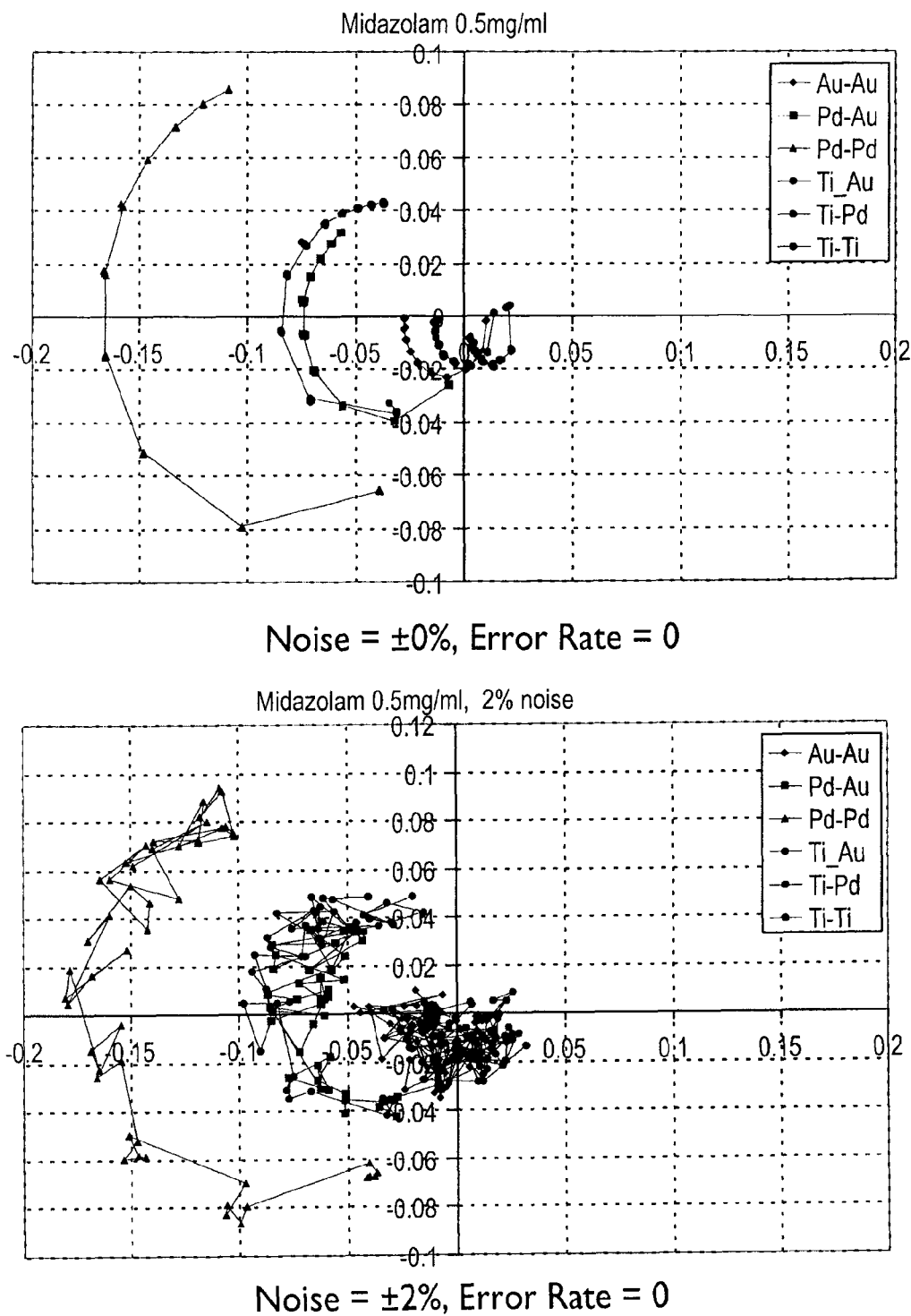
FIG. 96D shows the patterns with artificial noise added for Midazolam at 0.5 mg/ml (MID).
Figure 96D:
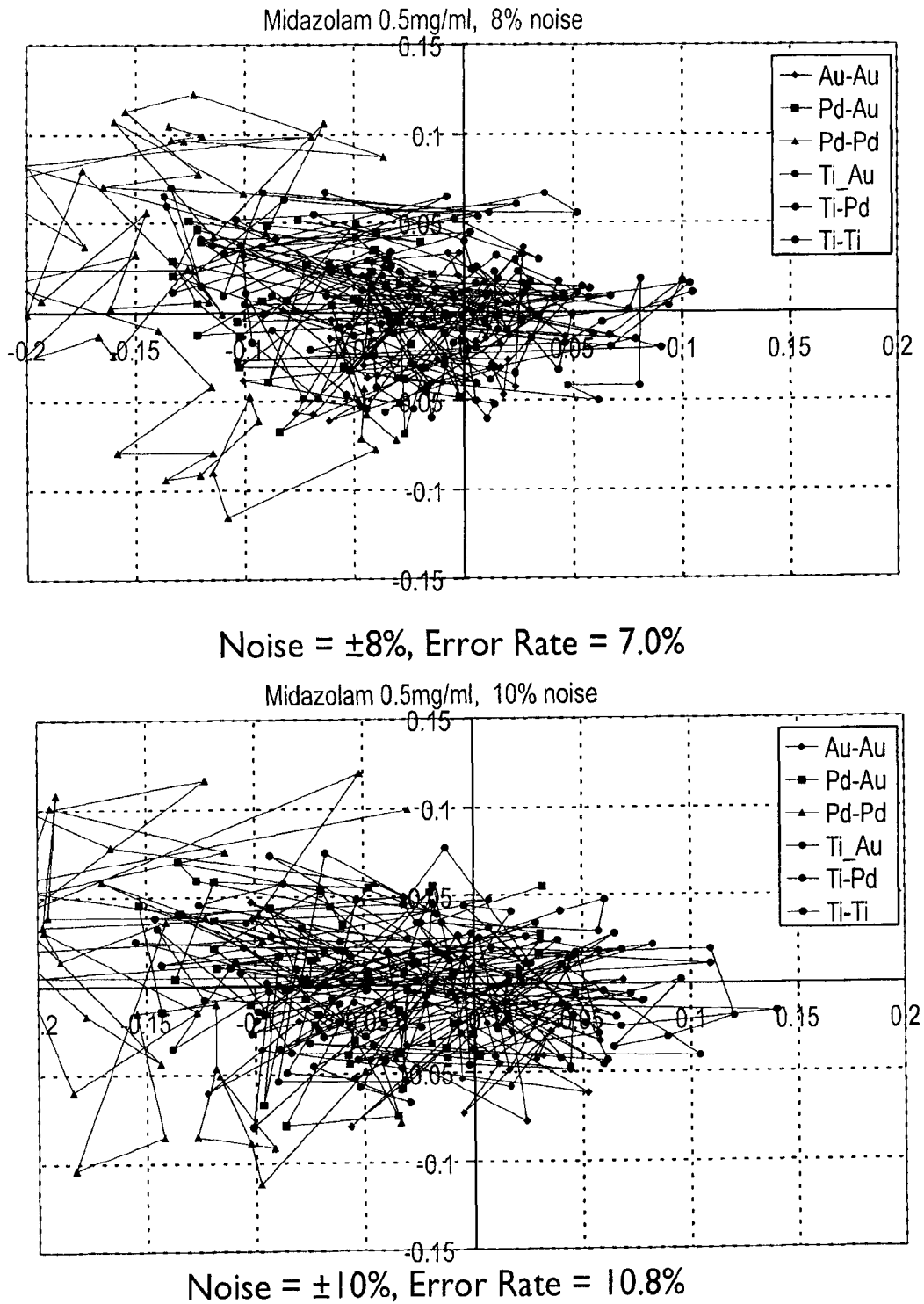

To provide a graphical representation of the noise amount added in the course of these tests, the original patterns and the "randomized" patterns are shown on FIG. 96A. through 96D. The EasyNN-plus software package demonstrated excellent noise rejection capabilities being able to recognize correctly the pattern that were visually substantially blurred by noise. Specifically, FIG. 96A shows patterns with artificial noise added for Vecuronium at 1 mg/ml (VEC); FIG. 96B shows the patterns with artificial noise added for Furocemide at 4 mg/ml (FUR); FIG. 96C shows the patterns with artificial noise added for Dopamine at 2 mg/ml (DOP); and FIG. 96D shows the patterns with artificial noise added for Midazolam at 0.5 mg/ml (MID).

The degree of the noise rejection is a direct reflection of the nature of neural network algorithms as predominantly space-partitioning engines that attempt to classify any unknown pattern as a member of one of the classes from the training set.

It is highly unlikely that the noise level of this magnitude will be ever encountered in the real life application. Even at 2% noise level it would be useful if the algorithm would flag such pattern as "unknown". Most neural network packages (such as EasyNN-plus) do not easily identify patterns as "unknown" and additional algorithms like Restricted Coulomb Energy (RCE) or similar can be added to better distinguish the "unknown" patterns.

The application of Neural Network pattern recognition methods for recognizing drug signatures has been tested with the prototype systems described herein. Examples of the application of neural network pattern recognition in other contexts include recognition of speech, facial features, images and in industrial parts recognition and sorting applications. The application of neural network techniques to the identification of IV drug solution compositions has not previously been described and offers a number of challenges.

The recognition of drug composition (e.g., both the drug identity and concentration) was implemented in our systems by creating two models based on a Probabilistic Neural Network (PNN). This model takes as input, the full data set of measurements from our admittance measurement across all metal pair combinations and frequencies. The first component is a drug recognition model to classify the drug/solvent combination from the measurements and the second component is a function approximation model to estimate the concentration of the drug from the measurements and the known drug/solvent that was being measured. In this implementation, the models were independent, but in use, the output of the drug recognition model could be fed as part of the input to the function approximation model to determine both the drug identity and its concentration. The models were trained on a set of drug data spanning a number of drugs, two diluents and a range of concentrations of each drug.

The table in FIG. 110 shows initial results from testing of this method against a set of drugs and concentration ranges. This table shows the result of processing drug signature data through the drug identification component and the table in FIG. 111 illustrates the concentration determination component output. In another implementation, both methods may be combined to give the drug and diluent identity as well as the concentration in the output and will be trained on a defined set of drugs, diluents and concentrations.

Method 2: Principal Component Analysis:

Principal component analysis (PCA) is a mathematical procedure for multivariate data decomposition that that transforms a number of partially correlated vector variables into a smaller number of uncorrelated vector variables called principal components. The multidimensional variables are processed so that the first principal component accounts for as much of the variability in the data as possible, and each succeeding component accounts for as much of the remaining variability as possible. It is often found that the size of the principal components diminishes quickly with each succeeding component and it is necessary to take into account only a few principle components to be able to account for the most significant portion of the observed variation in the original multivariate data.

The multivariate nature of the data coming out of the sensor reflects the method the data is gathered. The natural way of collecting admittance spectra is in form of in-phase X and quadrate Y components of admittance as a function of frequency within frequency range. Since the admittance is an analytical complex function of frequency, it immediately follows that X and Y components of complex admittance are not truly independent, but connected via Kramers-Kronig integral relation. Theoretically, if the whole spectrum of either one of the components were known within frequency range 0 to ∞, the other component could have been calculated by numerical integration. Since frequency range 0 to ∞ is difficult to attain experimentally, for drug recognition application it is more practical to measure both components within limited frequency range and utilize any resulting data redundancy for noise reduction.

As conventional in application of PCA, X and Y values at each frequency measured across a variety of metal pads are aligned to form a 120-element row (vector), which represents a particular measurement and can be considered a unique "observation". Multiple measurement rows are assembled into a matrix of observations and each column along the row is considered a variable vector. This approach allows for a relatively convenient way for numerical experimentation with the measured data by either adding or removing variables such as individual frequency columns or blocks of columns such as measurements across a certain metal pads or combinations to arrive at the minimalistic dataset that allows for reliable separation of observations taken, for example, at reduced set of frequencies without significant deterioration in signal-to-noise ratio (SNR).

The matrix of observations is treated as a set of points in Euclidean space. Each variable (column) is demeaned and scaled by subtracting mean along the column from each value in the column and dividing it by the column's standard deviation—procedure known as matrix centering and scaling. The first principal component is calculated as the vector with the largest length, which corresponds to a line that passes through the mean and minimizes sum squared error with all the observation points. The second principal component vector corresponds to the same after all variance between points along the first principal component vector has been subtracted out from the points. The calculations repeat for each succeeding vector. This process finds a number of orthogonal vectors starting from the mean of the dataset and rotated such that as much of the variance in the dataset as possible is aligned along these vectors. In most practical cases including S.E.A. sensor data the variance is substantial along a first few principal components and diminishes quickly with the increasing component's number in sequence. The variance along the remaining directions may be ignored with minimal loss of information and thus much more compact representative dataset of reduced dimensionality can be stored instead of the original data. In a sense PCA provides linear transformation of the original dataset for finding an optimal subspace that has largest variance.

Although PCA provides optimal linear transformation and reduction of data dimensionality, it is not the optimal algorithm for data classification and separability. For the patterns generated by both Smart IV and IV Check two approaches can be taken to data classification "local" or "individual PCA" or "global PCA". In the first case the training dataset is the data generated for a particular fluid with all variability that has to be taken into account (such as variability between sensors, electronics, different fluid manufacturers etc.). The orthogonal primary component basis is computed and stored in the library for each formulation that needs to be recognized. The data measured for the unknown fluid is projected onto the each basis from the library and classified based on the distance between the projection and the origin of the basis. If the distance from the origin is within expected limits defined by the variability in the training data set—the observation belongs to this class and can be identified as such. With the increasing distance from the origin the probability of current measurement being of different fluid increases. Alternatively, which may work better for the training sets with higher variability, the projected measurement data can be restored back from the projection and compared with the original measurement data. If the fluid belongs to the class onto which basis the measurement data was originally projected, the restored data will accurately trace the measurement data. The accuracy of restoration can be assessed by calculating of standard deviation (or some other measure of residuals) between the measured and restored datasets to see if it falls within or outside the deviations expected form the one reflecting the variability of the training set.

The attractive advantage of this first approach is in its additive nature—the library of known fluids is expandable by addition of training sets as they become available in the process of product development.

The second approach—"global PCA"—utilizes all training sets and generates a single space that encompasses all training sets available at the moment. In this approach the individual fluid training datasets appear as "clouds" of points in this global frame of reference reflecting variability within individual training sets. If a measurement data from an unknown fluid is projected into this global space as a single point that is found to be within or close to one of the training "clouds"—it belongs to that particular class and if not—it is an unknown fluid.

This "global PCA" is not additive as the optimal space has to be recalculated every time the next training set becomes available to be added to library. The separability of the classes are not optimal with this technique, but it can be naturally enhanced utilizing Fisher Linear Discriminant Analysis—FLDA—(to be discussed in the future reports). "Global PCA" also allows for more natural classification of fluids based on the whole dilution profile and relatively straightforward interpolation between different concentrations. Same dataset from the same set of IV fluids: 0.9% Saline (SAL), Dopamine at 2 mg/ml (DOP), Furocemide at 4 mg/ml (FUR), Midazolam at 0.5 mg/ml (MID) and Vecuronium at 1 mg/ml (VEC) was used in the calculations utilizing PCA.

Individual primary component spaces were calculated based on 5 instances of experimental data for each fluid. It was found that four primary components along with the mean vector provide a sufficient description of 99.98% of the variability on the patterns. Then for the unknown fluid the projections of the "unknown data" onto individual spaces has been generated and subsequently restored form the projection. Square root of sum of squares of the differences between the original data and the one restored from the projection has been calculated. This value should be close to zero if the experimental data "fits" the space, which it was projected onto and restored form. If the data has been projected onto the other's fluid space, data distortion caused by the mismatch will be substantial.

Figure 97:
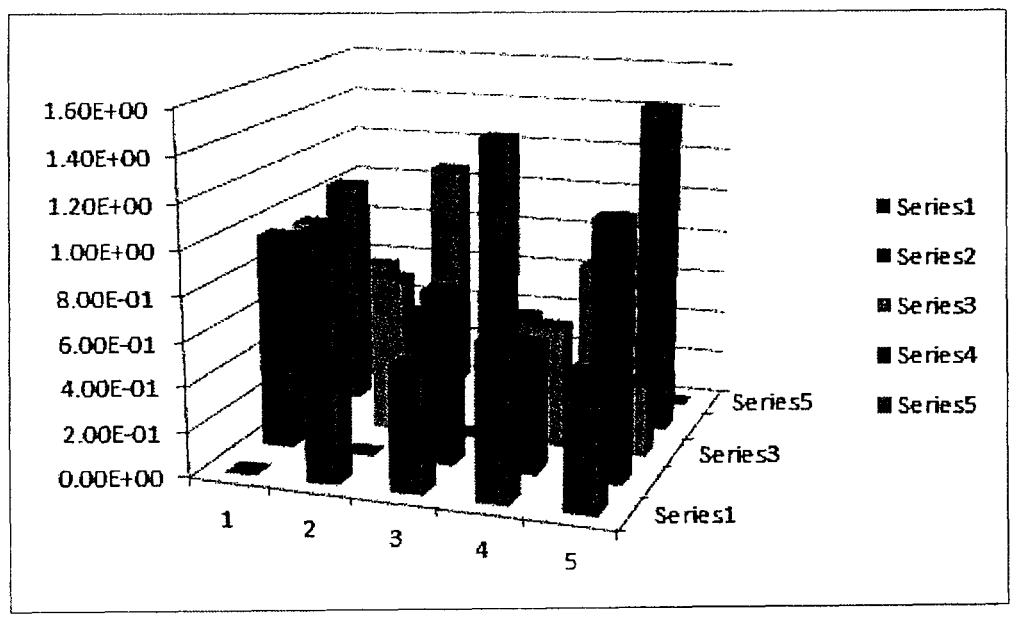
FIG. 97 shows the decomposition/restoration error using an individual principal component analysis.

The results of this procedure performed for the set of fluids above is shown on FIG. 97 below. FIG. 97 shows the decomposition/restoration error using the individual PCA technique just described. It is clearly visible in FIG. 97 that individual PCA allows for a very good discrimination between the patterns based on the discrepancy between the original data end the restored data. As more data is collected and all sources of the variability in the data are taken into account a realistic threshold levels can be calculated for the automated data classification based on this approach.

Figure 98:
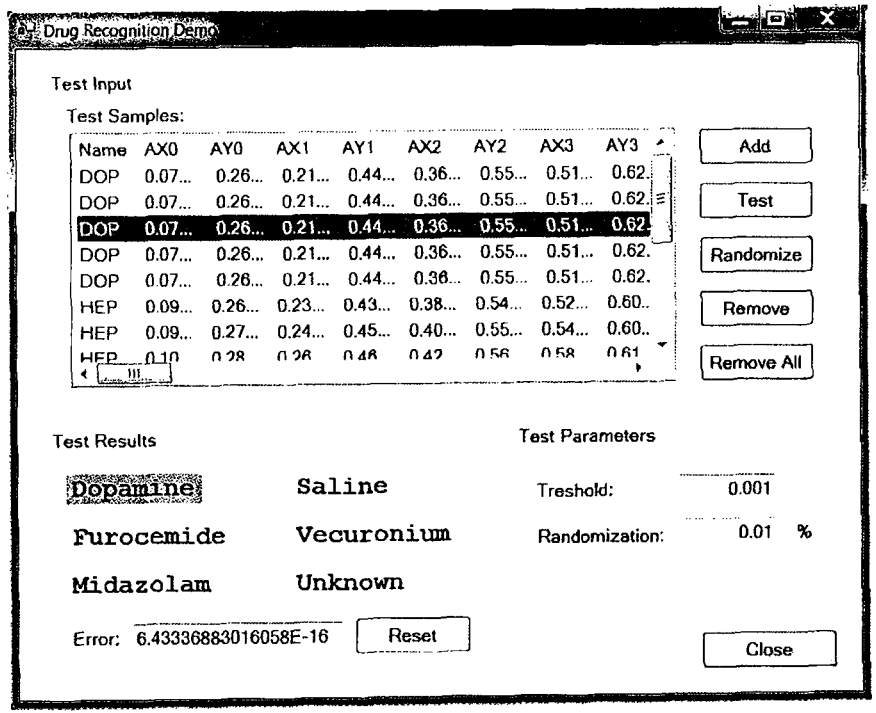
FIG. 98 is an exemplary screen shot showing the use of an individual PCA technique applied to drug recognition.
Figure 99:
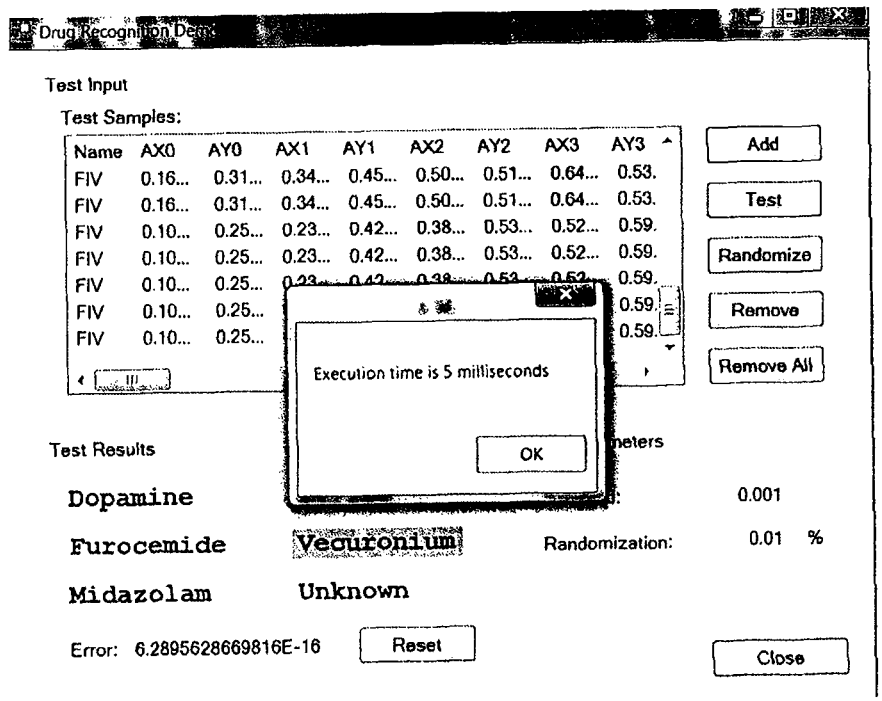
FIG. 99 indicates the timing of the method of FIG. 98.

Utilizing the individual PCA method an application for drug recognition has been developed (FIG. 98). It allows recognizing the 5 drugs described above as well as an unknown drugs that do not match any of the drug patterns in the training set. Running this program on a mid-power notebook and timing recognition demonstrated that it takes between 1 and 5 ms to recognize the drug or an unknown. Calculation time for one comparison with the drug from the training set is about 1 ms, and the worst case scenario is when the formulation matches the last drug in the sequence of attempts or when the formulation is unknown. For example, as shown in FIG. 99 it took 5 ms to recognize a fluid as Vecuronium—the fifth drug on the list an in the sequence of tests.

Figure 100:
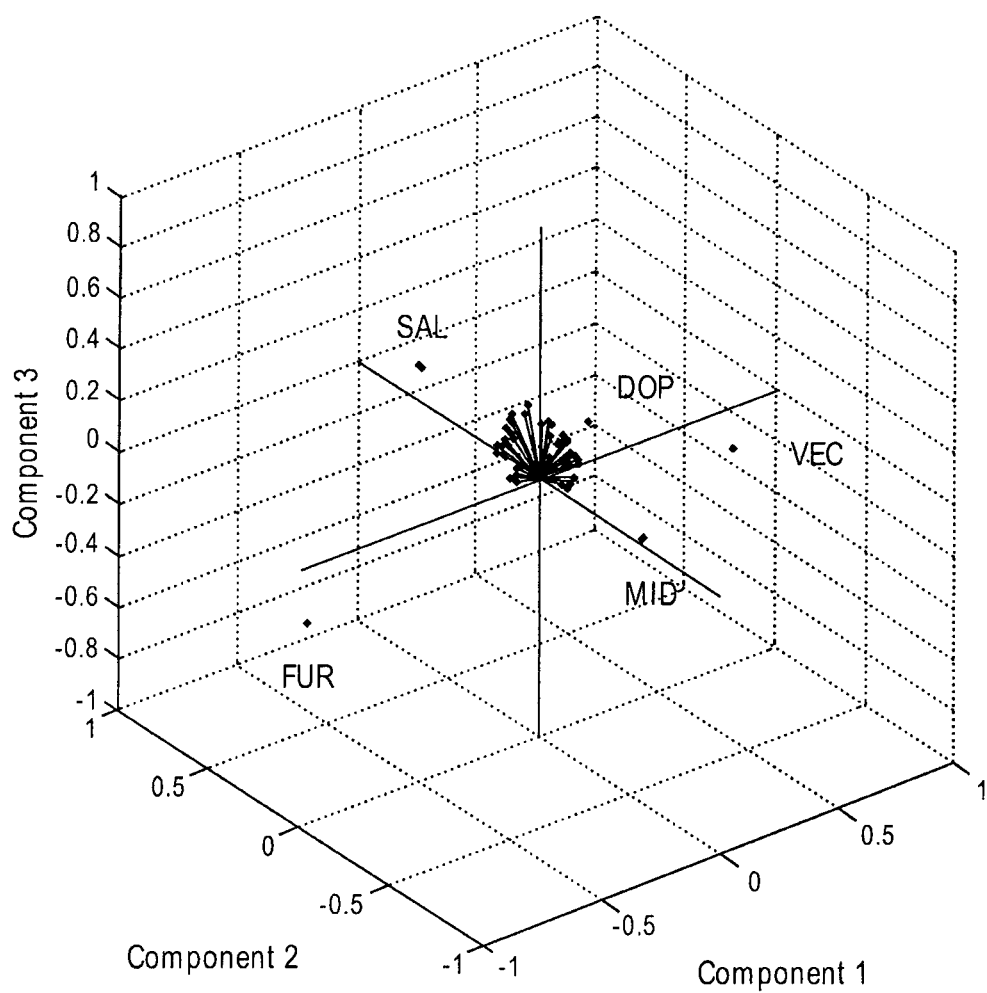
FIG. 100 is a BiPlot generated from a Global PCA analysis of 5 fluids to generate primary component space encompassing all five patterns.
Figure 101:
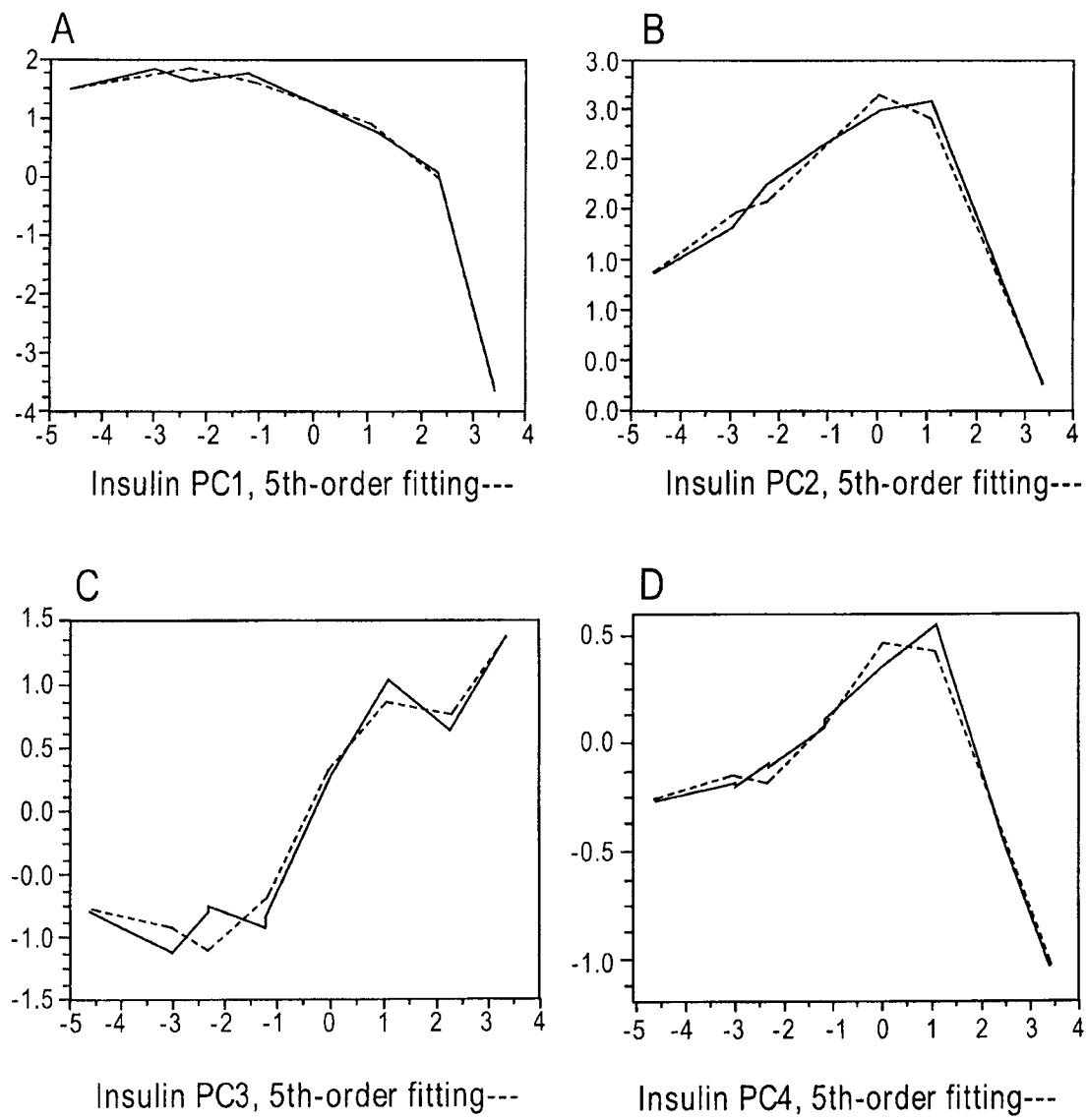
FIGS. 101A-D show examples of the principal component projections with the fitting by fifth-order polynomial curves for Insulin.
Figure 102:
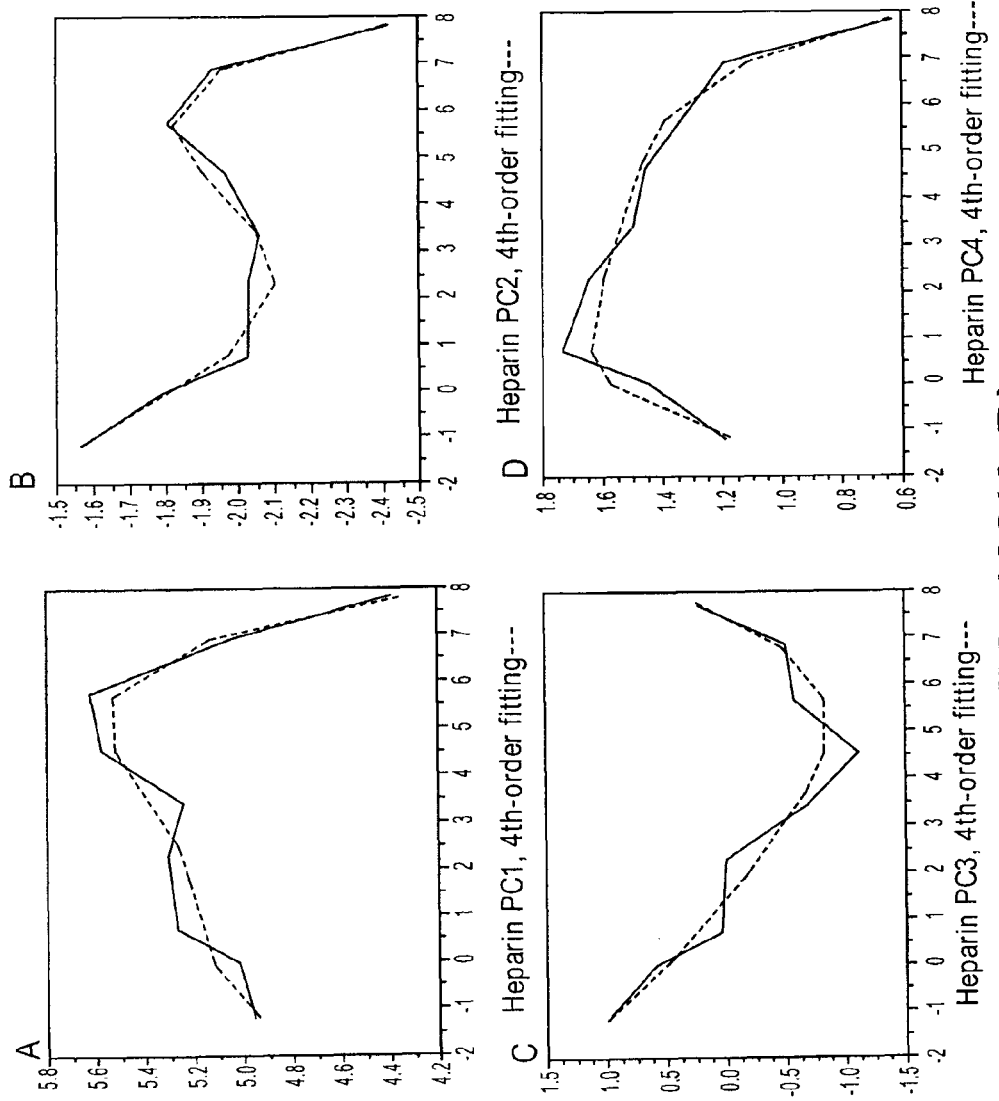
FIGS. 102A-D show examples of the principal component projections with the fitting by fifth-order polynomial curves for Heparin.

The technique of Global PCA described above was used with the same set of data for same 5 fluids to generate primary component space encompassing all five patterns. The BiPlot generated for this dataset is shown FIG. 100 below (only first 3 primary components are shown). In primary component space all patterns are points. All five individual measurements for each fluid are represented on this BiPlot, but lay so close to each other that appear as single data marker. Variability within data for individual fluids can be calculated and utilized as a measure of separation between different data classes.

TABLE 2

Various IV fluids in the common primary components' space.

| Drug | Variability | Distance from Origin | D to V ratio |
|---|---|---|---|
| DOP | 0.0197 | 8.2251 | 416.9393 |
| FUR | 0.0256 | 10.7262 | 418.417 |
| MID | 0.1879 | 4.3774 | 23.2955 |
| SAL | 0.0746 | 5.8154 | 77.9876 |
| VEC | 0.048 | 7.2233 | 150.5039 |

The coordinates of the center of mass for the individual class can be calculated as well as the distances between the center of mass and the coordinate's origin and between centers of masses of individual classes. Dividing these distances by the variability of data within one of the classes provides a proxy of a signal-to noise ratio in the primary components space. The variability, distances for the origin and their ratios were calculated for the 5 IV fluid datasets listed earlier, please see Table 2 above.

In some variations, the system may apply two steps to the drug recognition process: (1) dimension reduction; and (2) regression analysis. An overview of the available computational methods that may be applied to this method follows.
Dimension Reduction Drug signatures collected by the exemplary systems described above are multivariate. Each pattern could belong to 60, 120, 240 or even more dimensional spaces. Some of the variables could be linear combinations of other variables. It may be beneficial to reduce the high dimensional data to lower dimensional representation that captures the essential content in the original data. Two major types of dimension reduction methods are linear and non-linear.

Linear techniques result in each of the components of the new variable being a linear combination of the original variables. Enumerated in this paragraph are various types (and subtypes) of linear methods, additional methods may be used. For example, principal component analysis (PCA) is the best, in the mean-square error sense, linear dimension reduction technique. Factor analysis (FA) is also a linear method, based on the second-order statistical momentums. First suggested by psychologists, FA assumes that the measured variables depend on some unknown, and often immeasurable, common factors. Types of FA include: Principal Factor Analysis (PFA); and maximum likelihood factor analysis. Projection pursuit (PP) is a linear method that, unlike PCA and FA, can incorporate higher than second-order information, and thus is useful for non-Gaussian datasets. It is more computationally intensive than second-order methods. Independent component analysis (ICA) is a higher-order method that seeks linear projections, not necessarily orthogonal to each other, that are as nearly statistically independent as possible. Statistical independence is a much stronger condition than uncorrelatdness. It depends on all the higher-order statistics. Multi-unit objective functions. There are many different ways to specify objective functions: Maximum likelihood and network entropy. This method specifies the likelihood of the noise-free ICA model, and uses the maximum likelihood principle to estimate the parameters; Mutual information and Kullback-Leibler divergence. It attempts to find the variables that minimize the mutual information among the components; Non-linear cross-correlations; and Higher-order cumulant tensors. One-unit objective functions may include: Negentropy, which tries to find the direction of maximum negative entropy which is equivalent to finding the representation with minimum mutual information; higher-order cumulants; and General contrast functions. Optimization algorithms may also be used and include: Adaptive methods, which include the use of stochastic gradient-type algorithms; likelihood or other multi-unit contrast functions are optimized using gradient ascent of the objective function; Batch-mode (block) algorithms are much more computationally efficient than adaptive algorithms, and are more desirable in many practical situations where there is no need for adaptation. The Fast ICA is such a batch-mode algorithm using fixed-point iteration. Non-linear principal component analysis (NLPCA) is a technique that introduces non-linearity in the objective function, but the resulting components are still linear combinations of the original variables. Random projections method is a simple yet powerful dimension reduction technique that uses random projection matrices to project the data into lower dimensional spaces. It has been shown empirically that results with the random projection method are comparable with results obtained with PCA, and take a fraction of the time PCA requires.

Non-linear methods and extensions may also be used. The original variables in these methods are replaced with the new variables according to non-linear transformation:

$$(x_1, \ldots, x_p)^T = f(s_1, \ldots, s_k)^T$$

where f is an unknown real-valued p-component vector function. Non-linear techniques include, but are not limited to: Non-linear independent component analysis; Principal curves; Multidimensional scaling; and Topologically continuous maps. Topologically continuous maps include: Kohonen's self-organizing maps; Density networks; Neural networks; Vector quantization; and Genetic and evolutionary algorithms.

Regression analysis is the term used to describe a family of methods that seek to model the relationship between one (or more) dependent or response variables and a number of independent or predictor variables. Parametric methods may be applied when the regression function is defined in terms of a finite number of unknown parameters that are estimated from the data. For example types of regression analysis may include: Linear Regression—the model specification is that the dependent variable is a linear combination of the parameters (but need not be linear in the independent variables); Ordinary least squares (OLS); Generalized least squares (GLS); Iteratively reweighted least squares (IRLS); Instrumental variables regression (IV); Optimal instruments regression; Least absolute deviation (LAD); Quantile regression; Maximum likelihood estimation; Adaptive estimation; Principal component regression (PCR); Total least squares (TLS); Ridge regression; and Least angle regression.

Non-linear Regression is a form of regression analysis in which observational data are modeled by a function which is a nonlinear combination of the model parameters and depends on one or more independent variables. Examples of model functions are include exponential functions, logarithmic functions, trigonometric functions, power functions, Gaussian function, and Lorentzian curves. In general, there is no closed-form expression for the best-fitting parameters, as there is in linear regression. Usually numerical optimization algorithms are applied to determine the best-fitting parameters. Again in contrast to linear regression, there may be many local minima of the function to be optimized and even the global minimum may produce a biased estimate. In practice, estimated values of the parameters are used, in conjunction with the optimization algorithm, to attempt to find the global minimum of a sum of squares.

Non-parametric methods include nonparametric regression, which is a form of regression analysis in which the predictor does not take a predetermined form but is constructed according to information derived from the data. Non-parametric regression requires larger sample sizes than regression based on parametric models because the data must supply the model structure as well as the model estimates. Examples of non-parametric methods include: Kernel Regression; Multiplicative Regression; Regression Trees; and Multivariate Adaptive Regression Splines (MARS).

In one example, for the dimension reduction Principal Component Analysis (PCA) and Non-Linear PCA (or NLPCA) was applied to an initial test dataset for comparison to a library data space. This approach allows reduction from 60-dimensional space into 4-dimentional space. The analysis was implemented for recognition of seven different drugs. Linear Regression Analysis has been used for drug concentration calculation. Ordinary Least Squares technique was used to calculate parameters of fifth-order polynomial approximation. This method was applied to the concentration curves of two different drugs. The accuracy of concentration calculation was within 10%.

Other dimension reduction techniques as well as regression methods, including those mentioned above, such as Multivariate Adaptive Regression Splines (MARS), may be used to find the most optimal approach to the drug recognition problem.

Examples of the principal component projections with the fitting by fifth-order polynomial curves are shown in FIGS. 101A-D (Insulin) and FIG. 102A-D (Heparin), in which the principal component is indicated in capture as a function of logarithm of concentration.

An application has been developed for drug recognition software demonstration. The algorithm has been trained to recognize seven drugs—dopamine, furosemide, heparin, insulin, midazolam, saline, and vecuronium. The error threshold is configurable. The application has a randomization functionality injecting noise into the dataset, so that user can randomize the input data to test at what randomization factor the data still can be recognized as a pattern of a known drug.

Figure 103:
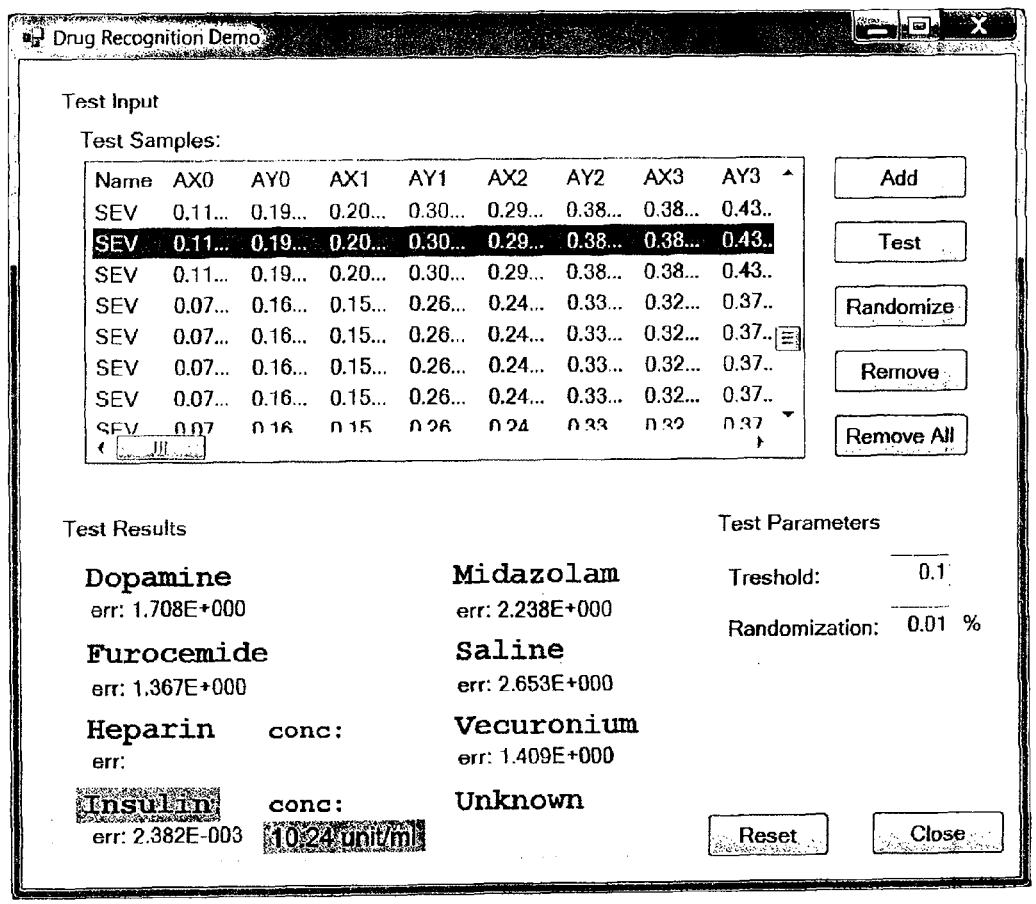
FIG. 103 is a screen capture showing the results of using a PCA technique to identify a drug from a library of immittance spectrographic fingerprints.

The application has been also trained to calculate the concentration of two drugs—insulin and heparin. As soon as an input sample is recognized as one of these two drugs, the concentration calculation procedure is invoked and the result is displayed next to the drug name. FIG. 103 illustrates a screen capture of some of the test results using this application in demonstrating the identification of drugs.

In addition to neural networks and Principal Component Analysis (PCA) techniques discussed above, we have considered the application of: data clustering, vector based approaches, as well as many conventional analysis techniques that it is clear could be applied to recognition of our sensor patterns.

Figure 104A:
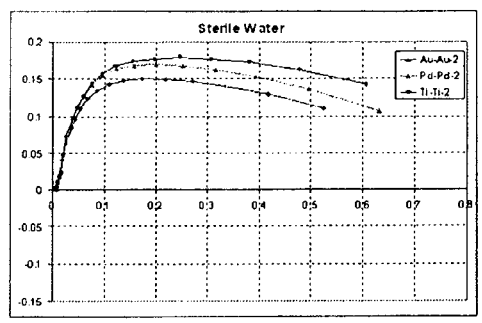
FIG. 104A is a plot of the complex immittance for sterile water.
Figure 104B:
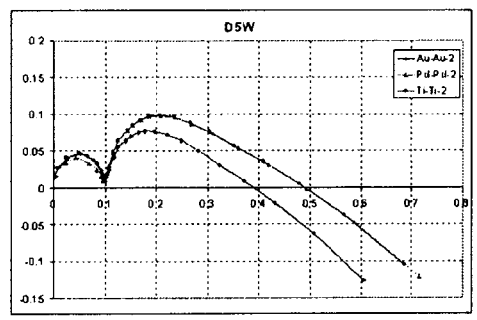
FIG. 104B is a plot of the complex immittance for D5W.

Another example of drug recognition using the systems described herein was used with both low and high ionic strength diluents, using the low-ionic strength electrodes described above. In this example, the low ionic strength (interdigitated electrode pattern) within the sensor allowed for clear distinction between very low ionic strength liquids: Sterile Water and D5W, as shown in FIGS. 104A and 104B.

FIGS. 105A-D show example of different sensor electrode patterns to Heparin of variable concentration in D5W, frequency scan from 100 HZ to 1 MHz taken with the low ionic-strength (interdigitated) electrodes. The same samples were then taken with small pad electrodes (high ionic strength electrodes); resulting traces are shown in FIGS. 106A-J. Finally, the same sample solutions were analyzed using cross-metal electrodes, as shown in FIGS. 107A-H. Note that the XY scale on all the above charts is dynamic (different) to make the complicated shape of the response clearly visible.

From the dilution curves of Heparin in D5W and Sterile Water, a limited demo "library" was generated and utilized in an interactive application program that is waiting for the data set from the measurement setup and recognizes the drug in the real time. Screenshots of this analysis are show in FIG. 108A-D. If the system is presented with a drug that is not in the library the system produces an alert and indicates that the drug could not be recognized.

Estimation of Drug Concentration

Patterns projected into multi-dimensional eigenvalue space define points in such space. A set of patterns obtained at various drug concentrations define a set of points in the eigenvalue space that can be treated as a "dilution" curve. All the available data on given drug dilution can be fit to a parametric function of concentration or, for many practical cases, logarithm of concentration. For a new measurement of the drug the concentration can be estimated from the previously measured data by minimizing distance from measured point to the approximating curve:

$$F(t) = (x_e - x(t))^2 + (y_e - y(t))^2 + (z_e - z(t))^2 + (u_e - u(t))^2 \xrightarrow[t]{} \min,$$

t—is log(c),
where c is the drug concentration: c=exp(t).

An example of this algorithm applied to the insulin dilution curve, where the curve was approximated by a $4^{th}$ and $5^{th}$ order polynomial function of logarithm of concentration is shown in FIG. 109A-D. The results depend on whether the dilution curve was constructed by fitting data of each primary component or all components altogether. For the dataset containing an outlier such as the third or fourth point in sequence the first approach tends to ignore the outlier and fit the rest of the data points accurately while the second approach tends to distribute disturbance produced by outlier to the neighboring points. Both approaches have demonstrated that concentration can be estimated with the accuracy of about 10-12% except for the concentration values in the vicinity of the outlier.

In the course of applying principal component analysis to the experimental data we have noted that 4 primary components account for 99.98% of observed variability in the data. This is a statistical indication that if the system is close to linear there should be 4 independent orthogonal sources of this variability. The physical model of the sensor-fluid interaction is an equivalent circuit that contains 4 independent lumped components—2 capacitors and 2 resistors. Thus the experimental data provides, although indirectly, empirical support for the 4-component physical model.

The systems and devices for determining the composition of aqueous solutions described herein may be particularly useful for medical applications, though not strictly limited to medical applications. The complex admittance devices, systems and methods described herein may also be useful for measurement or validation of key ingredients in complex fluids for manufacturing. In some variations the systems described herein may also be useful for determining water quality or other testing purposes.

While the methods, devices and systems for determining composition of a solution using admittance spectroscopy have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the invention.

What is claimed is:

1. A method of determining the identity of a drug or drug formulation by recognizing a pattern of complex immittance from a library of known complex immittances, the method comprising:
   receiving an initial dataset comprising complex immittance spectrographic information for an unknown liquid sample, the complex immittance spectrographic information taken from a plurality of different electrode pairs each at a plurality of different frequencies wherein each pair of electrodes had different surface properties arising from a different size, different shape, or different material relative to each other, and further wherein the complex immittance spectrographic information was recorded while the electrode pairs were in contact with the unknown liquid sample;
   using a processor to apply one or more pattern recognition techniques to compare the initial dataset to an identification space database comprising a plurality of identification datasets wherein the identification datasets comprise complex immittance data corresponding to known drug compositions to determine if the initial dataset matches an identification dataset from the identification space database within a threshold range; and
   reporting that the initial dataset does or does not match an identification dataset, and if the initial dataset does match an identification dataset within the threshold range, reporting which drug or drugs correspond to the identification dataset matched.

2. The method of claim 1, wherein using the processor to apply one or more pattern recognition techniques comprises using a Neural Network.

3. The method of claim 1, wherein using the processor to apply one or more pattern recognition techniques comprises using a Probabilistic Neural Network.

4. The method of claim 1, wherein using the processor to apply one or more pattern recognition techniques comprises reducing the dimension of the initial dataset and performing a regression analysis.

5. The method of claim 1, wherein receiving the initial dataset comprises receiving an initial dataset having greater than 30 dimensions.

6. The method of claim 1, further comprising setting the threshold range.

7. The method of claim 1, wherein using a processor to apply one or more pattern recognition techniques comprises applying two pattern recognition techniques.

8. The method of claim 1, wherein using the processor to apply one or more pattern recognition techniques comprises initially applying a PCA method to reduce the dimension of the data and then applying another pattern recognition technique to determine if the initial dataset matches an identification dataset.

9. The method of claim 1, wherein using the processor to apply one or more pattern recognition techniques comprises initially applying a PCA method to reduce the dimension of the dataset and then using a neural network to determine if the initial dataset matches an identification dataset.

10. The method of claim 1, wherein using the processor to apply one or more pattern recognition techniques comprises applying a linear technique selected from the group consisting of: principal component analysis, factor analysis, projection pursuit, independent component analysis, multi-objective functions, one-unit objective functions, adaptive methods, batch-mode algorithms, and random projections methods.

11. The method of claim 1, wherein using the processor to apply one or more pattern recognition techniques comprises applying a non-linear technique selected from the group consisting of: non-linear principle component analysis, non-linear independent component analysis, principle curves, multidimensional scaling, and topologically continuous maps.

12. The method of claim 1, further comprising interpolating to get an estimate of the concentration of the drug or drug corresponding to the matching identification dataset when the initial dataset matches the identification dataset within the threshold range.

13. The method of claim 1, wherein reporting that the initial dataset does or does not match an identification dataset comprises reporting the concentration of the drug or drugs correspond to the identification dataset when the initial dataset does match the identification dataset within the threshold range.

14. The method of claim 1, wherein using the processor to apply one or more pattern recognition techniques comprises reducing the initial dataset down to four dimensions.

15. A method of determining the identity of a drug or drug formulation by recognizing a pattern of complex immittance from a library of known complex immittances, the method comprising:
   receiving an initial dataset comprising multi-dimensional, complex immittance spectrographic information for an unknown liquid sample, the complex immittance spectrographic information taken from a plurality of different electrode pairs each at a plurality of different frequencies wherein each pair of electrodes had different surface properties arising from a different size, different shape, or different material relative to each other, and further wherein the complex immittance spectrographic information was recorded while the electrode pairs were in contact with the unknown liquid sample;
   reducing the dimensions of the initial dataset using a linear or non-linear technique to form a reduced dataset;
   determining how closely the reduced dataset matches an identification dataset of an identification space database, wherein the identification space database comprises a plurality of identification datasets corresponding to known drug compositions; and
   reporting that the known drug composition corresponding to the identification space database having the closest match to the reduced dataset if the closeness of the match is within a threshold range, or report that the unknown liquid sample does not match a known drug composition of those drugs included in the identification space database if the closeness of match is outside of the threshold range.

16. The method of claim 15, wherein reducing the dimensions of the initial dataset comprises applying a linear technique selected from the group consisting of: principal component analysis, factor analysis, projection pursuit, independent component analysis, multi-objective functions, one-unit objective functions, adaptive methods, batch-mode algorithms, and random projections methods.

17. The method of claim 15, wherein reducing the dimensions of the initial dataset comprises applying a non-linear technique selected from the group consisting of: non-linear principle component analysis, non-linear independent component analysis, principle curves, multidimensional scaling, and topologically continuous maps.

18. The method of claim 15, wherein reducing the dimensions of the initial dataset comprises reducing the initial dataset down to four dimensions.

19. A method of determining the identity and concentration of a drug by recognizing a pattern of complex immittance from a library of known complex immittances, the method comprising:
- receiving an initial dataset comprising multi-dimensional, complex immittance spectrographic information for an unknown liquid sample, the complex immittance spectrographic information taken from a plurality of different electrode pairs each at a plurality of different frequencies wherein each pair of electrodes had different surface properties arising from a different size, different shape, or different material relative to each other, and further wherein the complex immittance spectrographic information was recorded while the electrode pairs were in contact with the unknown liquid sample;
- reducing the dimensions of the initial dataset using a linear or non-linear technique to form a reduced dataset;
- matching the reduced dataset to an identification space database, the identification space database comprising a plurality of identification datasets corresponding to known drug compositions;
- determining the closeness of the match for the reduced dataset relative to each of the identification datasets;
- determining a proposed drug composition by applying a threshold to the closeness of the match for each of the identification datasets, wherein the proposed drug composition is unknown if the closeness of match is outside of the threshold range; and
- determining a concentration of drug in the unknown liquid sample by applying a regression of the proposed drug composition for the known drug composition.

* * * * *